US012698275B2

(12) United States Patent
Kwon et al.

(10) Patent No.: US 12,698,275 B2
(45) Date of Patent: Aug. 4, 2026

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Jiyun Kwon, Suwon-si (KR); Dong Min Kang, Suwon-si (KR); Byungku Kim, Suwon-si (KR); Jin Sook Kim, Suwon-si (KR); Byoungkwan Lee, Suwon-si (KR); Kipo Jang, Suwon-si (KR); Suyong Lim, Suwon-si (KR); Sung-Hyun Jung, Suwon-si (KR); Ho Kuk Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 966 days.

(21) Appl. No.: 17/965,074

(22) Filed: Oct. 13, 2022

(65) Prior Publication Data

US 2023/0119772 A1 Apr. 20, 2023

(30) Foreign Application Priority Data

Oct. 13, 2021 (KR) ........................ 10-2021-0135987
Oct. 13, 2022 (KR) ........................ 10-2022-0131396

(51) Int. Cl.
*C07D 405/04* (2006.01)
*C07D 405/14* (2006.01)
(Continued)

(52) U.S. Cl.
CPC ......... *C07D 405/04* (2013.01); *C07D 405/14* (2013.01); *C07D 409/14* (2013.01);
(Continued)

(58) Field of Classification Search
CPC ............. H10K 85/654; H10K 85/6574; H10K 85/6576; C07D 405/04; C07D 405/10;
(Continued)

(56) References Cited

U.S. PATENT DOCUMENTS 5,061,569 A 10/1991 Vanslyke et al.
2019/0312215 A1 10/2019 Kang et al.
(Continued)

FOREIGN PATENT DOCUMENTS

CN 112080273 A 12/2020
CN 112159397 A 1/2021
(Continued)

OTHER PUBLICATIONS

Machine-generated English-language translation of CN-113549059-A.*
(Continued)

*Primary Examiner* — Vu A Nguyen
(74) *Attorney, Agent, or Firm* — Lee IP Law, P.C.

(57) ABSTRACT

A compound for an organic optoelectronic device, a composition for an organic optoelectronic device including the same, an organic optoelectronic device, and a display device, the compound being represented by Chemical Formula 1:
(Continued)

[Chemical Formula 1]

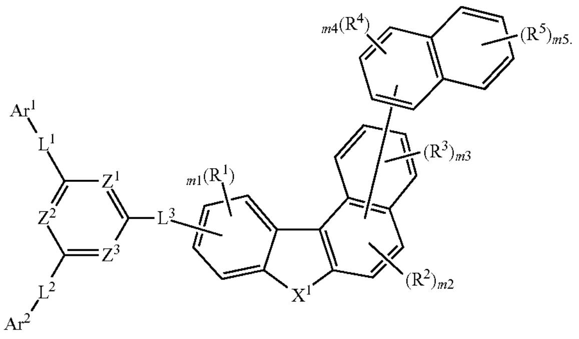

19 Claims, 1 Drawing Sheet

(51) Int. Cl.

| | |
|---|---|
| ***C07D 409/14*** | (2006.01) |
| ***C07D 413/14*** | (2006.01) |
| ***C07D 417/14*** | (2006.01) |
| ***C07F 7/08*** | (2006.01) |
| ***H10K 50/12*** | (2023.01) |
| ***H10K 85/40*** | (2023.01) |
| ***H10K 85/60*** | (2023.01) |

(52) U.S. Cl.
CPC ......... *C07D 413/14* (2013.01); *C07D 417/14* (2013.01); *C07F 7/0812* (2013.01); *H10K 50/12* (2023.02); *H10K 85/40* (2023.02); *H10K 85/615* (2023.02); *H10K 85/622* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *C07B 2200/05* (2013.01)

(58) Field of Classification Search
CPC .. C07D 405/14; C07D 409/04; C07D 409/10; C07D 409/14
See application file for complete search history.

(56) References Cited

U.S. PATENT DOCUMENTS

| | | | | |
|---|---|---|---|---|
| 2021/0009894 | A1 | 1/2021 | Ha et al. | |
| 2021/0273176 | A1 | 9/2021 | Kang et al. | |
| 2022/0085298 | A1 | 3/2022 | Lee et al. | |
| 2022/0089610 | A1* | 3/2022 | Mo .................... | C07D 491/048 |
| 2022/0131081 | A1 | 4/2022 | Moon et al. | |
| 2023/0048456 | A1* | 2/2023 | Kwon .................. | H10K 85/631 |

FOREIGN PATENT DOCUMENTS

| | | | | | |
|---|---|---|---|---|---|
| CN | 112292767 | A | | 1/2021 | |
| CN | 113004295 | A | | 6/2021 | |
| CN | 113260615 | A | | 8/2021 | |
| CN | 113330016 | A | | 8/2021 | |
| CN | 113549059 | A | * | 10/2021 | ........... C07D 405/04 |
| JP | 1993-009471 | A | | 1/1993 | |
| JP | 1995-126615 | A | | 5/1995 | |
| JP | 1998-095973 | A | | 4/1998 | |
| KR | 10-2018-0051355 | A | | 5/2018 | |
| KR | 10-2019-0103765 | A | | 9/2019 | |
| KR | 10-2021294 | B1 | | 9/2019 | |
| KR | 10-2019-0118392 | A | | 10/2019 | |
| KR | 10-2019-0124162 | A | | 11/2019 | |
| KR | 10-2019-0127272 | A | | 11/2019 | |
| KR | 10-2019-0140732 | A | | 12/2019 | |
| KR | 10-2020-0042851 | A | | 4/2020 | |
| KR | 10-2020-0070462 | A | | 6/2020 | |
| KR | 10-2020-0081300 | A | | 7/2020 | |
| KR | 10-2134383 | B1 | | 7/2020 | |
| KR | 10-2020-0092633 | A | | 8/2020 | |
| KR | 10-2020-0092879 | A | | 8/2020 | |
| KR | 10-2021-0056935 | A | | 5/2021 | |
| KR | 10-2021-0084715 | A | | 7/2021 | |
| KR | 10-2021-0135987 | A | | 11/2021 | |
| WO | WO 1995/009147 | A1 | | 4/1995 | |
| WO | WO-2020138944 | A1 | * | 7/2020 | ........... C07D 519/00 |
| WO | WO-2021096331 | A1 | * | 5/2021 | ............. H10K 50/11 |
| WO | WO-2021132995 | A1 | * | 7/2021 | ......... H10K 85/6574 |

OTHER PUBLICATIONS

Korean Office action dated Oct. 22, 2024.
Chinese Office action dated Dec. 27, 2024.
Korean Notice of Allowance dated Jun. 24, 2025.

* cited by examiner

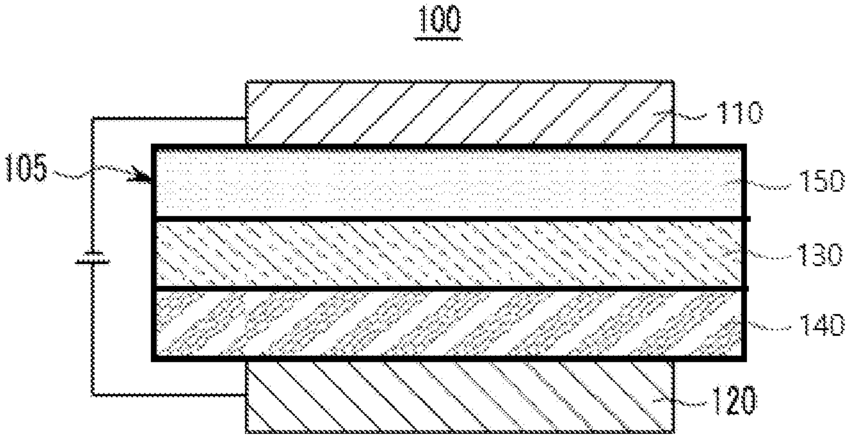
100
110
105
150
130
140
120

COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

CROSS-REFERENCE TO RELATED APPLICATION

This application claims priority to and the benefit of Korean Patent Application No. 10-2021-0135987 filed in the Korean Intellectual Property Office on Oct. 13, 2021, and Korean Patent Application No. 10-2022-0131396, filed in the Korean Intellectual Property Office on Oct. 13, 2022, the entire contents of which are incorporated herein by reference.

BACKGROUND

1. Field

Embodiments relate to a compound for an organic optoelectronic device, a composition for an organic optoelectronic device, an organic optoelectronic device, and a display device.

2. Description of the Related Art

An organic optoelectronic device (e.g., organic optoelectronic diode) is a device capable of converting electrical energy and optical energy to each other.

Organic optoelectronic devices may be largely divided into two types according to a principle of operation. One is a photoelectric device that generates electrical energy by separating excitons formed by light energy into electrons and holes, and transferring the electrons and holes to different electrodes, respectively and the other is light emitting device that generates light energy from electrical energy by supplying voltage or current to the electrodes.

Examples of the organic optoelectronic device may include an organic photoelectric device, an organic light emitting diode, an organic solar cell, and an organic photo conductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode is greatly influenced by an organic material between electrodes.

SUMMARY

The embodiments may be realized by providing a compound for an organic optoelectronic device, the compound being represented by Chemical Formula 1:

[Chemical Formula 1]

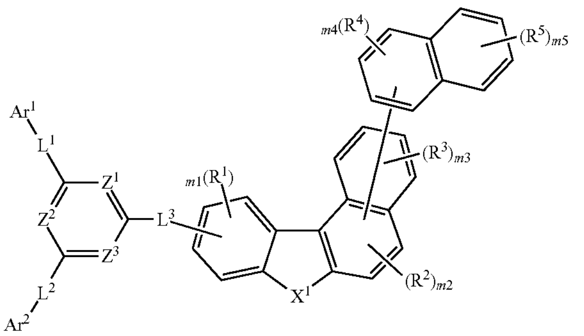

wherein, in Chemical Formula 1, $X^1$ is O or S, $Z^1$ to $Z^3$ are each independently N or $CR^a$, at least two of $Z^1$ to $Z^3$ being N, $L^1$ and $L^2$ are each independently a single bond, a substituted or unsubstituted C6 to C30 arylene group, or a substituted or unsubstituted C2 to C30 heterocyclic group, $L^3$ is a single bond, a substituted or unsubstituted C6 to C30 arylene group, or a substituted or unsubstituted C2 to C30 heterocyclic group, $Ar^1$ and $Ar^2$ are each independently a substituted or unsubstituted C6 to C30 aryl group or a substituted or unsubstituted C2 to C30 heterocyclic group, $R^a$ and $R^1$ to $R^5$ are each independently hydrogen, deuterium, a substituted or unsubstituted C1 to C20 alkyl group, or a substituted or unsubstituted C6 to C20 aryl group, m1 and m4 are each independently an integer of 1 to 3, m2 is 1 or 2, and m3 and m5 are each independently an integer of 1 to 4.

The embodiments may be realized by providing a composition for an organic optoelectronic device, the composition including a first compound; and a second compound, wherein the first compound is the compound for the organic optoelectronic device according to an embodiment, and the second compound is represented by Chemical Formula 2:

[Chemical Formula 2]

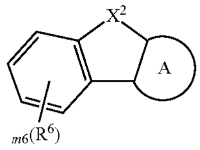

in Chemical Formula 2, $X^2$ is O, S, $NR^b$, $CR^cR^d$, or $SiR^eR^f$, $R^b$, $R^c$, $R^d$, $R^e$, $R^f$, and $R^6$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, m6 is an integer of 1 to 4, and ring A is a ring of Group II,

[Group II]

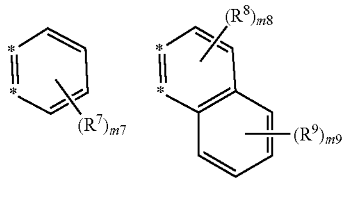

-continued

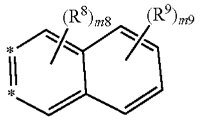

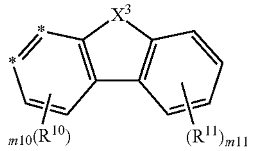

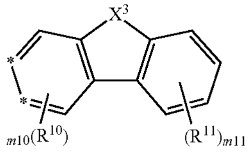

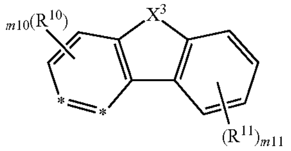

in Group II,*is a linking point, $X^3$ is O, S, $NR^g$, $CR^hR^i$, or $SiR^jR^k$, $R^h$, $R^i$, $R^j$, $R^k$, and $R^7$ to $R^{11}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, m7, m9, and m11 are each independently an integer of 1 to 4, m8 and m10 are each independently 1 or 2, and at least one of $R^6$ to $R^{11}$ is a group represented by Chemical Formula a,

[Chemical Formula a]

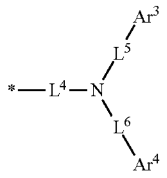

in Chemical Formula a, $L^4$ to $L^6$ are each independently a single bond or a substituted or unsubstituted C6 to C30 arylene group, $Ar^3$ and $Ar^4$ are each independently a substituted or unsubstituted amine group, a substituted or unsubstituted C6 to C30 aryl group, or a substituted or unsubstituted C2 to C30 heterocyclic group, and*is a linking point.

The embodiments may be realized by providing an organic optoelectronic device including an anode and a cathode facing each other, and at least one organic layer between the anode and the cathode, wherein the at least one organic layer includes a light emitting layer, and the light emitting layer includes the compound for the organic optoelectronic device according to an embodiment.

The embodiments may be realized by providing an organic optoelectronic device including an anode and a cathode facing each other, and at least one organic layer between the anode and the cathode, wherein the at least one organic layer includes a light emitting layer, and the light emitting layer includes the composition for the organic optoelectronic device according to an embodiment.

The embodiments may be realized by providing a display device including the organic optoelectronic device according to an embodiment.

BRIEF DESCRIPTION OF THE DRAWING

Features will be apparent to those of skill in the art by describing in detail exemplary embodiments with reference to the attached drawing in which:

the FIGURE a cross-sectional view illustrating an organic light emitting diode according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout. As used herein, the term "or" is not an exclusive term, e.g., "A or B" would include A, B, or A and B.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in specific examples of the present invention, "substituted" refers to replacement of at least one hydrogen of a substituent or a compound by deuterium, a C1 to C20 alkyl group, a C6 to C30 aryl group, or a cyano group. In addition, in specific examples of the present invention, "substituted" refers to replacement of at least one hydrogen of a substituent or a compound by deuterium, a C1 to C5 alkyl group, a C6 to C18 aryl group, or a cyano group. In addition, in specific examples of the present invention, "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, "unsubstituted" refers to non-replacement of a hydrogen atom by another substituent and remaining of the hydrogen atom.

As used herein, "hydrogen substitution (—H)" may include deuterium substitution (-D) or "tritium substitution (-T).

As used herein, when a definition is not otherwise provided, "hetero" refers to one including one to three heteroatoms selected from N, O, S, P, and Si, and remaining carbons in one functional group.

As used herein, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring, for example, a fluorenyl group, and the like.

The aryl group may include a monocyclic, polycyclic or fused ring polycyclic (i.e., rings sharing adjacent pairs of carbon atoms) functional group.

As used herein, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but is not limited thereto.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, a substituted or unsubstituted dibenzothiophenyl group, a substituted or unsubstituted benzonaphthofuranyl group, a substituted or unsubstituted benzonaphthothiophenyl group, a substituted or unsubstituted dibenzosilolyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

The compound for an organic optoelectronic device according to an embodiment may be represented by, e.g., Chemical Formula 1.

[Chemical Formula 1]

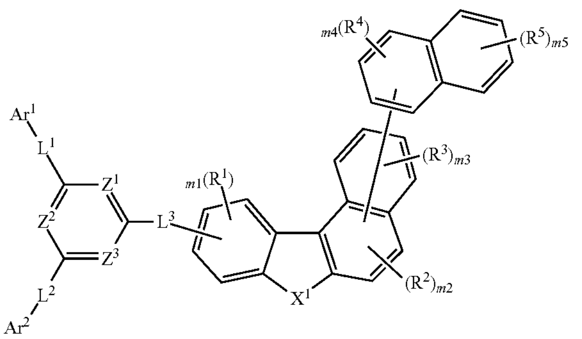

In Chemical Formula 1, $X^1$ may be, e.g., O or S.

- $Z^1$ to $Z^3$ may each independently be, e.g., N or $CR^a$. In an implementation, at least two of $Z^1$ to $Z^3$ are N.
- $L^1$ and $L^2$ may each independently be or include, e.g., a single bond, a substituted or unsubstituted C6 to C30 arylene group, or a substituted or unsubstituted C2 to C30 heterocyclic group.
- $L^3$ may be or may include, e.g., a single bond, a substituted or unsubstituted C6 to C30 arylene group, or a substituted or unsubstituted C2 to C30 heterocyclic group.
- $Ar^1$ and $Ar^2$ may each independently be or include, e.g., a substituted or unsubstituted C6 to C30 aryl group or a substituted or unsubstituted C2 to C30 heterocyclic group.
- $R^a$, and $R^1$ to $R^5$ may each independently be or include, e.g., hydrogen, deuterium, a substituted or unsubstituted C1 to C20 alkyl group, or a substituted or unsubstituted C6 to C20 aryl group.
- m1 and m4 may each independently be, e.g., an integer of 1 to 3.

m2 may be, e.g., 1 or 2.

m3 and m5 may each independently be, e.g., an integer of 1 to 4.

The compound represented by Chemical Formula 1 may have a structure in which at least one naphthalene is substituted in the naphtho direction of a benzo[b]naphtho[1,2-d]furan (or benzo[b]naphtho[1,2-d]thiophene) and at least one nitrogen-containing 6-membered ring is substituted in the benzo direction of the benzo[b]naphtho[1,2-d]furan (or benzo[b]naphtho[1,2-d]thiophene) in the center of benzo[b]naphtho[1,2-d]furan (or benzo[b]naphtho[1,2-d]thiophene) core in which benzene is further fused at 1st and 2nd positions.

By further substituting naphthalene for the benzo[b]naphtho[1,2-d]furan (or benzo[b]naphtho[1,2-d]thiophene) core, a sterically distorted effect may be provided to help improve stability between host-host and host-dopant, thereby inducing a reduction in a full width at half maximum (FWHM) of the dopant and improving the efficiency and life-span of a device to which the same is applied.

In an implementation, the compound represented by Chemical Formula 1 may be represented by, e.g., Chemical Formula 1A or Chemical Formula 1B, according to a specific substitution position of naphthalene substituted on the core.

[Chemical Formula 1A]

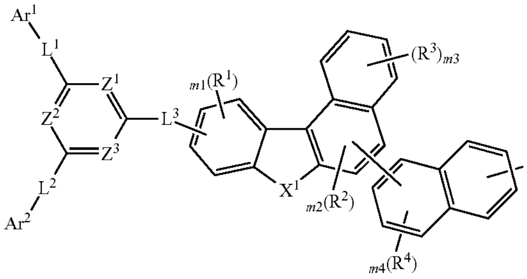

[Chemical Formula 1B]

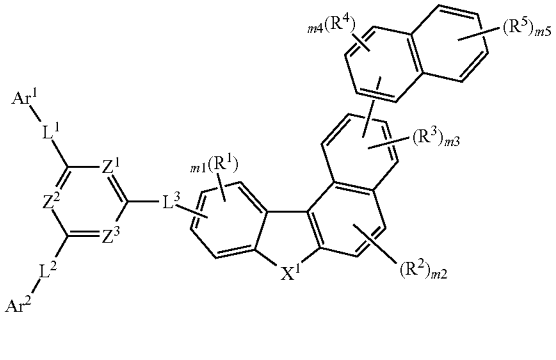

In Chemical Formula 1A and Chemical Formula 1B, $X^1$, $Z^1$ to $Z^3$, $L^1$ to $L^3$, $Ar^1$, $Ar^2$, $R^1$ to $R^5$, and m1 to m5 may be defined the same as those described above.

In an implementation, Chemical Formula 1A may be represented by, e.g., Chemical Formula 1A-1 or Chemical Formula 1A-2 according to a specific substitution point of the core to which naphthalene is substituted.

[Chemical Formula 1A-1]

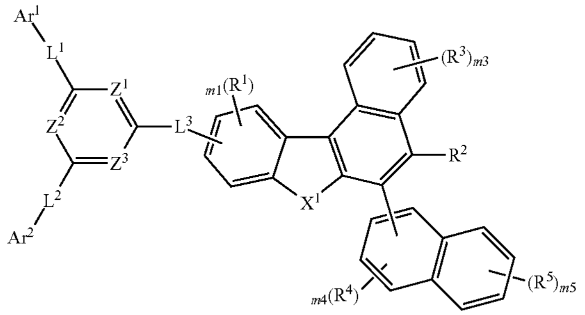

[Chemical Formula 1A-2]

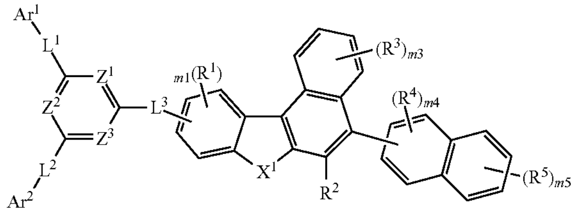

In Chemical Formula 1A-1 and Chemical Formula 1A-2, $X^1$, $Z^1$ to $Z^3$, $L^1$ to $L^3$, $Ar^1$, $Ar^2$, $R^1$ to $R^5$, m1, and m3 to m5 may be defined the same as those described above.

In an implementation, Chemical Formula 1A may be represented by, e.g., Chemical Formula 1A-1-1, Chemical Formula 1A-1-2, Chemical Formula 1A-2-1, or Chemical Formula 1A-2-2, depending on specific substitution positions of the core and naphthalene.

[Chemical Formula 1A-1-1]

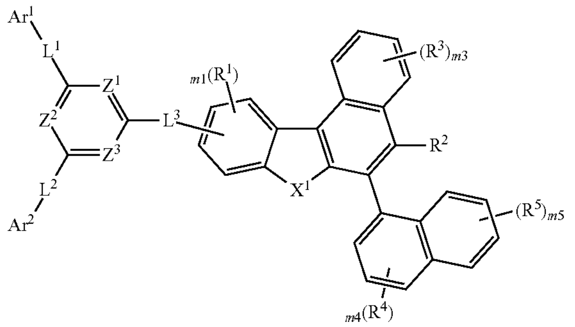

[Chemical Formula 1A-1-2]

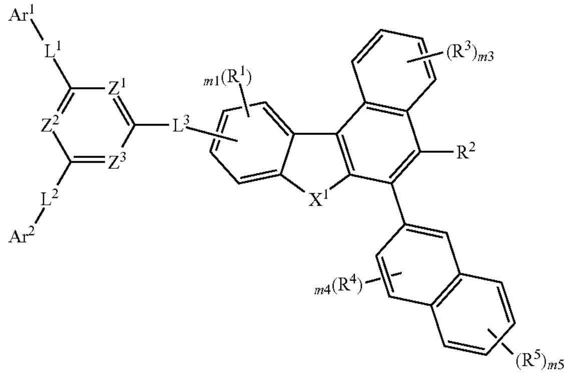

-continued

[Chemical Formula 1A-2-1]

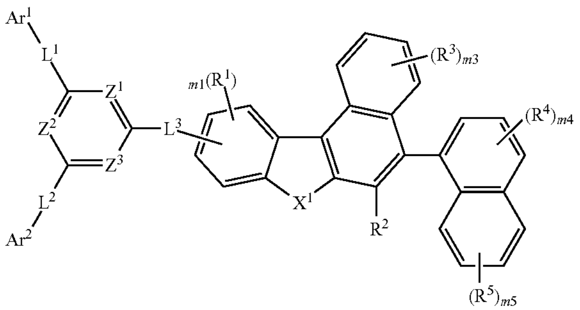

[Chemical Formula 1A-2-2]

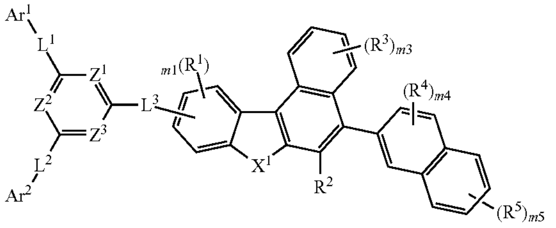

In Chemical Formula 1A-1-1, Chemical Formula 1A-1-2, Chemical Formula 1A-2-1, and Chemical Formula 1A-2-2, $X^1$, $Z^1$ to $Z^3$, $L^1$ to $L^3$, $Ar^1$, $Ar^2$, $R^1$ to $R^5$, m1, and m3 to m5 may be defined the same as those described above.

In an implementation, Chemical Formula 1B may be represented by, e.g., one of Chemical Formula 1B-1 to Chemical Formula 1B-4, according to a specific substitution point of the core to which naphthalene is substituted.

[Chemical Formula 1B-1]

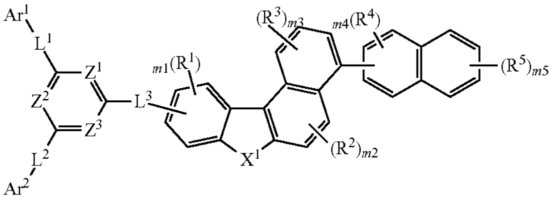

[Chemical Formula 1B-2]

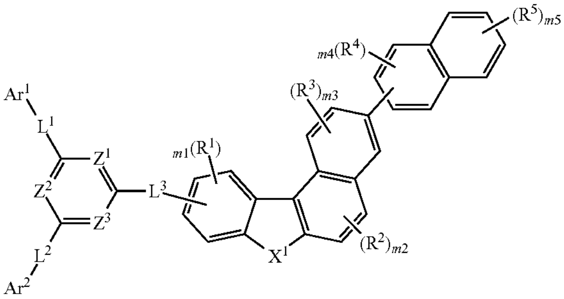

-continued

[Chemical Formula 1B-3]

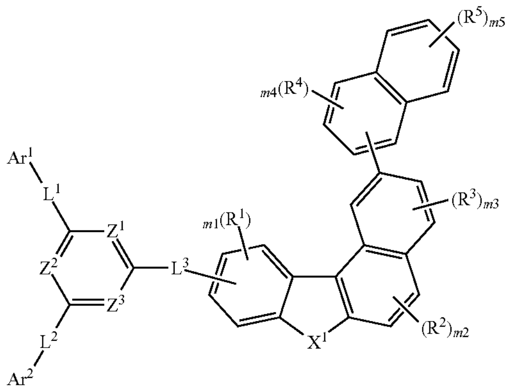

[Chemical Formula 1B-4]

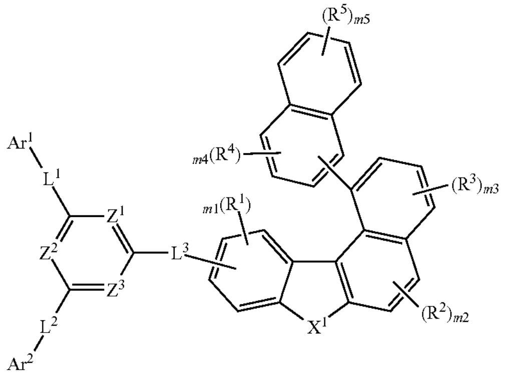

In Chemical Formula 1B-1 to Chemical Formula 1B-4, $X^1$, $Z^1$ to $Z^3$, $L^1$ to $L^3$, $Ar^1$, $Ar^2$, $R^1$ to $R^5$, m1, m2, m4, and m5 may be defined the same as those described above, and m3 may be, e.g., an integer of 1 to 3.

In an implementation, Chemical Formula 1B may be represented by, e.g., Chemical Formula 1B-1-1, Chemical Formula 1B-1-2, Chemical Formula 1B-2-1, Chemical Formula 1B-2-2, Chemical Formula 1B-3-1, Chemical Formula 1B-3-2, Chemical Formula 1B-4-1, or Chemical Formula 1B-4-2, according to specific substitution positions of the core and naphthalene.

[Chemical Formula 1B-1-1]

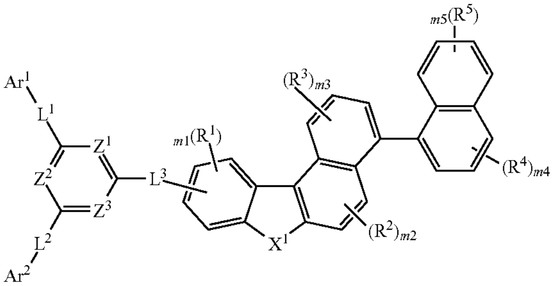

-continued

[Chemical Formula 1B-1-2]

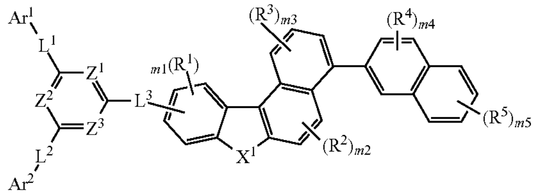

[Chemical Formula 1B-2-1]

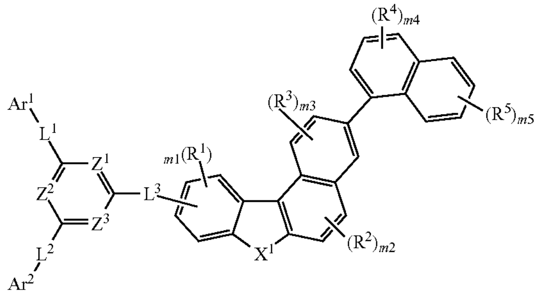

[Chemical Formula 1B-2-2]

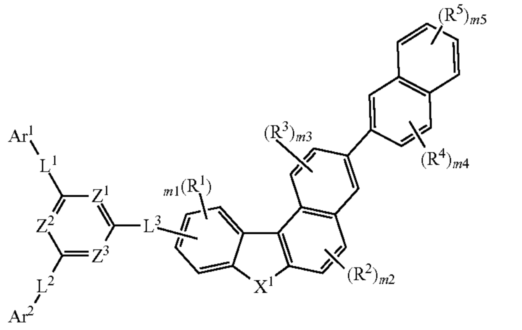

[Chemical 1B-3-1]

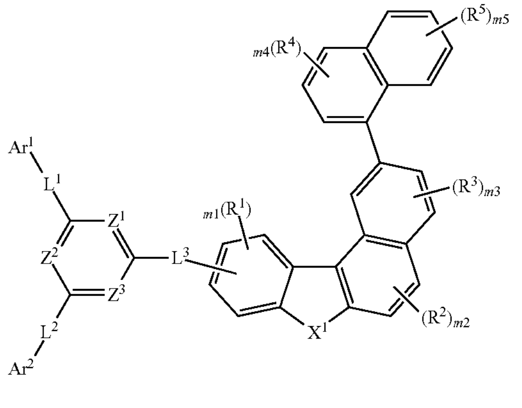

-continued

[Chemical 1B-3-2]

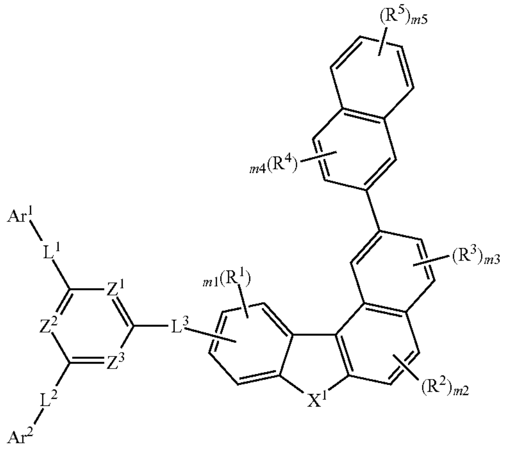

[Chemical 1B-4-1]

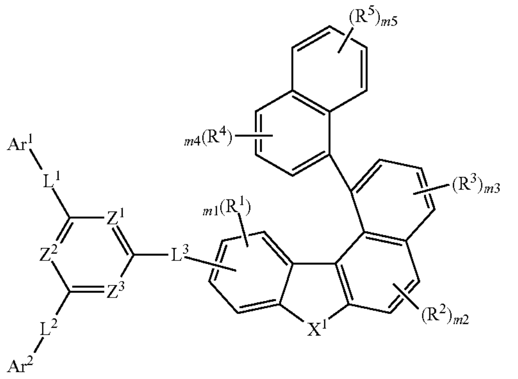

[Chemical 1B-4-2]

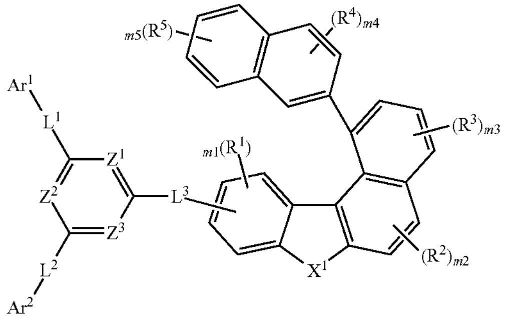

In Chemical Formula 1B-1-1, Chemical Formula 1B-1-2, Chemical Formula 1B-2-1, Chemical Formula 1B-2-2, Chemical Formula 1B-3-1, Chemical Formula 1B-3-2. Chemical Formula 1B-4-1, and Chemical Formula 1B-4-2, $X^1$. $Z^1$ to $Z^3$, $L^1$ to $L^3$, $Ar^1$, $Ar^2$, $R^1$ to $R^5$, m1, m2, m4, and m5 may be defined the same as those described above, and m3 may be, e.g., an integer of 1 to 3.

In an implementation, $Ar^1$ and $Ar^2$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted chrysenyl group, a substituted or unsubstituted benzophenanthrenyl group, a substituted or unsubstituted acridinyl group, a substituted or unsubstituted xanthenyl group, substituted or unsubstituted 10-phenyl-10H-spiro[acridine-9,9'-fluorenyl group], a substituted or unsubstituted 10H-spiro[acridine-9,9'-fluorenyl group], a substituted or unsubstituted spiro[fluorene-9,9'-xanthenyl group], a substituted or unsubstituted dibenzosilolyl group, a substituted or unsubstituted dibenzofuranyl group, a substituted or unsubstituted dibenzothiophenyl group, a substituted or unsubstituted benzonaphthofuranyl group, a substituted or unsubstituted benzonaphthothiophenyl group, a substituted or unsubstituted carbazolyl group, a substituted or unsubstituted benzocarbazolyl group, a substituted or unsubstituted dibenzocarbazolyl group, a substituted or unsubstituted dinaphthofuranyl group, a substituted or unsubstituted dinaphthothiophenyl group, a substituted or unsubstituted benzofuranofluorenyl group, a substituted or unsubstituted benzothiophenofluorenyl group, a substituted or unsubstituted phenoxazinyl group, a substituted or unsubstituted thiophenoxazinyl group, a substituted or unsubstituted benzophenoxazinyl group, or a substituted or unsubstituted benzothiophenoxazinyl group.

In an implementation, $Ar^1$ and $Ar^2$ may each independently be, e.g., a substituted or unsubstituted phenyl group, a substituted or unsubstituted biphenyl group, a substituted or unsubstituted naphthyl group, a substituted or unsubstituted dibenzofuranyl group, a substituted or unsubstituted dibenzothiophenyl group, or a substituted or unsubstituted carbazolyl group.

In an implementation, $L^1$ and $L^2$ may each independently be, e.g., a single bond, a substituted or unsubstituted phenylene group, or a substituted or unsubstituted naphthylene group.

In an implementation, $L^1$ and $L^2$ may each independently be, e.g., a single bond or a substituted or unsubstituted phenylene group.

In an implementation, moieties *-$L^1$-$Ar^1$ and *-$L^2$-$Ar^2$ may each independently be, e.g., a moiety of Group I.

[Group I]

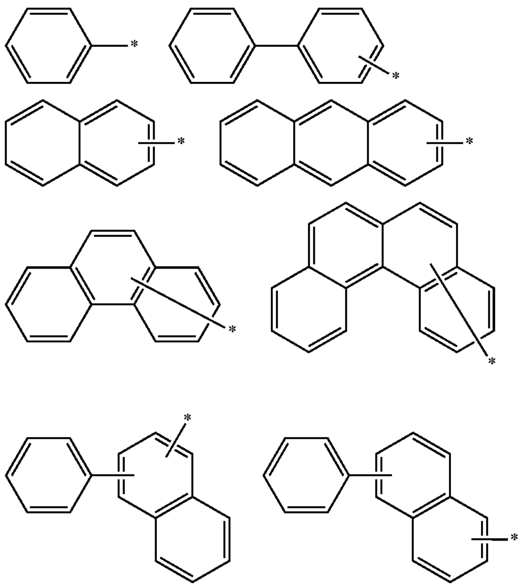

-continued

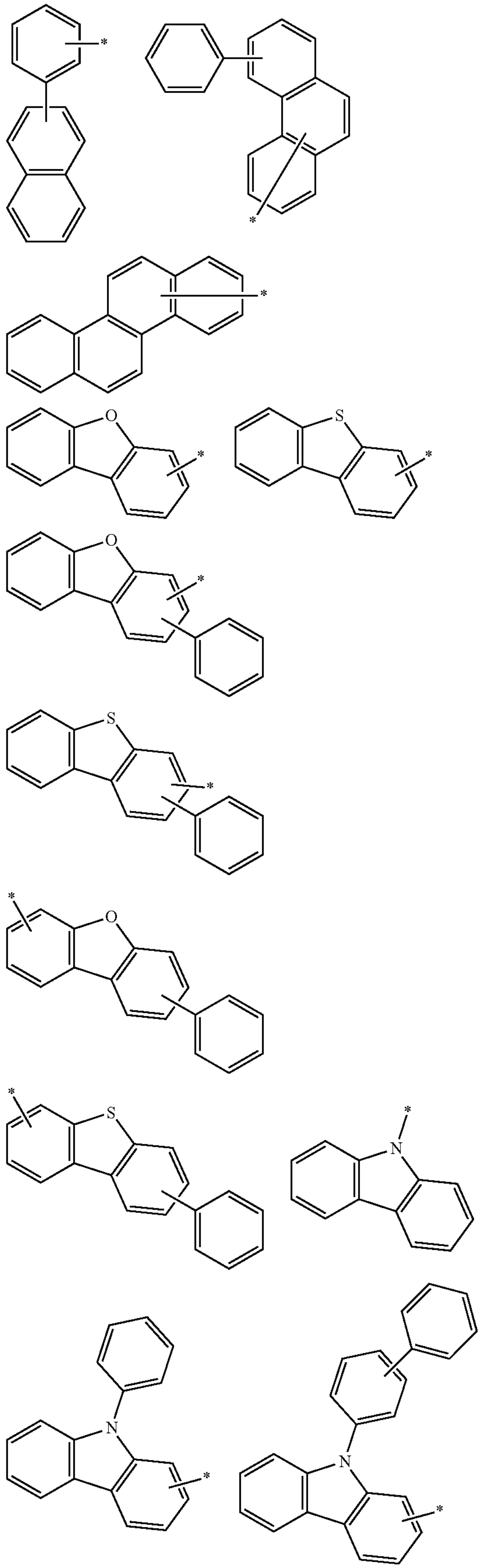

-continued
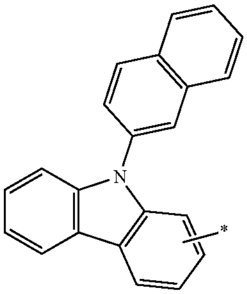
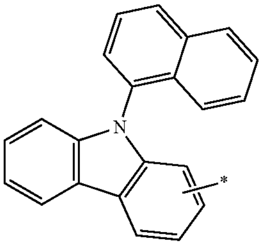
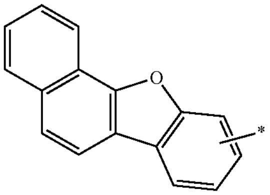
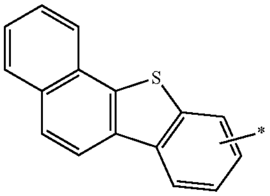
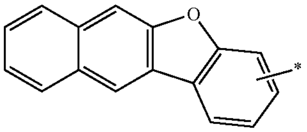
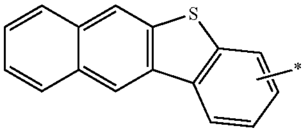
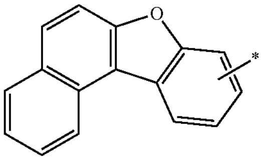
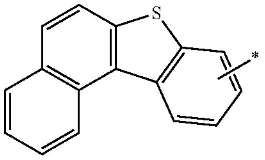
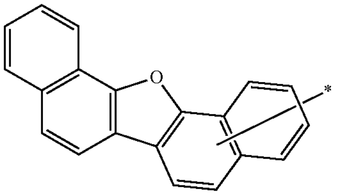
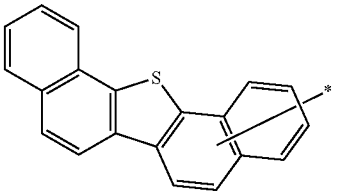
-continued
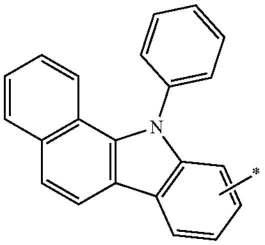
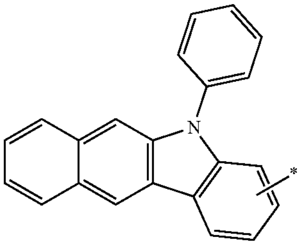
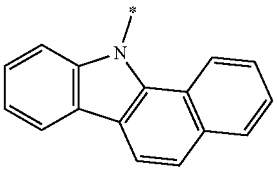
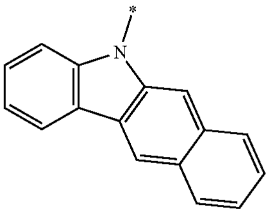
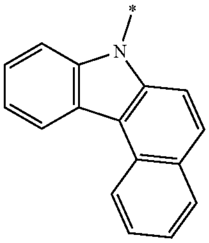
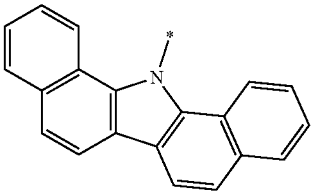
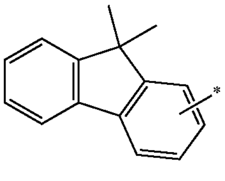
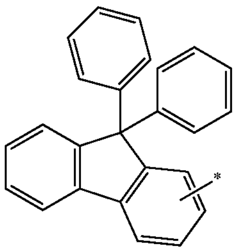
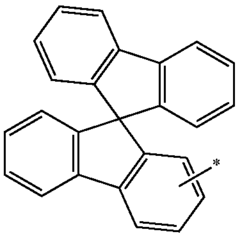

-continued
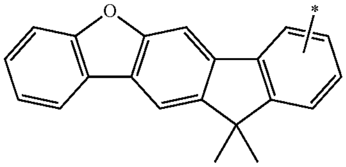
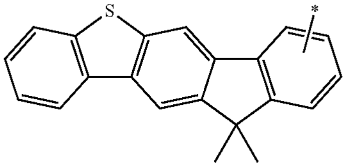
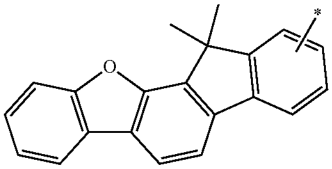
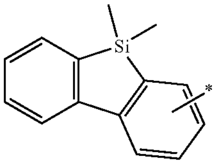
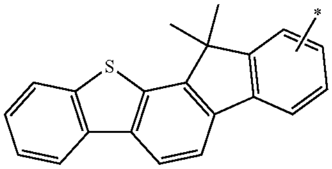
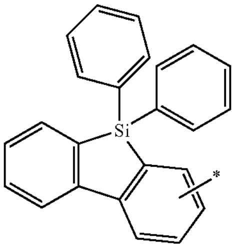
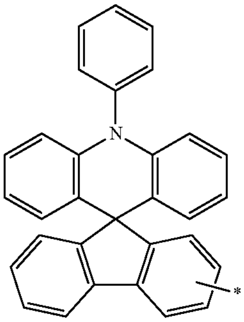
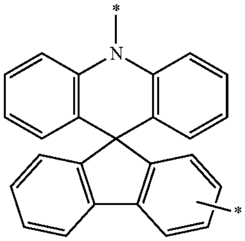
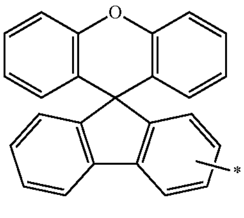
-continued
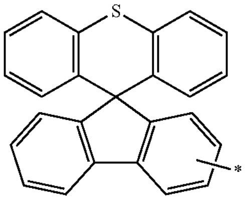
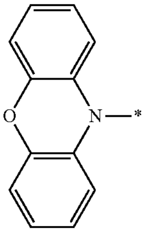
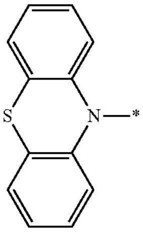
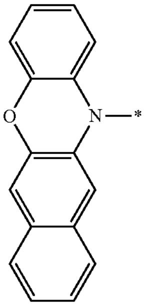
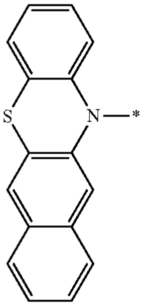
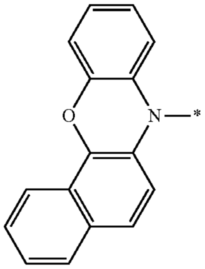
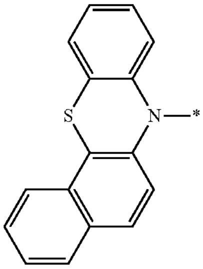
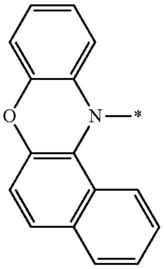
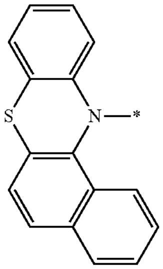
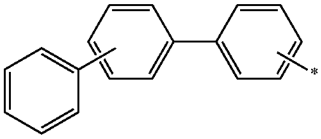
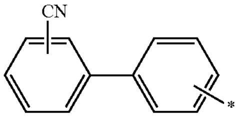
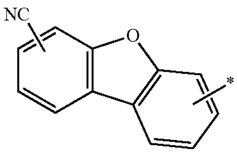
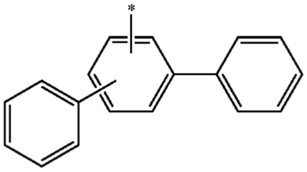

-continued

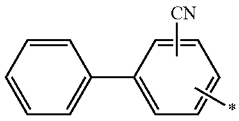

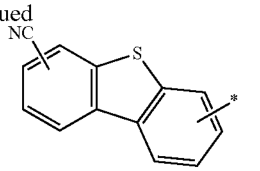

In Group I,*is a linking point.

The moieties of Group I may be unsubstituted (e.g., as illustrated above) or may be substituted with a substituent.

The substituent may be, e.g., deuterium, a C1 to C10 alkyl group, or a C6 to C12 aryl group.

In an implementation, $L^3$ may be, e.g., a single bond, a substituted or unsubstituted phenylene group, a substituted or unsubstituted naphthylene group, a substituted or unsubstituted anthracenylene group, a substituted or unsubstituted phenanthrenylene group, a substituted or unsubstituted dibenzofuranylene group, or a substituted or unsubstituted dibenzothiophenylene group.

In an implementation, $L^3$ may be a single bond.

In an implementation, $R^1$ to $R^5$ may each independently be, e.g., hydrogen, deuterium, a substituted or unsubstituted C1 to C10 alkyl group, or a substituted or unsubstituted C6 to C12 aryl group.

In an implementation, $R^1$ to $R^5$ may each independently be, e.g., hydrogen or deuterium.

In an implementation, Chemical Formula 1 may be represented by, e.g., Chemical Formula 1A-2-1.

In an implementation, Chemical Formula 1A-2-1 may be represented by, e.g., Chemical Formula 1A-2-1-a, Chemical Formula 1A-2-1-b, Chemical Formula 1A-2-1-c, or Chemical Formula 1A-2-1-d.

[Chemical Formula 1A-2-1-a]

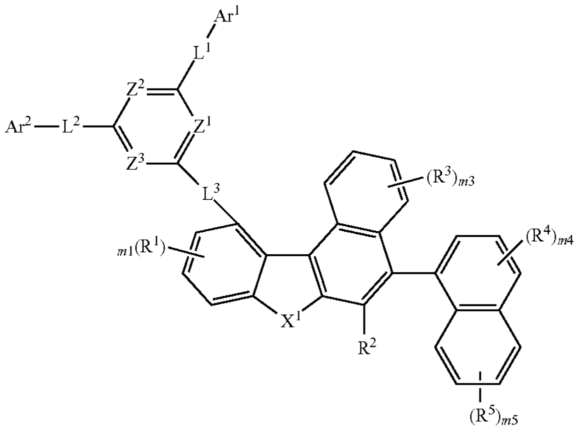

-continued

[Chemical Formula 1A-2-1-b]

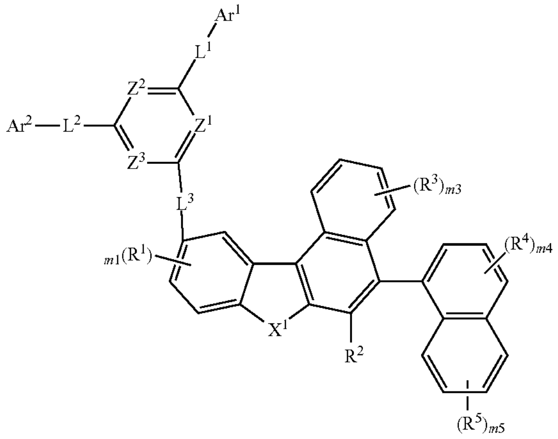

[Chemical Formula 1A-2-1-c]

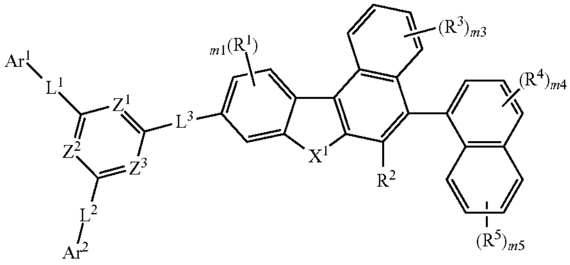

[Chemical Formula 1A-2-1-d]

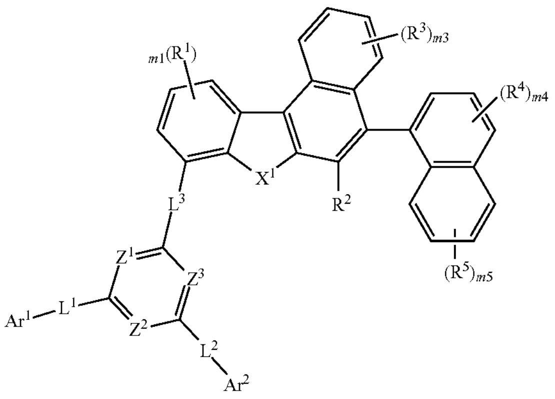

In Chemical Formula 1A-2-1-a, Chemical Formula 1A-2-1-b, Chemical Formula 1A-2-1-c, and Chemical Formula 1A-2-1-d, $X^1$, $Z^1$ to $Z^3$, $L^1$ to $L^3$, $Ar^1$, $Ar^2$, $R^1$ to $R^5$, m3, m4, and m5 may be defined the same as those described above, and m1 may be, e.g., an integer of 1 to 3.

In an implementation, Chemical Formula 1 may be represented by, e.g., Chemical Formula 1A-2-1-b.

In an implementation, the compound for the organic optoelectronic device represented by Chemical Formula 1 may be, e.g., a compound of Group 1.

[Group 1]
[1]
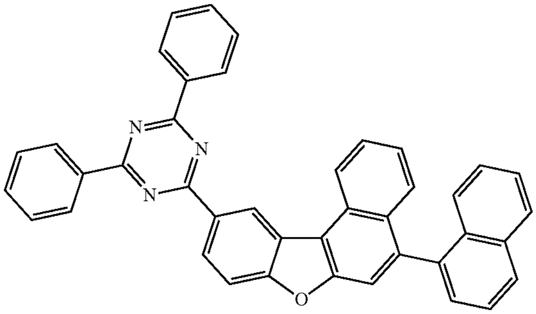
[2]
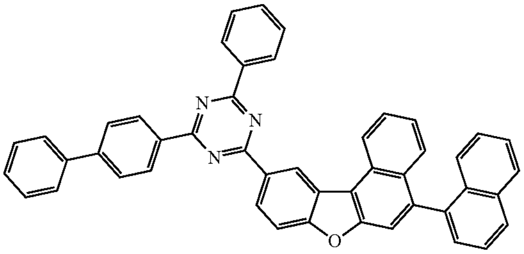
[3]
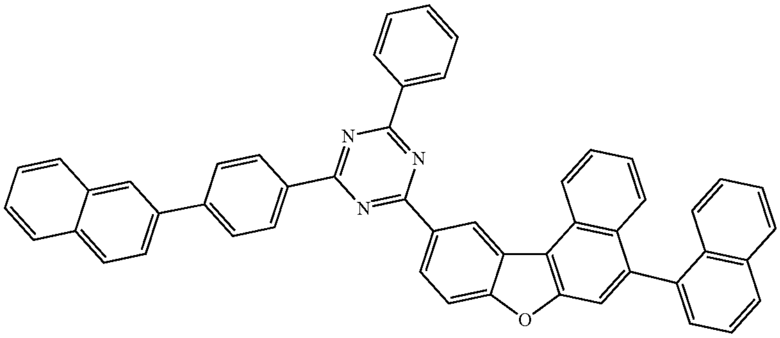
[4]
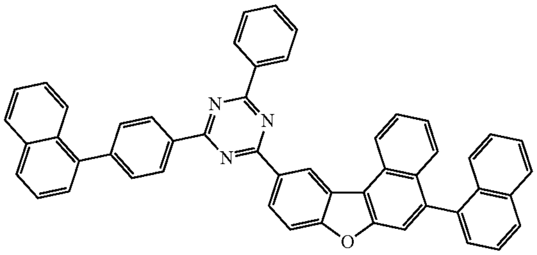
[5]
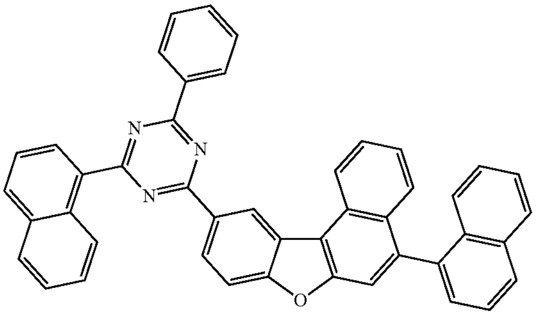
[6]
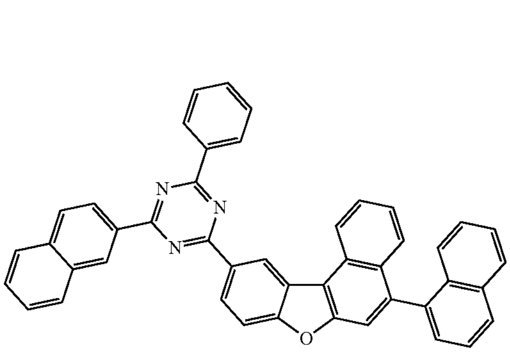
[7]
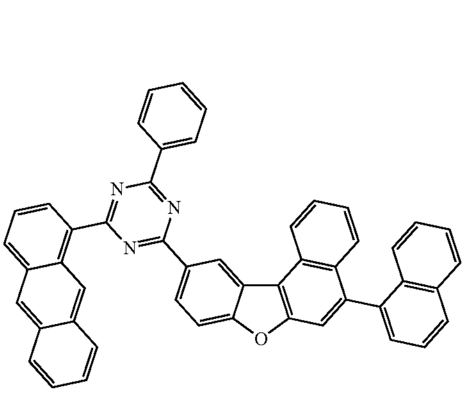

-continued
[8]
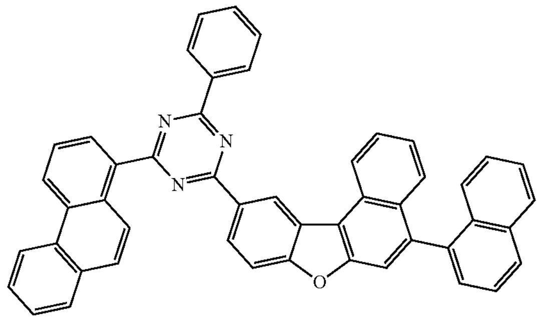
[9]
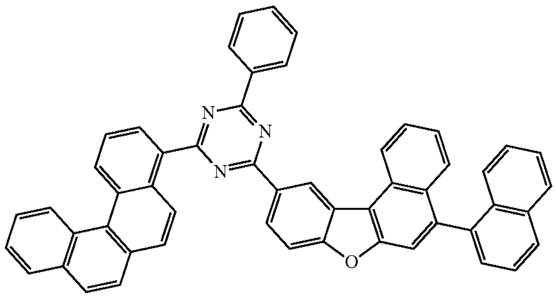
[10]
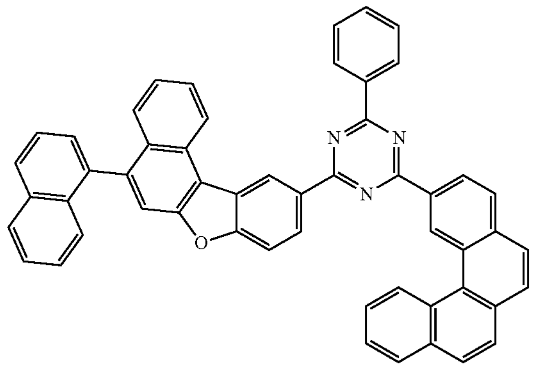
[11]
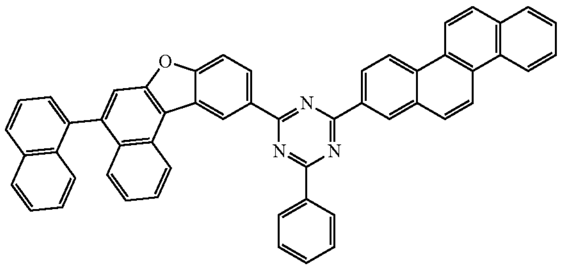
[12]
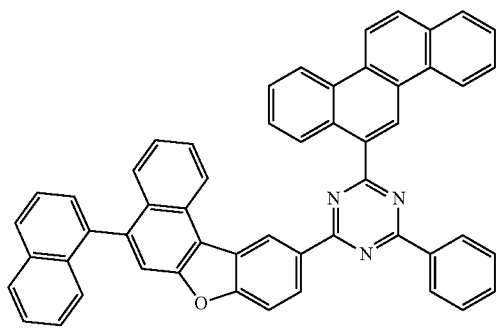
[13]
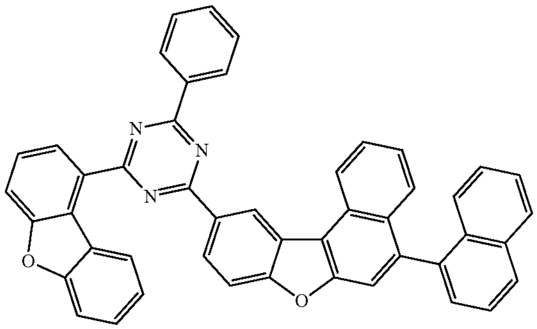
[14]
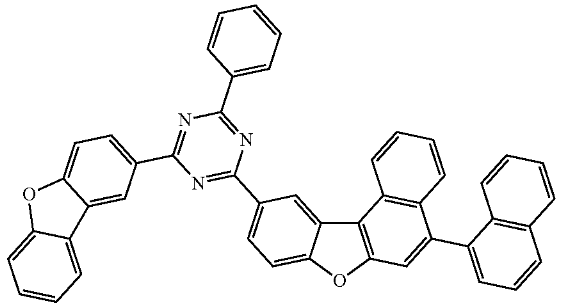
[15]
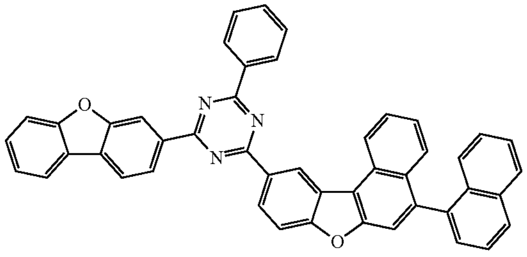

-continued
[16]
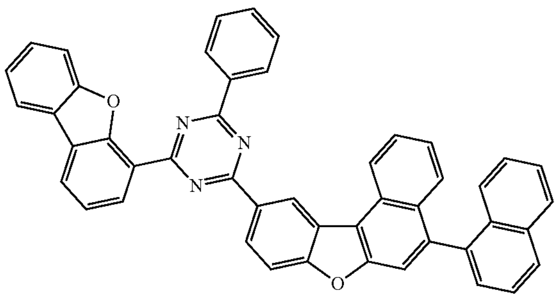
[17]
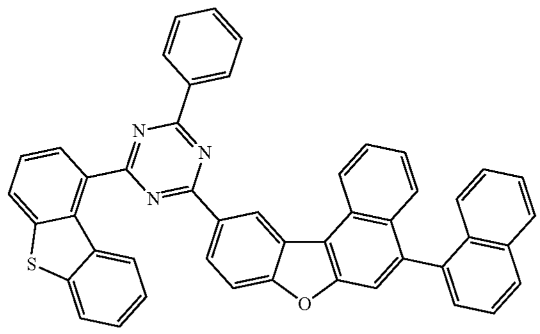
[18]
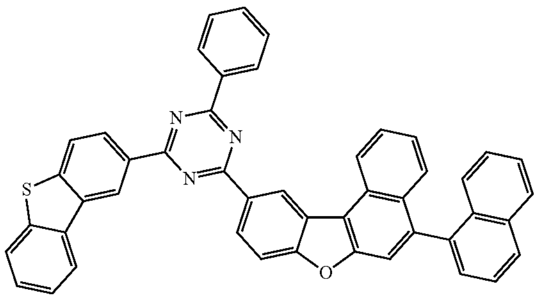
[19]
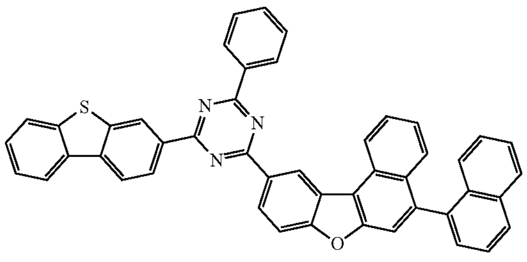
[20]
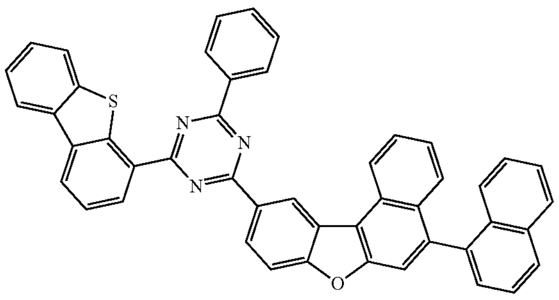
[21]
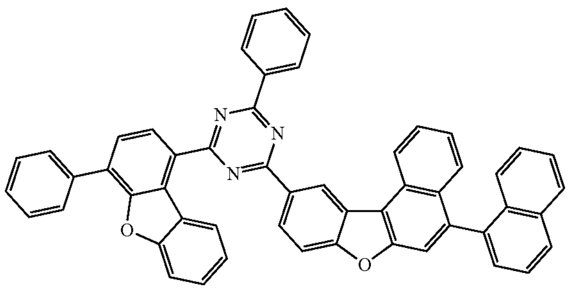
[22]
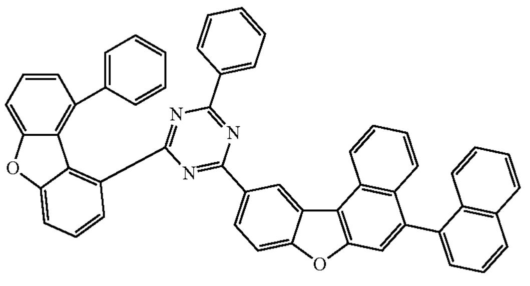
[23]
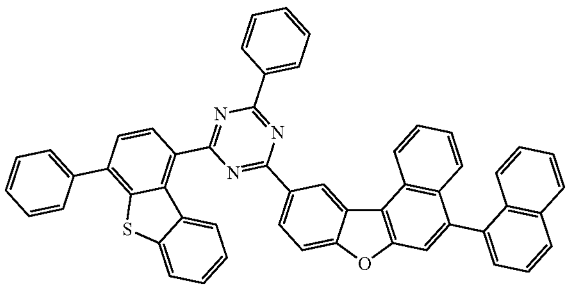
[24]
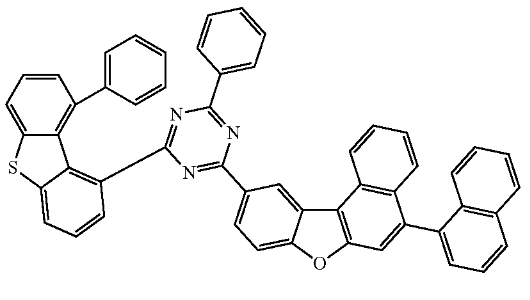
[25]
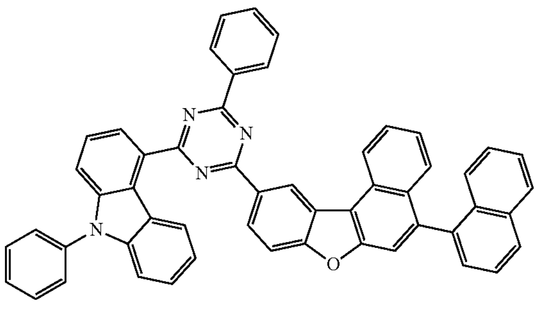

-continued
[26]
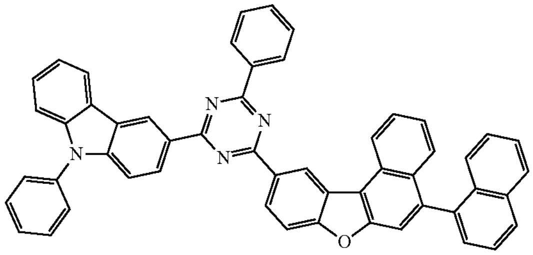
[27]
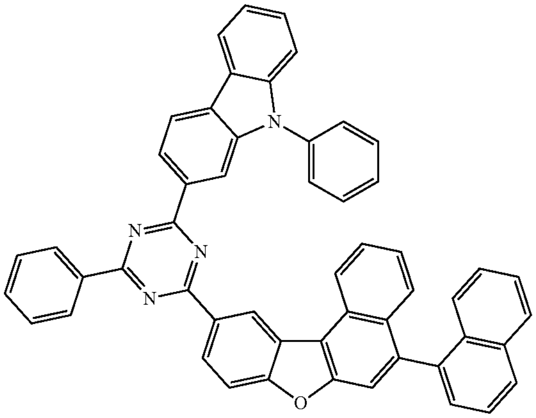
[28]
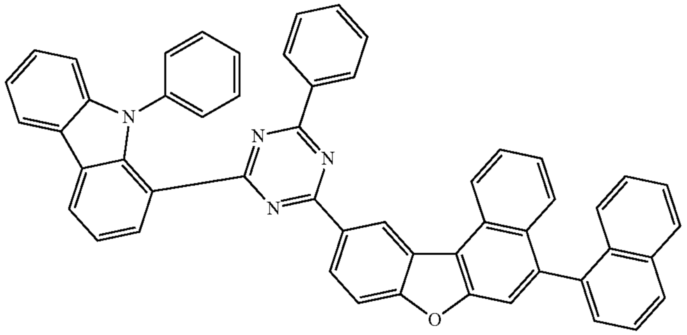
[29]
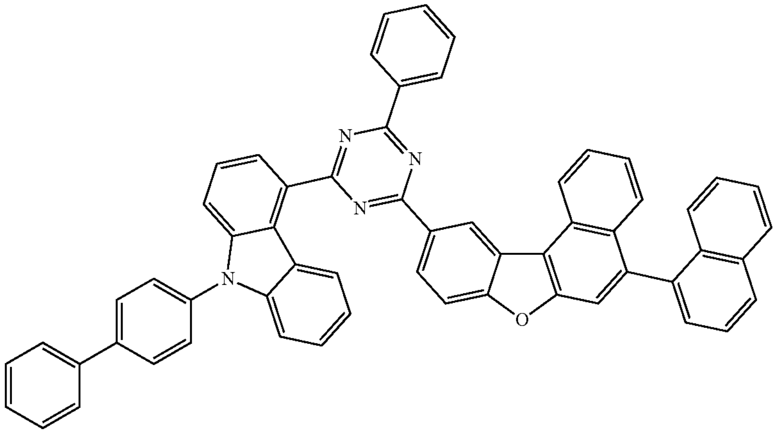
[30]
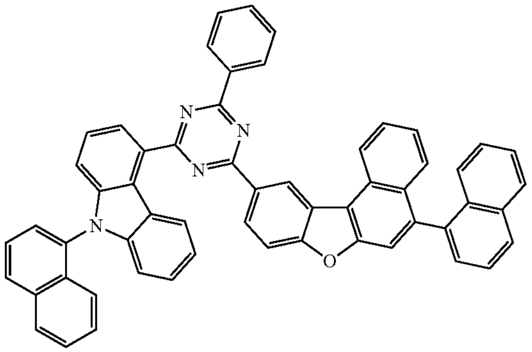
[31]
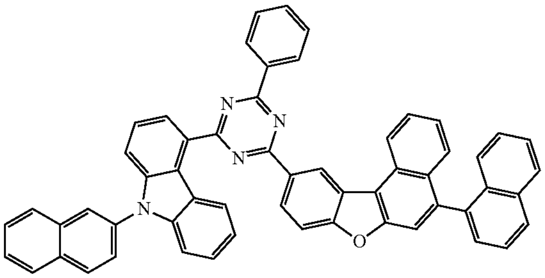

-continued
[32]
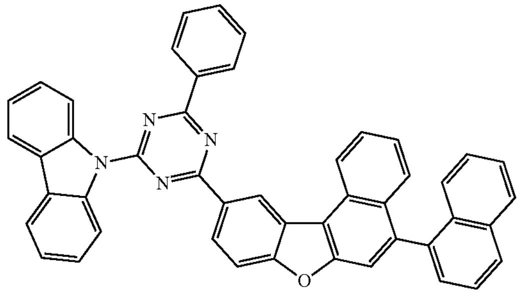
[33]
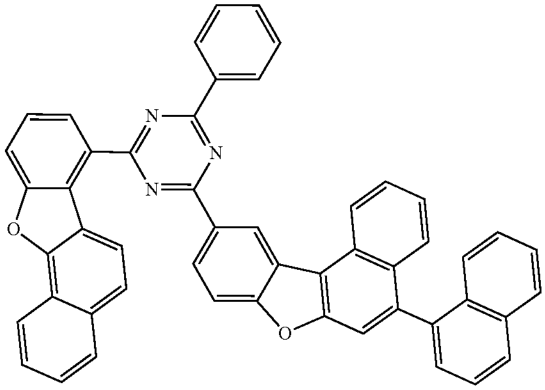
[34]
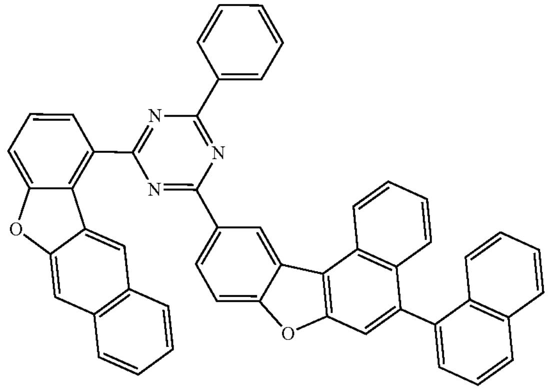
[35]
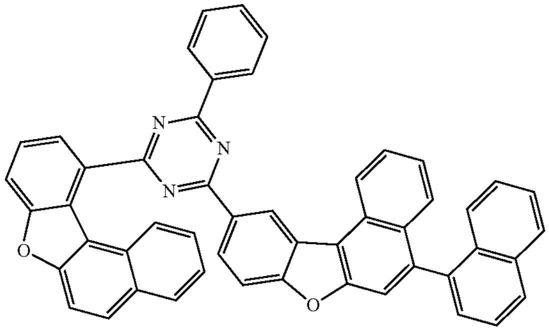
[36]
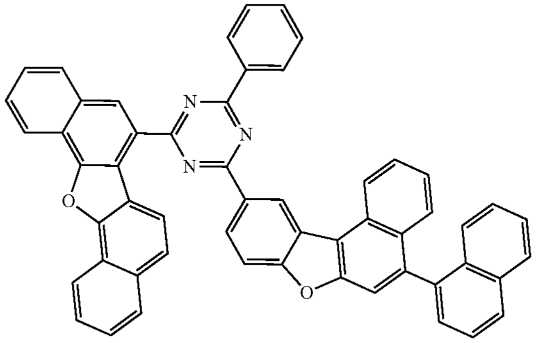
[37]
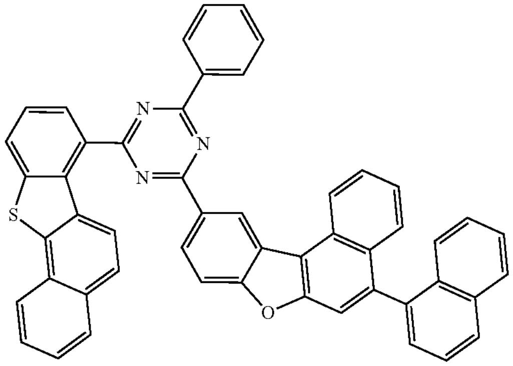
[38]
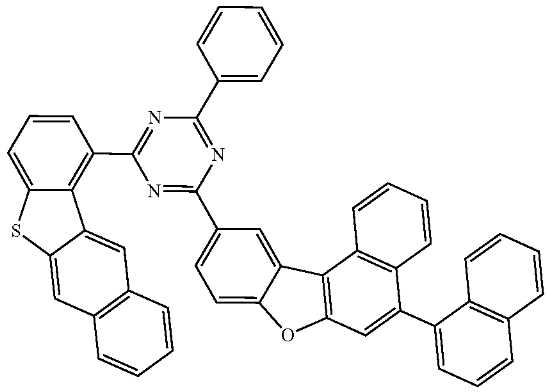
[39]
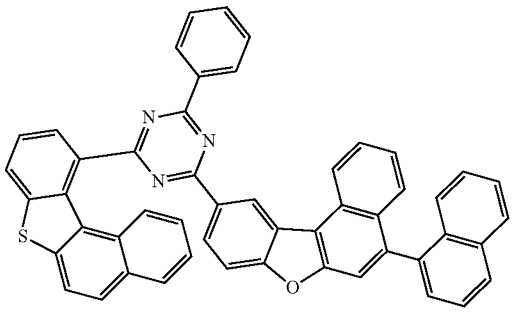

-continued
[40]
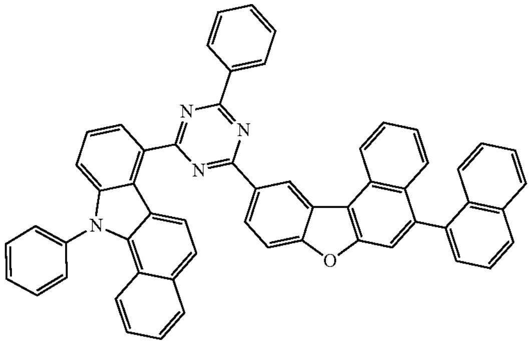
[41]
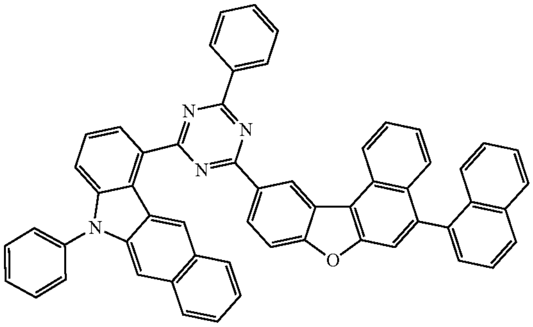
[42]
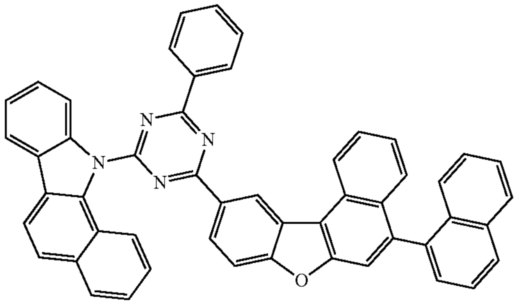
[43]
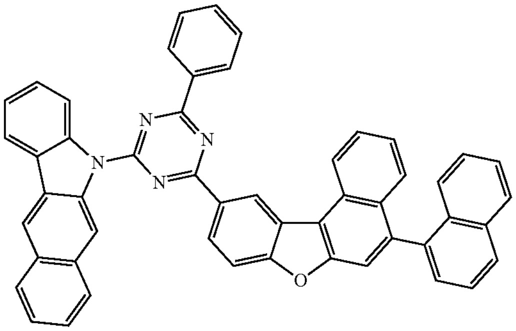
[44]
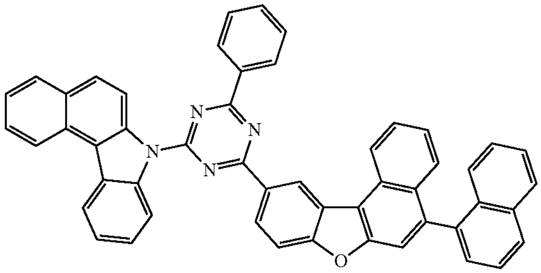
[45]
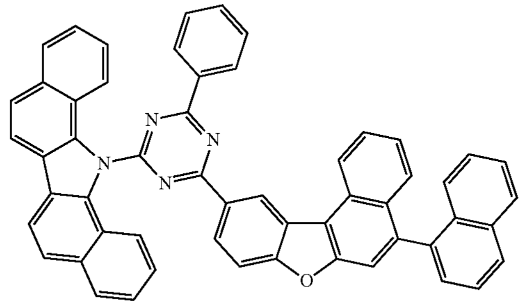
[46]
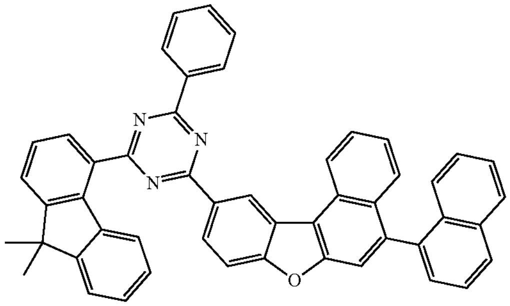
[47]
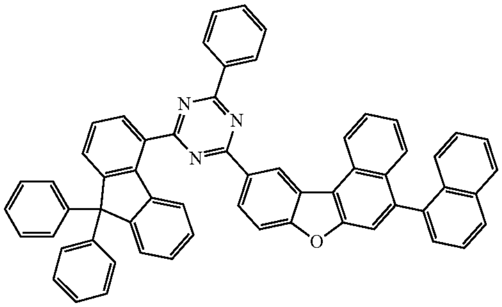

-continued
[48]
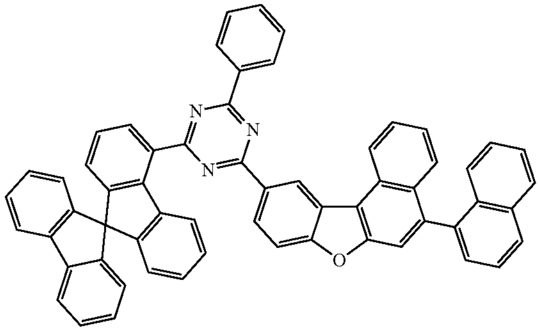
[49]
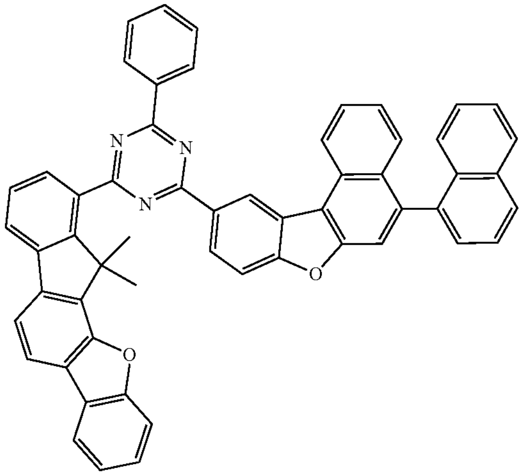
[50]
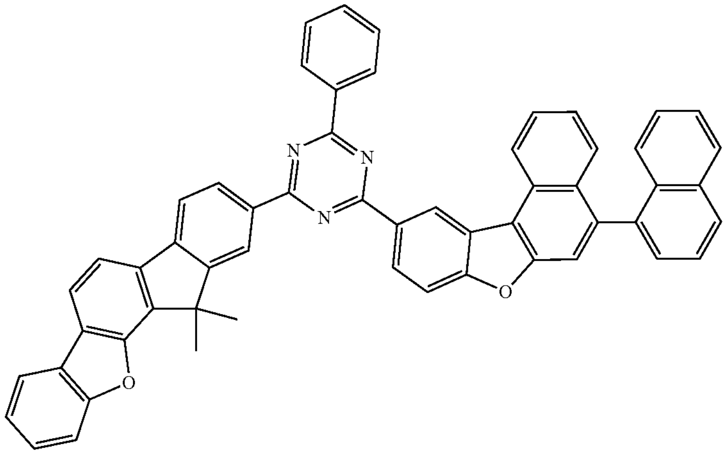
[51]
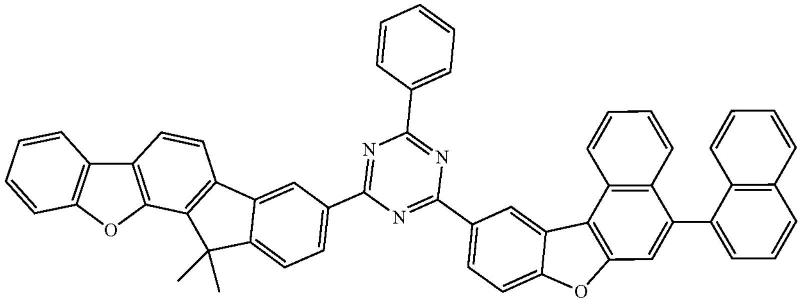
[52]
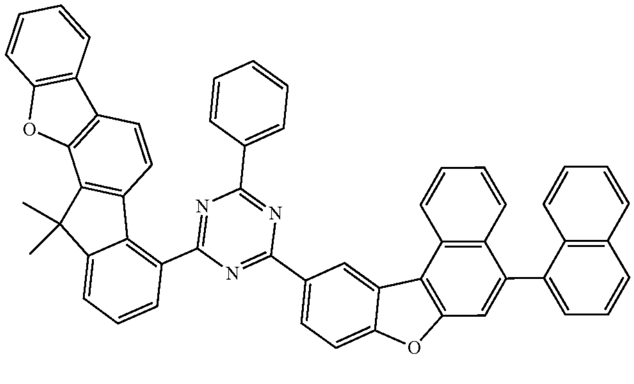

-continued
[53]
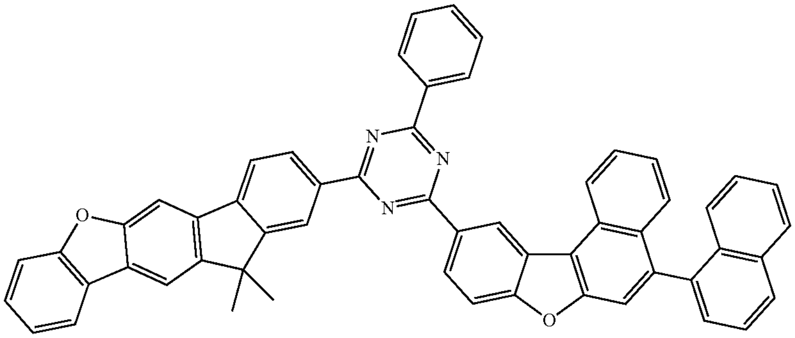
[54]
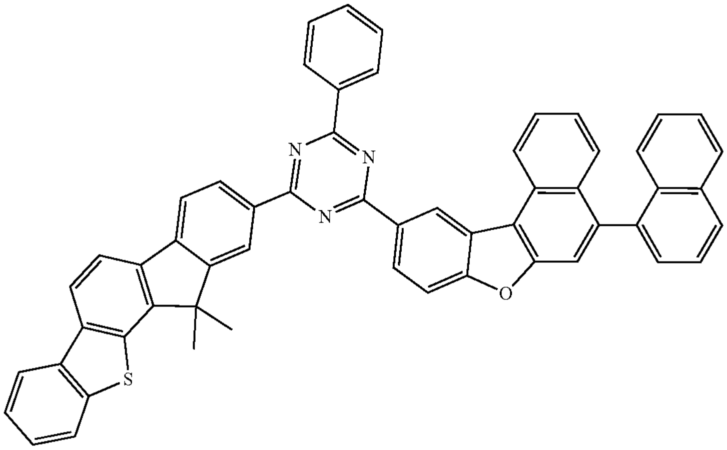
[55]
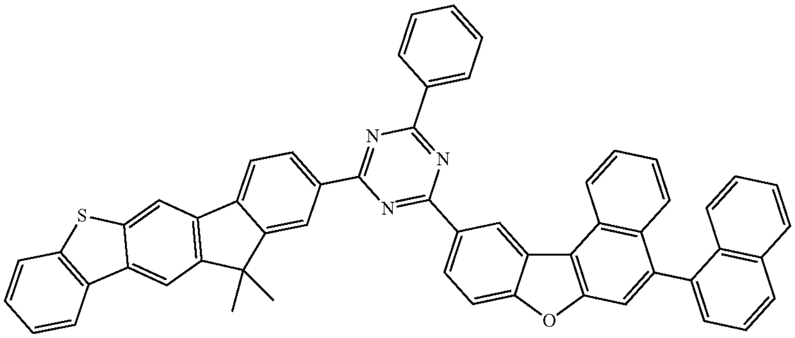
[56]
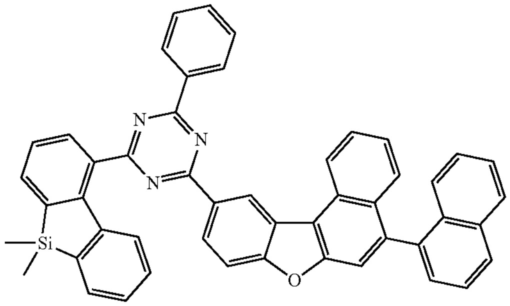
[57]
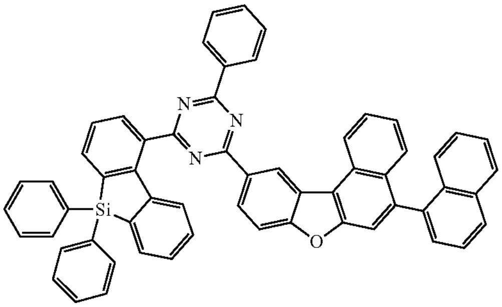

-continued
[58]
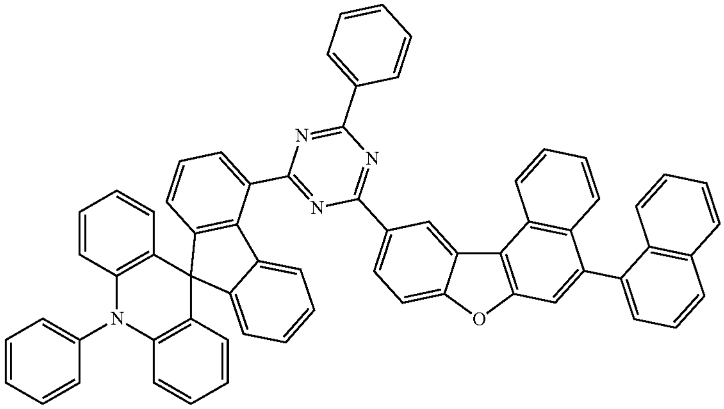
[59]
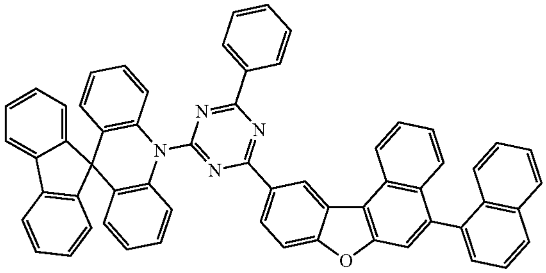
[60]
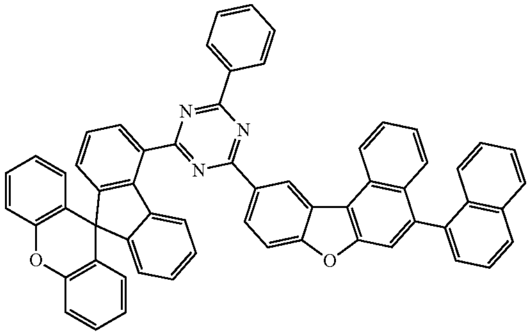
[61]
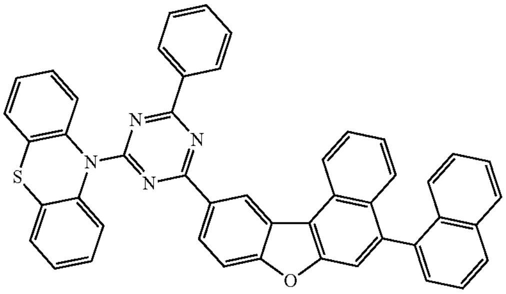
[62]
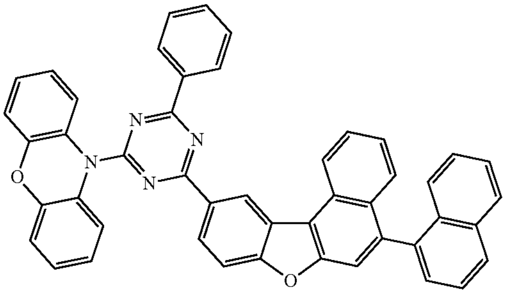

-continued
[63]
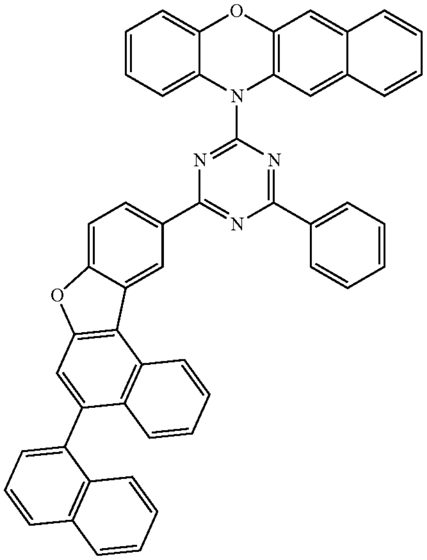
[64]
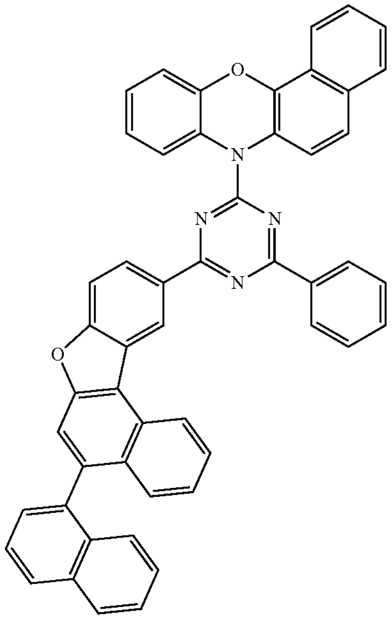
[65]
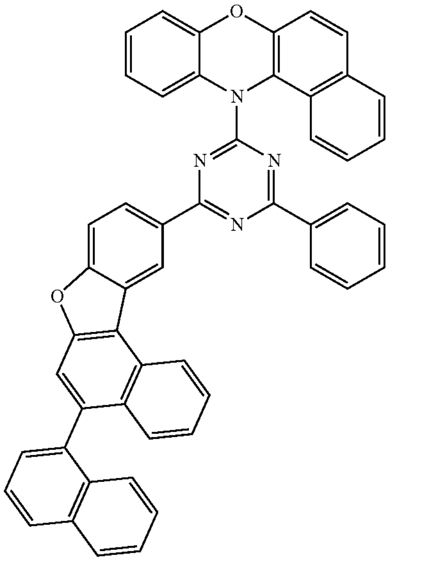
[66]
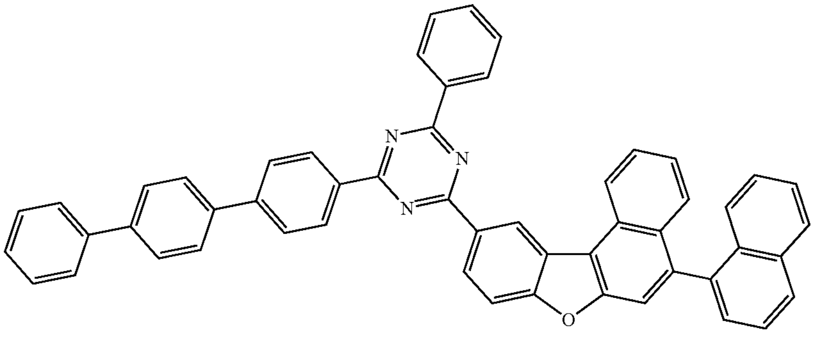

-continued
[67]
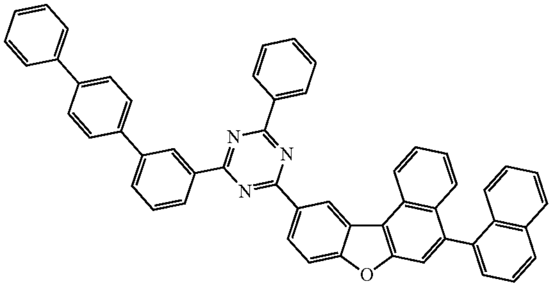
[68]
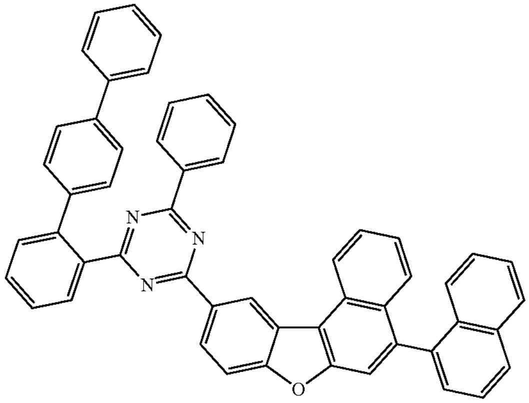
[69]
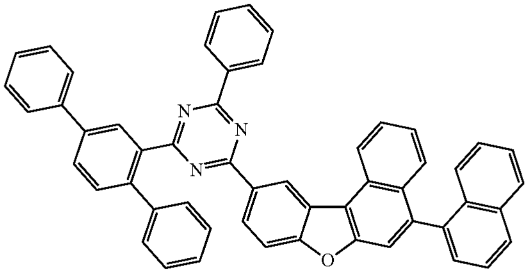
[70]
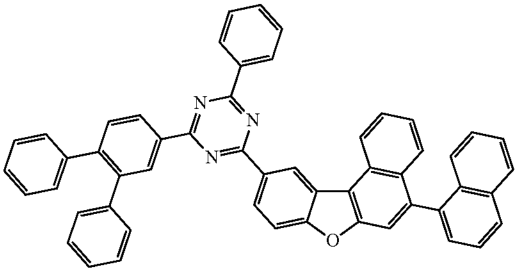
[71]
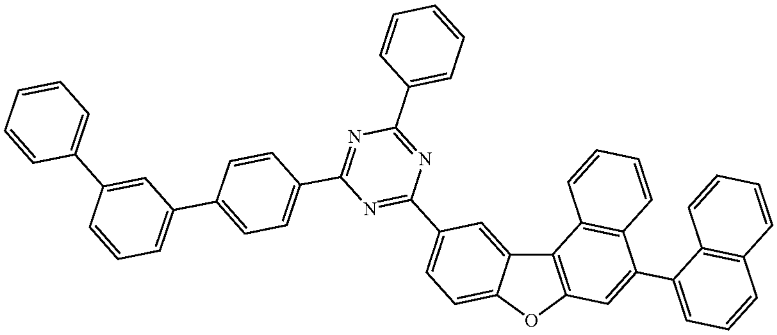
[72]
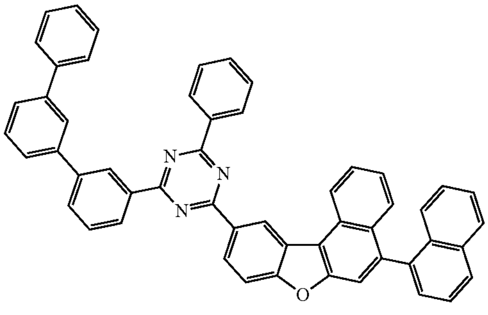
[73]
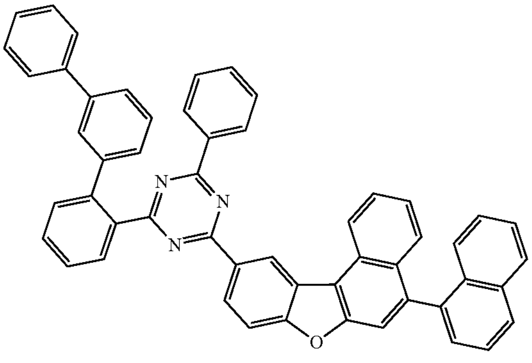

-continued
[74]
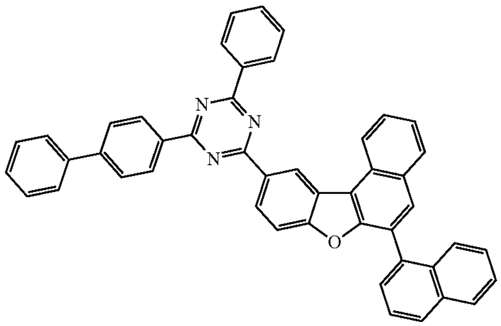
[75]
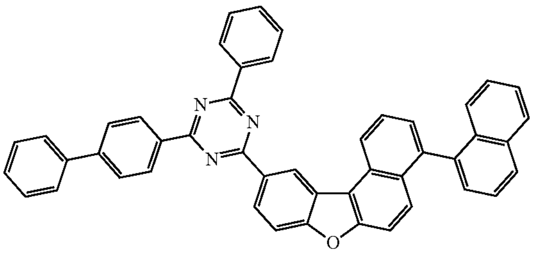
[76]
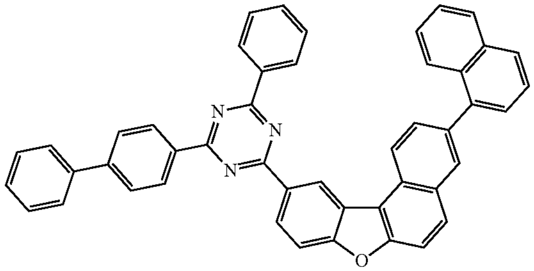
[77]
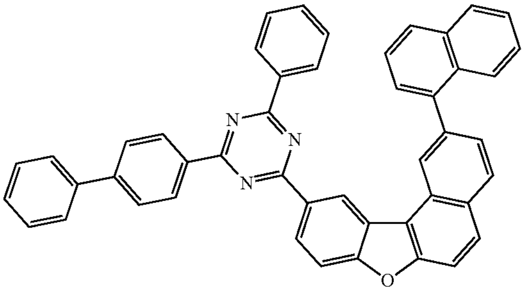
[78]
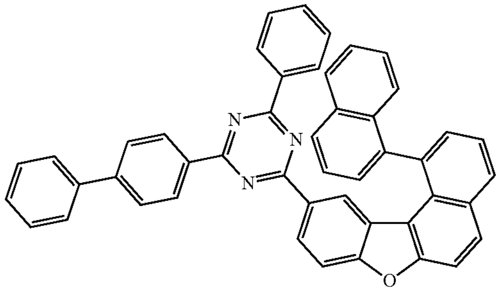
[79]
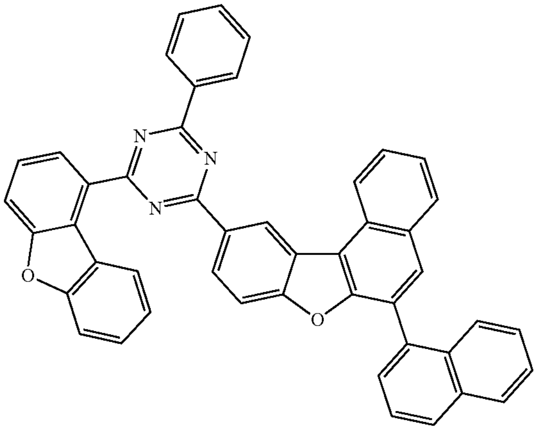
[80]
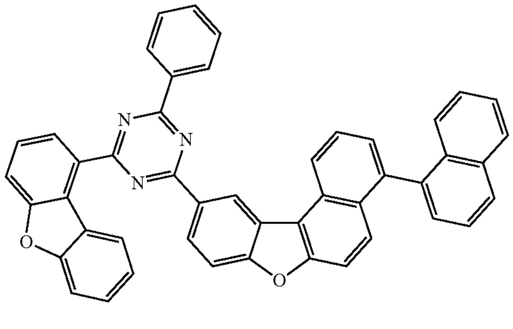
[81]
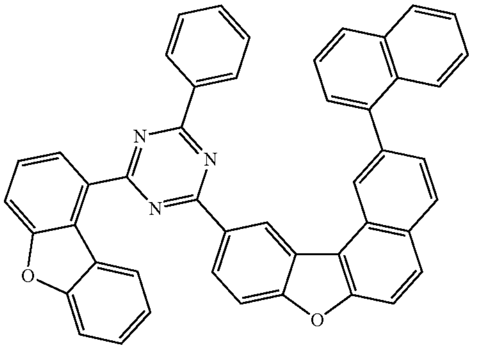

-continued
[82]
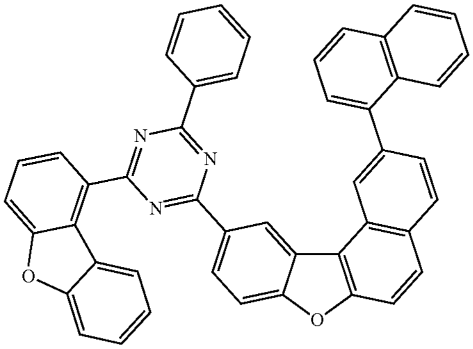
[83]
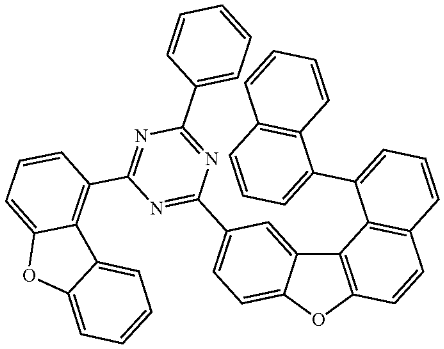
[84]
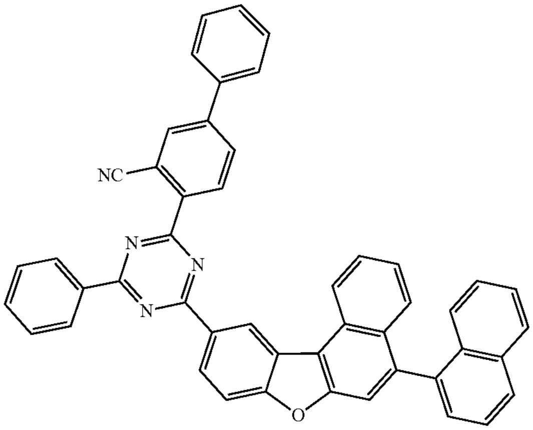
[85]
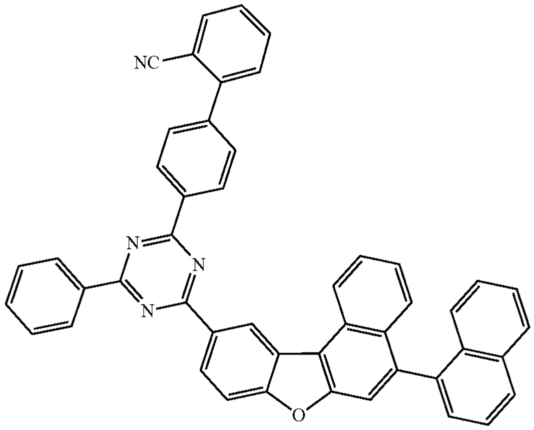
[86]
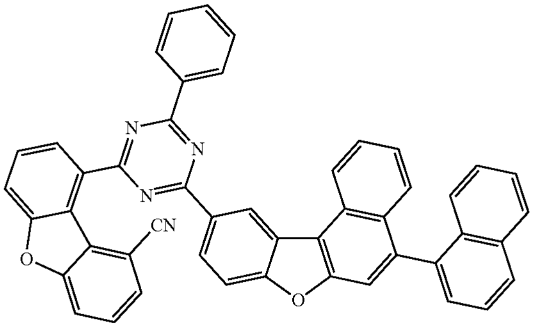
[87]
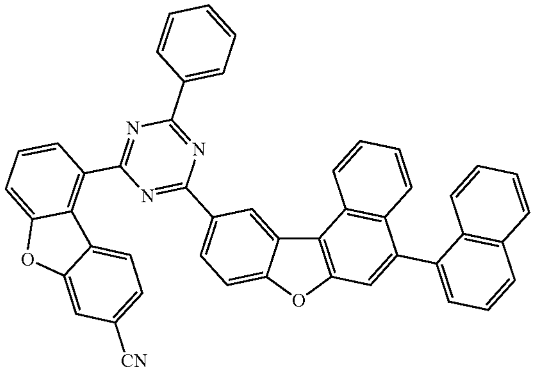
[88]
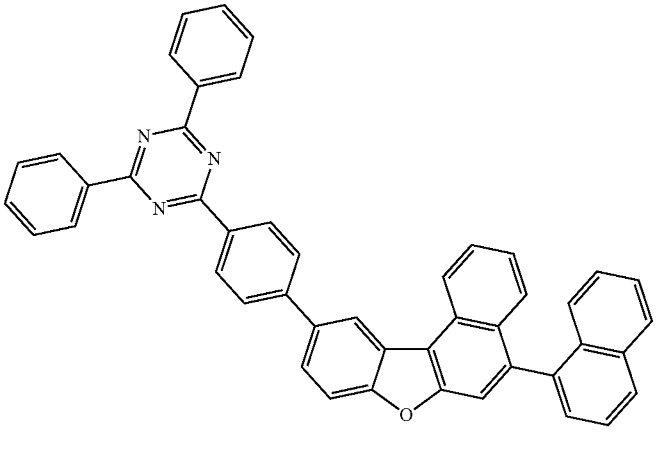

-continued
[89]
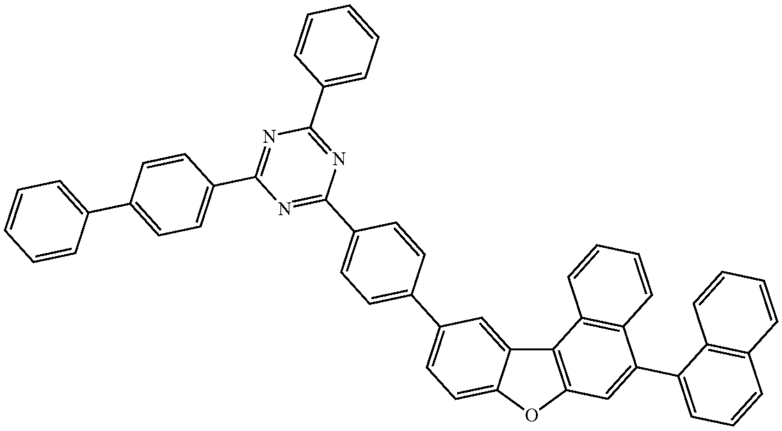
[90]
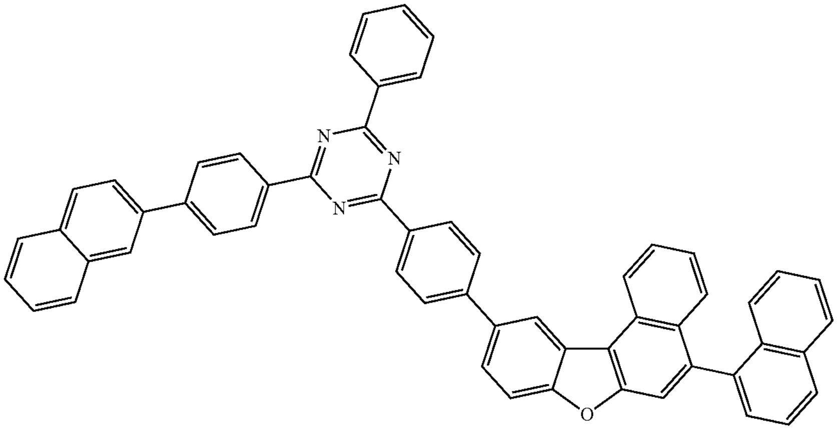
[91]
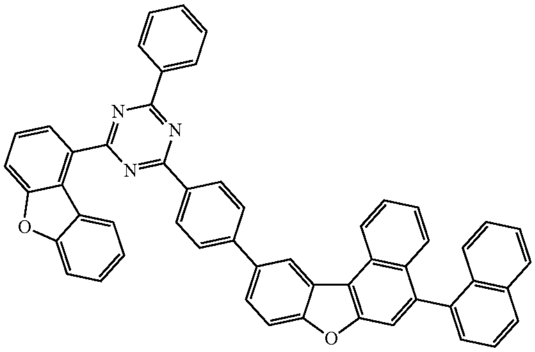
[92]
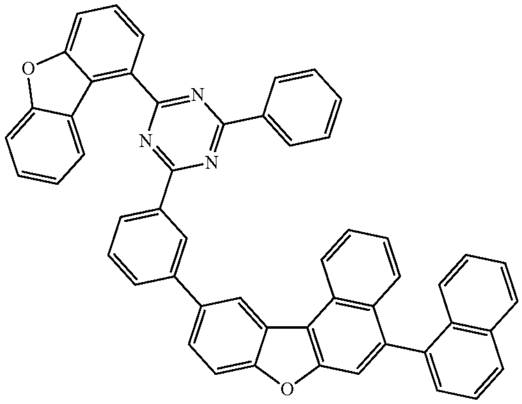
[93]
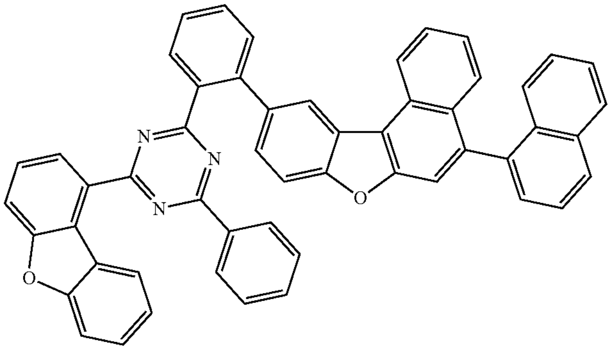

-continued
[94]
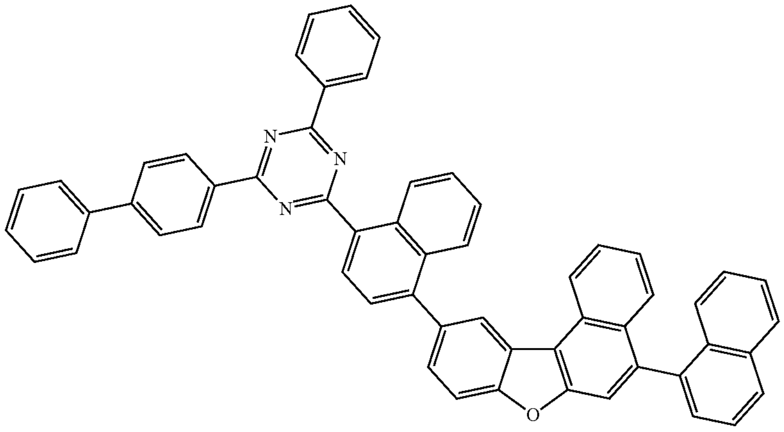
[95]
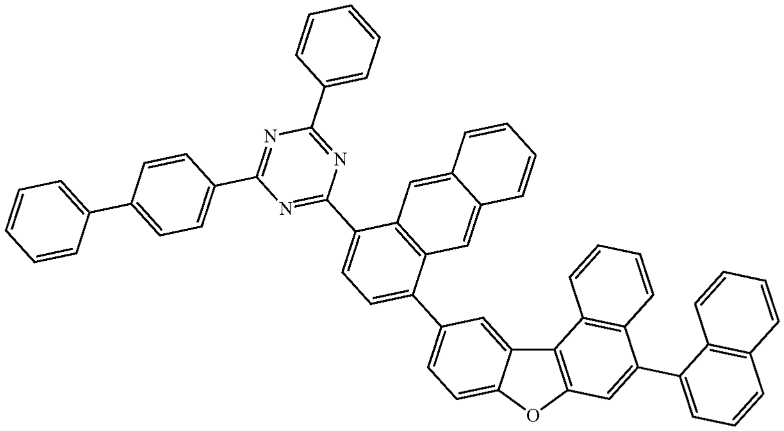
[96]
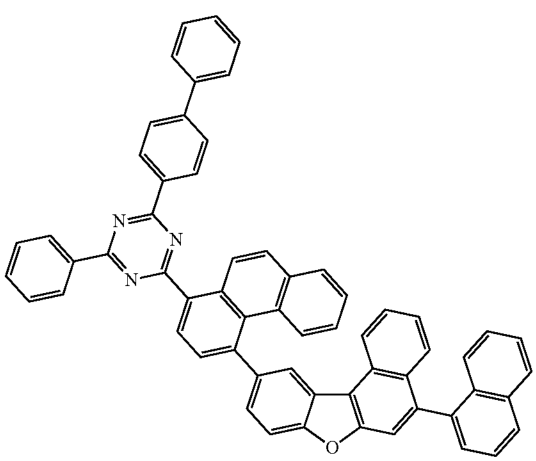
[97]
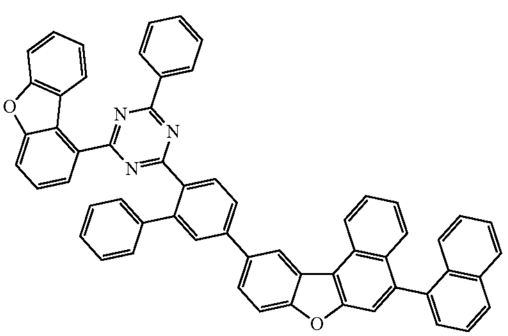

-continued
[98]
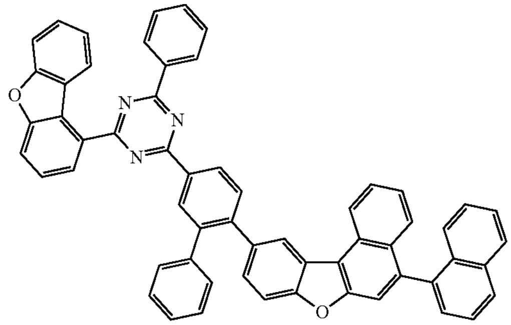
[99]
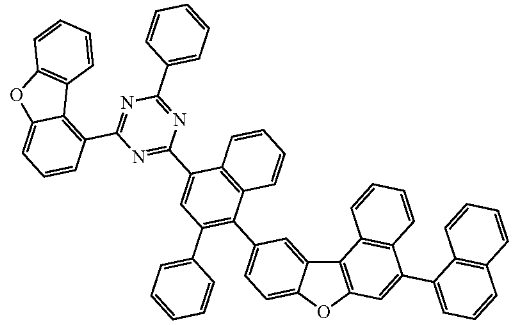
[100]
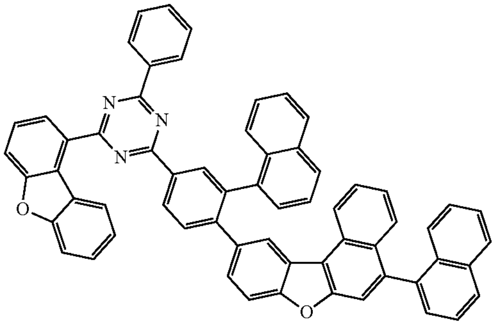
[101]
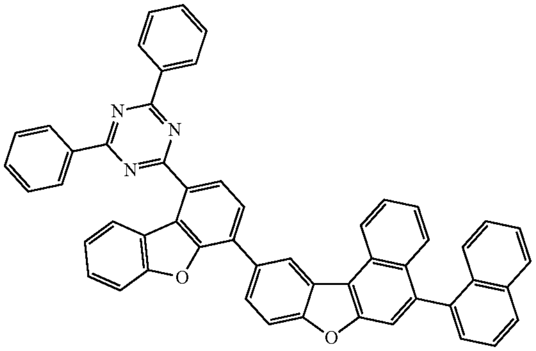
[102]
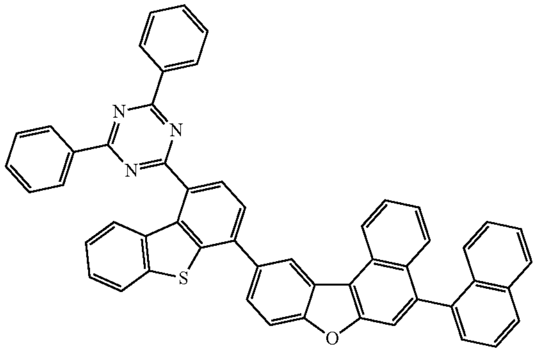
[103]
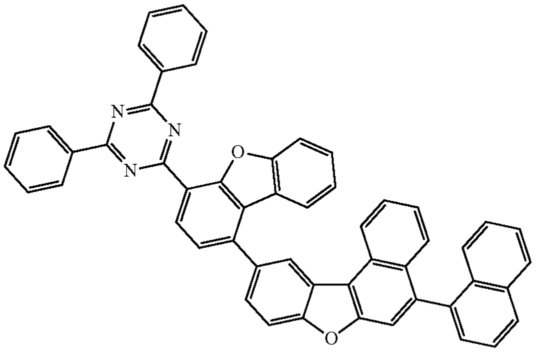
[104]
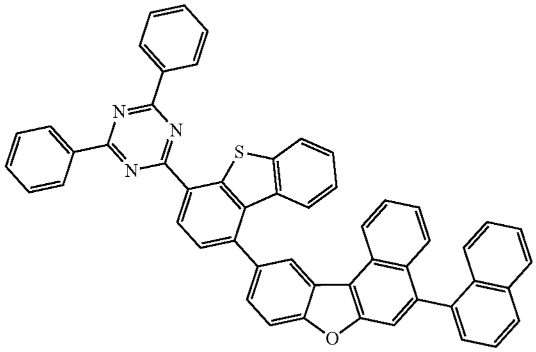
[105]
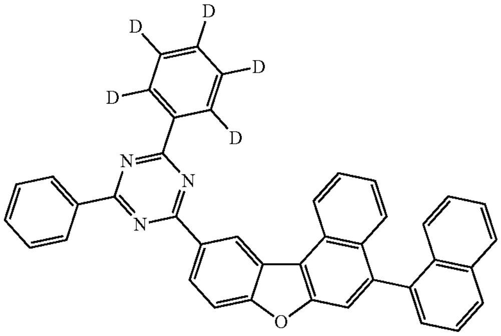

-continued
[106]
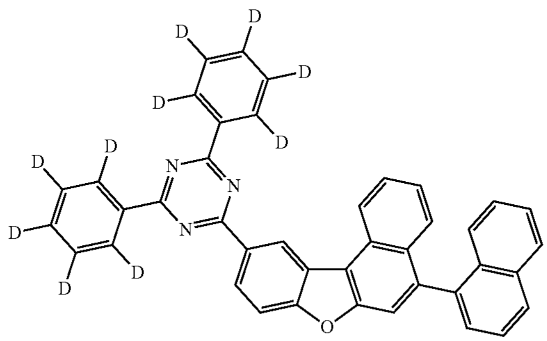
[107]
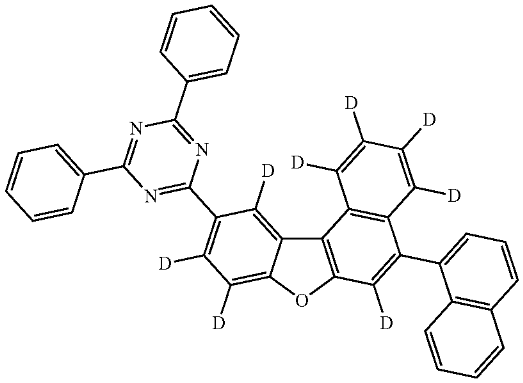
[108]
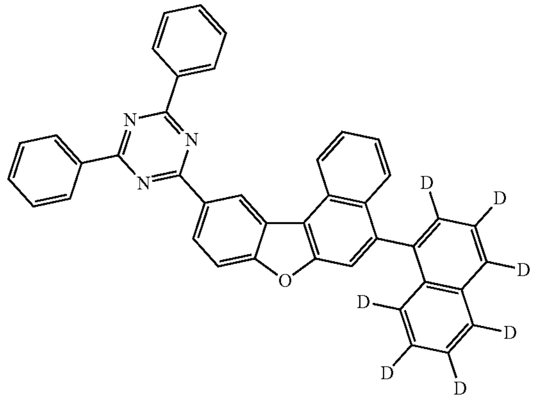
[109]
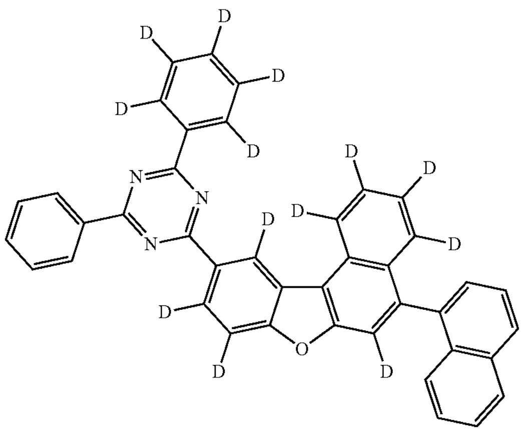
[110]
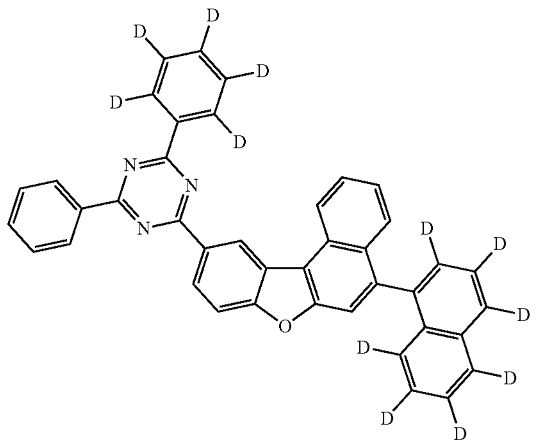
[111]
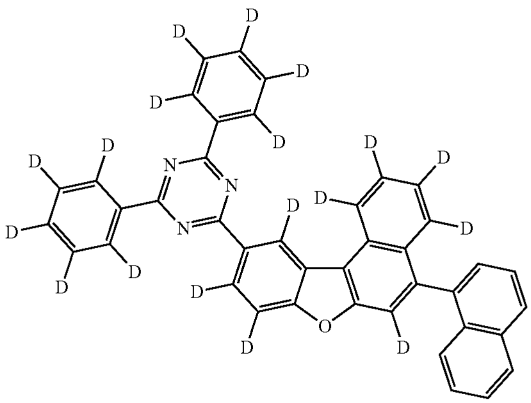

-continued
[112]
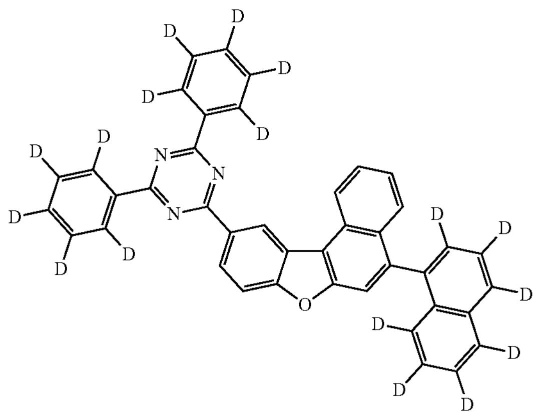
[113]
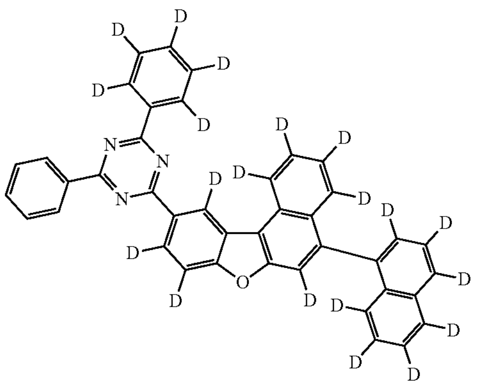
[114]
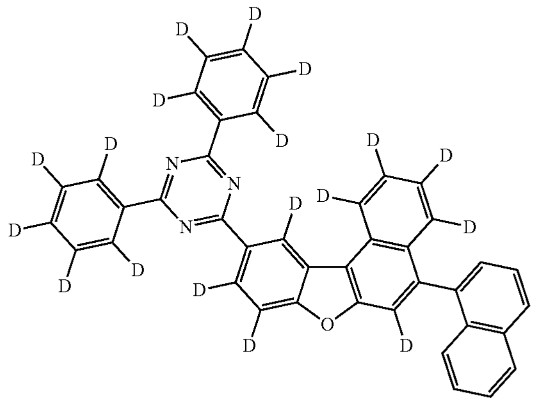
[115]
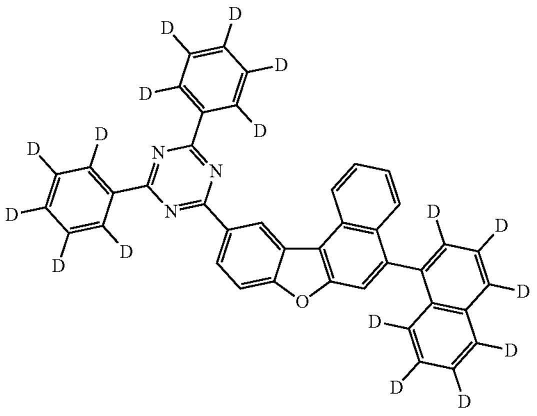
[116]
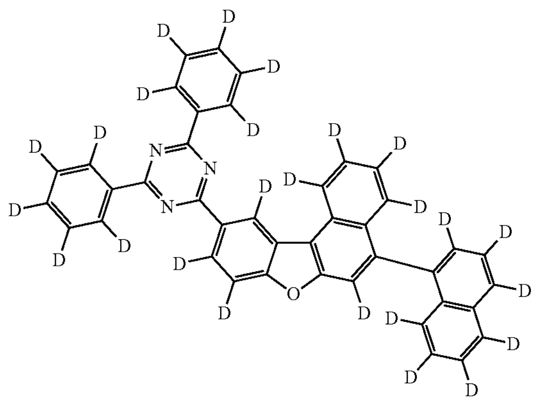
[117]
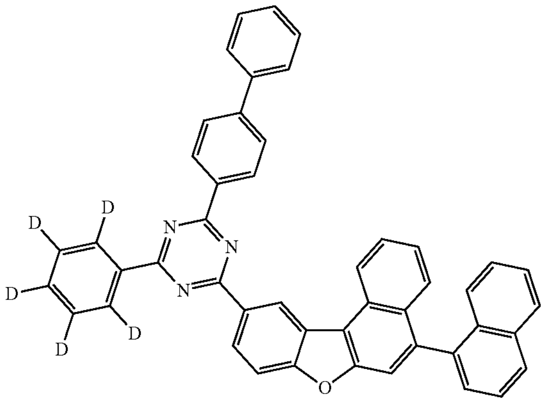

-continued
[118]
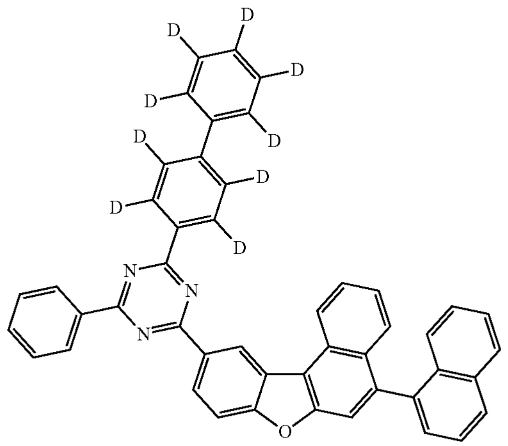
[119]
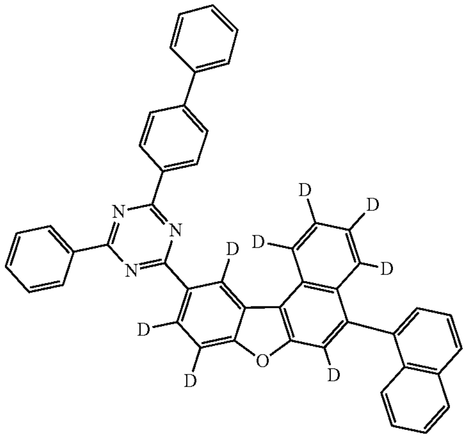
[120]
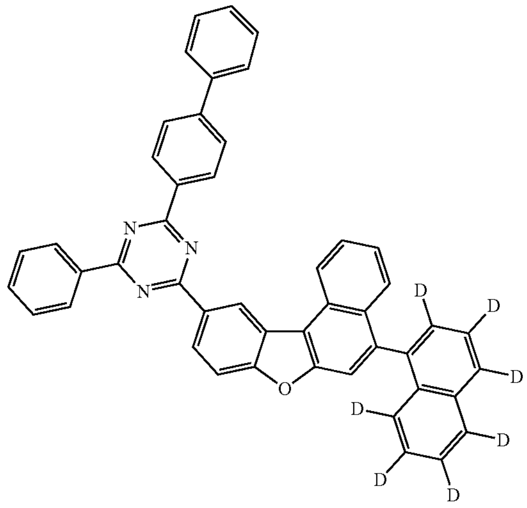
[121]
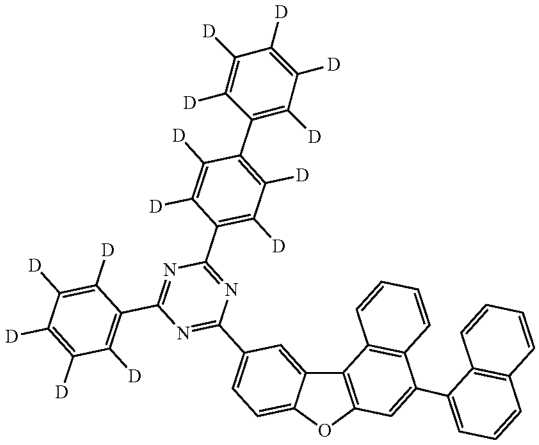
[122]
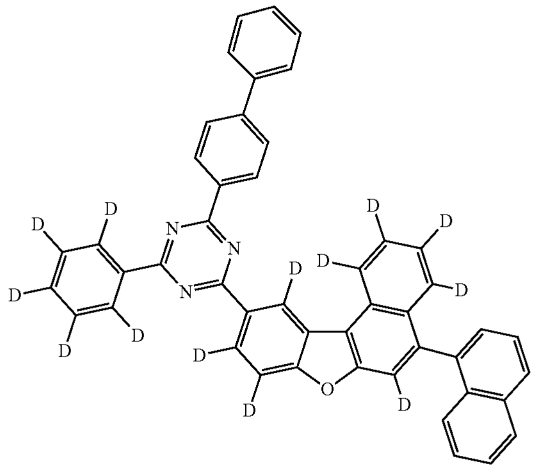
[123]
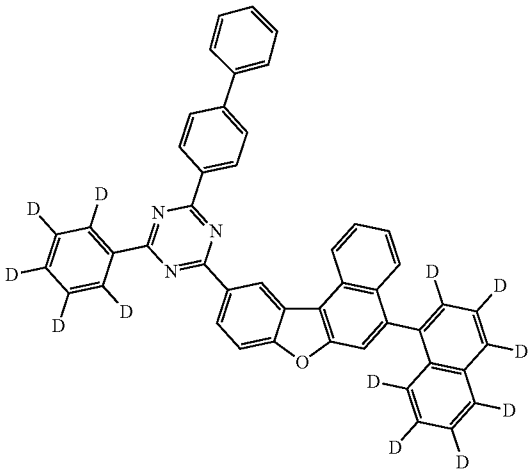

-continued
[124]
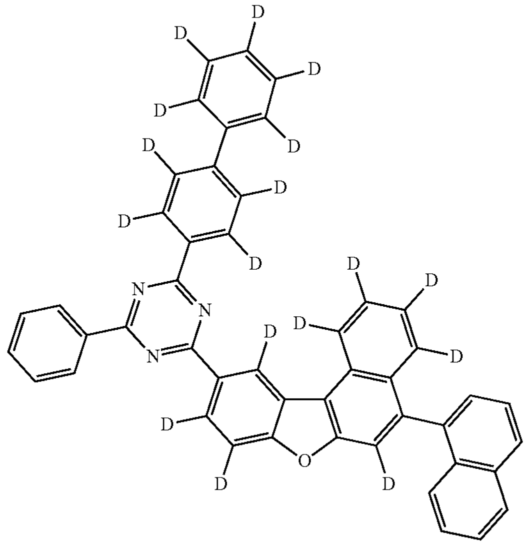
[125]
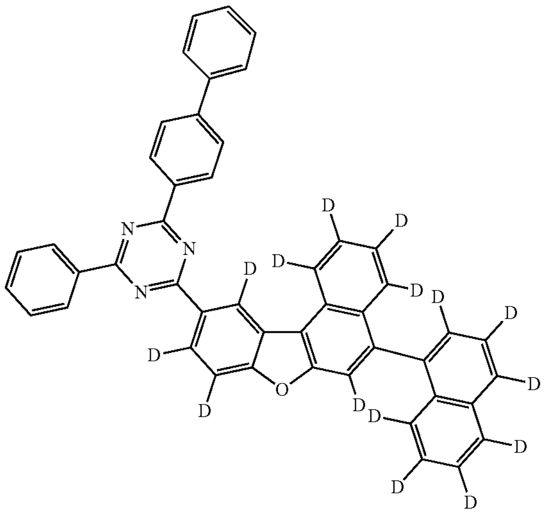
[126]
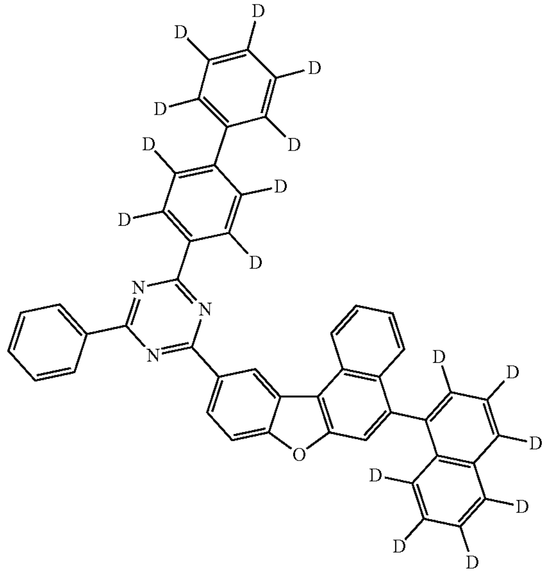
[127]
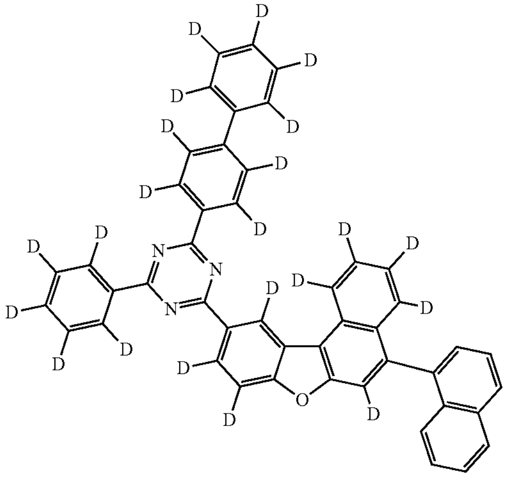
[128]
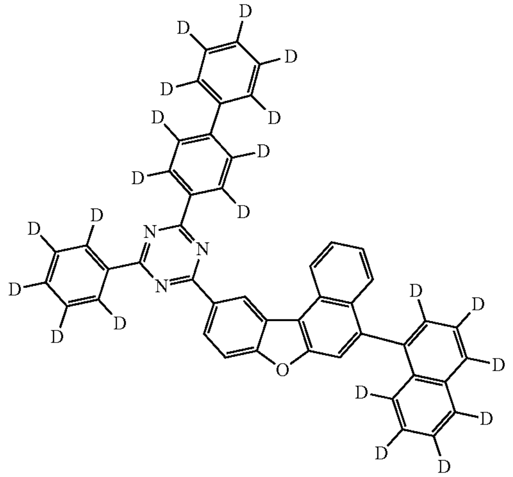
[129]
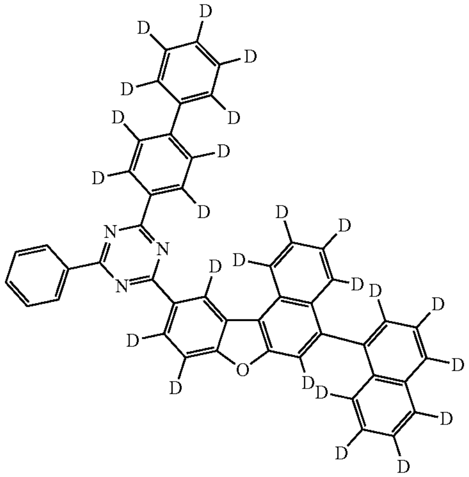

-continued
[130]
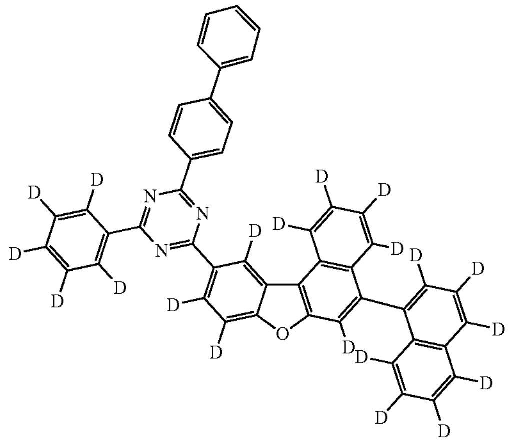
[131]
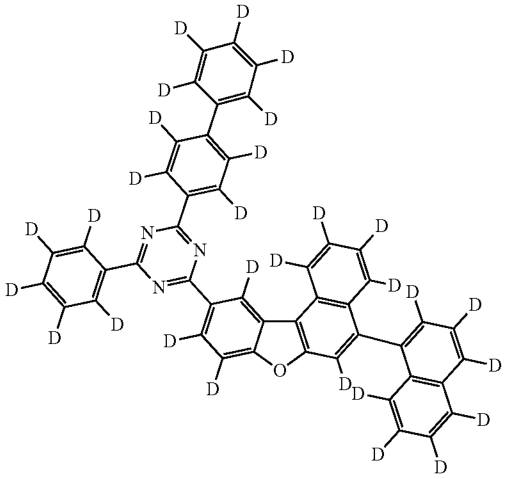
[132]
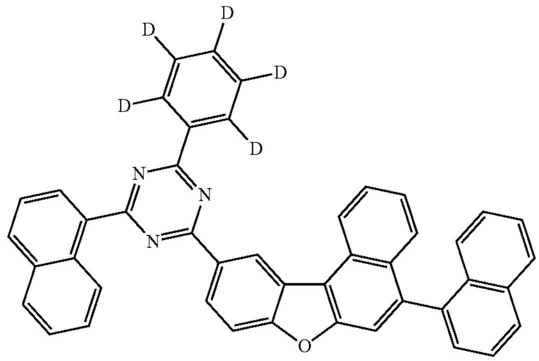
[133]
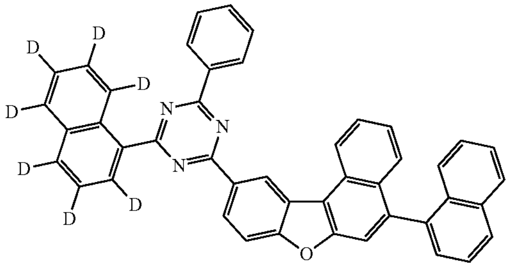
[134]
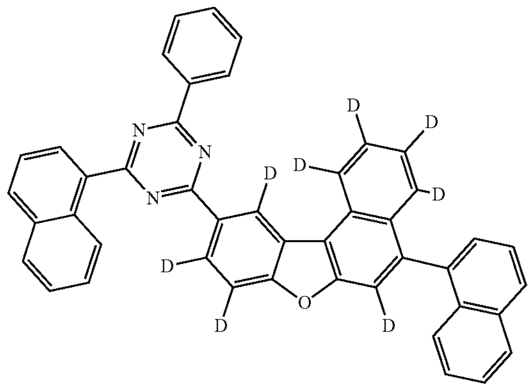
[135]
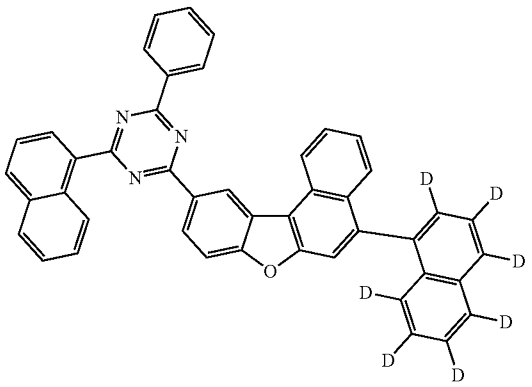

-continued
[136]
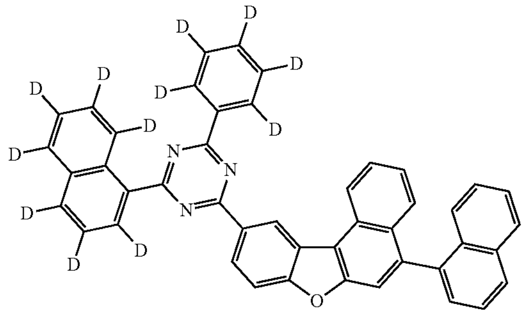
[137]
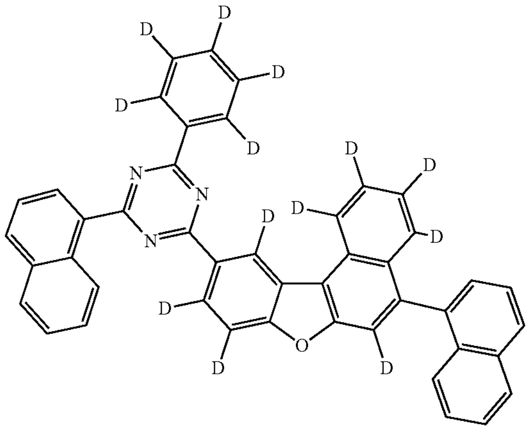
[138]
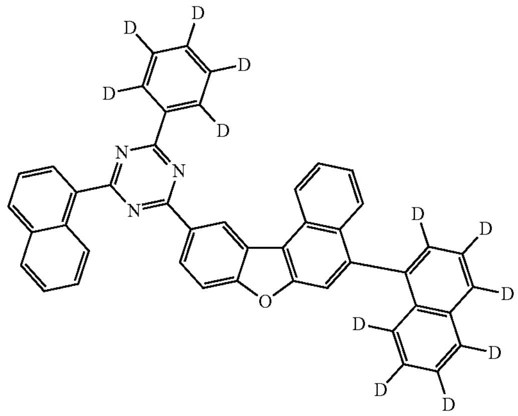
[139]
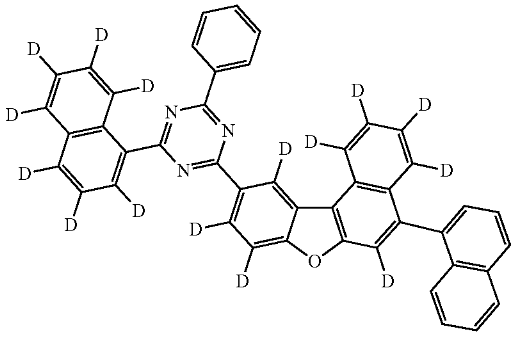
[140]
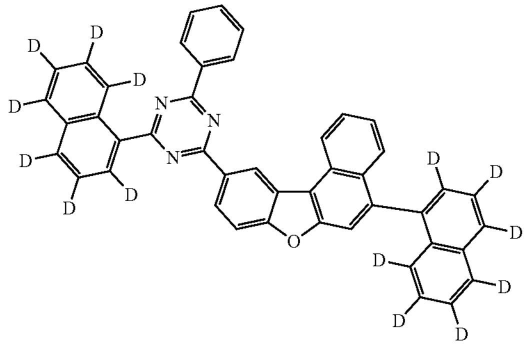
[141]
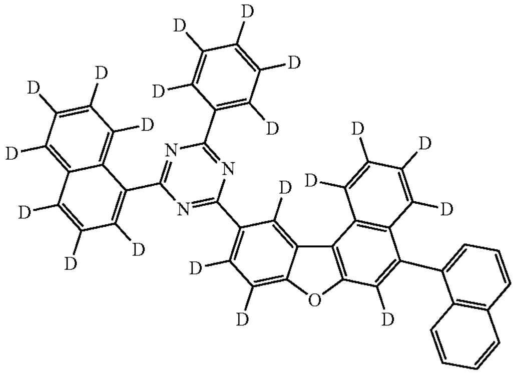

-continued
[142]
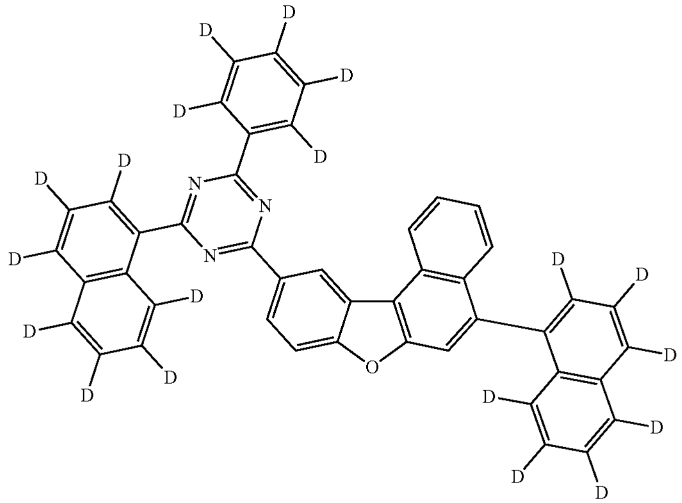
[143]
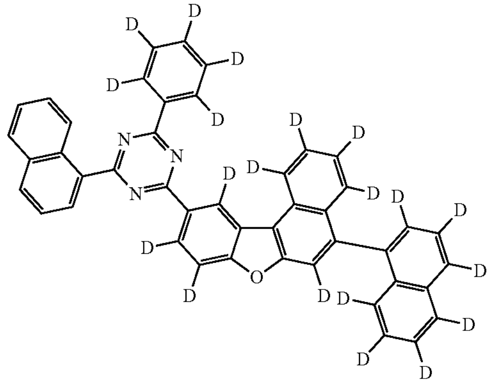
[144]
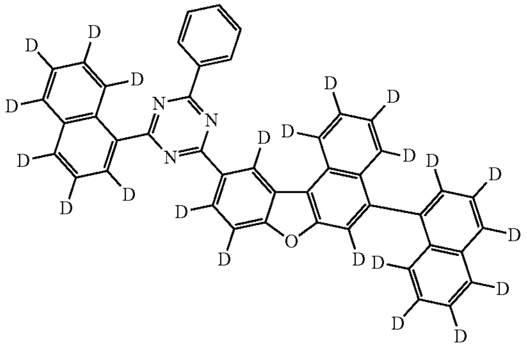
[145]
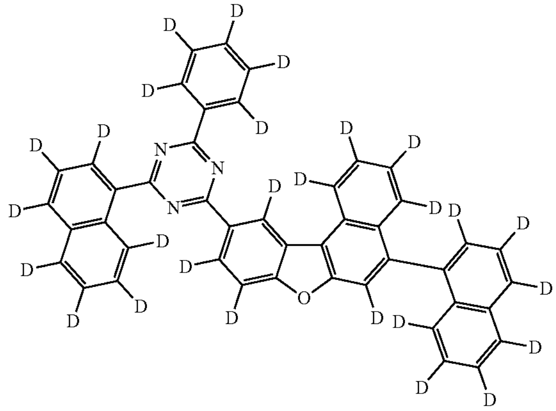
[146]
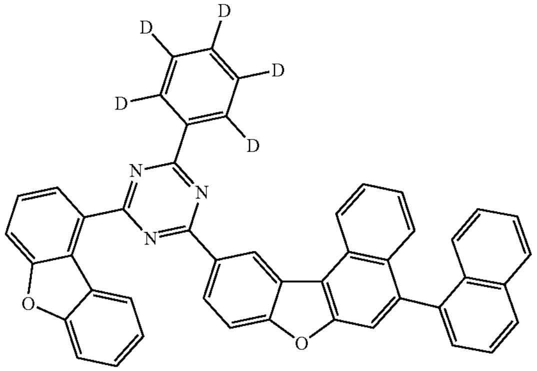

-continued
[147]
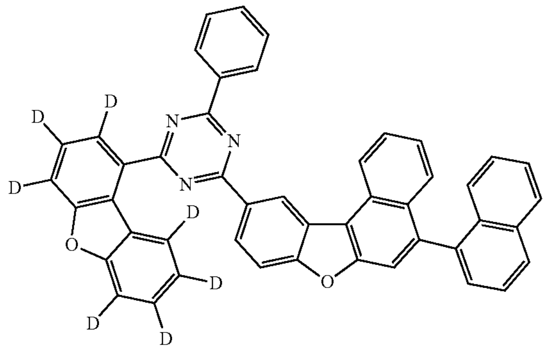
[148]
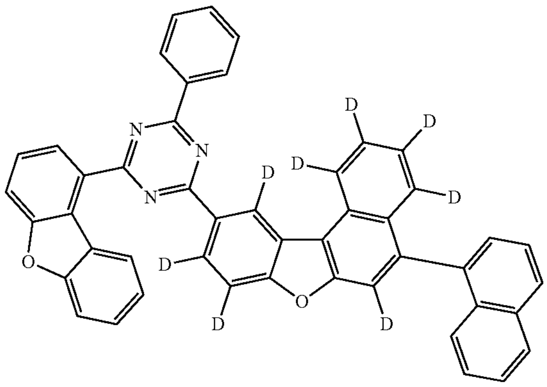
[149]
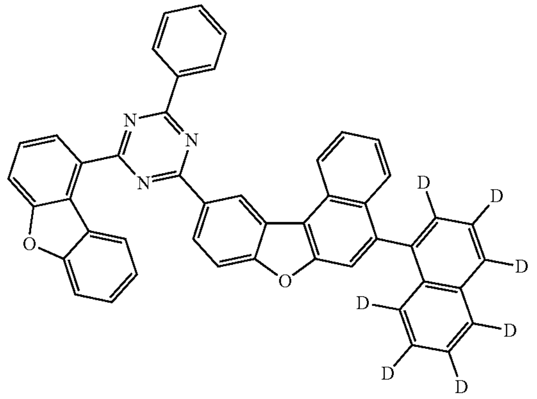
[150]
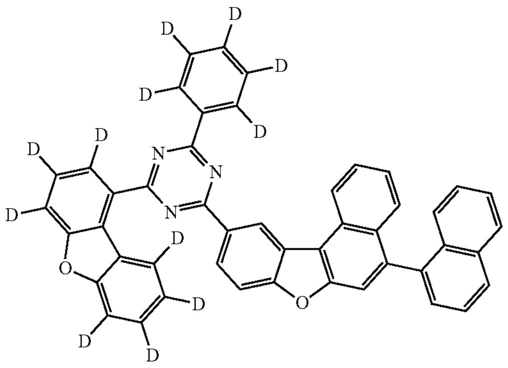
[151]
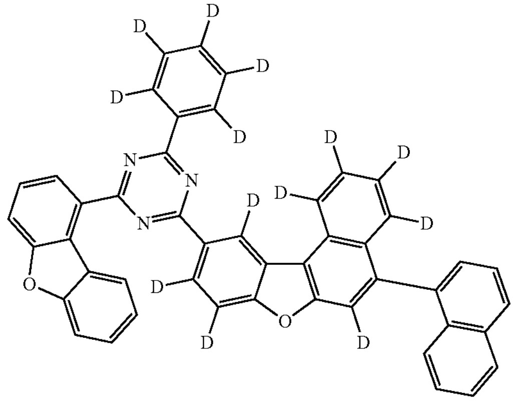
[152]
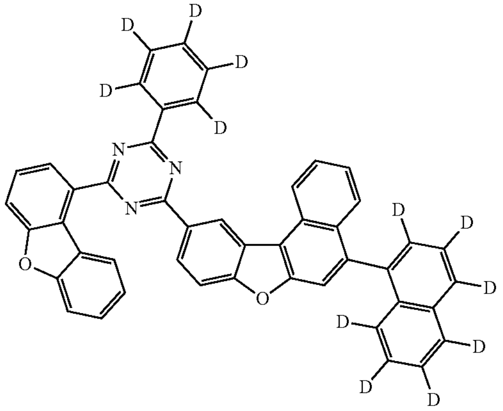
[153]
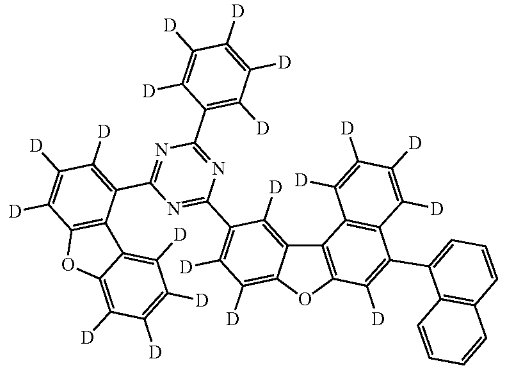
[154]
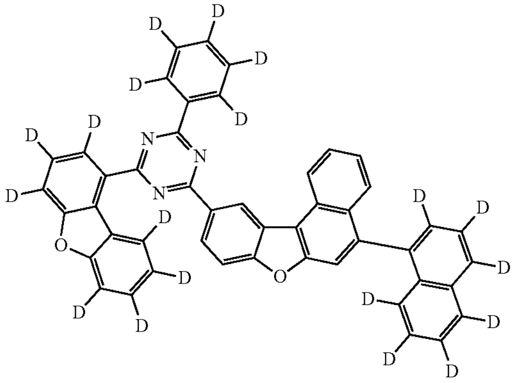

-continued
[155]
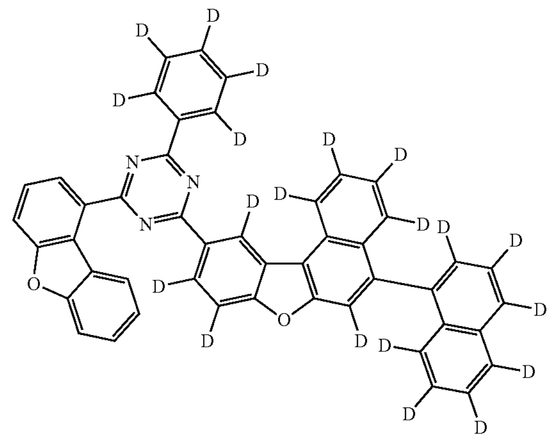
[156]
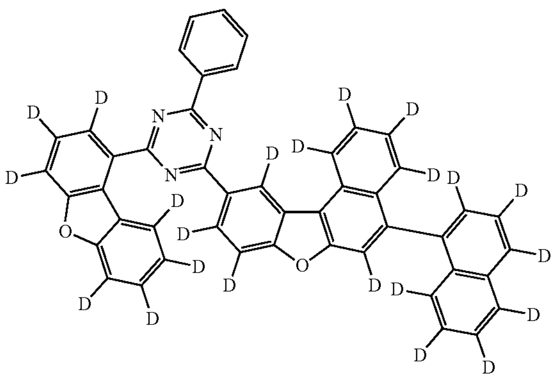
[157]
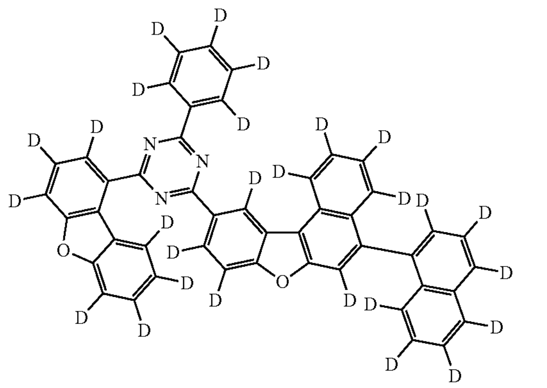
[158]
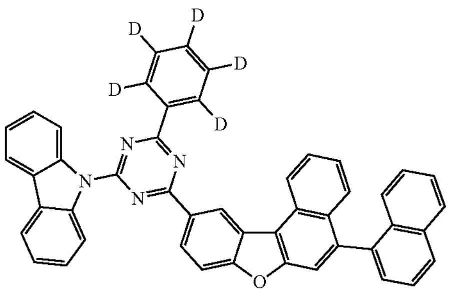
[159]
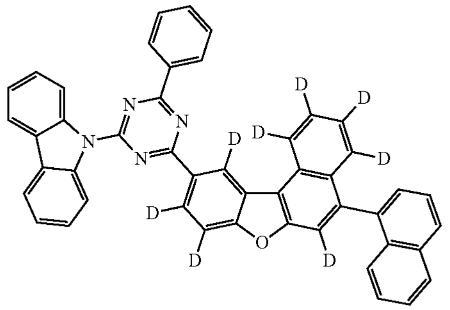
[160]
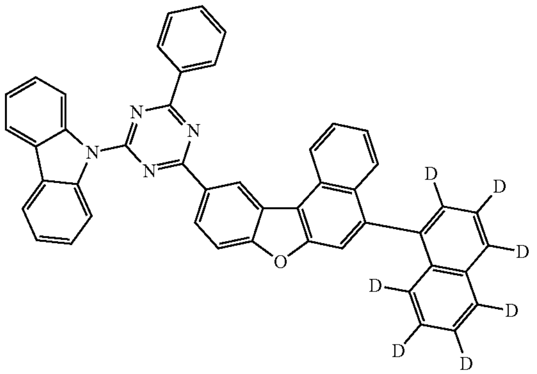
[161]
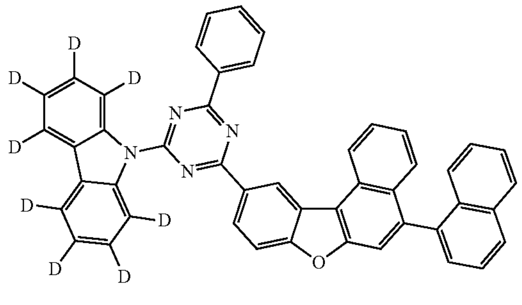
[162]
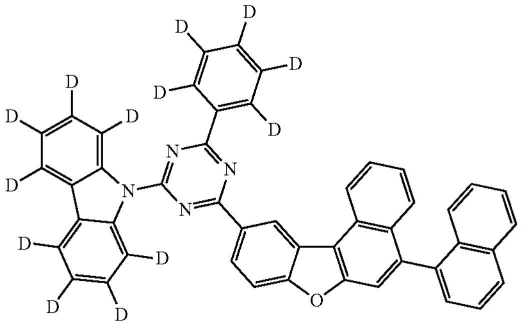

-continued
[163]
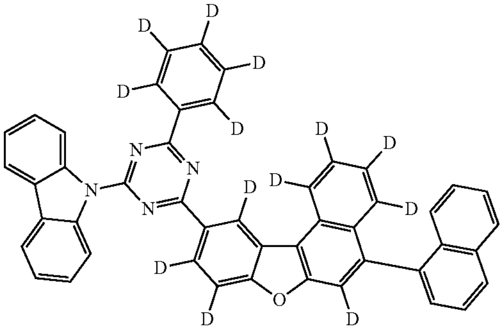
[164]
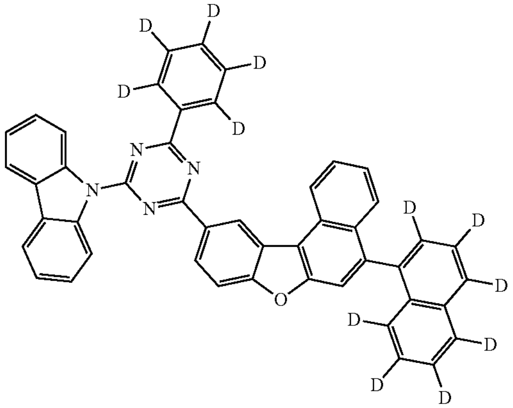
[165]
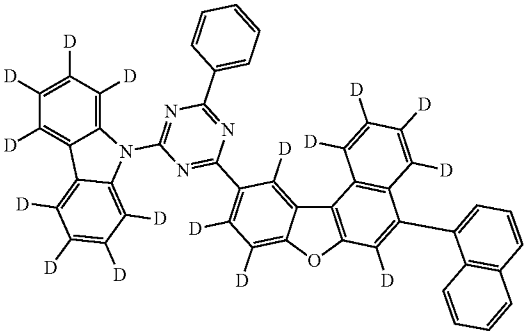
[166]
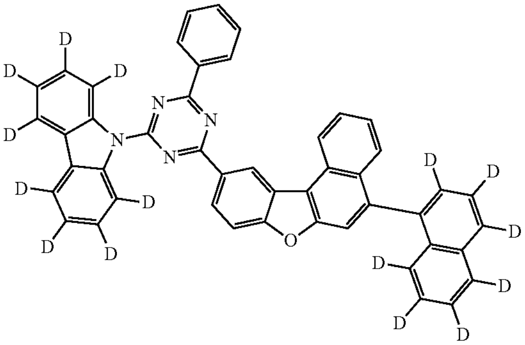
[167]
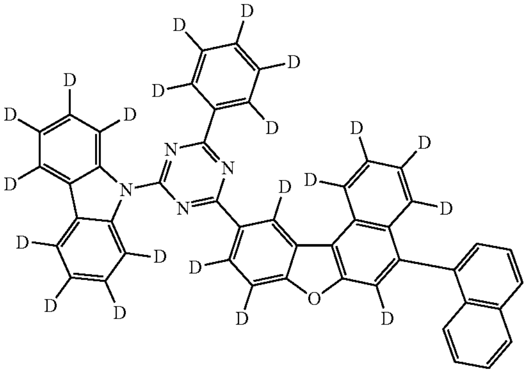
[168]
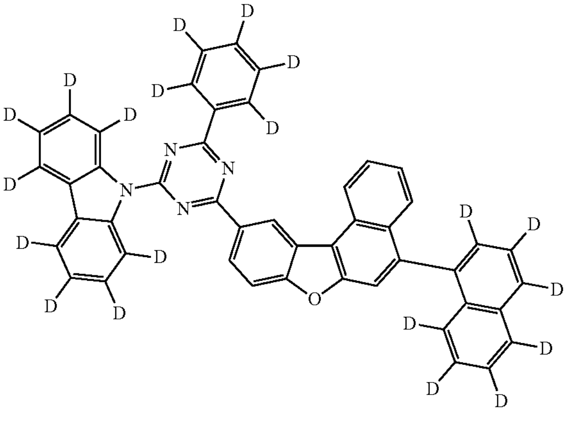

-continued

[169]

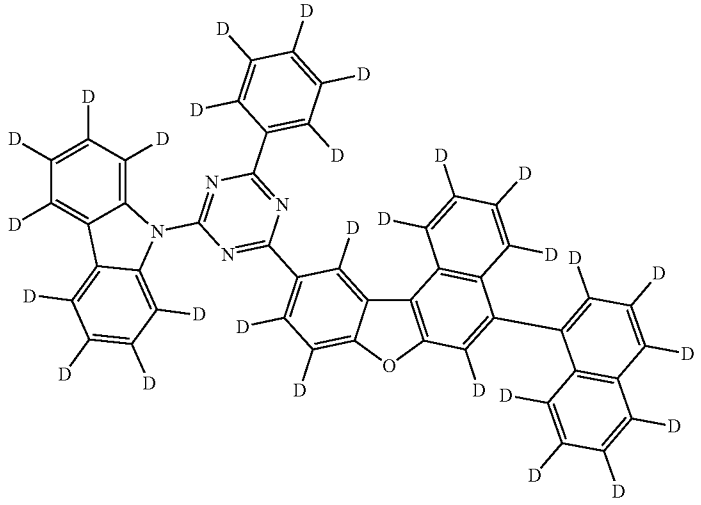

A composition or the organic optoelectronic device according to another embodiment may include a first compound and a second compound. In an implementation, the first compound may be the aforementioned compound for the organic optoelectronic device, and the second compound may be represented by, e.g., Chemical Formula 2.

[Chemical Formula 2]

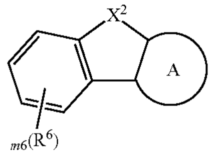

In Chemical Formula 2, $X^2$ may be, e.g., O, S, NR, $CR^cR^d$, or $SiR^eR^f$.

$R^b$, $R^c$, $R^d$, $R^e$, $R^f$, and $R^6$ may each independently be or include, e.g., hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

m6 may be, e.g., an integer of 1 to 4.

Ring A may be, e.g., a ring of Group II.

[Group II]

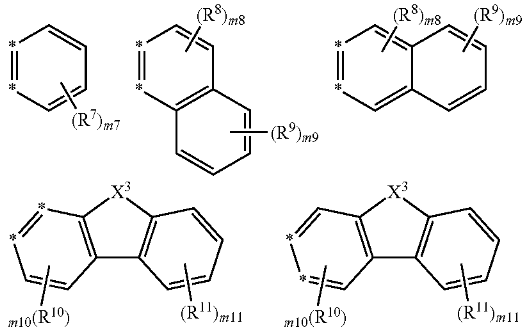

-continued

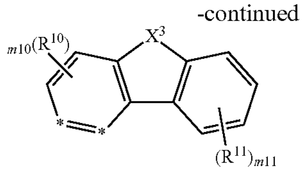

In Group II,*is a linking point (e.g., a shared carbon with the $X^2$-containing ring of Chemical Formula 2).

$X^3$ may be, e.g., O, S, $NR^g$, $CR^hR^i$, or $SiR^jR^k$, $R^g$, $R^h$, $R^i$, $R^j$, $R^k$, and $R^7$ to $R^{11}$ may each independently be or include, e.g., hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

m7, m9, and m11 may each independently be, e.g., an integer of 1 to 4.

m8 and m10 may each independently be, e.g., 1 or 2.

In an implementation, at least one of $R^6$ to $R^{11}$ may be, e.g., a group (e.g., a substituted amine group) represented by Chemical Formula a.

[Chemical Formula a]

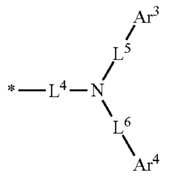

In Chemical Formula a, $L^4$ to $L^6$ may each independently be or include, e.g., a single bond or a substituted or unsubstituted C6 to C30 arylene group.

$Ar^3$ and $Ar^4$ may each independently be or include, e.g., a substituted or unsubstituted amine group, a substituted or unsubstituted C6 to C30 aryl group, or a substituted or unsubstituted C2 to C30 heterocyclic group.

* is a linking point.

The second compound may have a structure in which carbazole/fused carbazole/fused dibenzofuran/fused dibenzothiophene/fused dibenzosilole is substituted with an amine. In an implementation, the second compound may be represented by, e.g., one of Chemical Formula 2-I to Chemical Formula 2-IX, depending on the type and fusion position of the additional benzene ring.

[Chemical Formula 2-I]

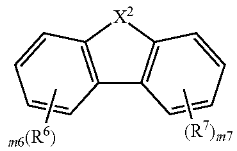

[Chemical Formula 2-II]

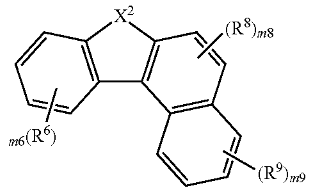

[Chemical Formula 2-III]

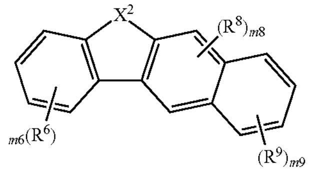

[Chemical Formula 2-IV]

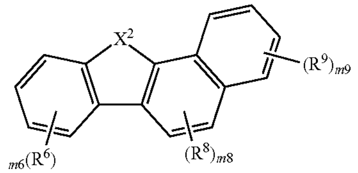

[Chemical Formula 2-V]

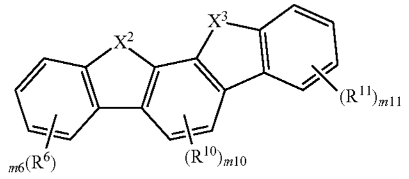

[Chemical Formula 2-VI]

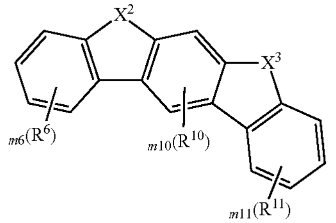

-continued

[Chemical Formula 2-VII]

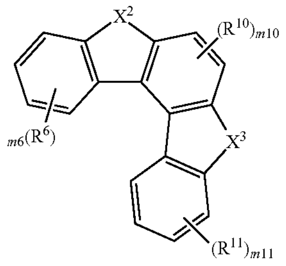

[Chemical Formula 2-VIII]

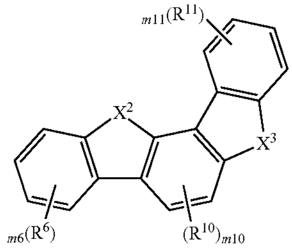

[Chemical Formula 2-IX]

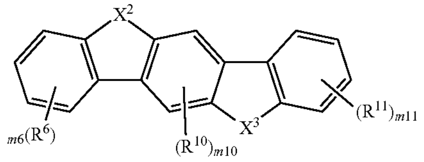

In Chemical Formula 2-I to Chemical Formula 2-IX, $X^2$, $X^3$, m6 to m11, and $R^6$ to $R^{11}$ may be defined the same as those described above.

In an implementation, the second compound may be represented by, e.g., one of Chemical Formula 2-IA to Chemical Formula 2-IXA, Chemical Formula 2-TB to Chemical Formula 2-IXB, and Chemical Formula 2-IIC to Chemical Formula 2-IVC, depending on the substitution direction of the amine group.

[Chemical Formula 2-IA]

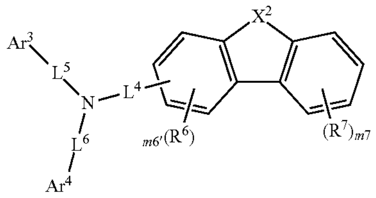

[Chemical Formula 2-IIA]

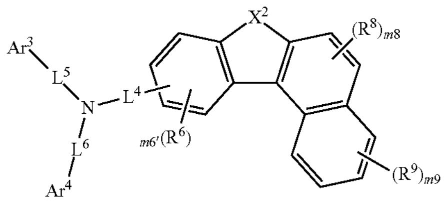

-continued
[Chemical Formula 2-IIIA]
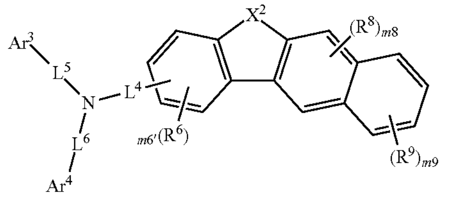
[Chemical Formula 2-IVA]
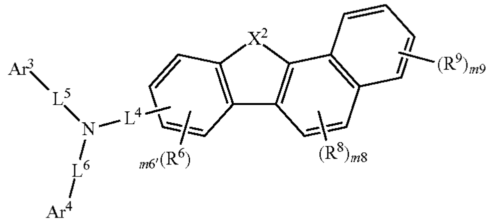
[Chemical Formula 2-VA]
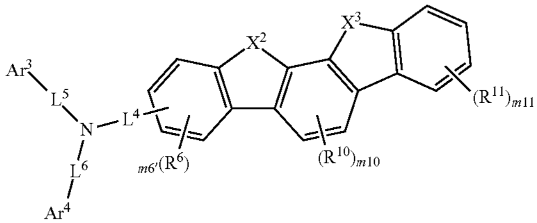
[Chemical Formula 2-VIA]
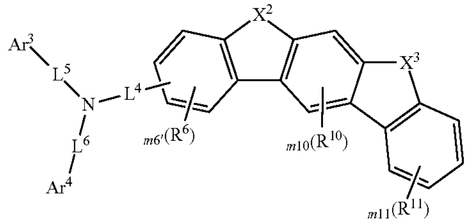
[Chemical Formula 2-VIIA]
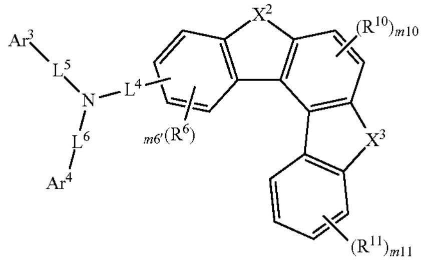
[Chemical Formula 2-VIIIA]
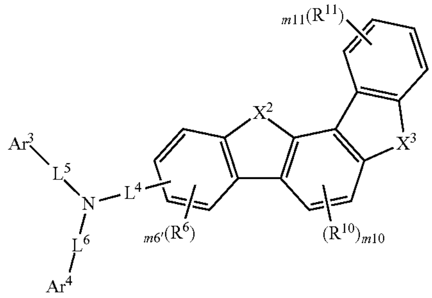
-continued
[Chemical Formula 2-IXA]
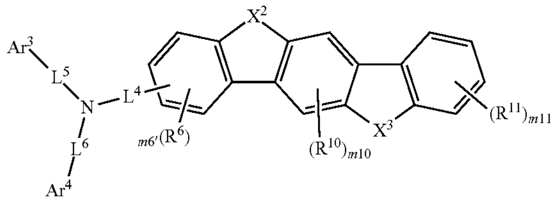
[Chemical Formula 2-IB]
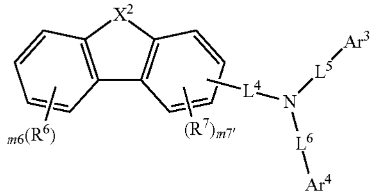
[Chemical Formula 2-IIB]
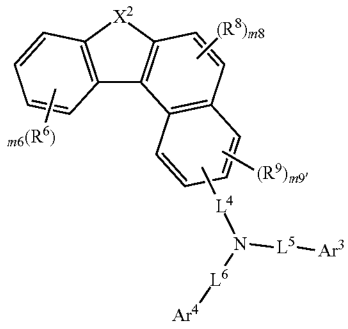
[Chemical Formula 2-IIIB]
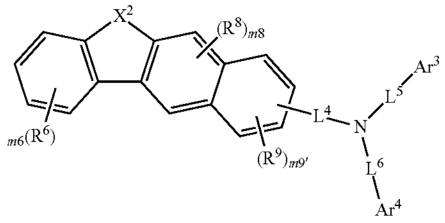
[Chemical Formula 2-IVB]
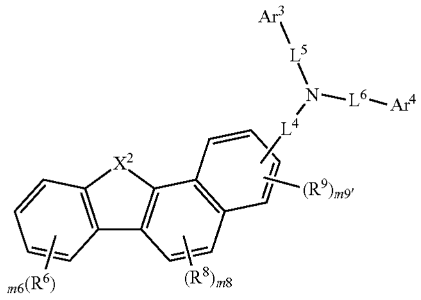

-continued

[Chemical Formula 2-VB]

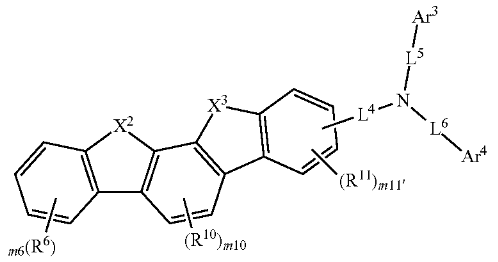

[Chemical Formula 2-VIB]

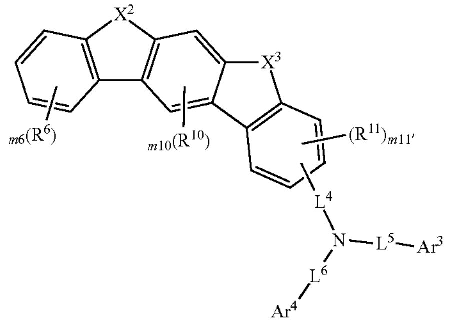

[Chemical Formula 2-VIIB]

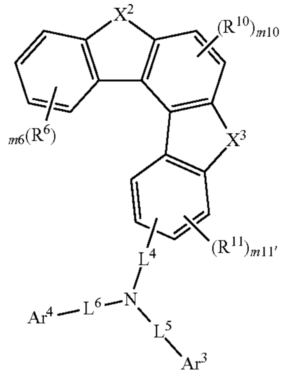

[Chemical Formula 2-VIIIB]

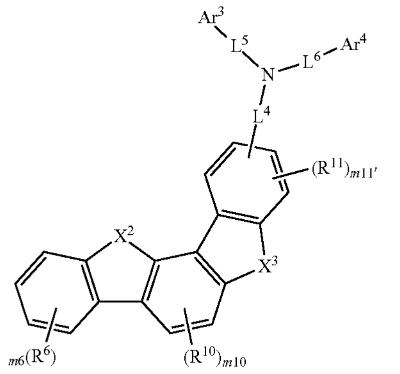

-continued

[Chemical Formula 2-IXB]

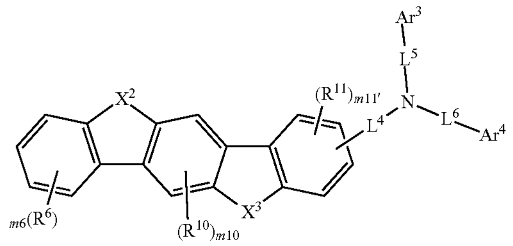

[Chemical Formula 2-IIC]

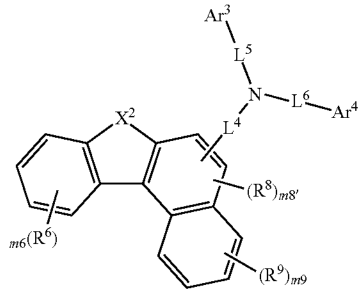

[Chemical Formula 2-IIIC]

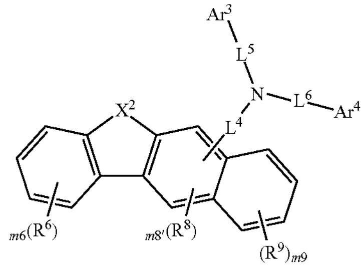

[Chemical Formula 2-IVC]

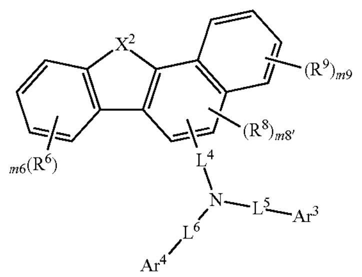

In Chemical Formula 2-IA to Chemical Formula 2-IXA, Chemical Formula 2-IB to Chemical Formula 2-IXB, and Chemical Formula 2-IIC to Chemical Formula 2-IVC, $X^2$, $X^3$, $L^4$ to $L^6$, m6 to m11, $Ar^3$, and $Ar^4$ may be defined the same as those described above.

$R^6$ to $R^{11}$ may each independently be, e.g., hydrogen, deuterium, a substituted or unsubstituted C1 to C30 alkyl group, or a substituted or unsubstituted C6 to C30 aryl group.

m6', m7', m9', and m11' may each independently be, e.g., an integer of 1 to 3.

m8' may be, e.g., 1.

In an implementation, the second compound may be represented by, e.g., Chemical Formula 2-IVB or Chemical Formula 2-VIIIB.

In an implementation, $X^2$ of Chemical Formula 2-IVB may be, e.g., $NR^b$.

In an implementation, in Chemical Formula 2-VIIIB, $X^2$ may be, e.g., O or S, and $X^3$ may be, e.g., $CR^hR^i$ or $SiR^jR^k$.

In an implementation, $R^b$, $R^h$, $R^i$, $R^j$, and $R^k$ may each independently be, e.g., a substituted or unsubstituted C1 to C10 alkyl group, or a substituted or unsubstituted C6 to C20 aryl group.

In an implementation, the second compound may be represented by, e.g., Chemical Formula 2-IVB-2 or Chemical Formula 2-VITIB-2.

[Chemical Formula 2-IVB-2]

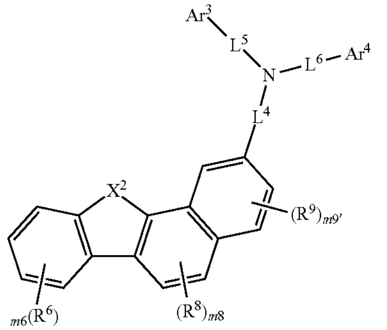

[Chemical Formula 2-VIIIB-2]

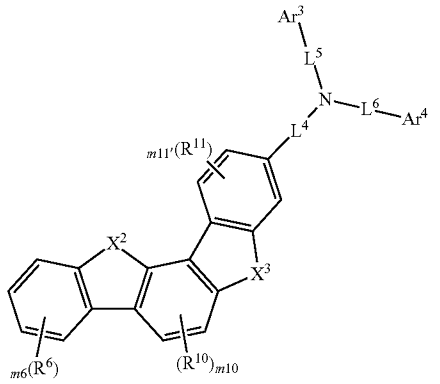

In Chemical Formula 2-IVB-2 and Chemical Formula 2-VIIIB-2, $L^4$ to $L^6$ may each independently be, e.g., a single bond or a substituted or unsubstituted phenylene group.

$Ar^3$ and $Ar^4$ may each independently be, e.g., a substituted or unsubstituted phenyl group, a substituted or unsubstituted biphenyl group, or a substituted or unsubstituted naphthyl group.

$X^2$ may be, e.g., $NR^b$, O, or S.

$X^3$ may be, e.g., $CR^hR^i$ or $SiR^jR^k$.

$R^b$, $R^h$, $R^i$, $R^j$, and $R^k$ may each independently be, e.g., a substituted or unsubstituted C1 to C10 alkyl group, or a substituted or unsubstituted C6 to C20 aryl group.

$R^6$, $R^8$, $R^9$, $R^{10}$, and $R^{11}$ may each independently be, e.g., hydrogen, deuterium, a substituted or unsubstituted C1 to C30 alkyl group, or a substituted or unsubstituted C6 to C30 aryl group.

m6 may be, e.g., an integer of 1 to 4.

m8 and m10 may each independently be, e.g., 1 or 2.

m9' and m11 may each independently be, e.g., an integer of 1 to 3.

In an implementation, $L^4$ to $L^6$ may each independently be, e.g., a single bond, a substituted or unsubstituted phenylene group, or a substituted or unsubstituted biphenylene group.

In an implementation, $Ar^3$ and $Ar^4$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, a substituted or unsubstituted dibenzothiophenyl group, a substituted or unsubstituted benzofuranofluorenyl group, or a substituted or unsubstituted benzothiophenofluorenyl group.

In an implementation, the second compound may be, e.g., a compound of Group 2.

[Group 2]

A-1

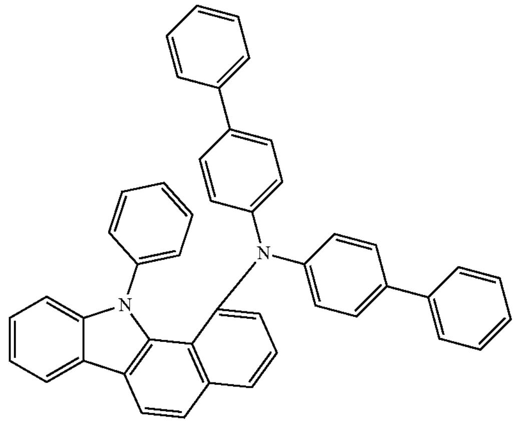

A-2

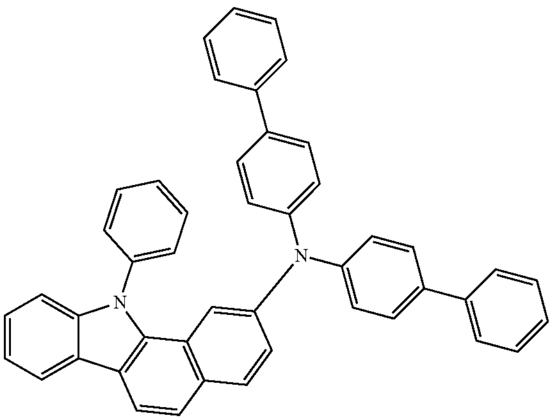

-continued
A-3
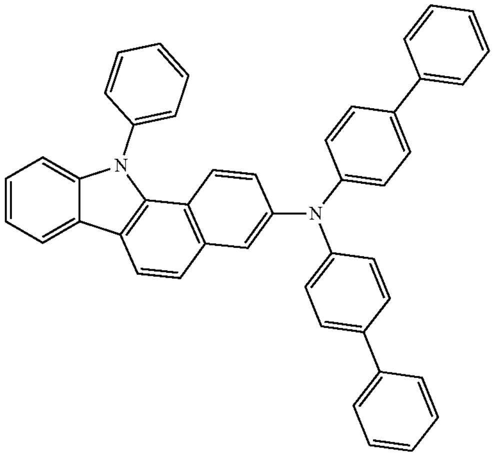
A-4
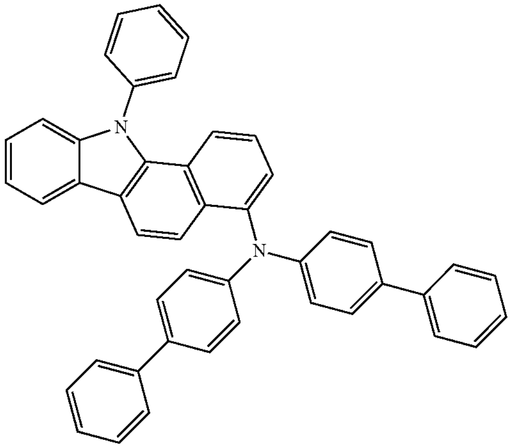
A-5
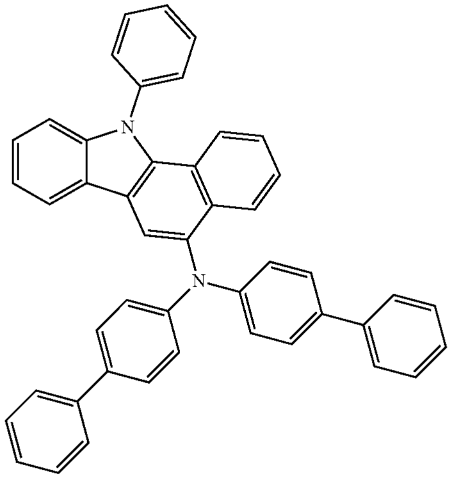
-continued
A-6
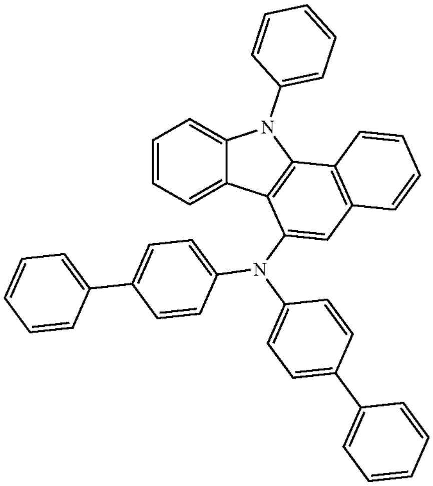
A-7
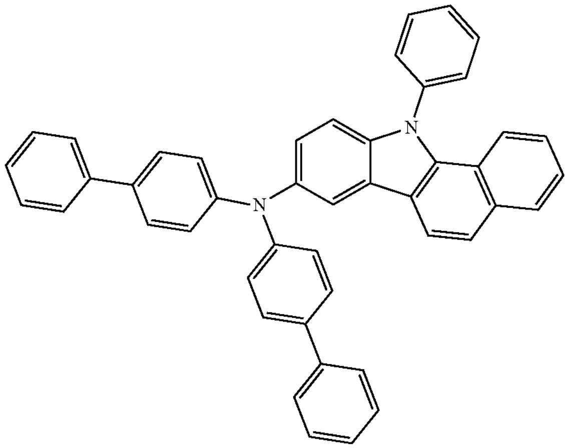
A-8
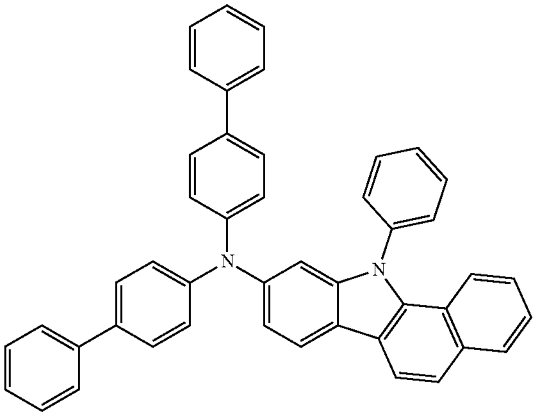

-continued
A-9
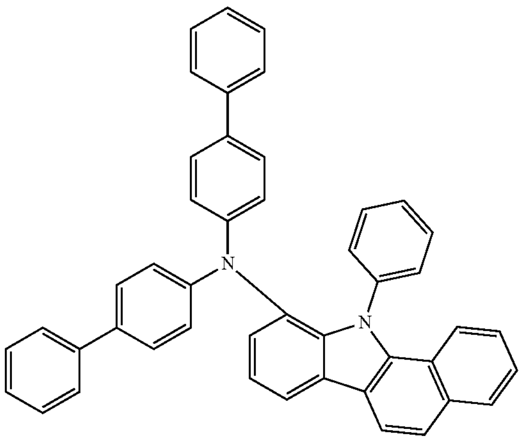
A-10
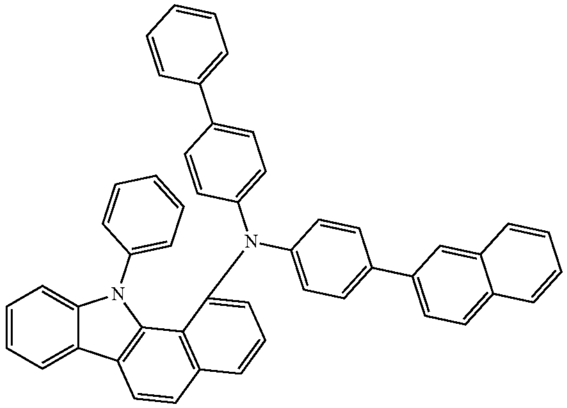
A-11
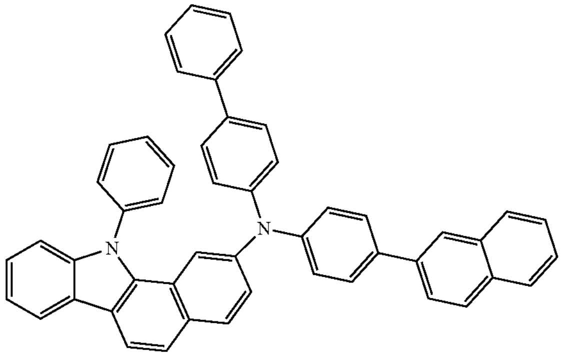
-continued
A-12
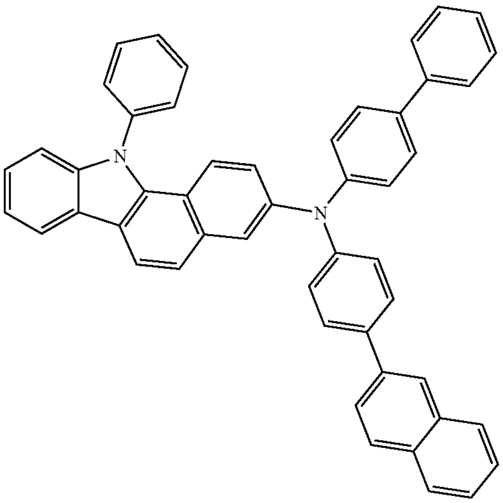
A-13
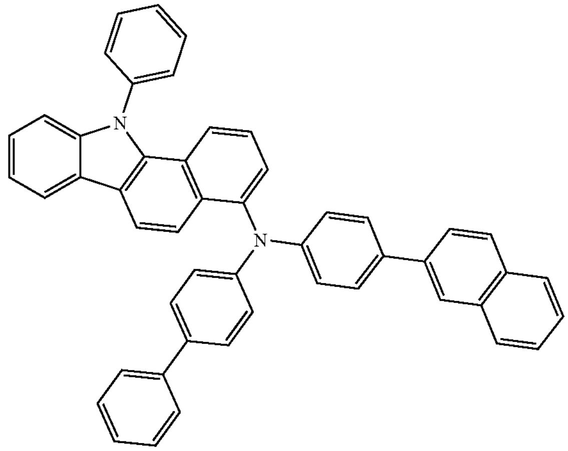
A-14
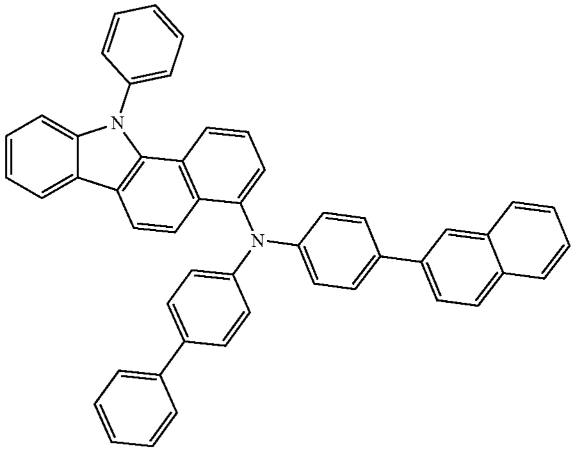

-continued
A-15
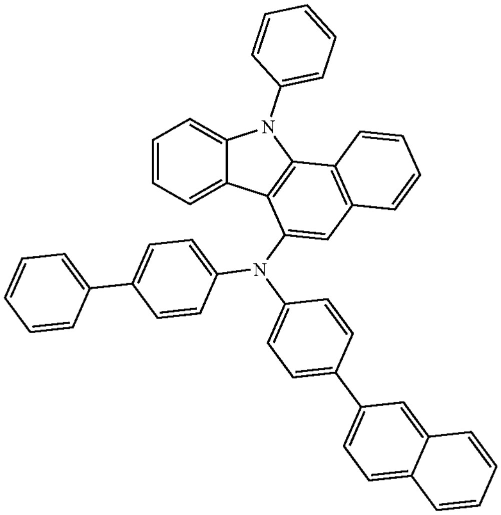
A-16
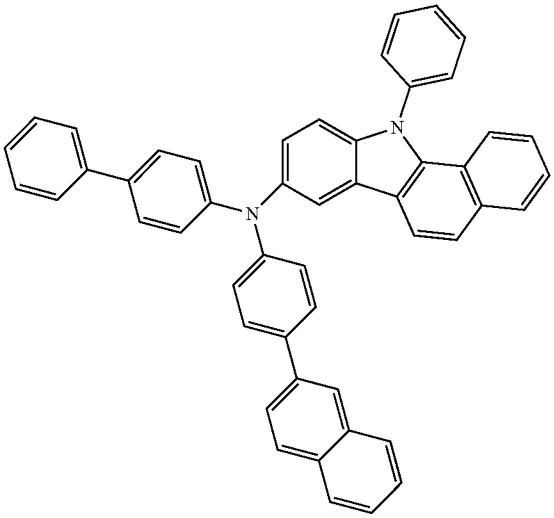
A-17
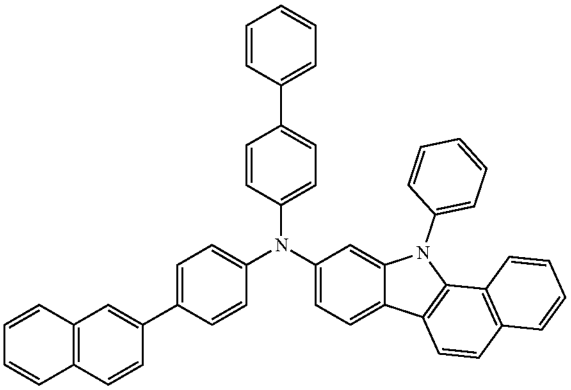
-continued
A-18
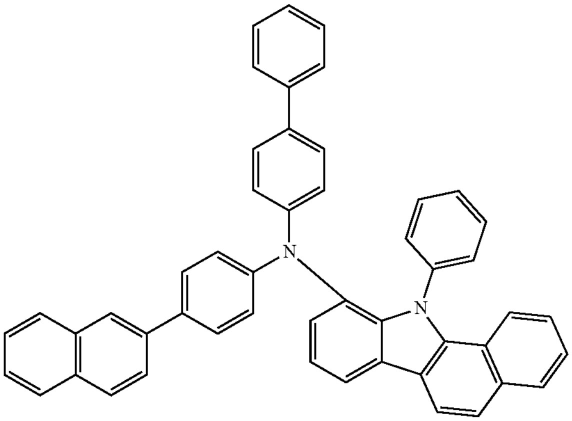
A-19
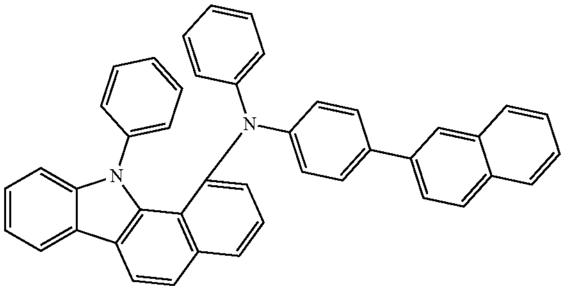
A-20
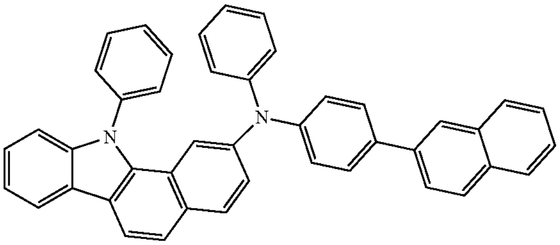
A-21
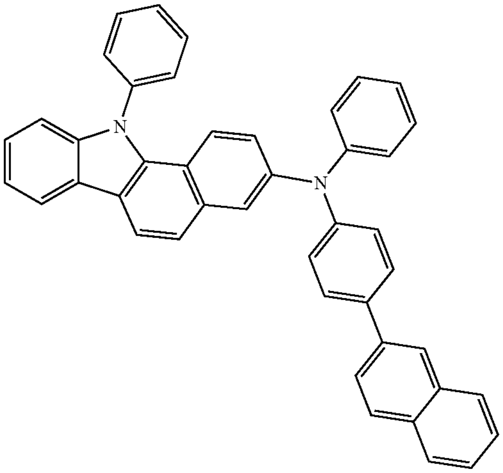

-continued
A-22
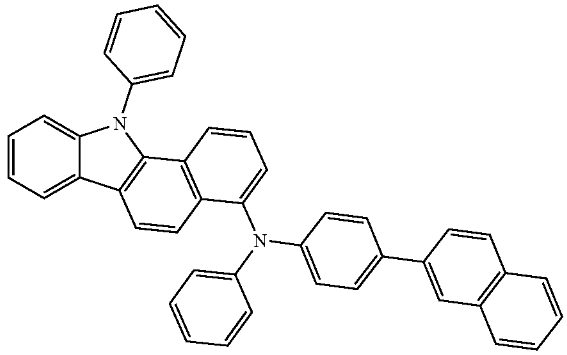
A-23
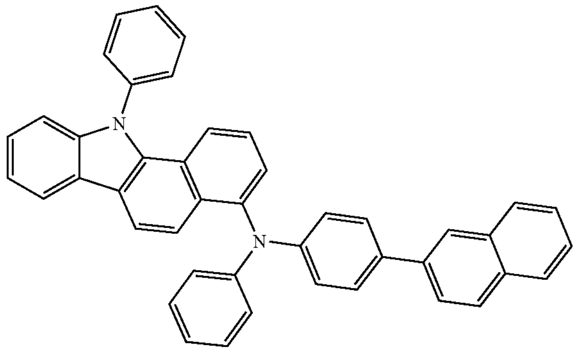
A-24
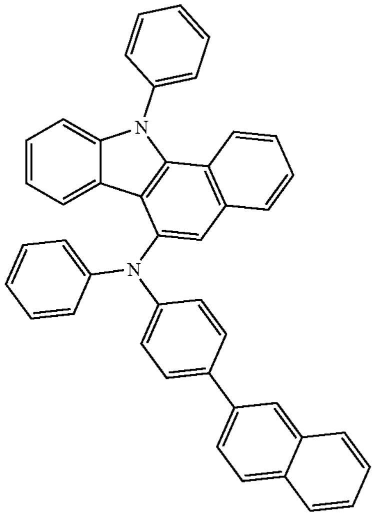
-continued
A-25
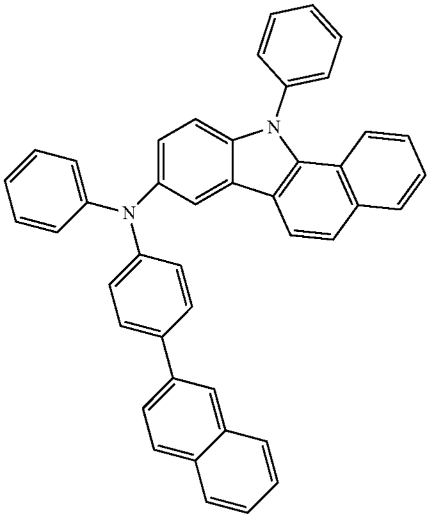
A-26
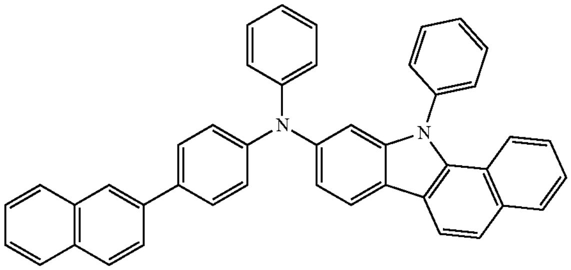
A-27
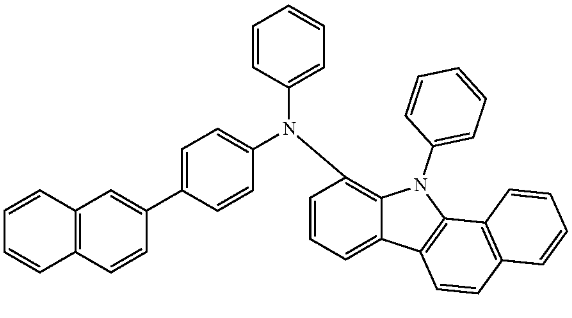
A-28
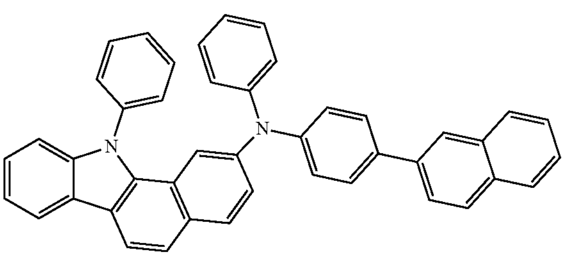

-continued
A-45
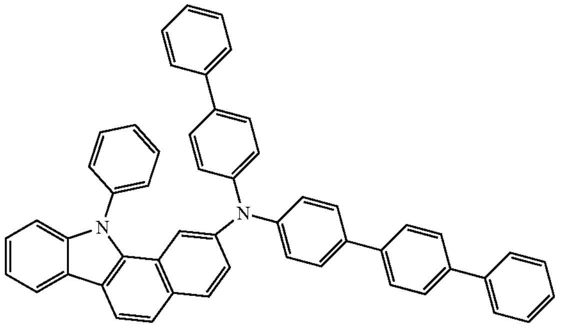
A-46
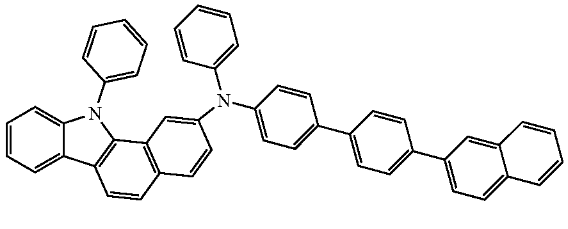
A-47
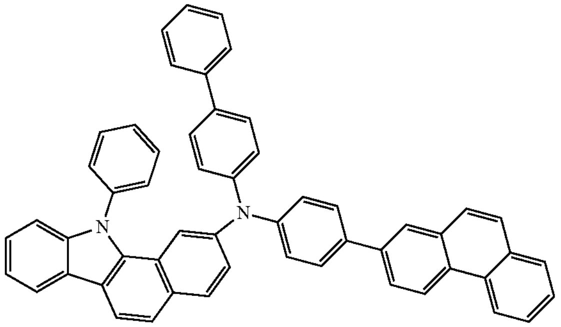
A-48
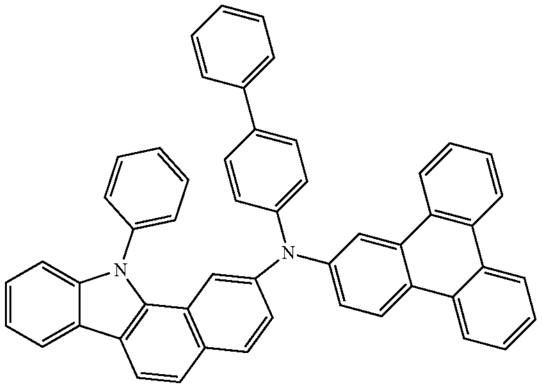
-continued
A-49
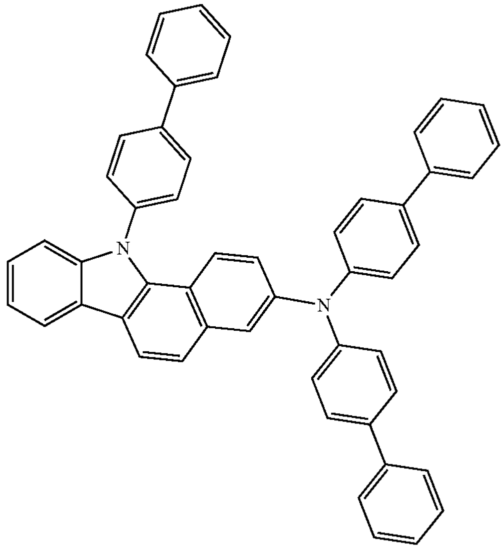
A-50
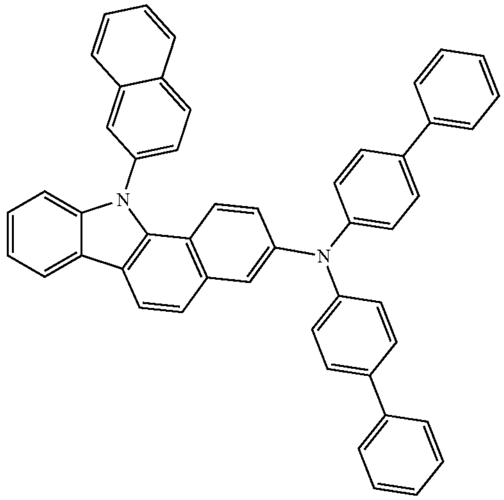
A-51
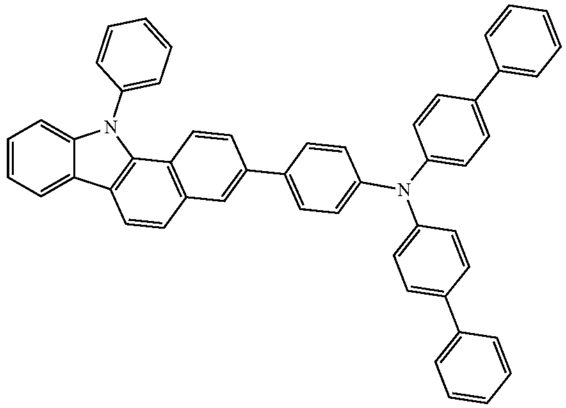

-continued
A-52
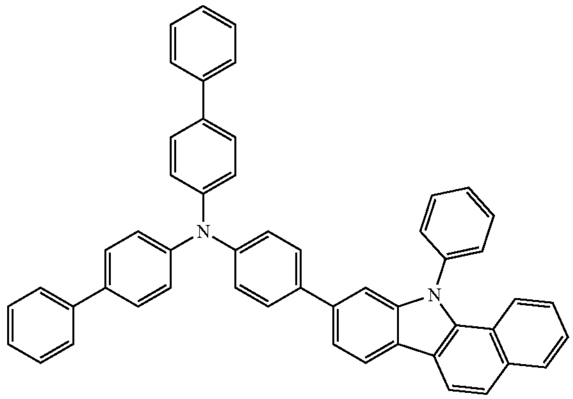
A-53
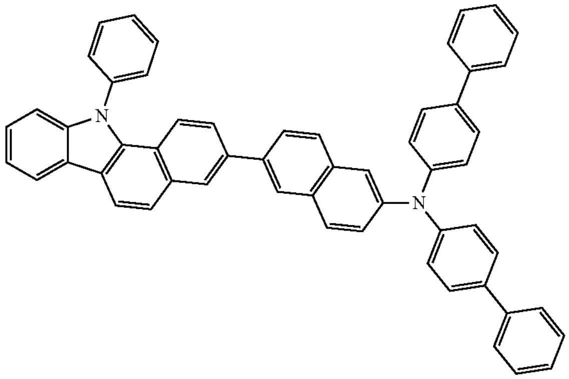
A-54
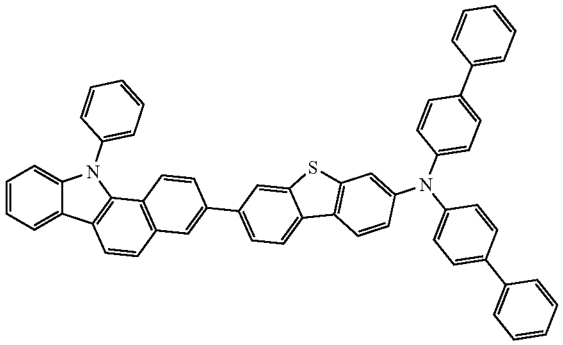
A-55
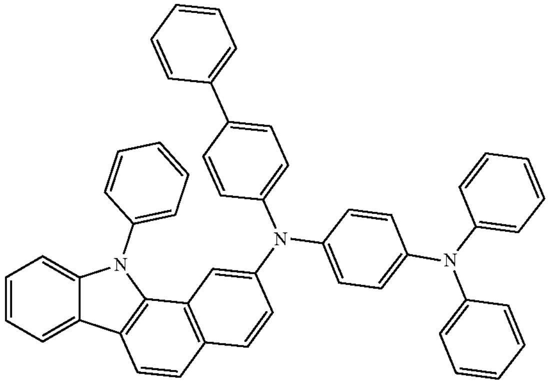
-continued
A-56
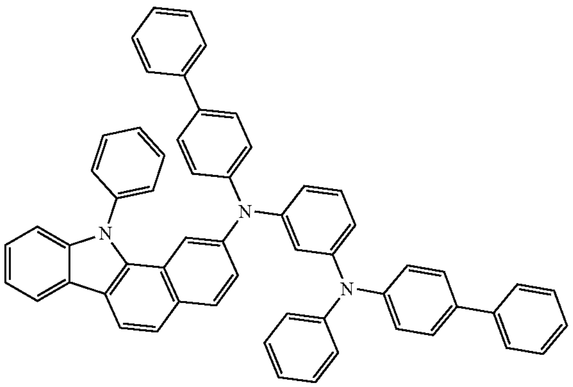
A-57
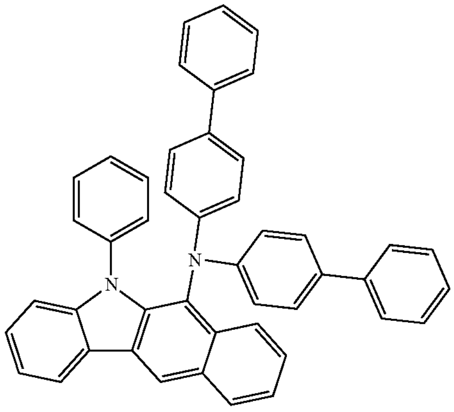
A-58
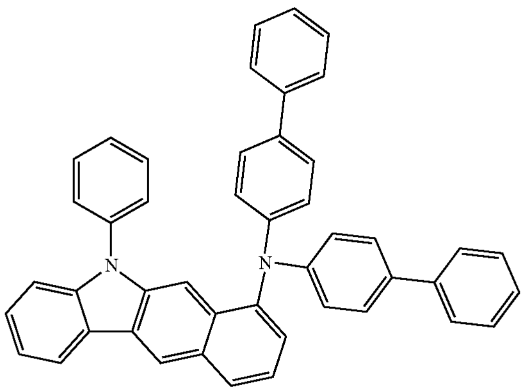
A-59
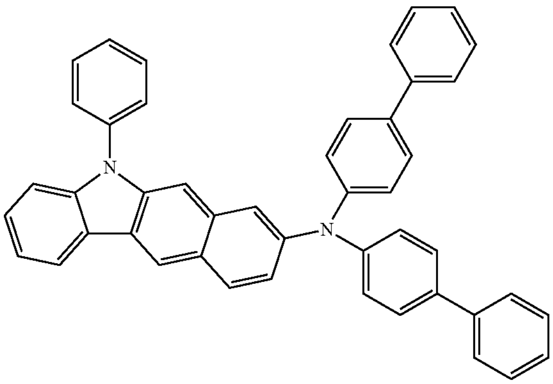

-continued
A-60
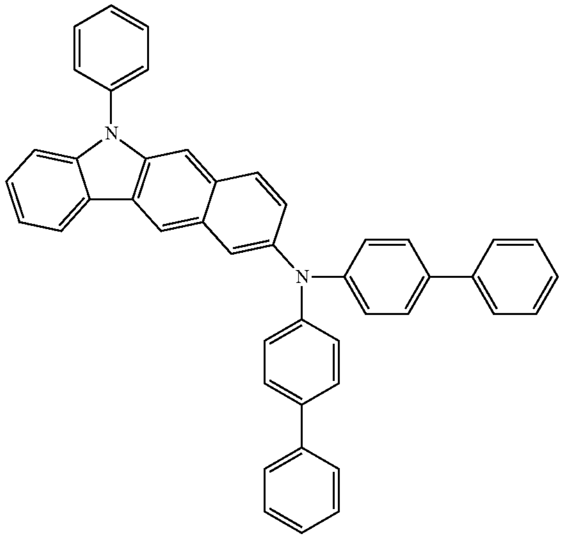
A-61
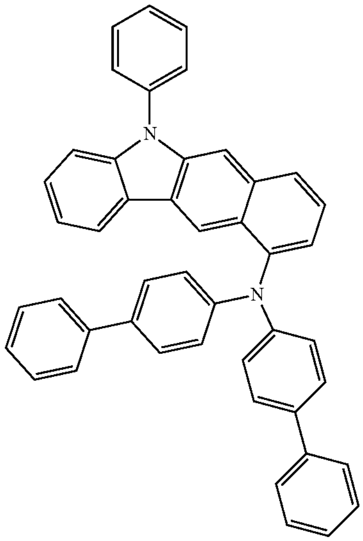
A-62
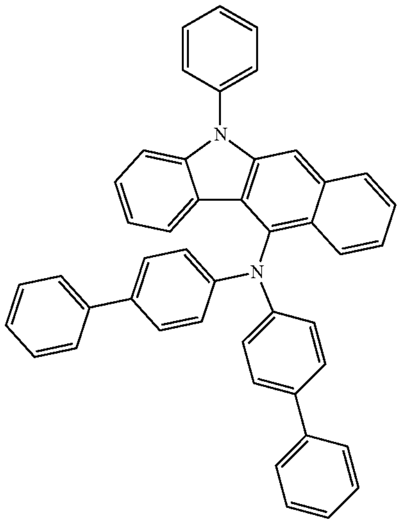
-continued
A-63
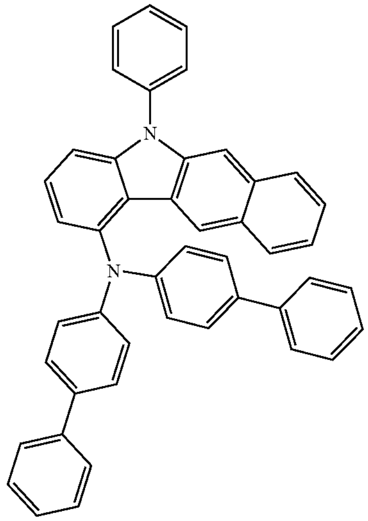
A-64
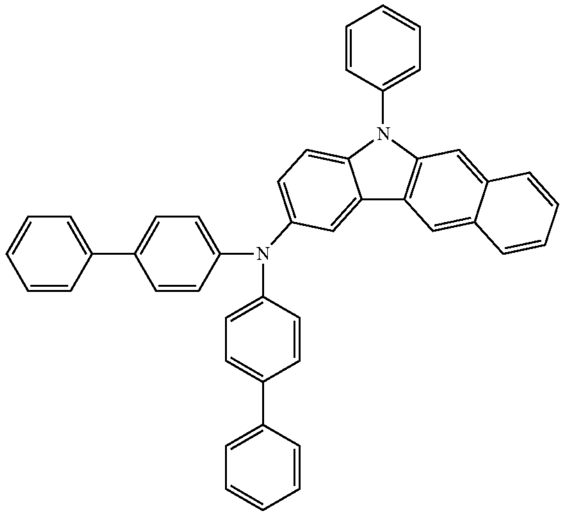
A-65
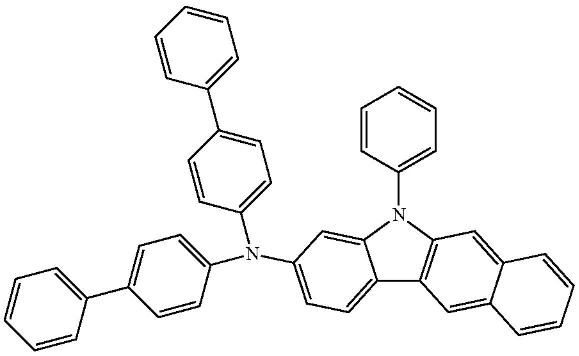

A-66
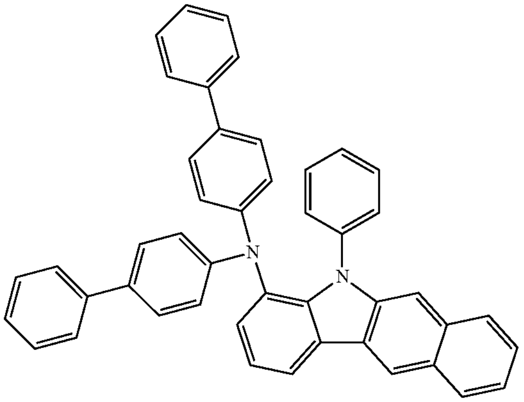
A-67
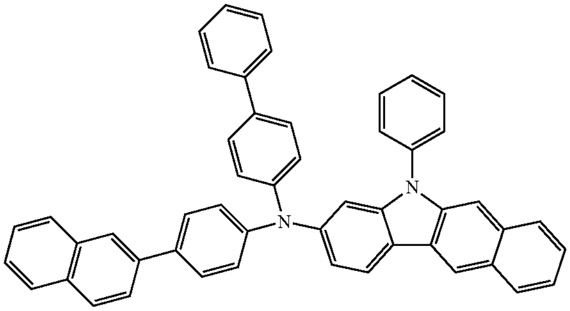
A-68
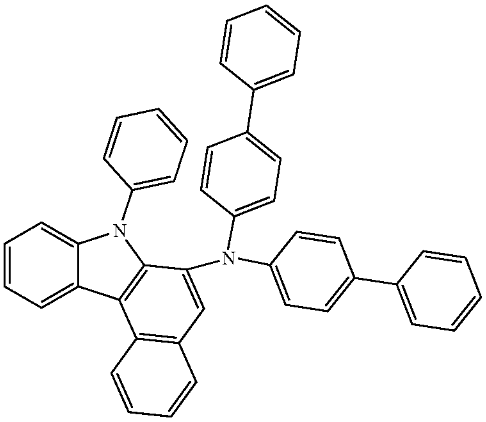
A-69
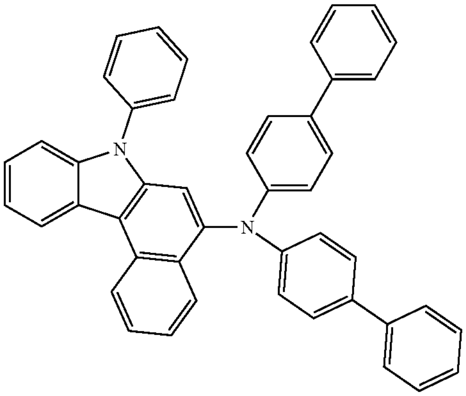
A-70
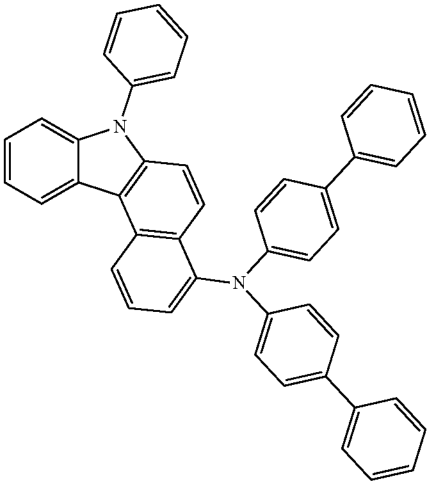
A-71
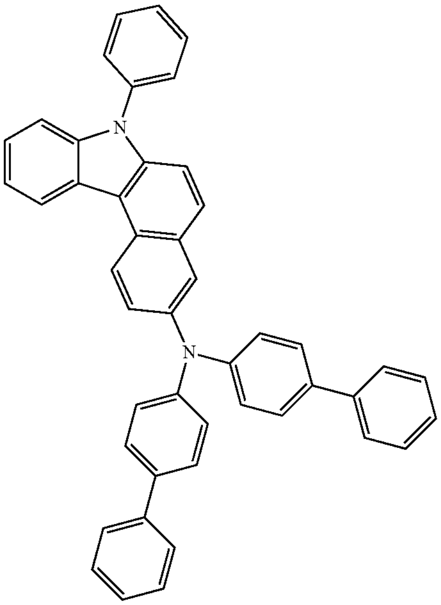

-continued
A-72
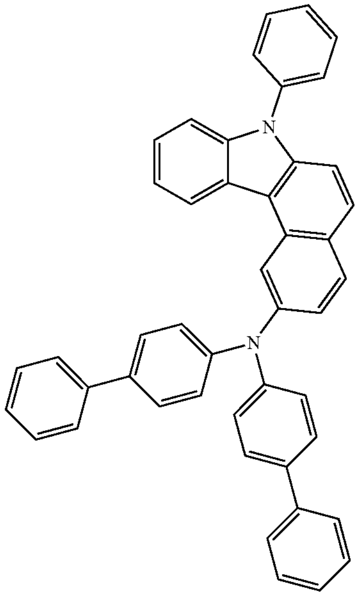
A-73
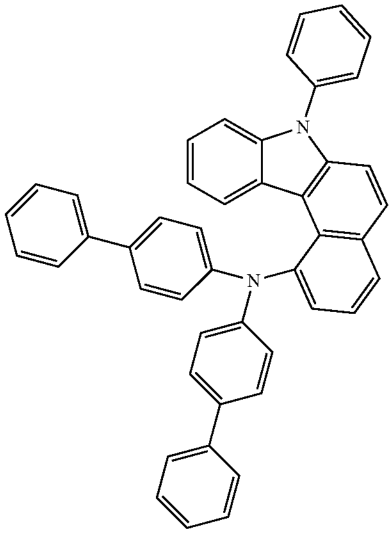
A-74
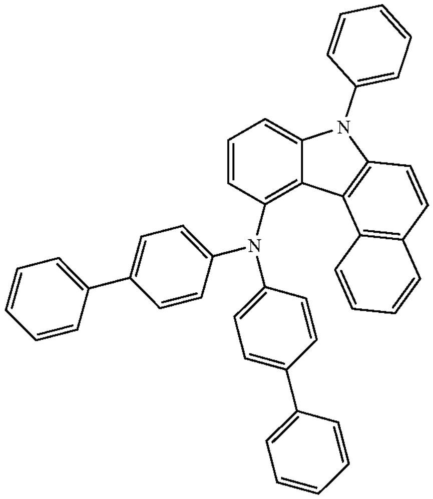
-continued
A-75
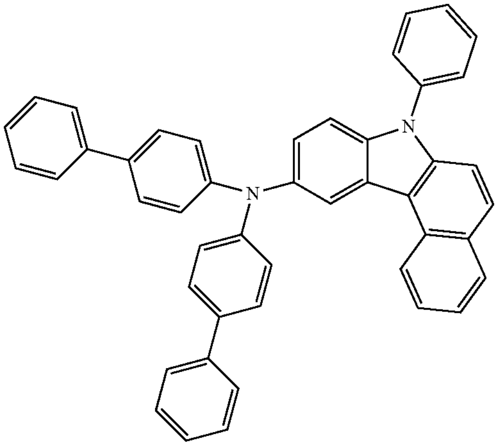
A-76
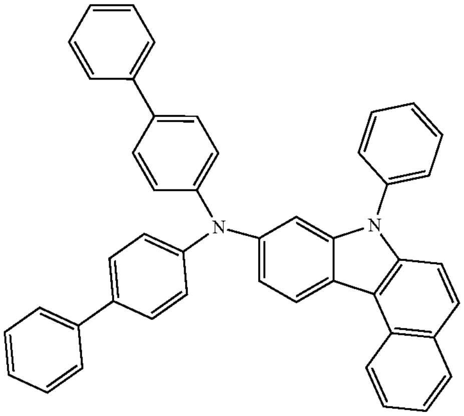
A-77
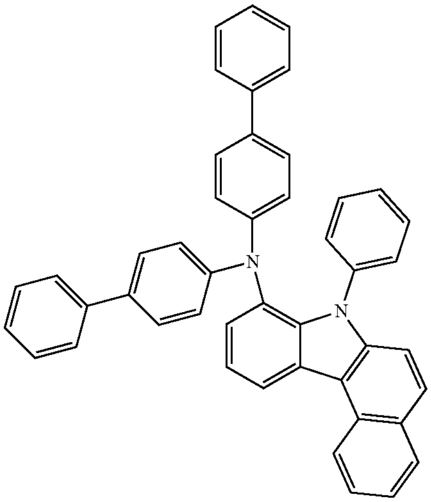

-continued
A-78
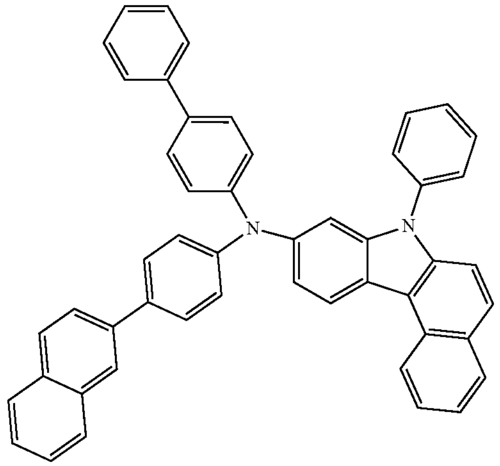
A-79
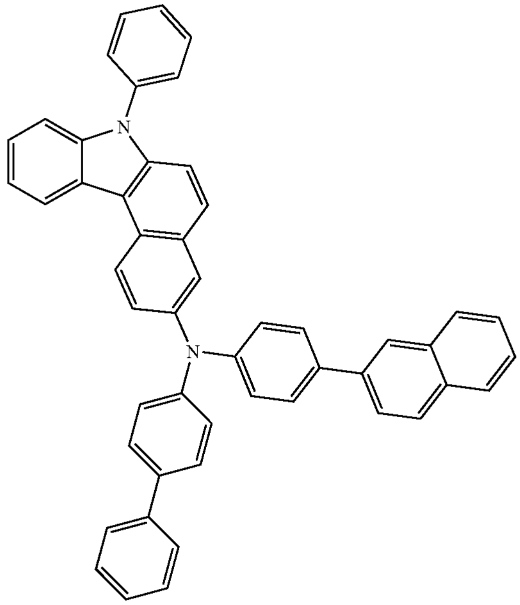
A-80
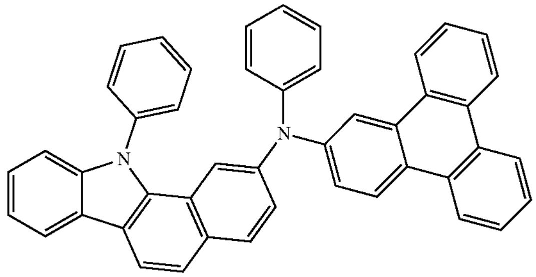
-continued
A-81
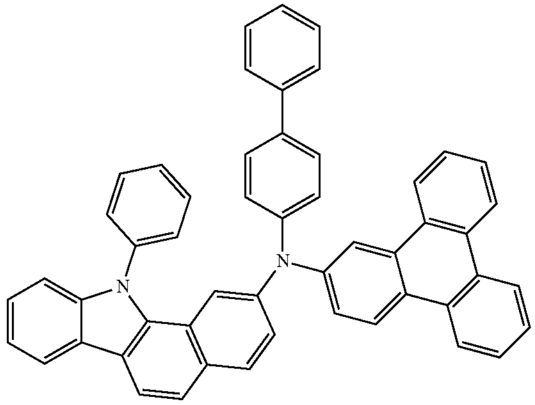
A-82
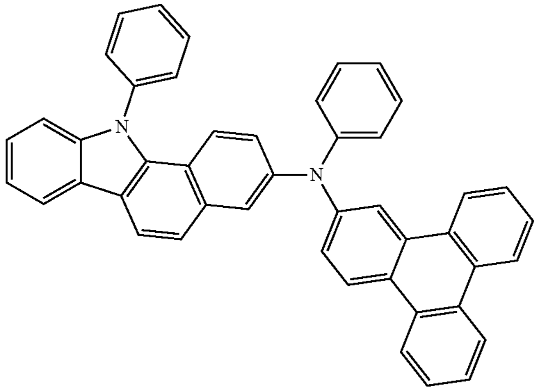
A-83
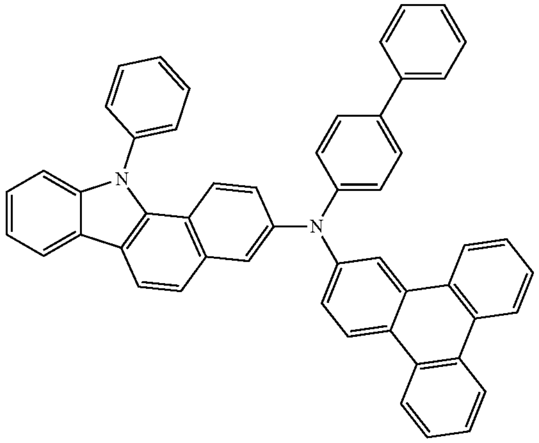

-continued
A-84
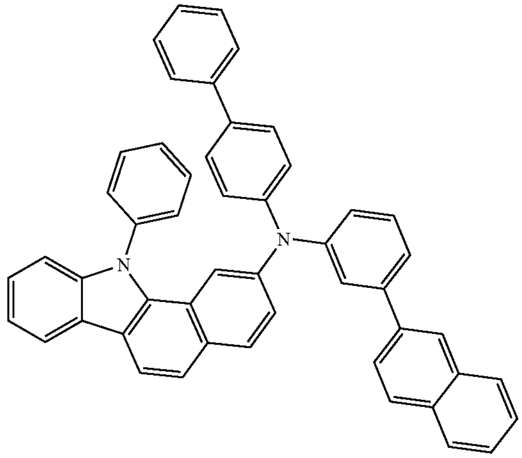
A-85
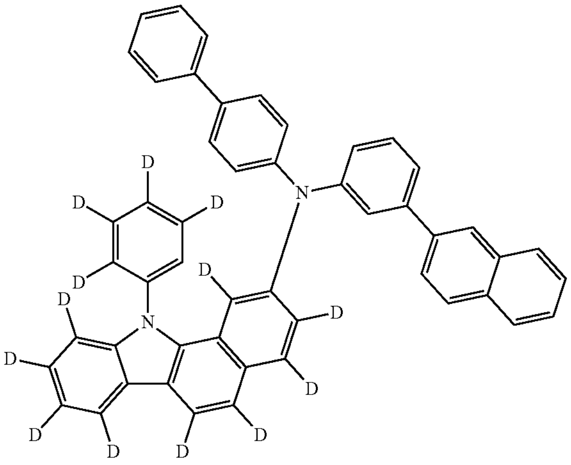
A-86
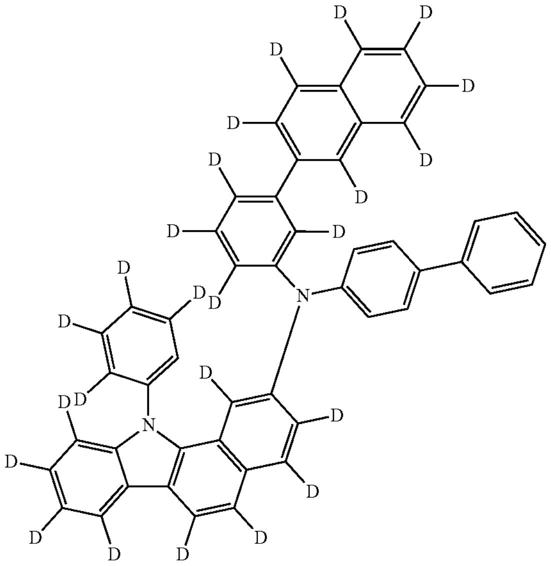
-continued
A-87
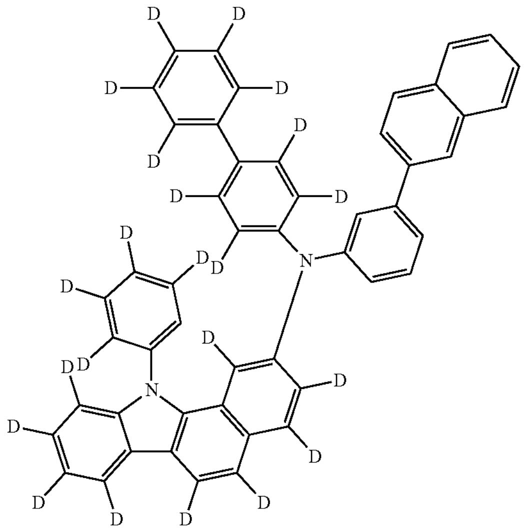
A-88
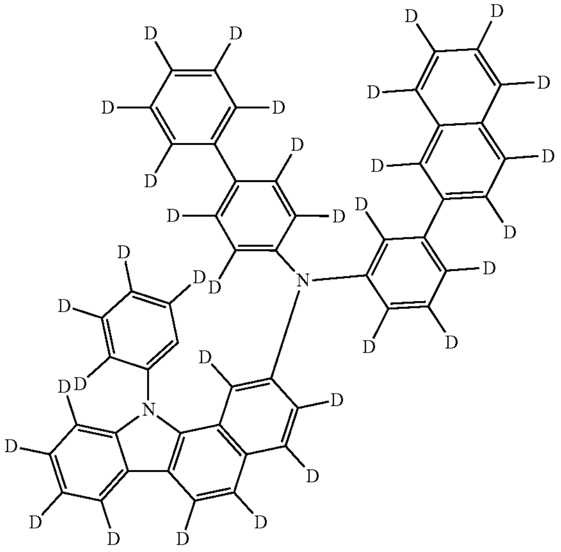
[2-1]
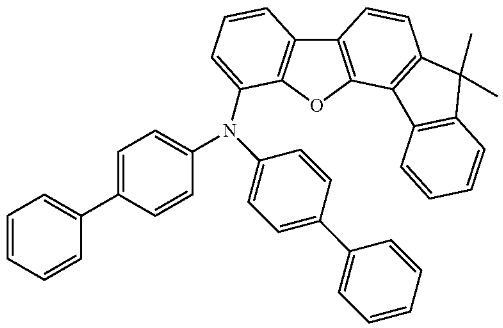

-continued
[2-2]
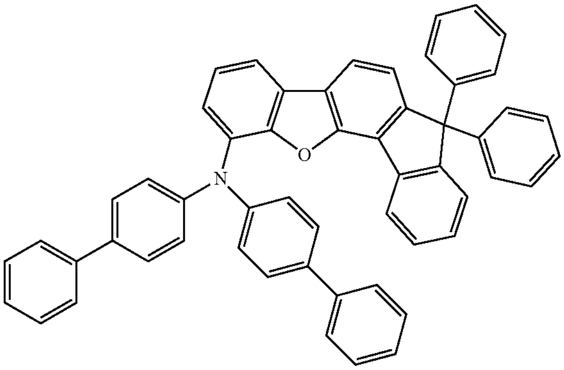
[2-3]
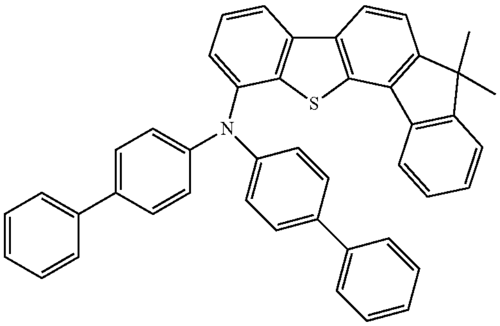
[2-4]
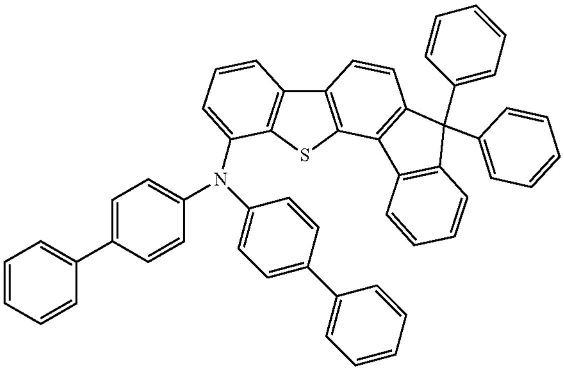
[2-5]
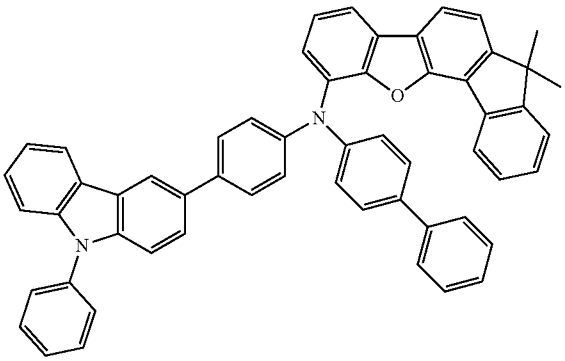
-continued
[2-6]
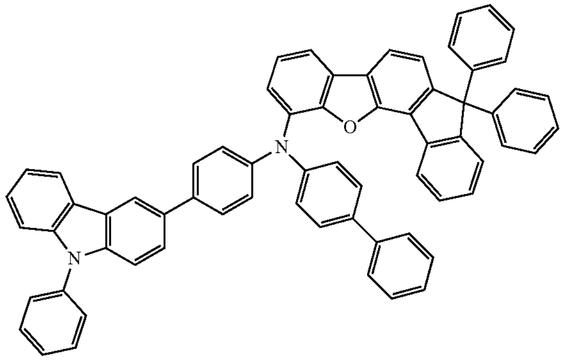
[2-7]
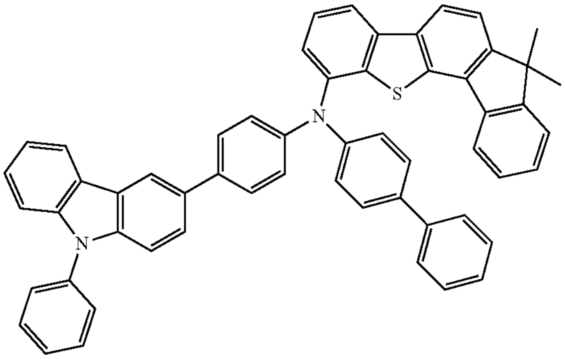
[2-8]
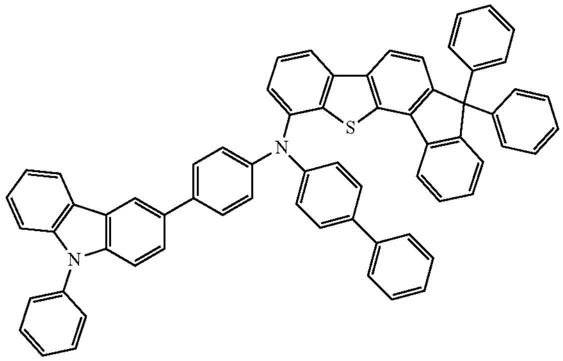
[2-9]
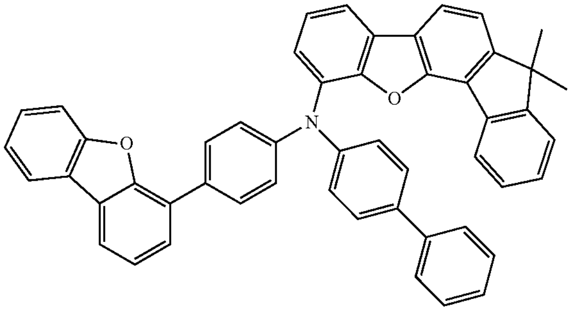

-continued
[2-10]
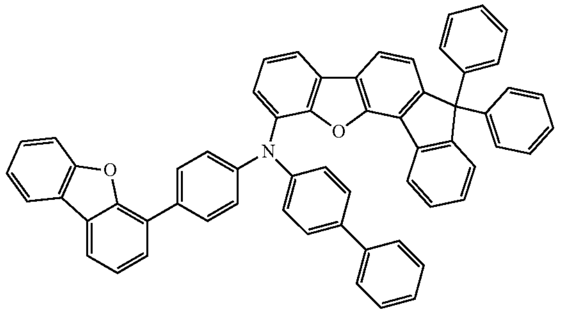
[2-11]
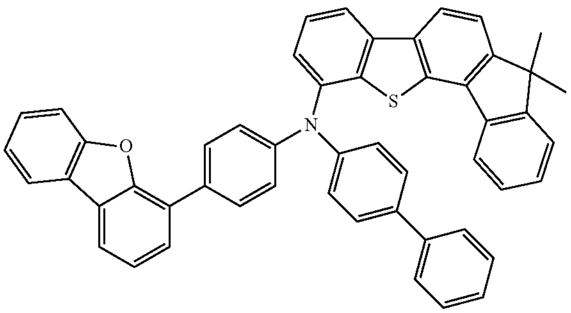
[2-12]
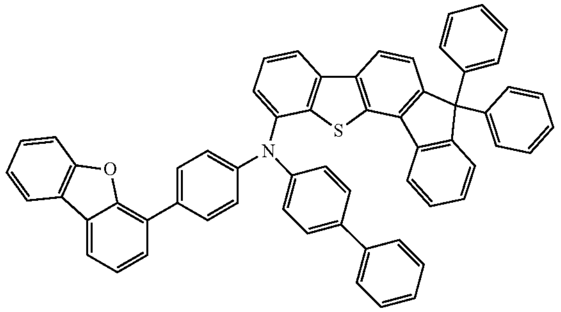
[2-13]
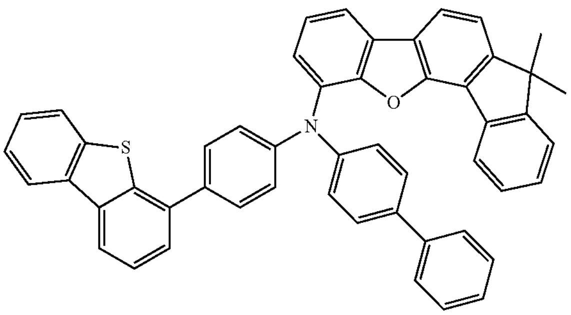
-continued
[2-14]
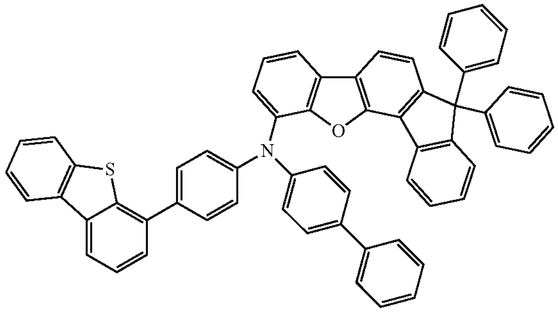
[2-15]
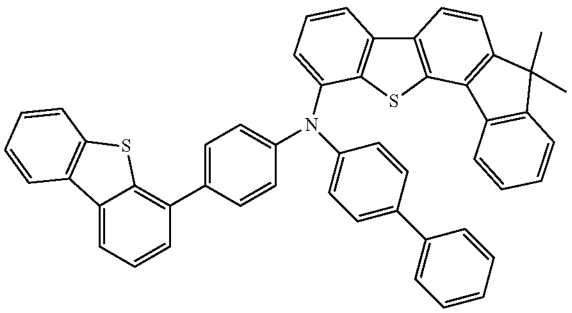
[2-16]
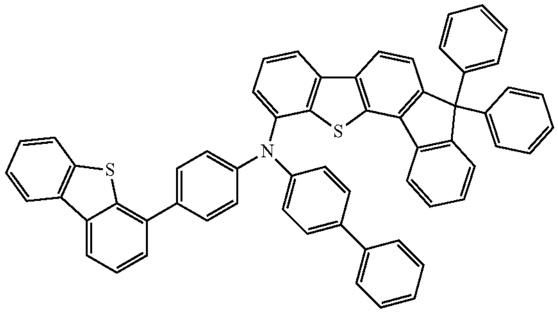
[2-17]
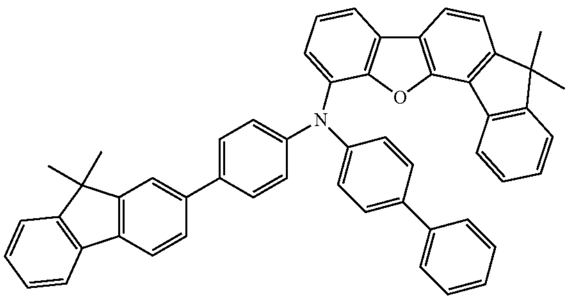

-continued
[2-18]
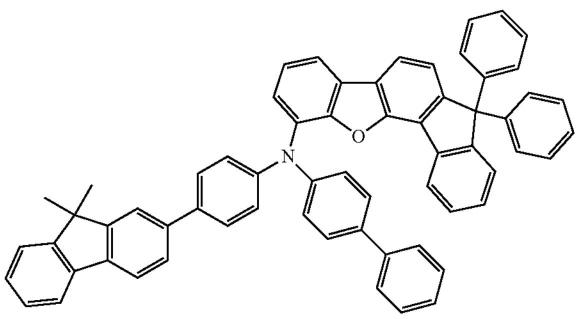
[2-19]
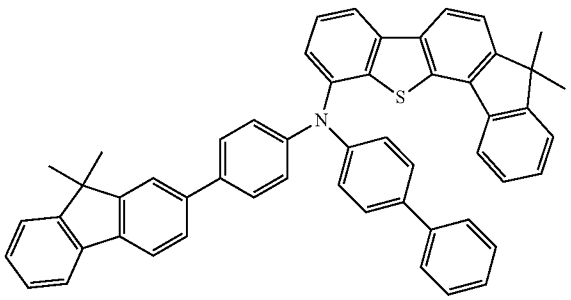
[2-20]
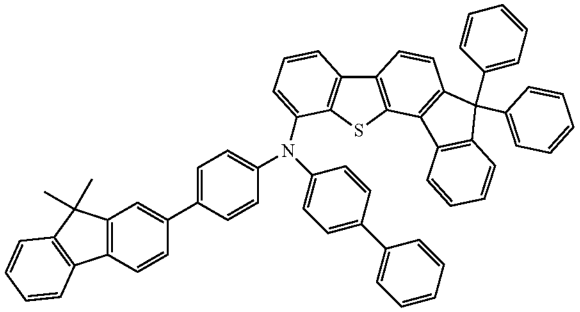
[2-21]
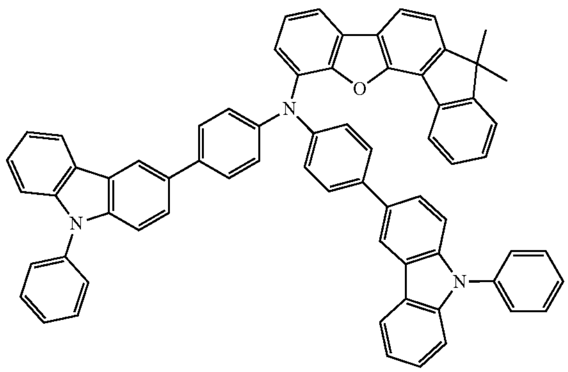
-continued
[2-22]
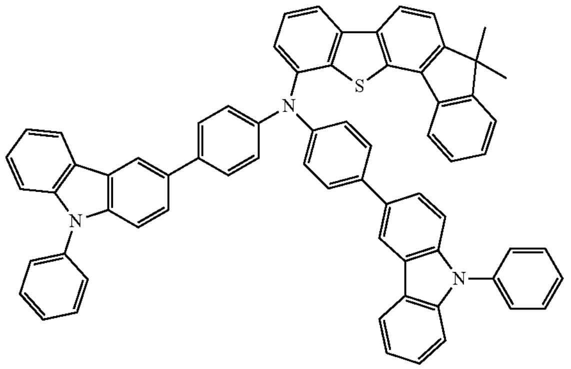
[2-23]
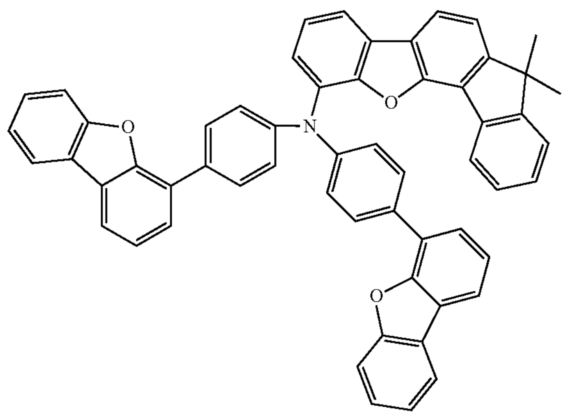
[2-24]
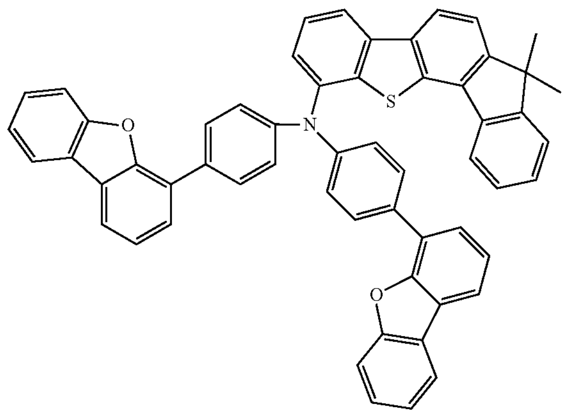

[2-25]
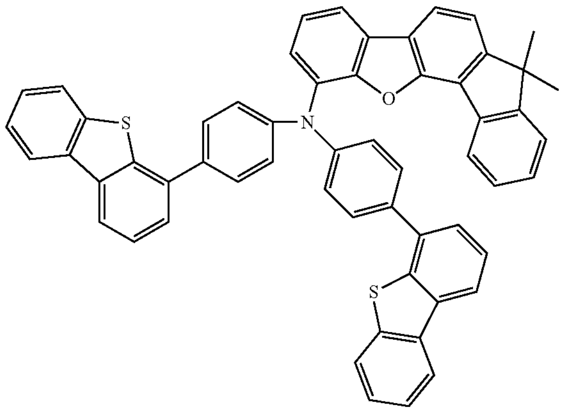
[2-26]
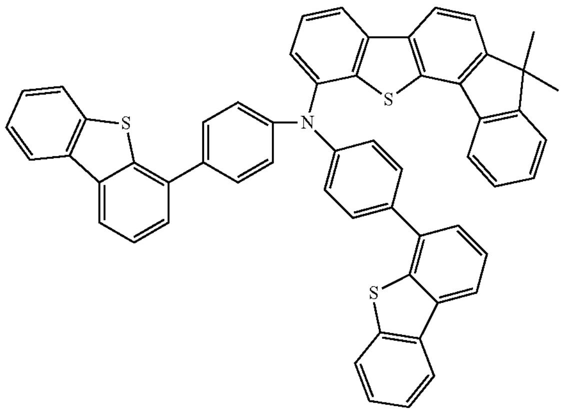
[2-27]
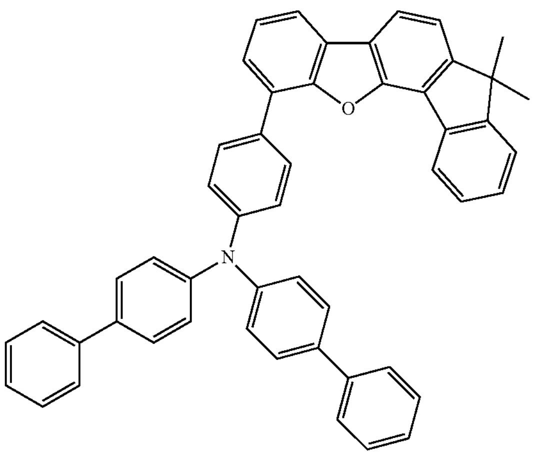
[2-28]
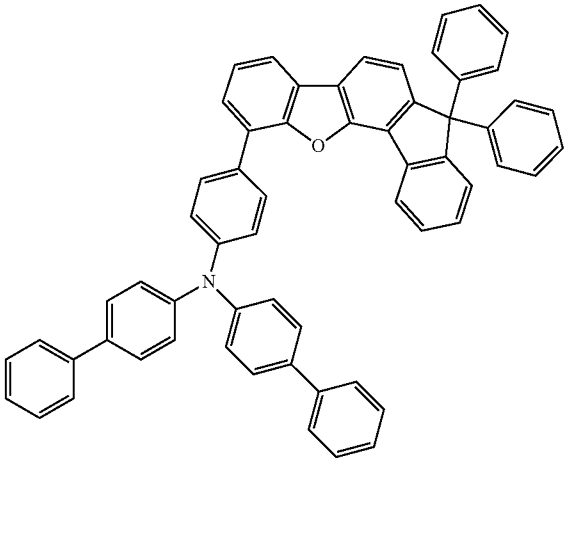
[2-29]
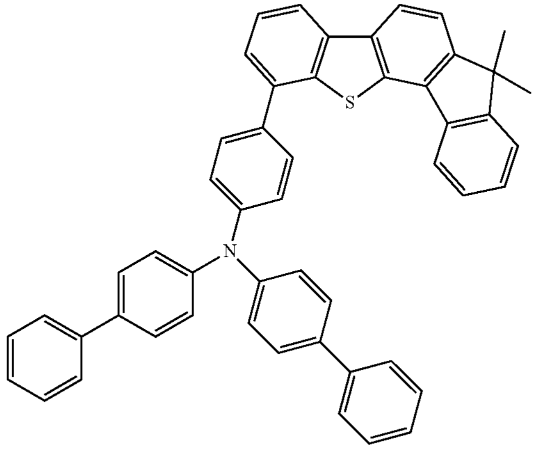
[2-30]
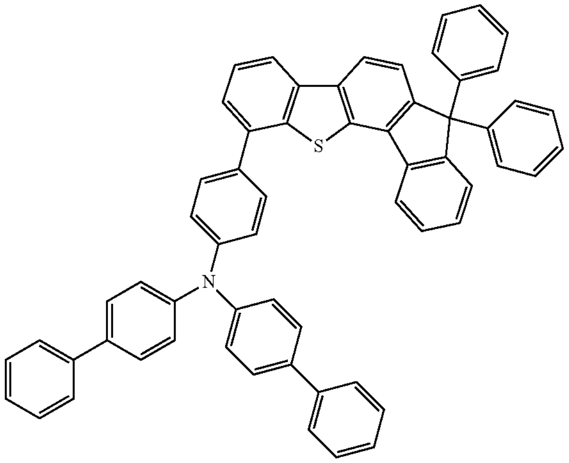

-continued
[2-31]
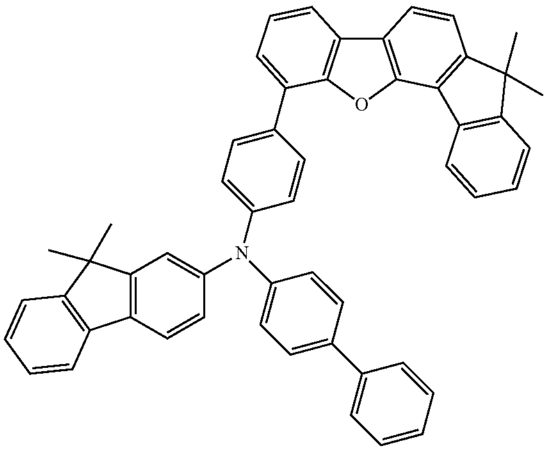
[2-32]
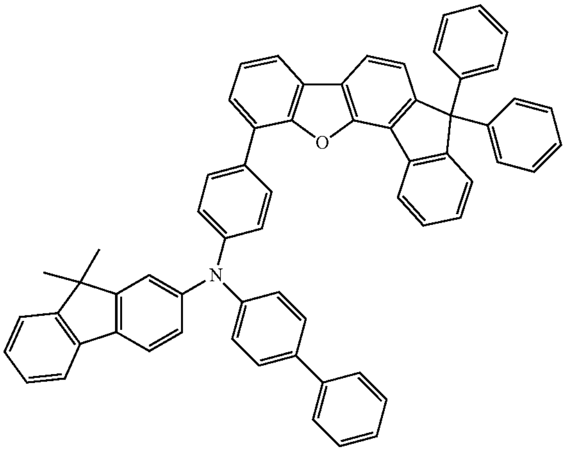
[2-33]
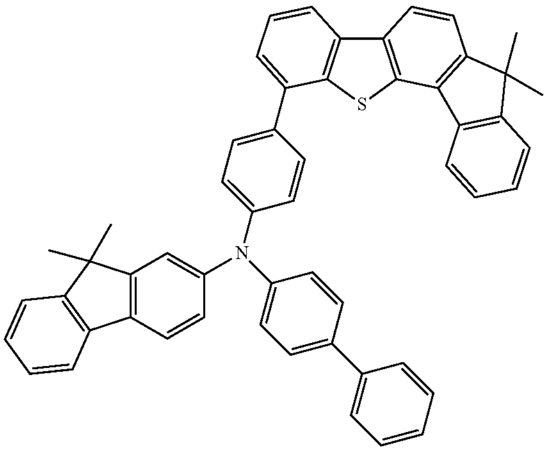
-continued
[2-34]
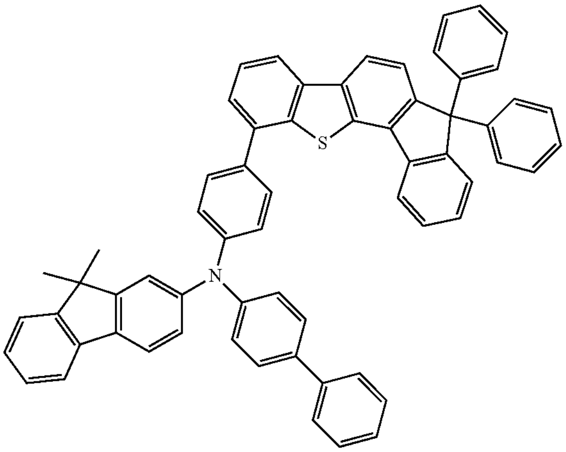
[2-35]
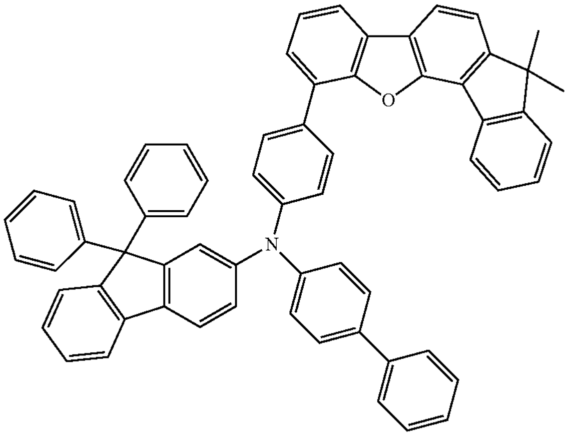
[2-36]
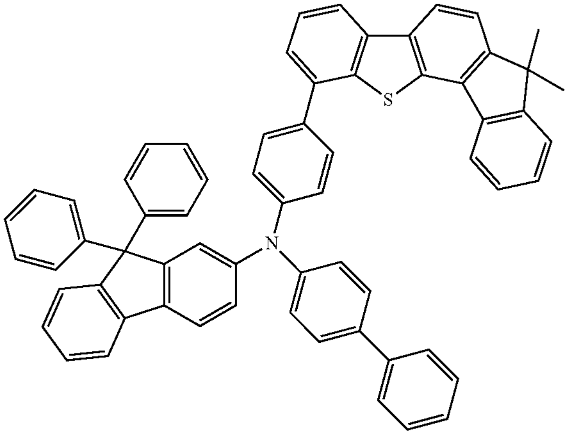

-continued
[2-37]
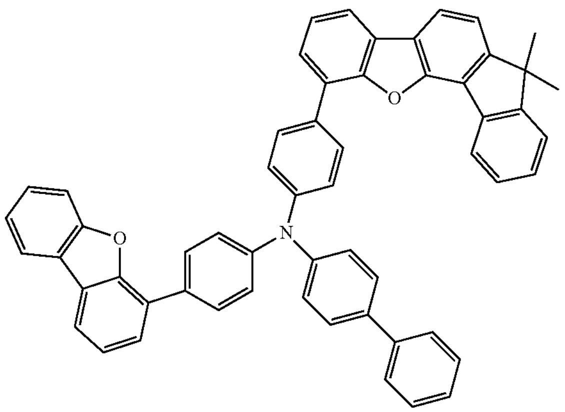
[2-38]
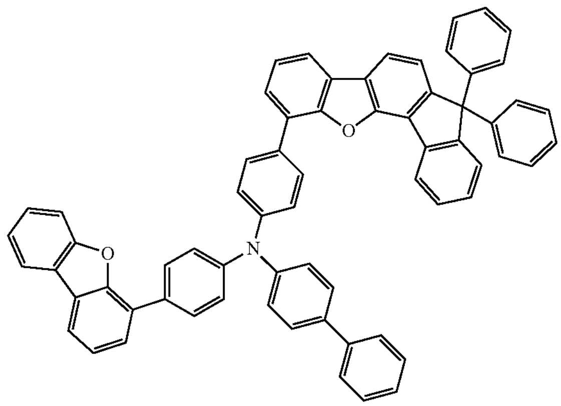
[2-39]
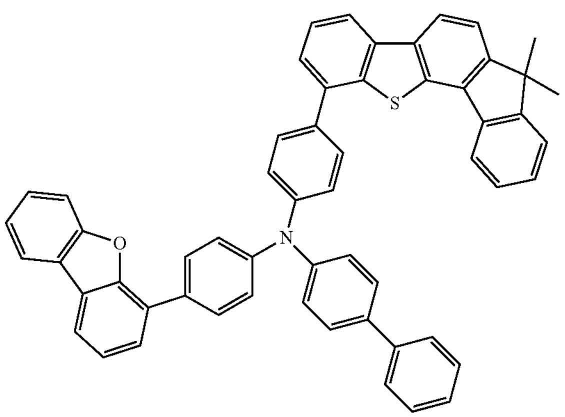
-continued
[2-40]
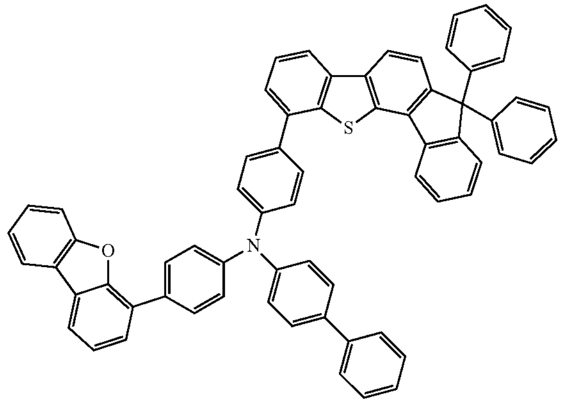
[2-41]
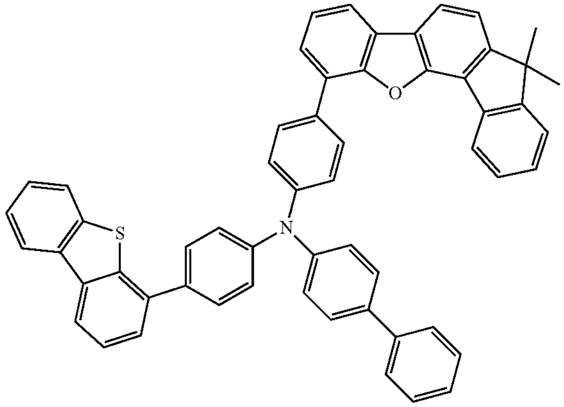
[2-42]
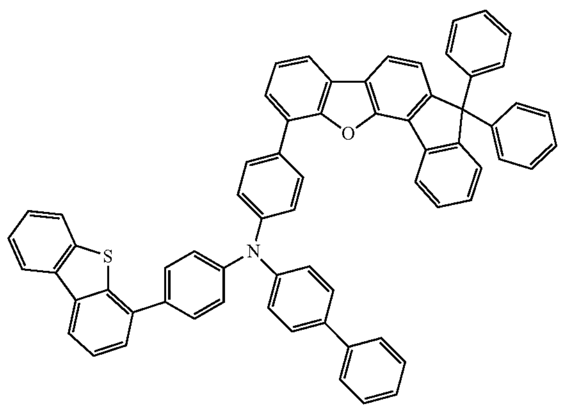

-continued
[2-43]
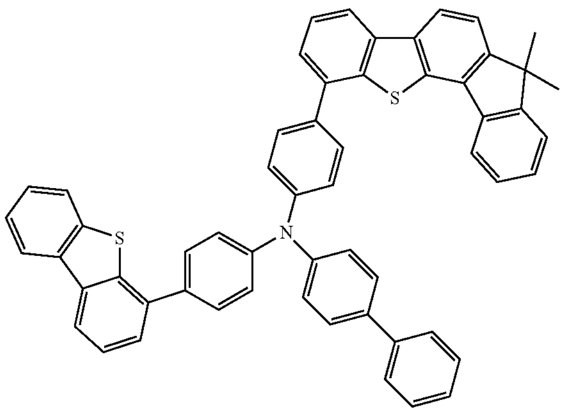
[2-44]
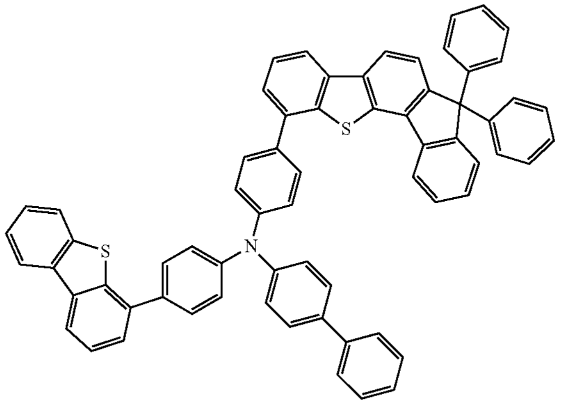
[2-45]
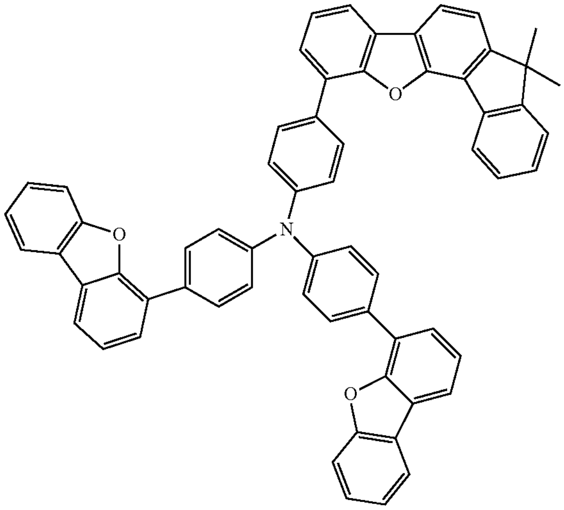
-continued
[2-46]
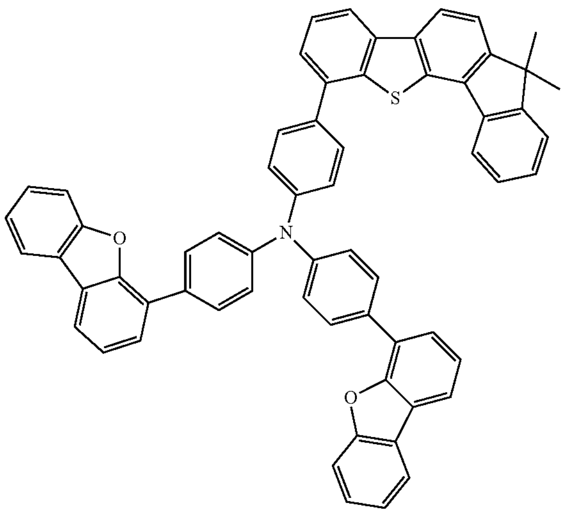
[2-47]
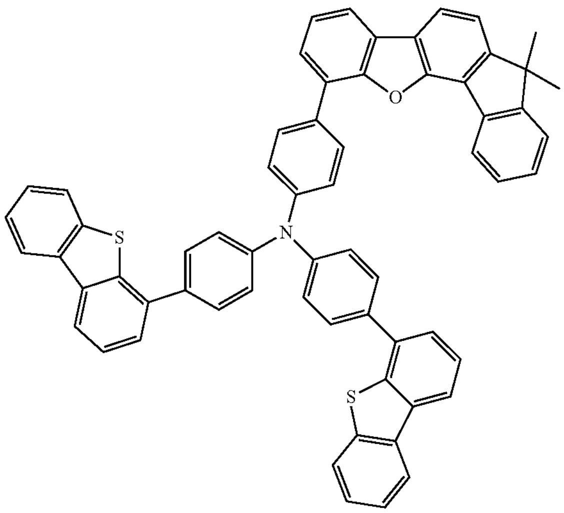
[2-48]
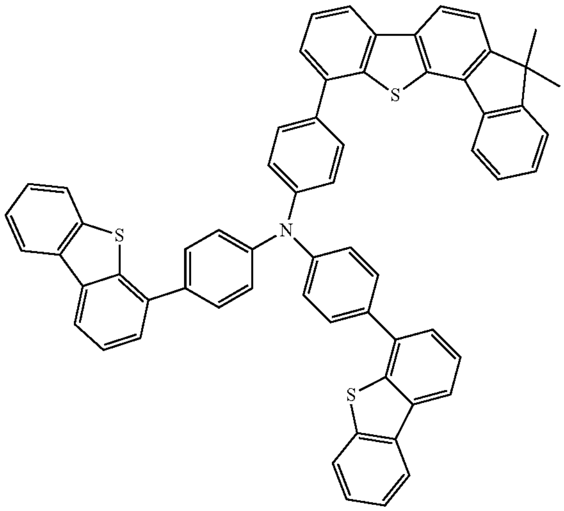

[2-49]
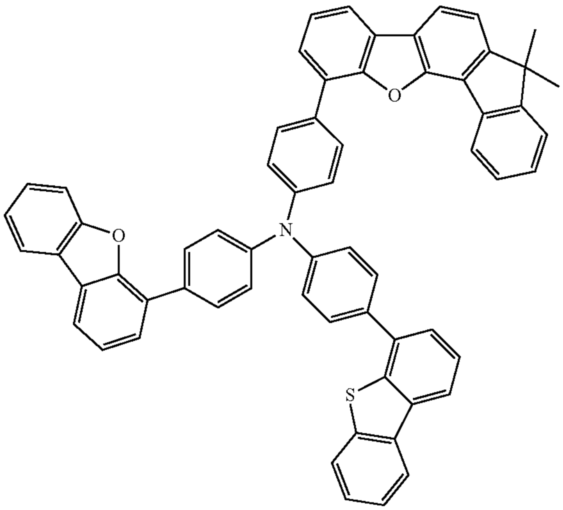
[2-50]
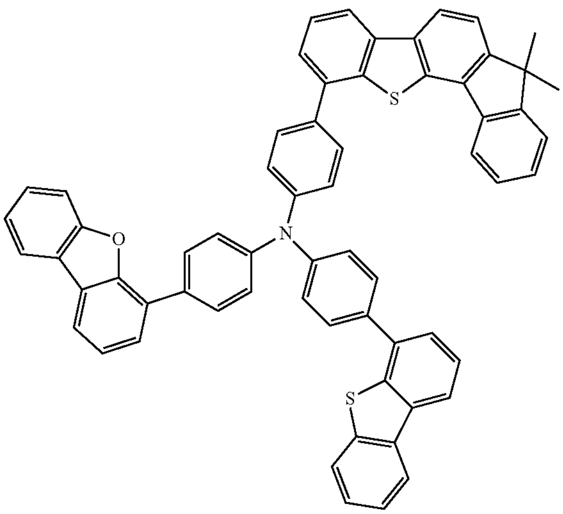
[2-51]
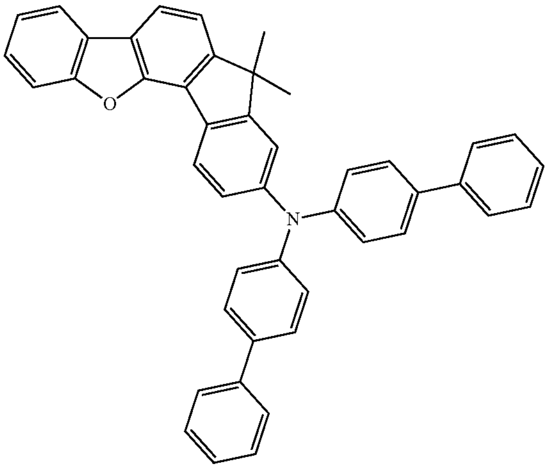
[2-52]
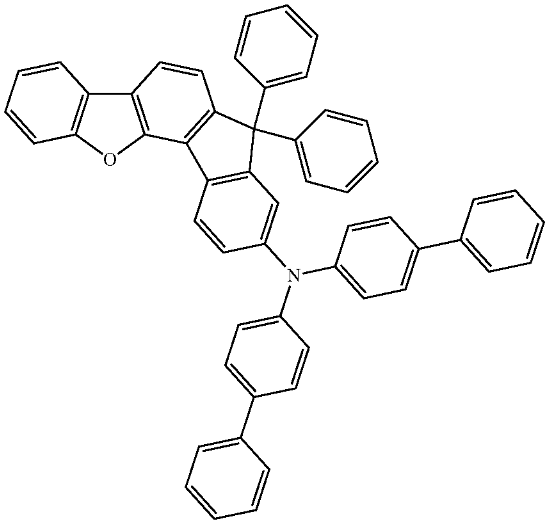
[2-53]
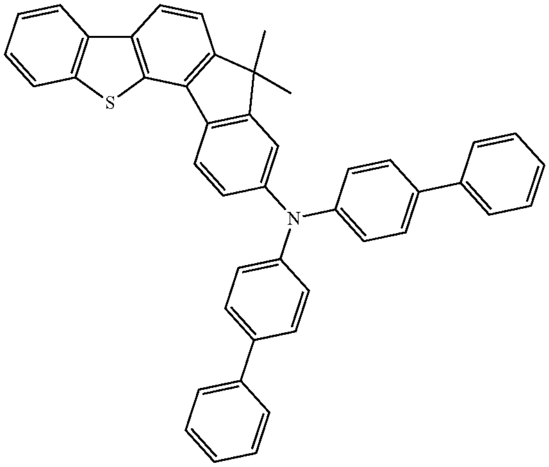
[2-54]
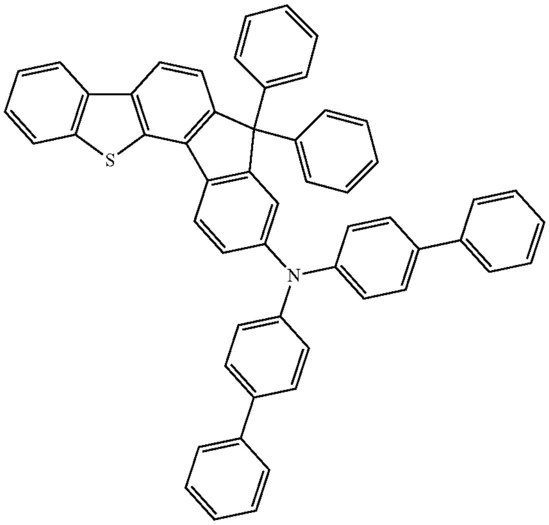

-continued
[2-55]
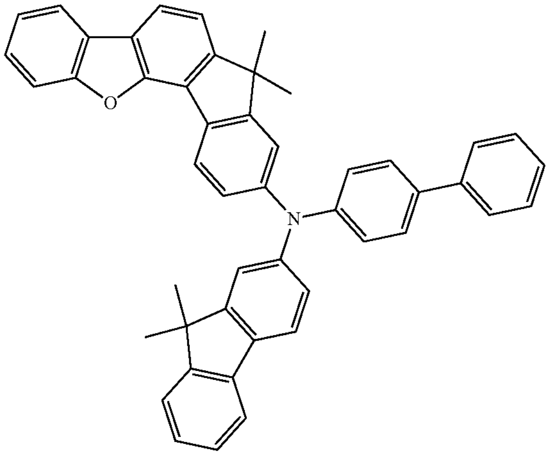
[2-56]
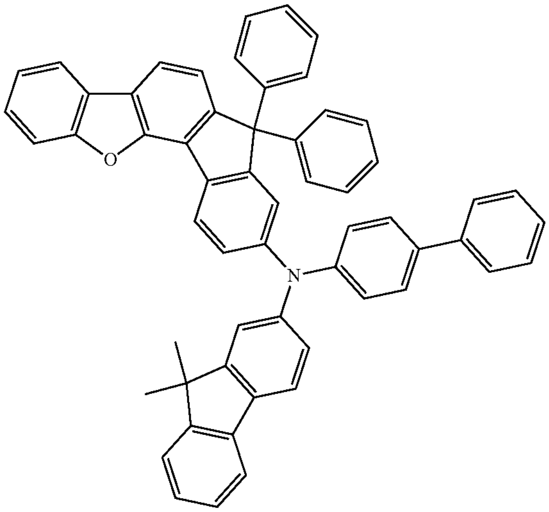
[2-57]
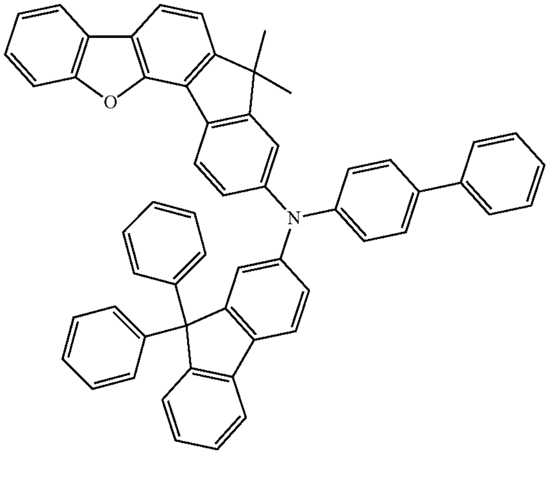
-continued
[2-58]
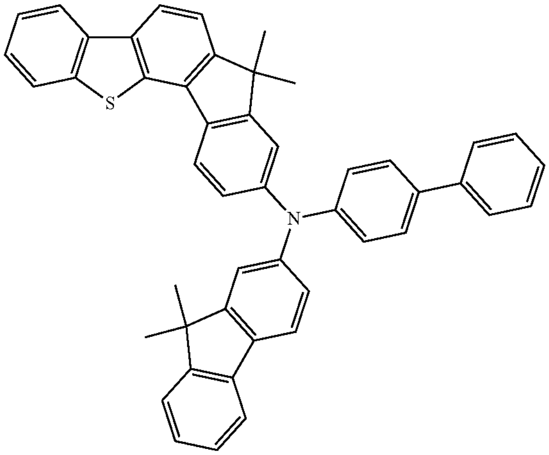
[2-59]
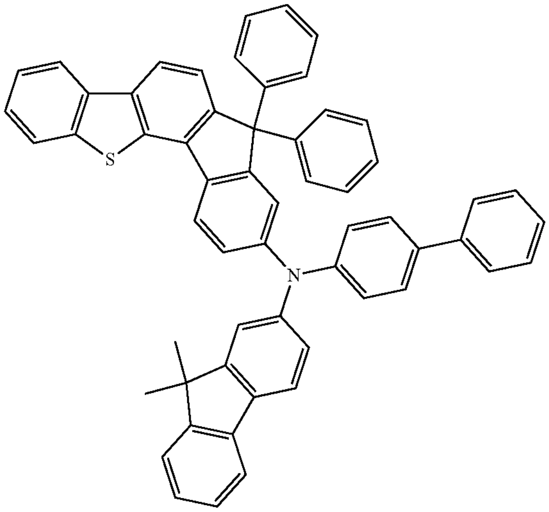
[2-60]
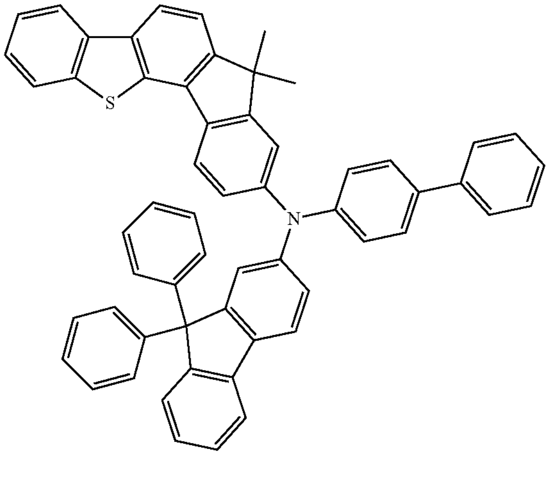

-continued
[2-61]
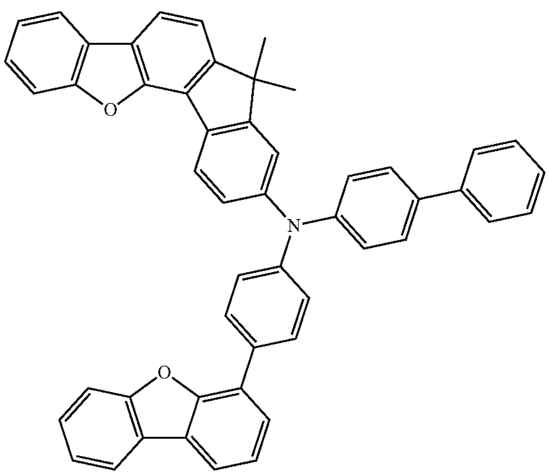
[2-62]
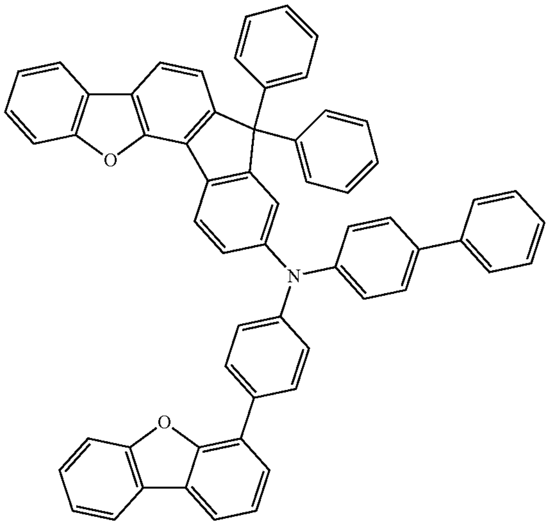
[2-63]
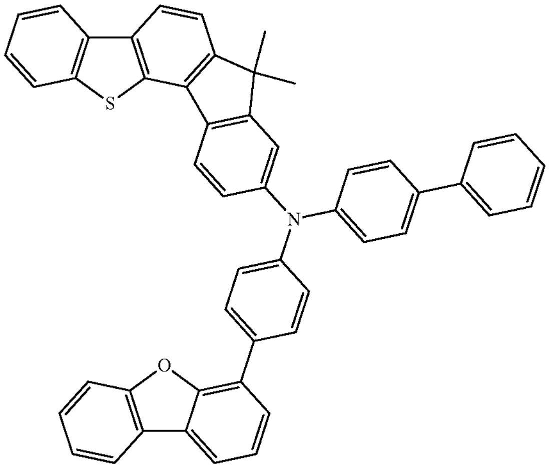
-continued
[2-64]
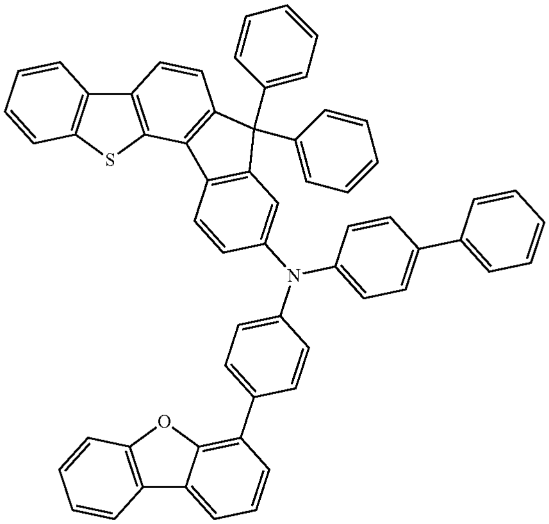
[2-65]
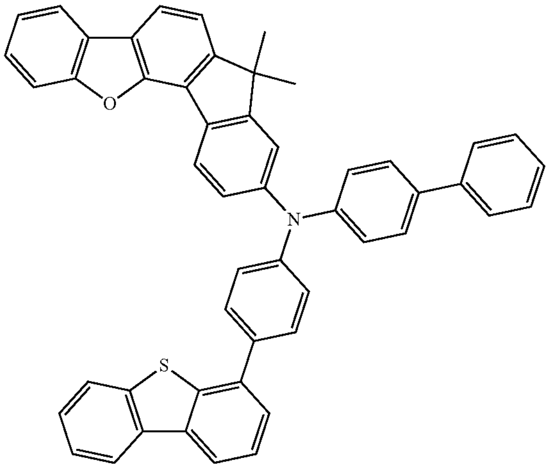
[2-66]
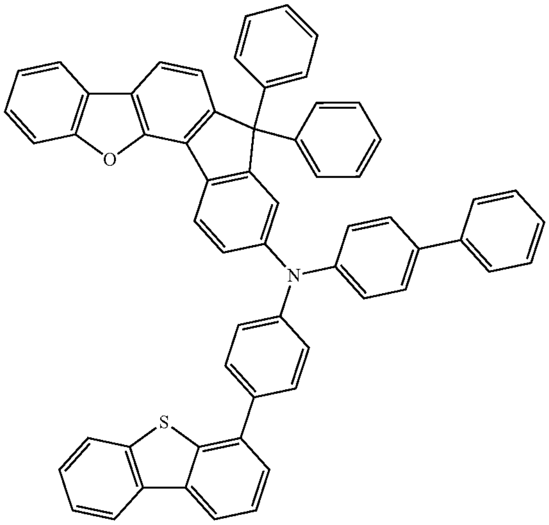

-continued
[2-67]
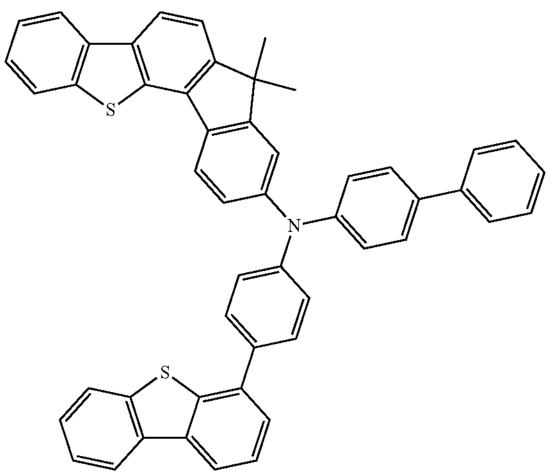
[2-68]
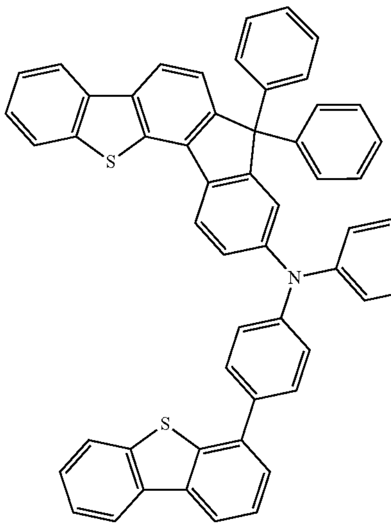
[2-69]
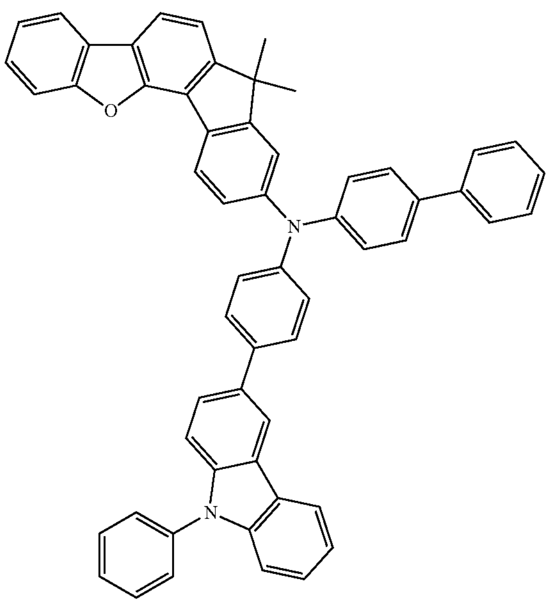
-continued
[2-70]
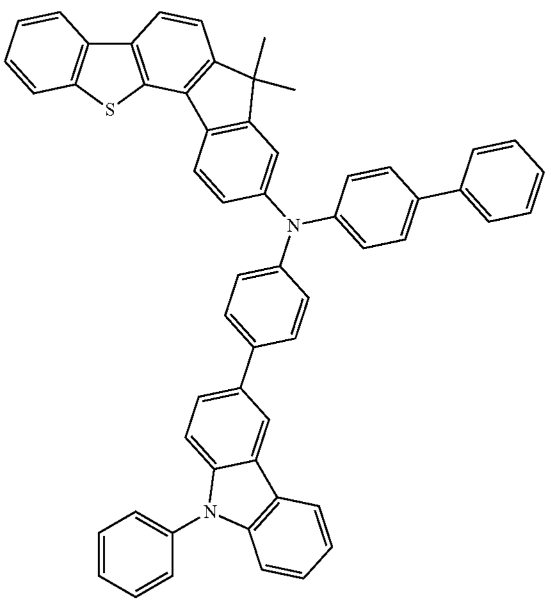
[2-71]
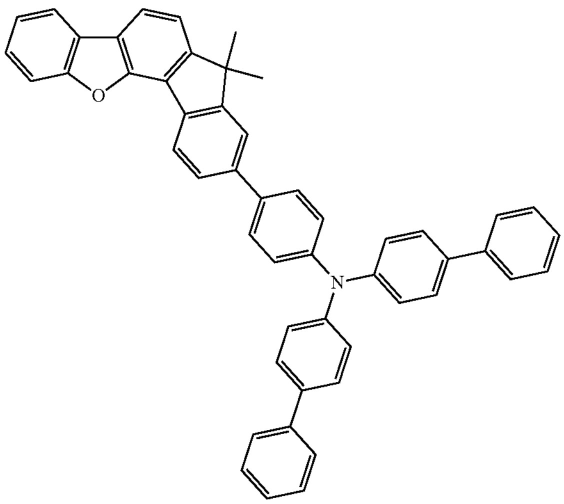
[2-72]
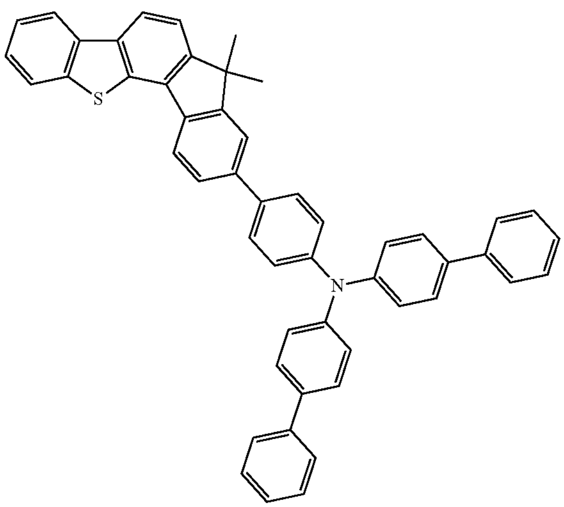

-continued
[2-73]
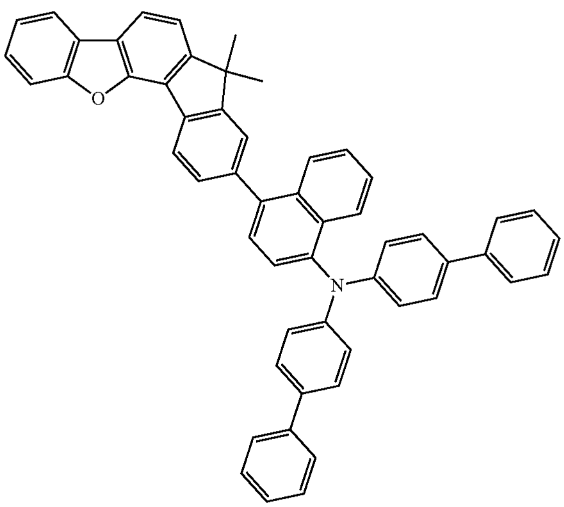
[2-74]
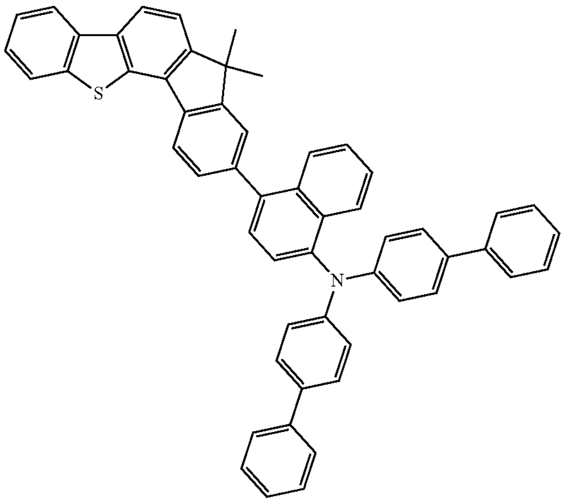
[2-75]
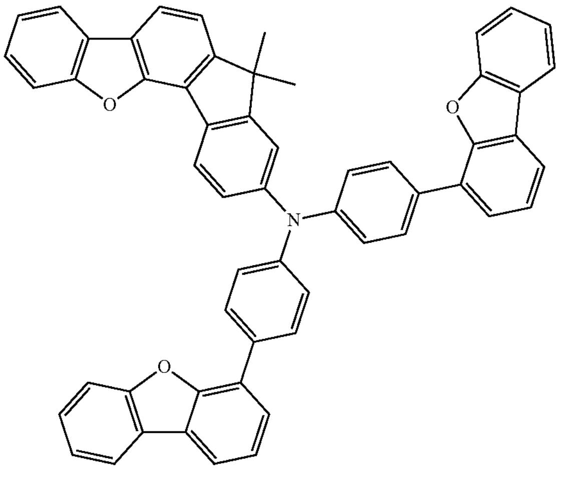
-continued
[2-76]
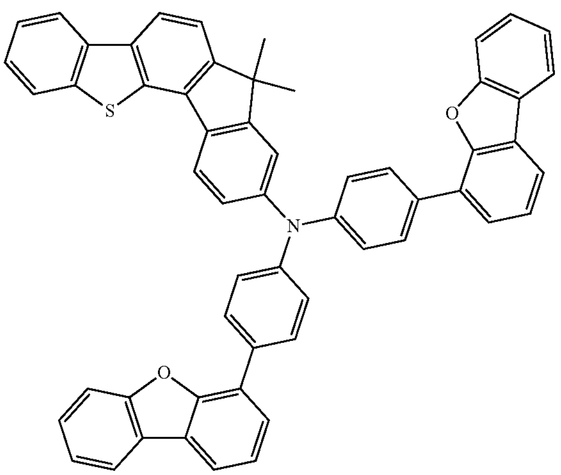
[2-77]
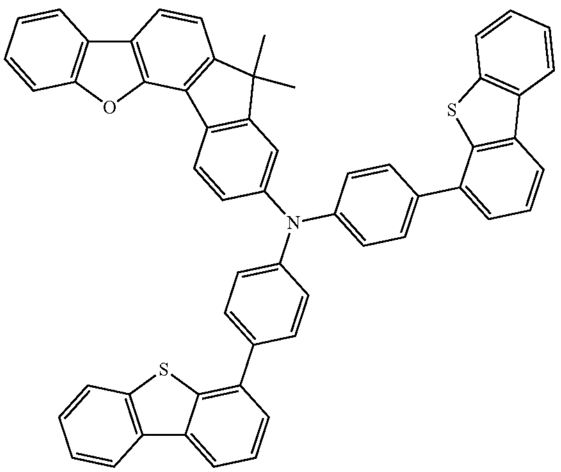
[2-78]
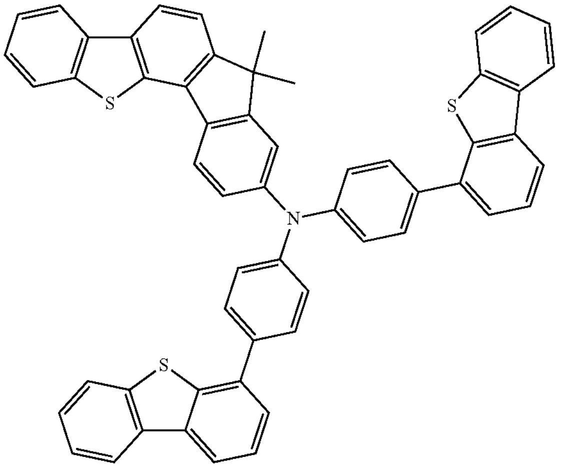

-continued
[2-79]
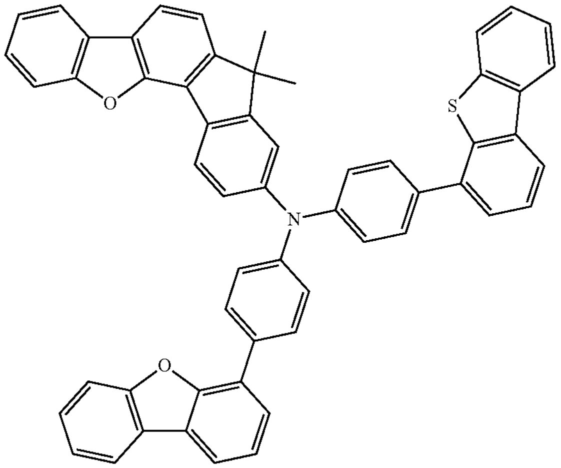
[2-80]
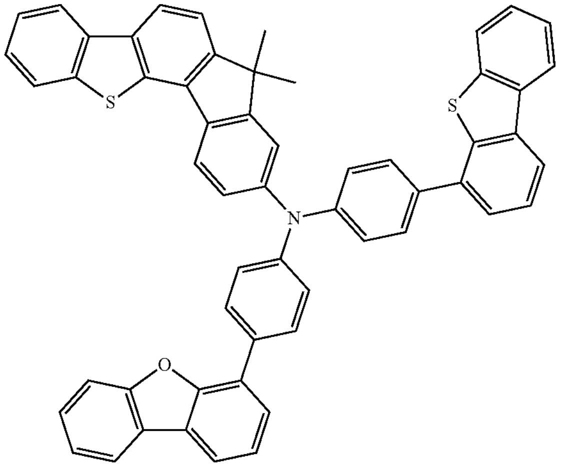
[2-81]
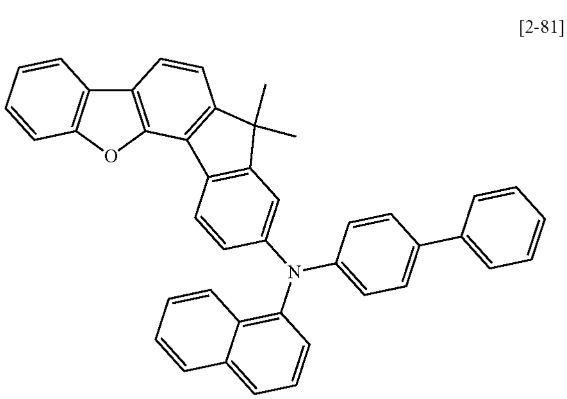
-continued
[2-82]
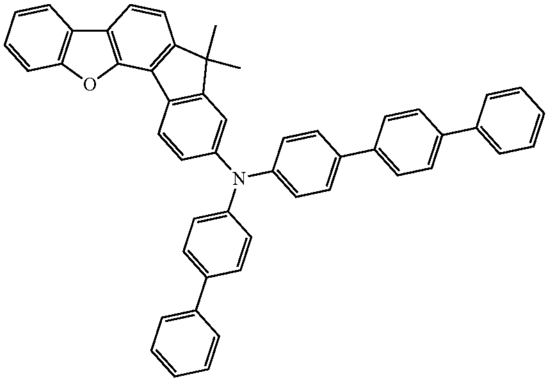
[2-83]
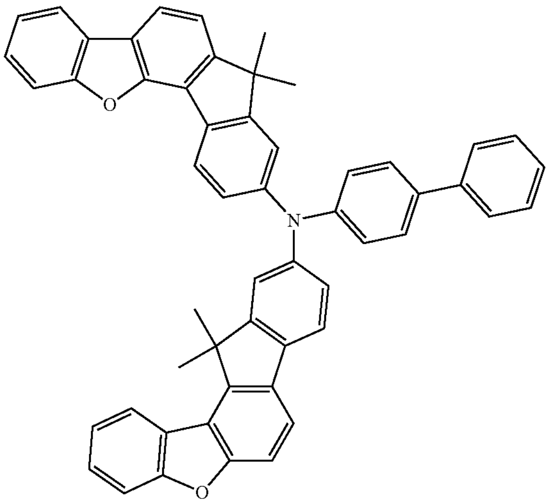
[2-84]
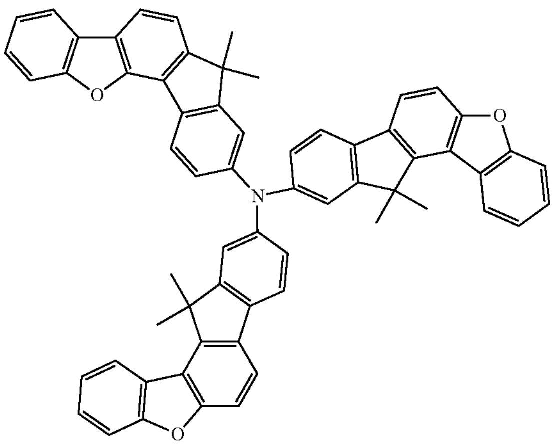

-continued
[2-85]
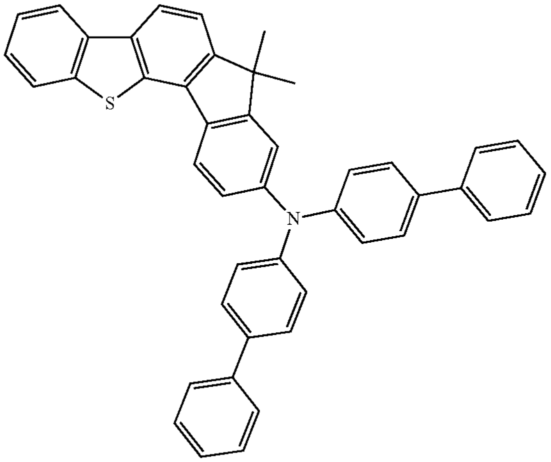
[2-86]
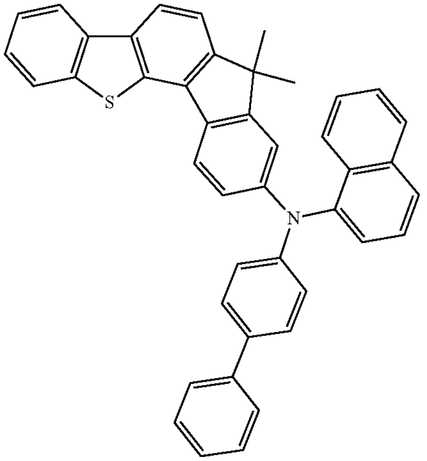
[2-87]
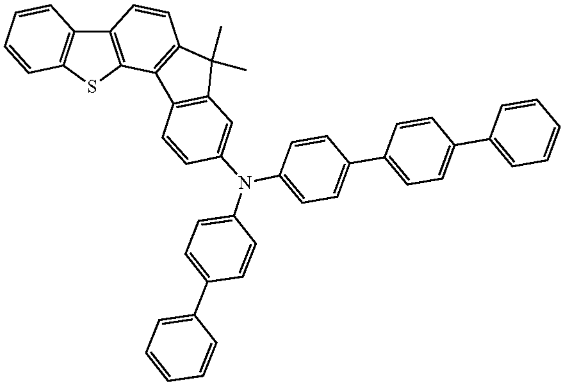
-continued
[2-88]
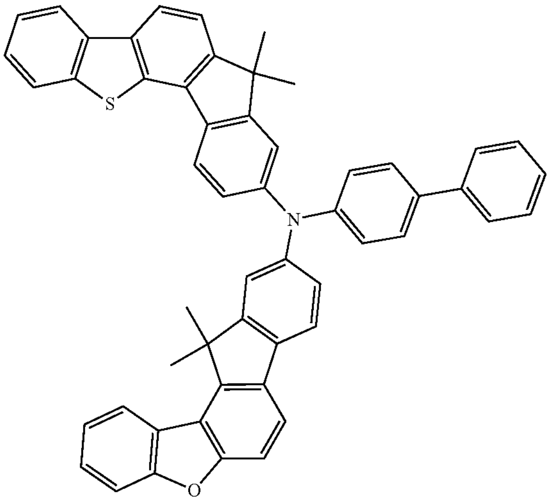
[2-89]
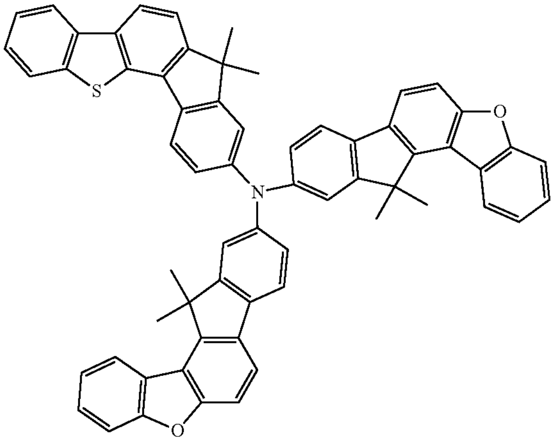
[2-90]
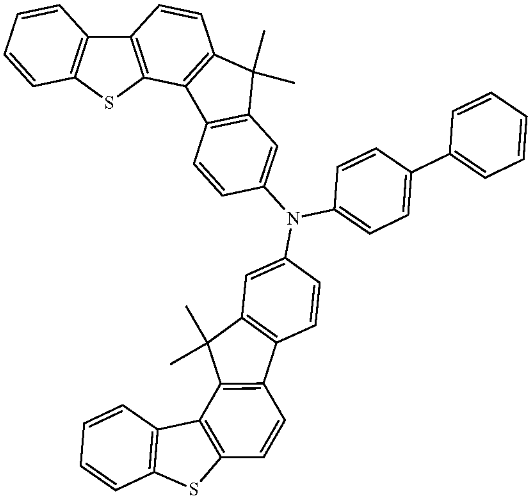

-continued
[2-91]
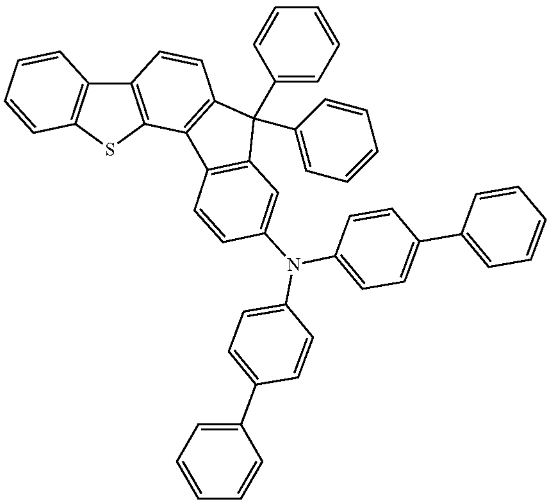
]2-92]
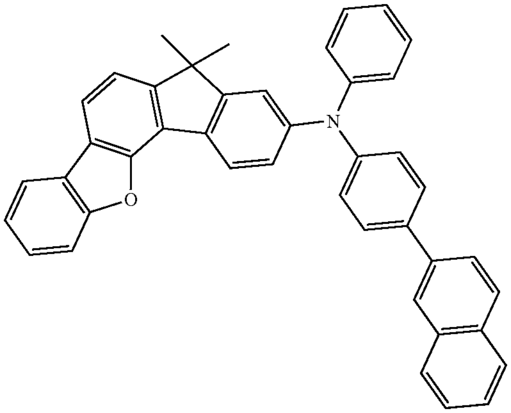
[2-93]
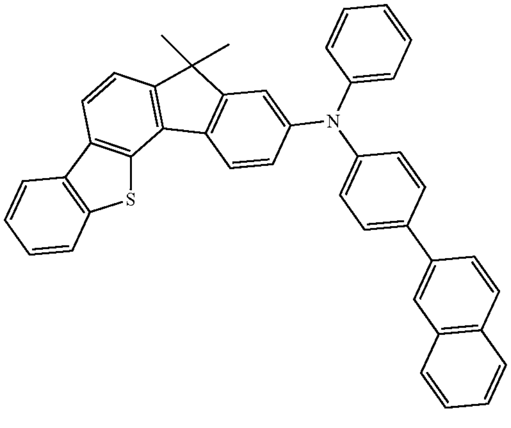
-continued
[2-94]
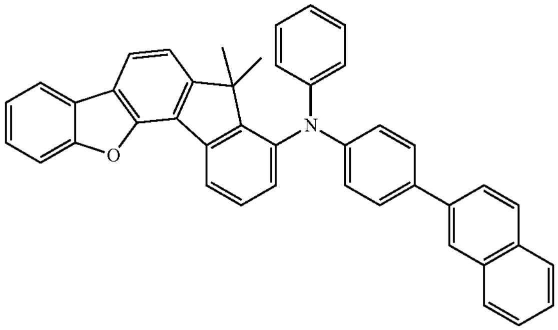
[2-95]
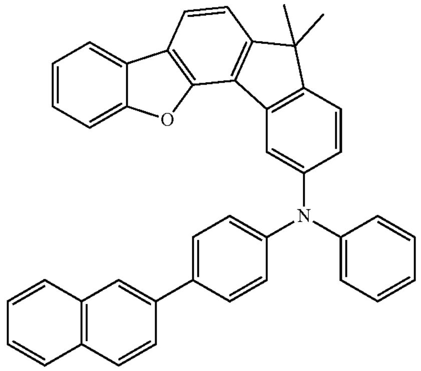
[2-96]
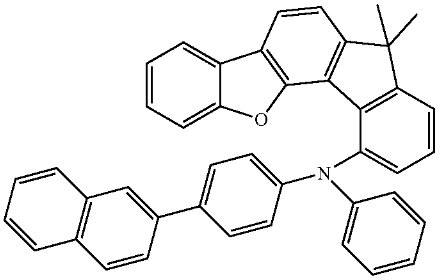
[2-97]
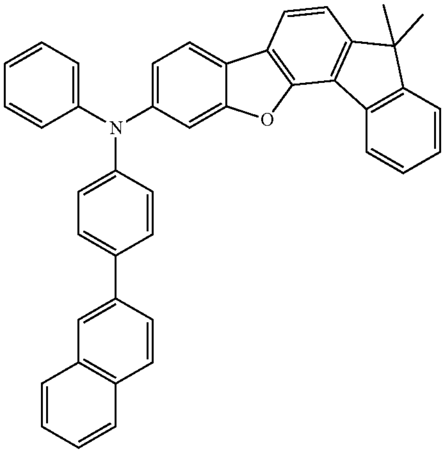

-continued
[2-98]
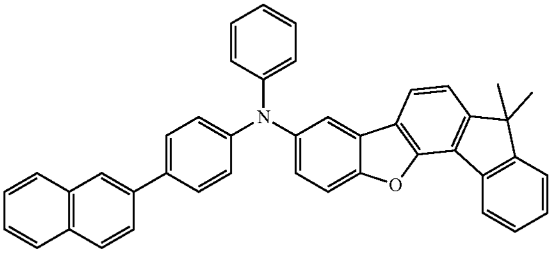
[2-99]
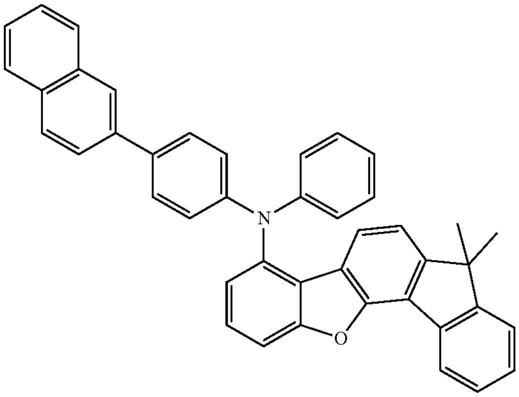
[2-100]
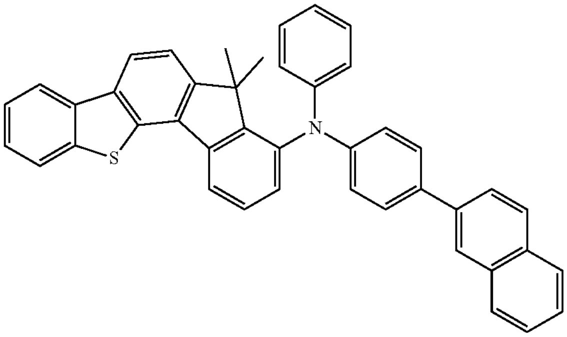
[2-101]
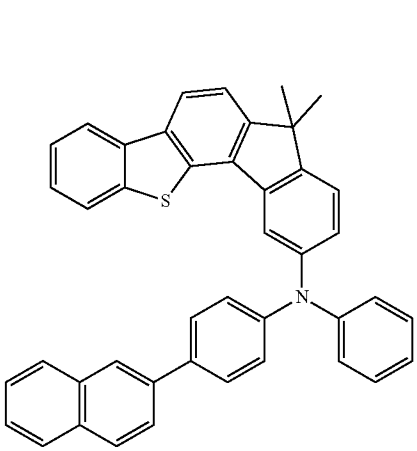
-continued
[2-102]
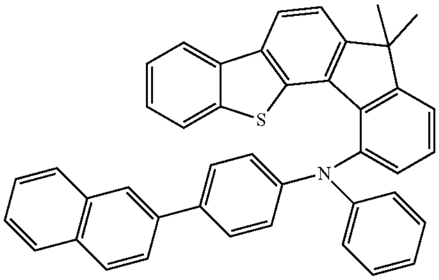
[2-103]
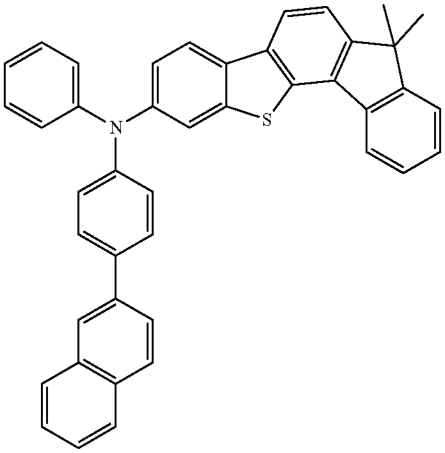
[2-104]
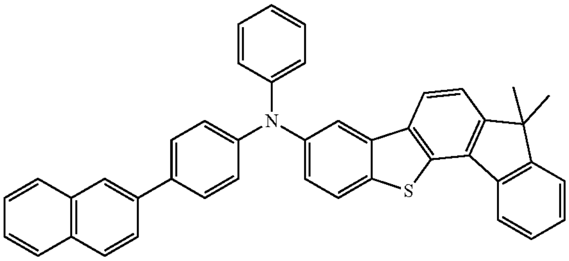
[2-105]
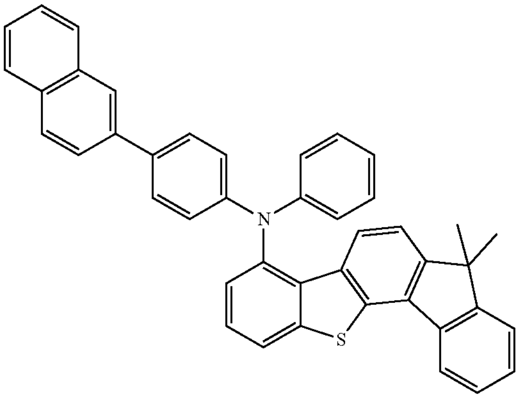

-continued
[2-106]
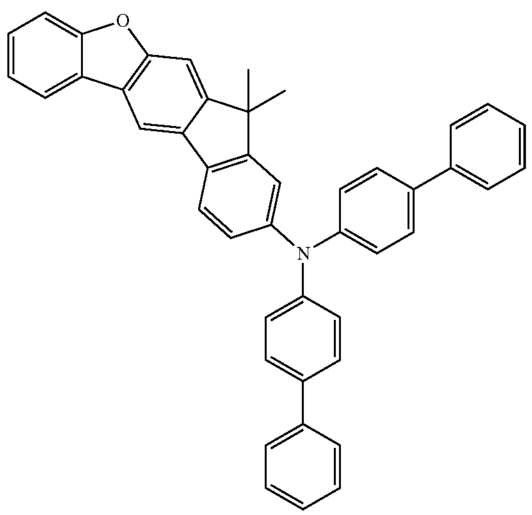
[2-107]
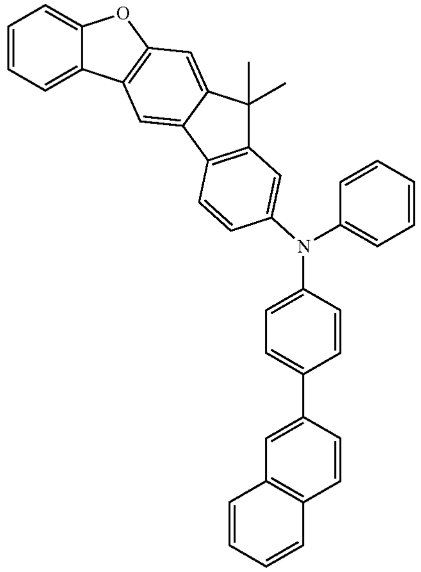
[2-108]
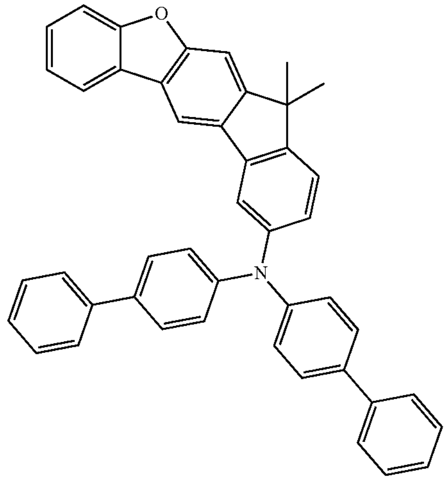
-continued
[2-109]
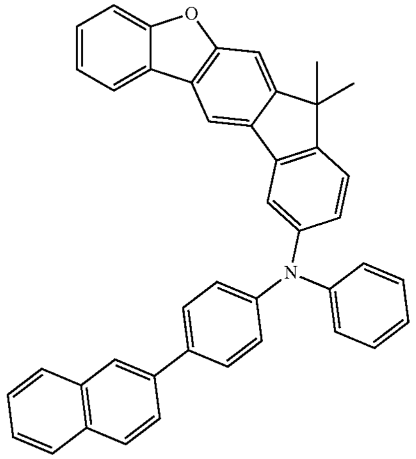
[2-110]
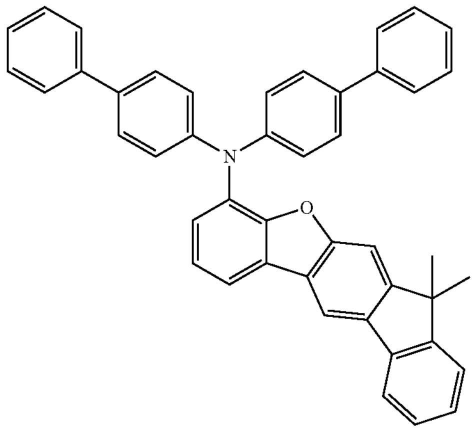
[2-111]
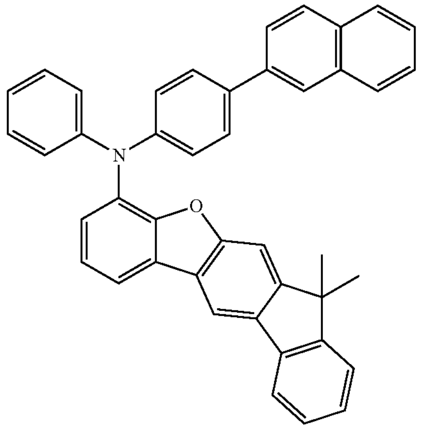

-continued
[2-112]
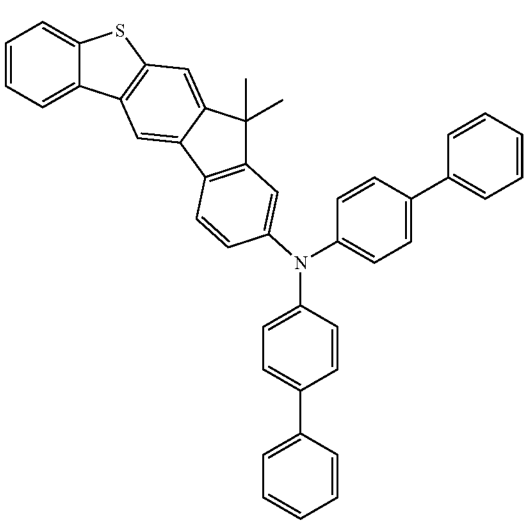
[2-113]
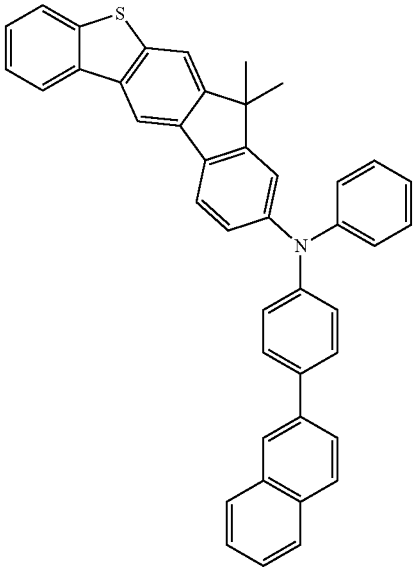
[2-114]
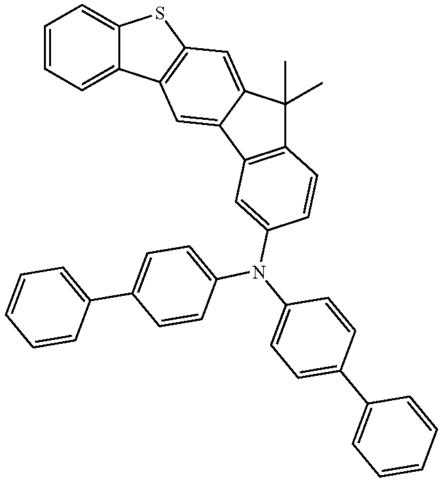
-continued
[2-115]
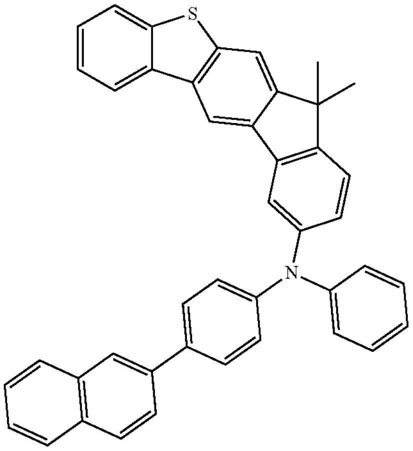
[2-116]
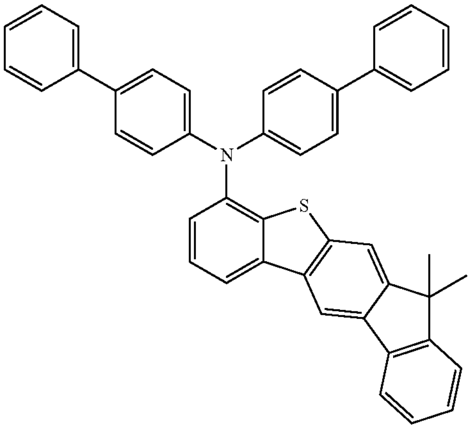
[2-117]
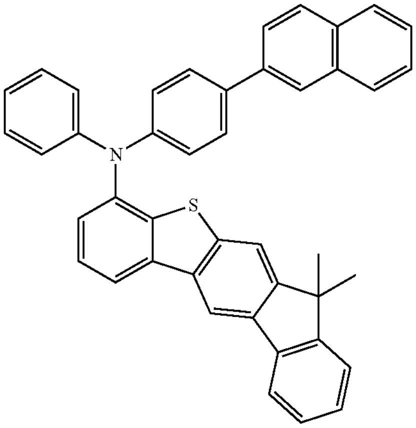

-continued
[2-118]
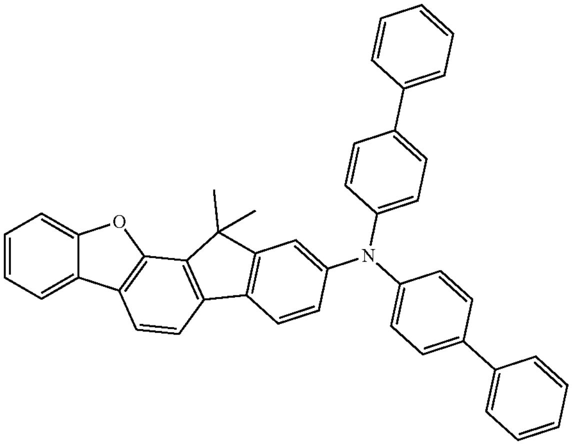
[2-119]
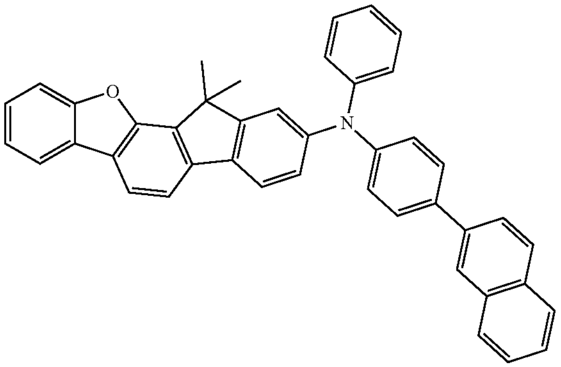
[2-120]
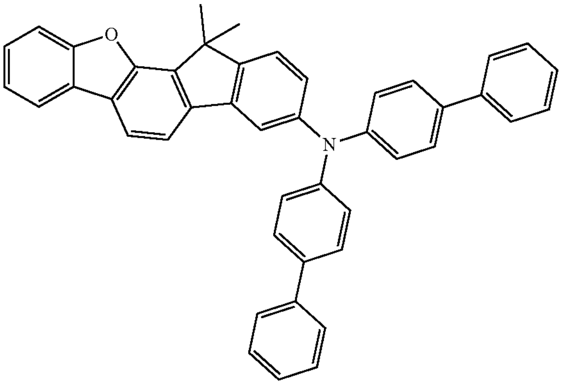
-continued
[2-121]
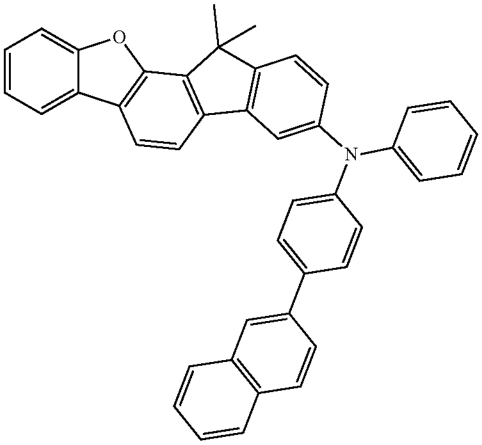
[2-122]
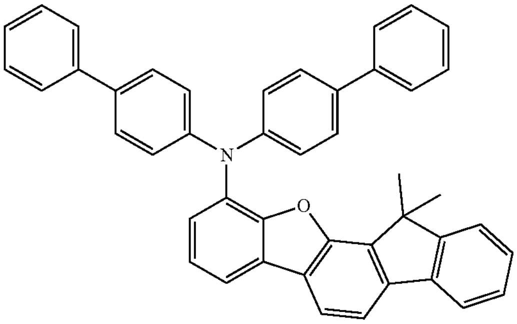
[2-123]
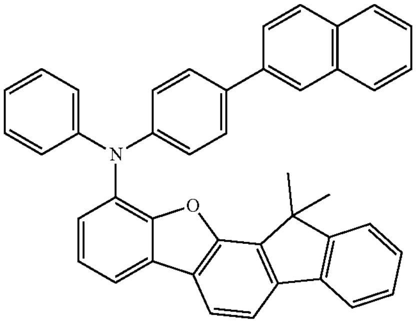
[2-124]
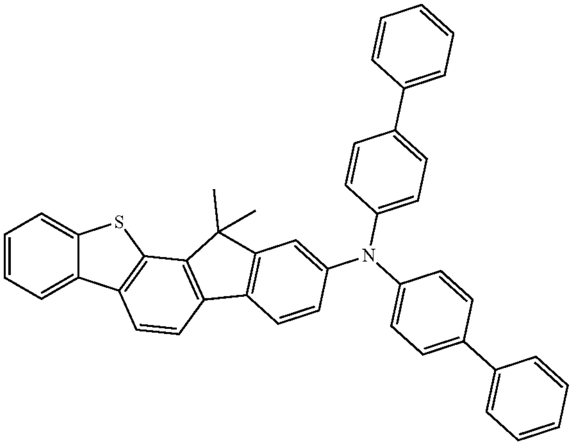

-continued
[2-125]
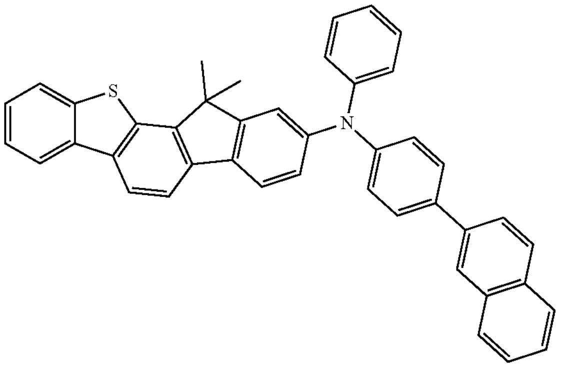
[2-126]
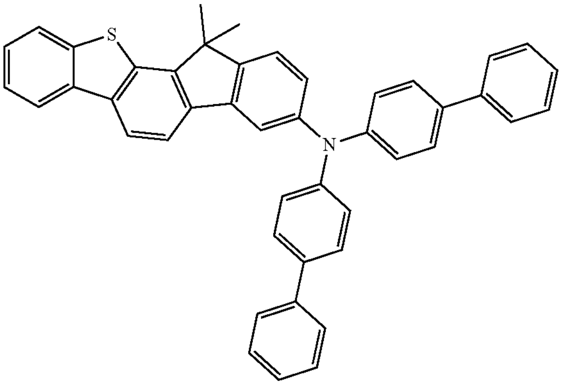
[2-127]
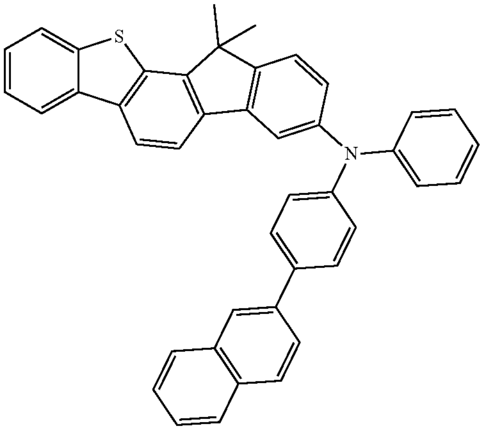
[2-128]
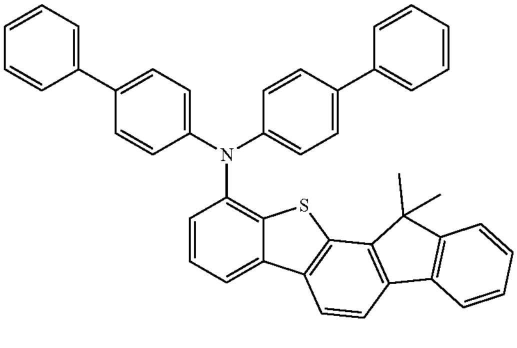
-continued
[2-129]
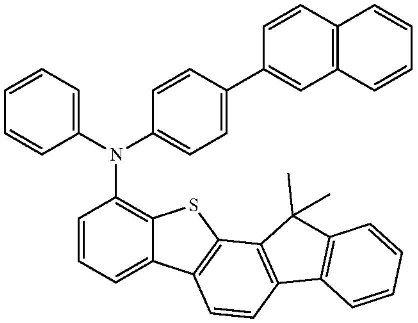
[2-130]
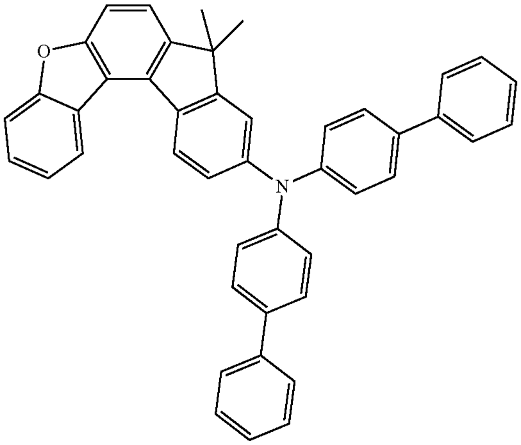
[2-131]
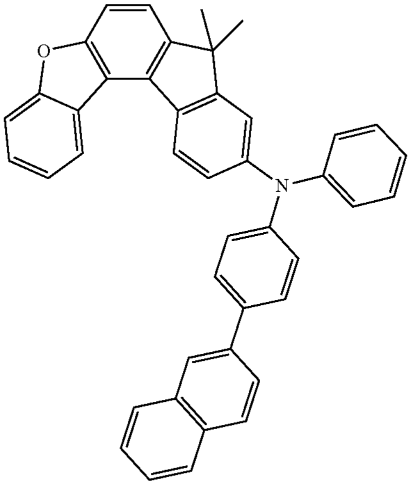

-continued
[2-132]
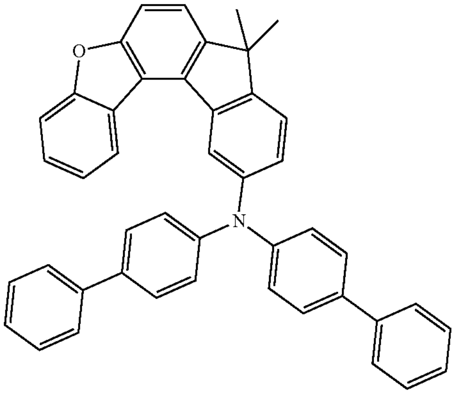
[2-133]
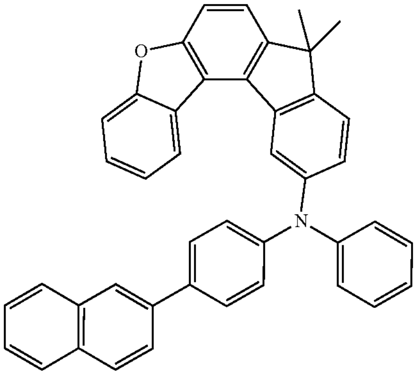
[2-134]
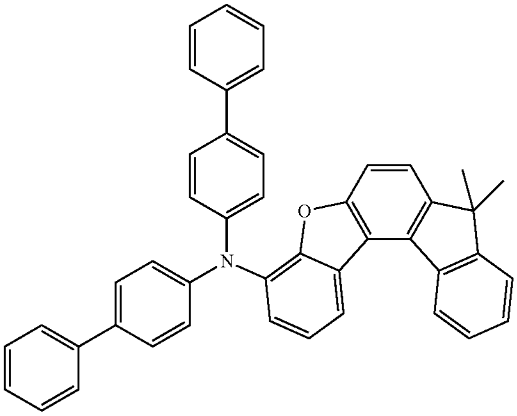
[2-135]
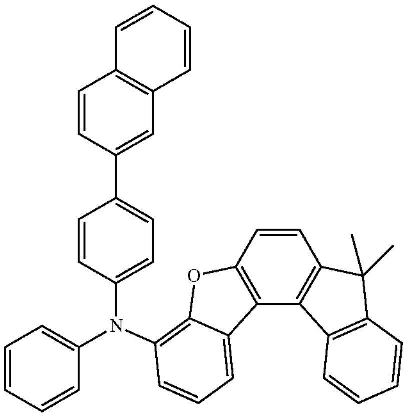
-continued
[2-136]
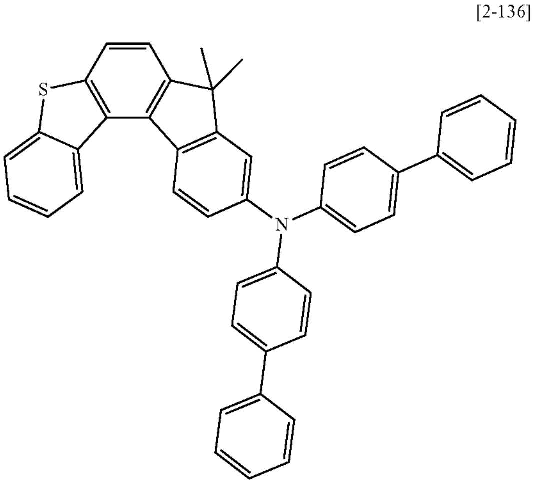
[2-137]
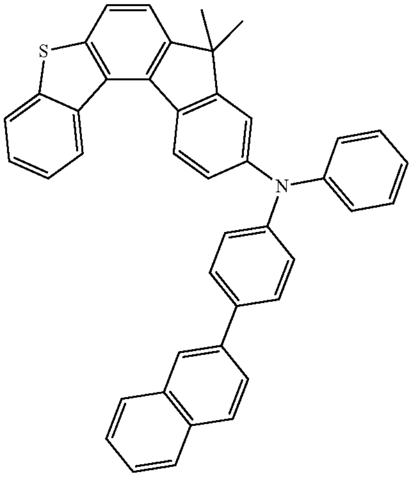
[2-138]
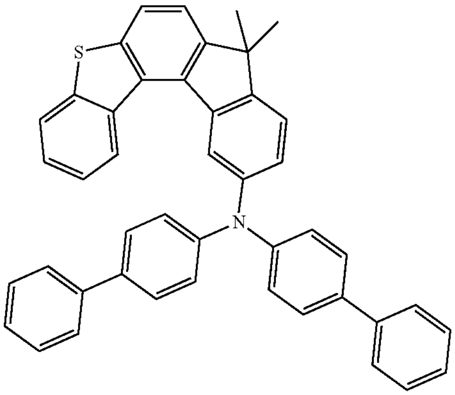

[2-139]
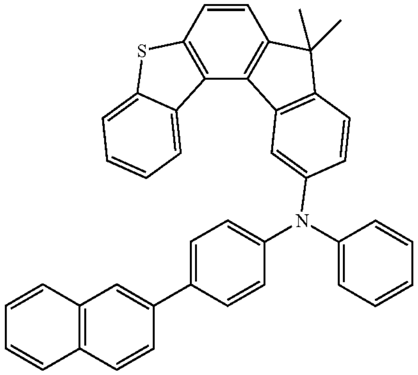
[2-140]
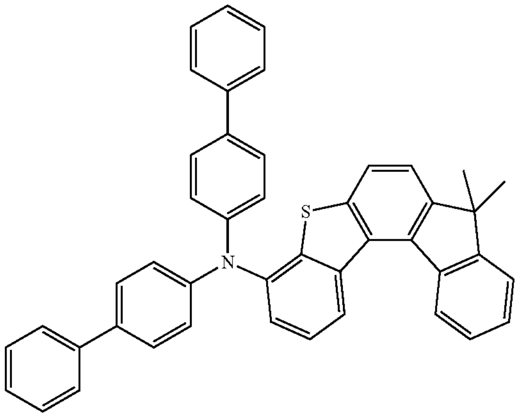
[2-141]
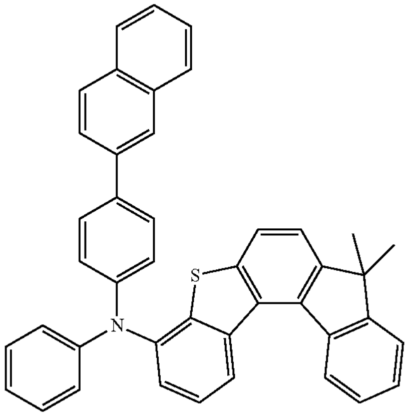
[2-142]
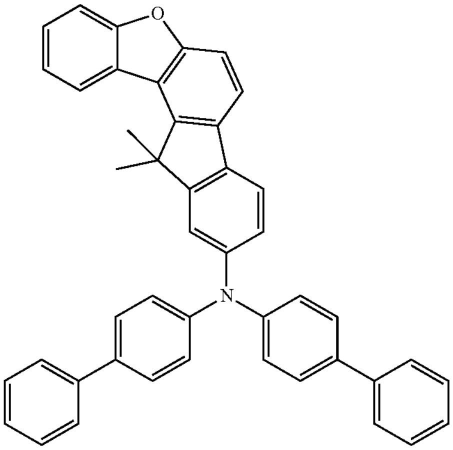
[2-143]
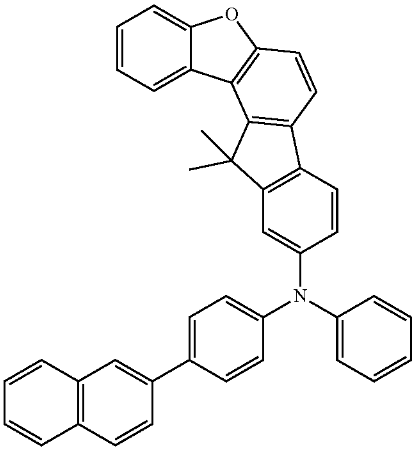
[2-144]
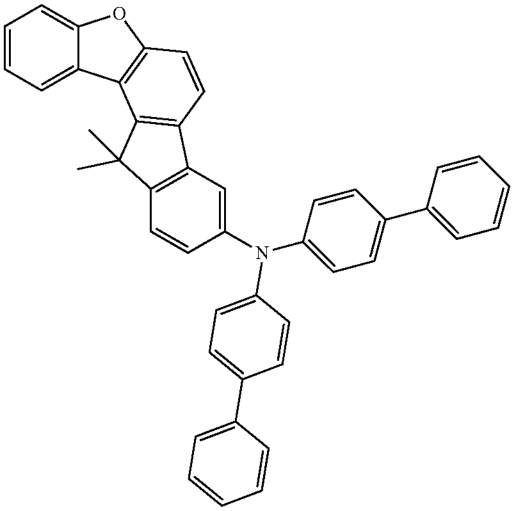

-continued
[2-145]
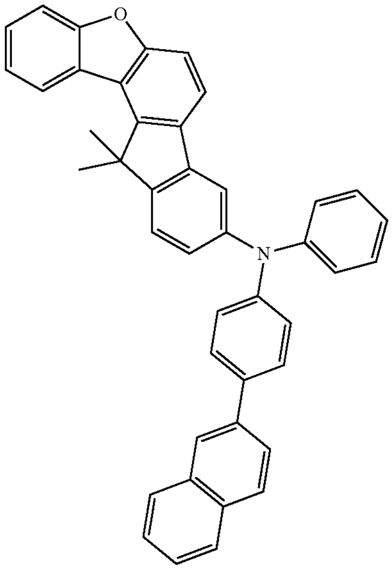
[2-146]
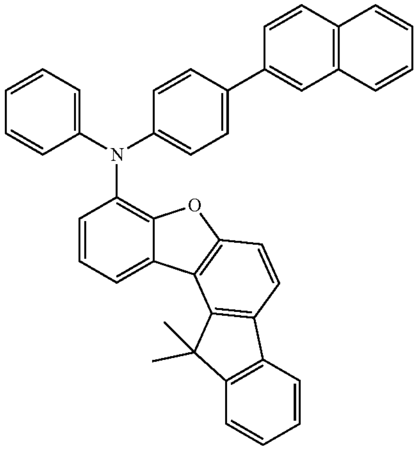
[2-147]
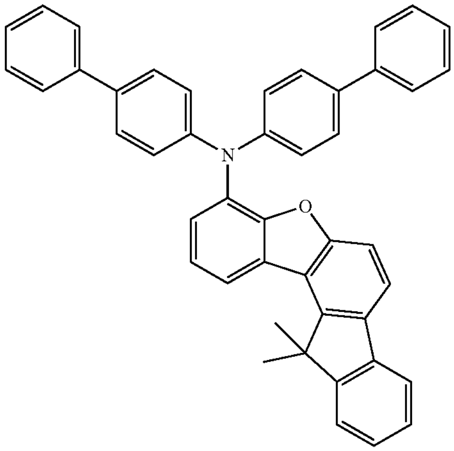
-continued
[2-148]
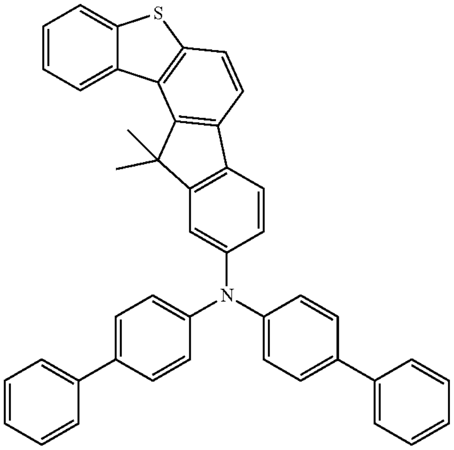
[2-149]
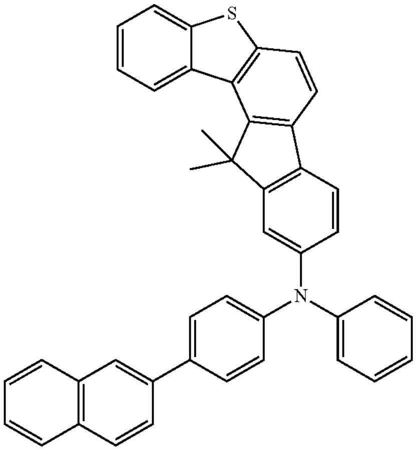
[2-150]
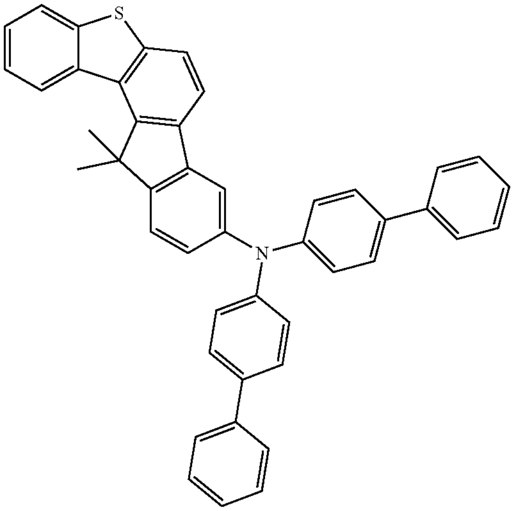

-continued
[2-151]
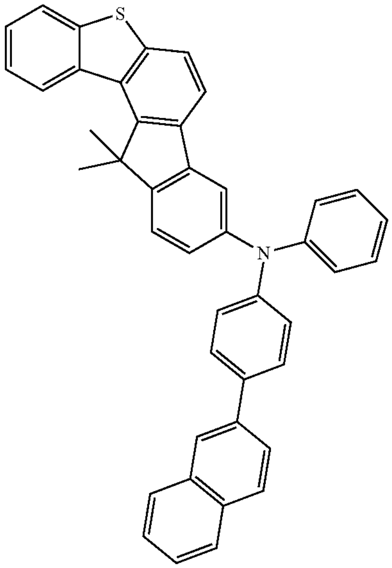
[2-152]
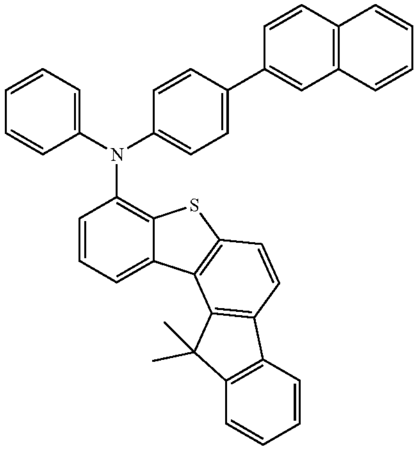
[2-153]
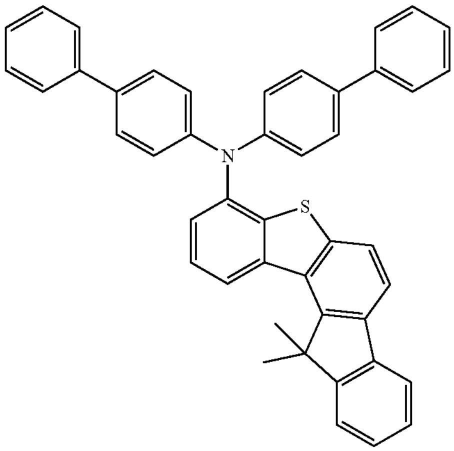
-continued
[2-154]
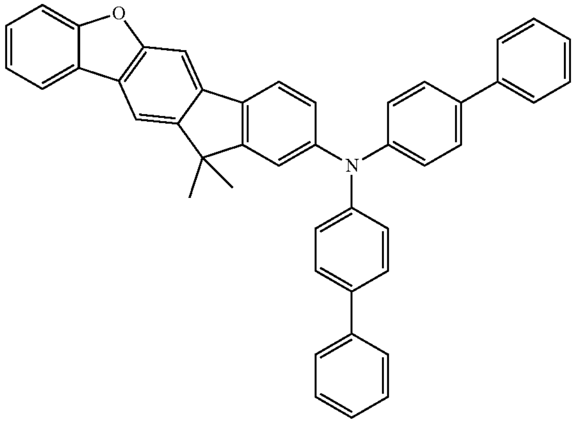
[2-155]
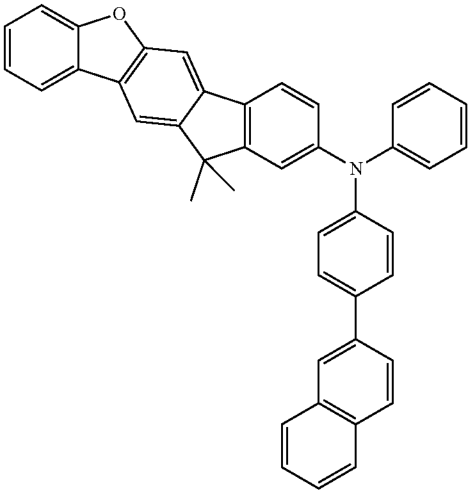
[2-156]
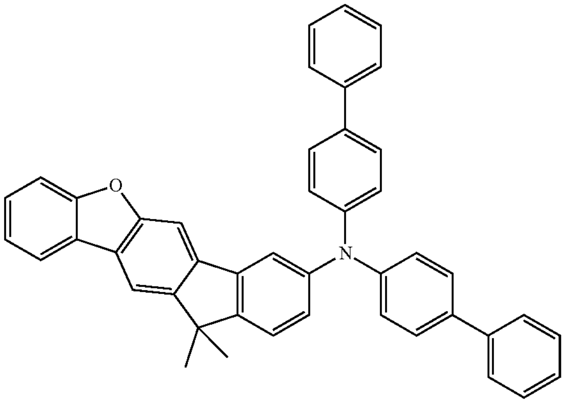

-continued
[2-157]
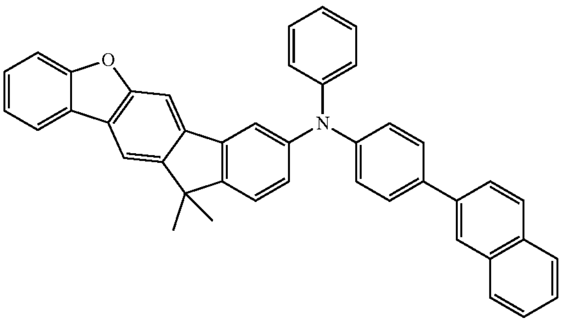
[2-158]
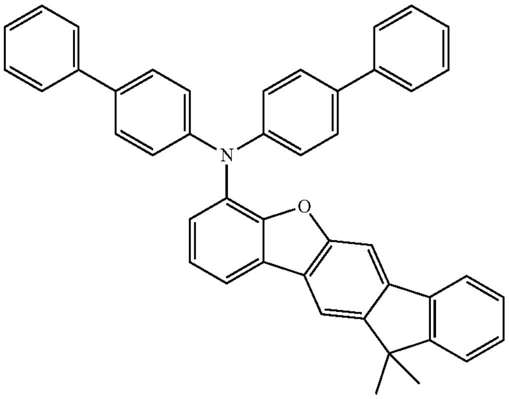
[2-159]
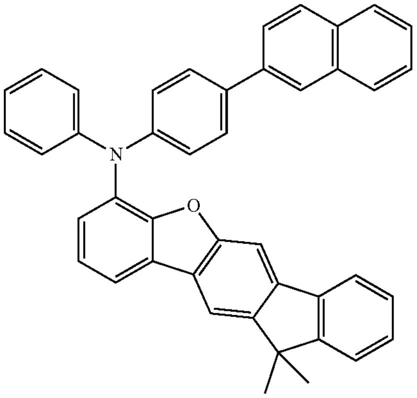
[2-160]
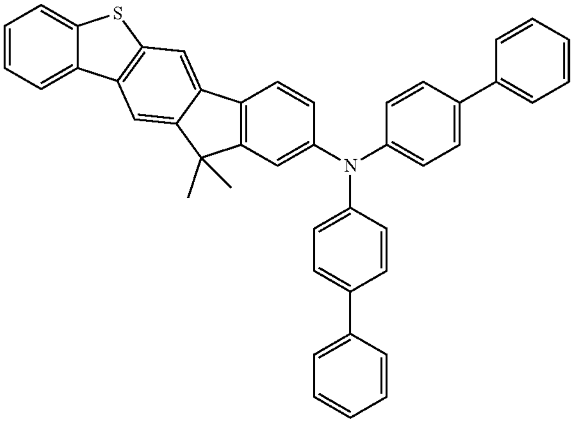
-continued
[2-161]
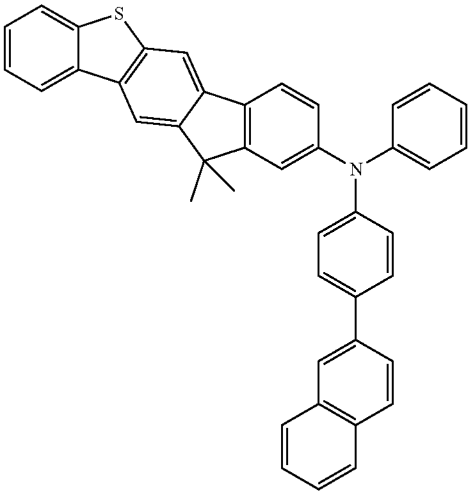
[2-162]
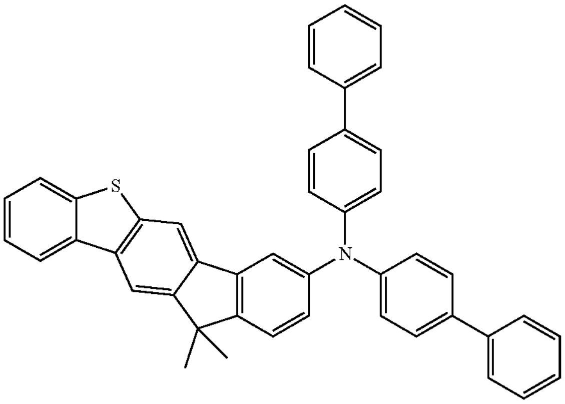
[2-163]
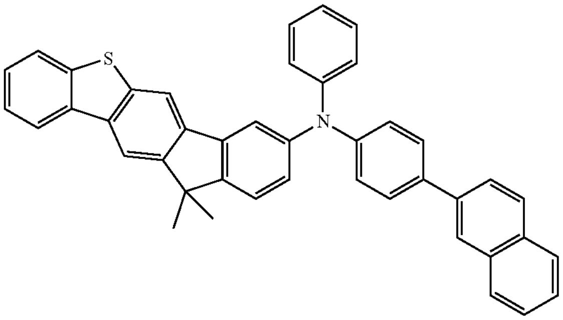

-continued
[2-164]
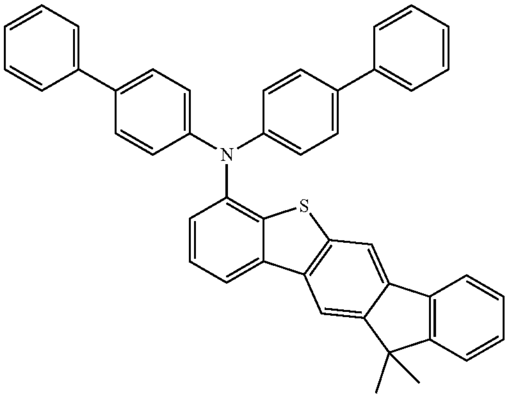
[2-165]
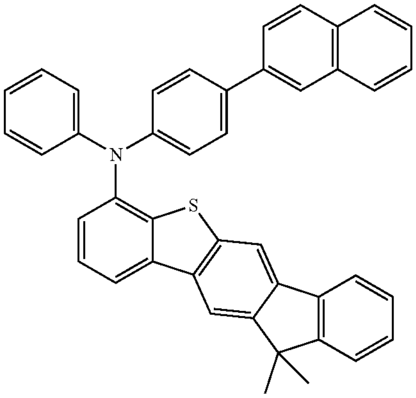
[2-166]
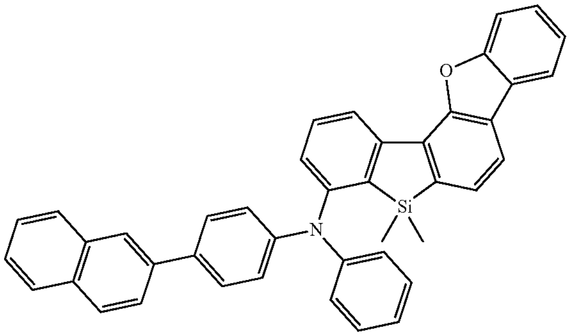
[2-167]
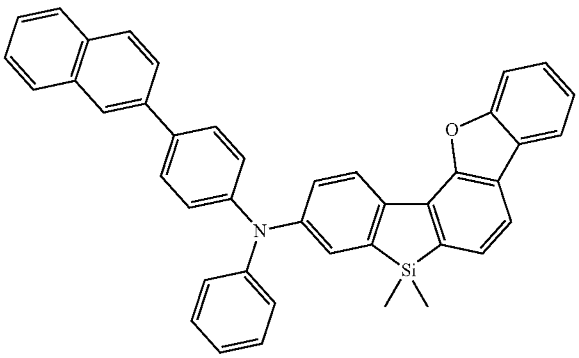
-continued
[2-168]
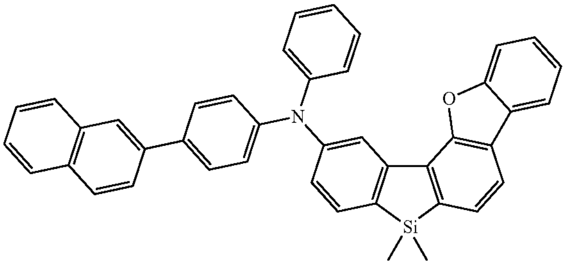
[2-169]
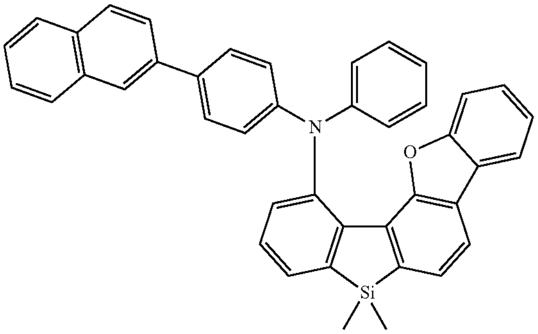
[2-170]
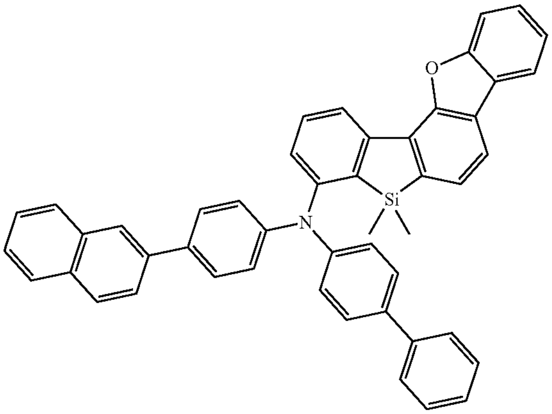
[2-171]
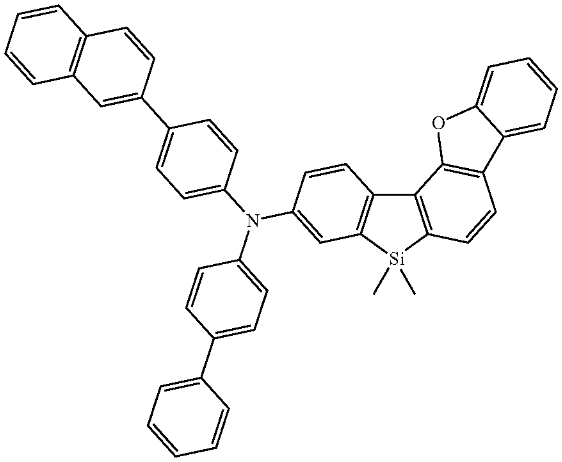

-continued
[2-172]
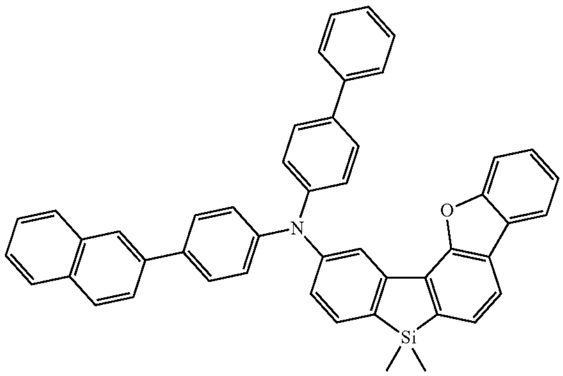
[2-173]
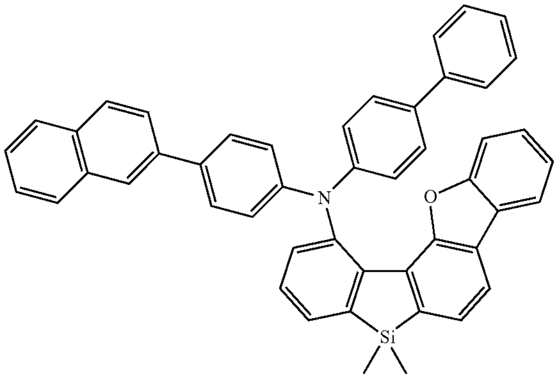
[2-174]
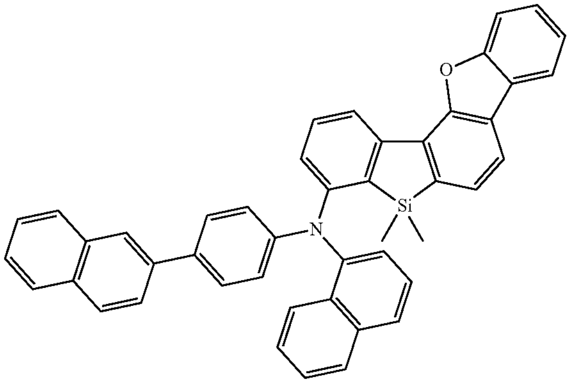
[2-175]
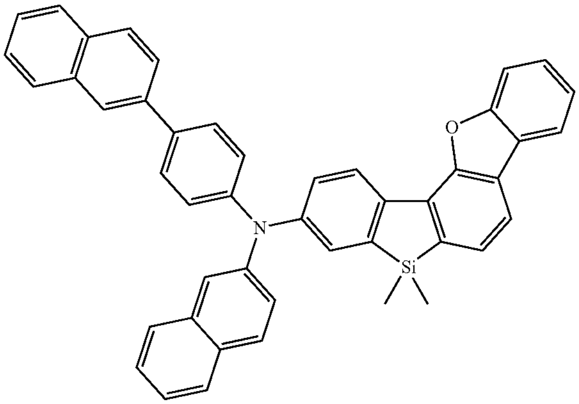
-continued
[2-176]
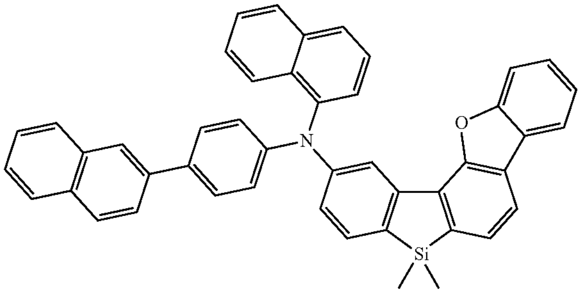
[2-177]
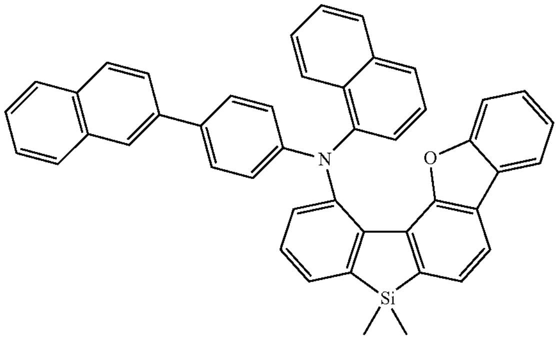
[2-178]
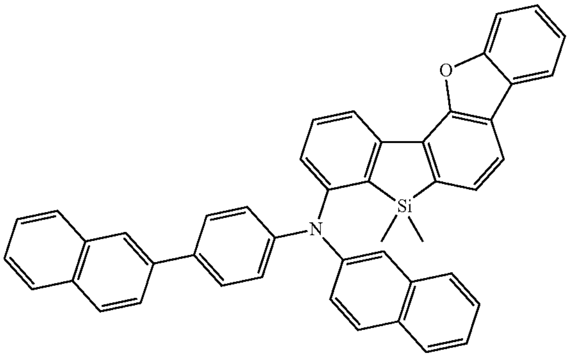
[2-179]
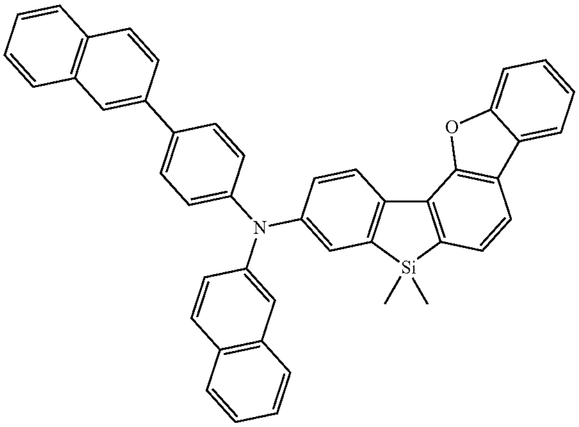

-continued
[2-180]
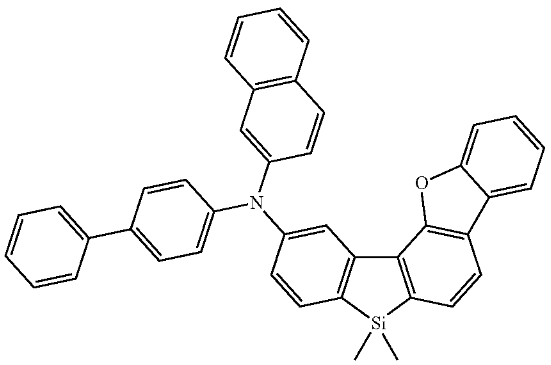
[2-181]
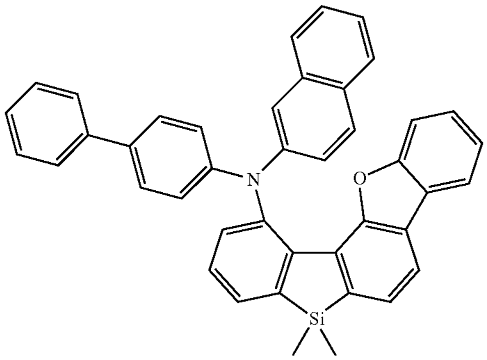
[2-182]
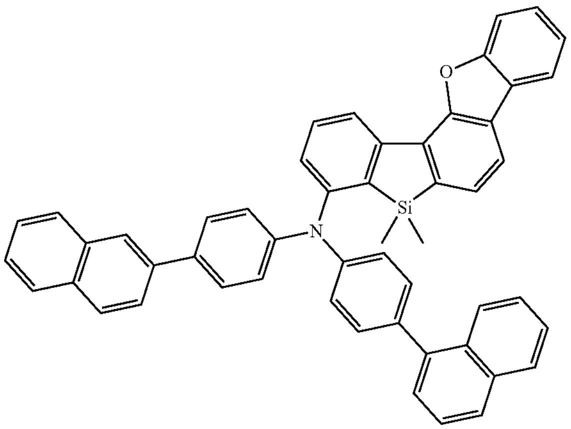
-continued
[2-183]
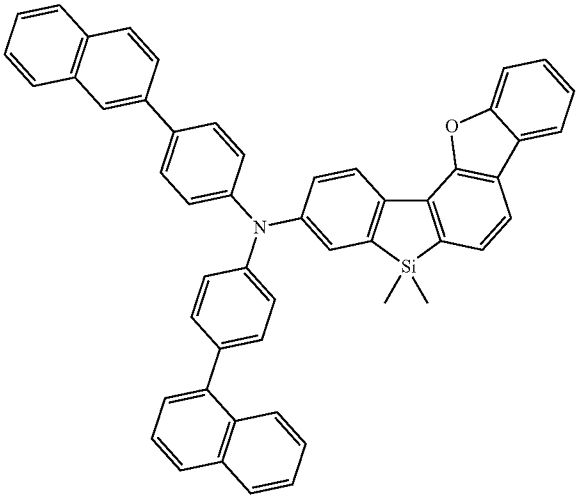
[2-184]
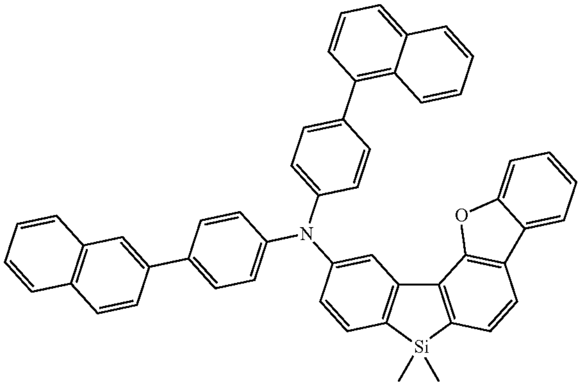
[2-185]
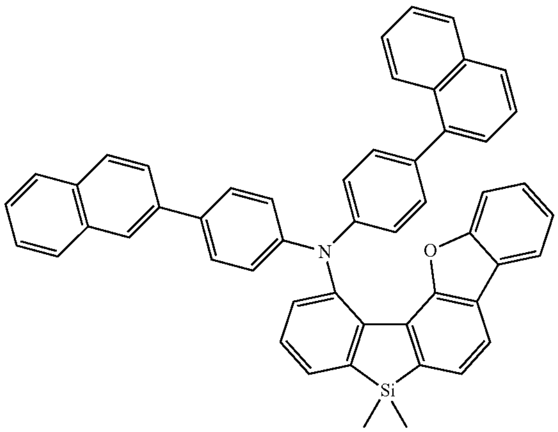

-continued
[2-186]
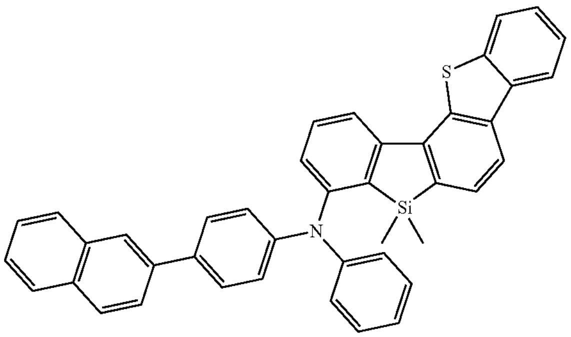
[2-187]
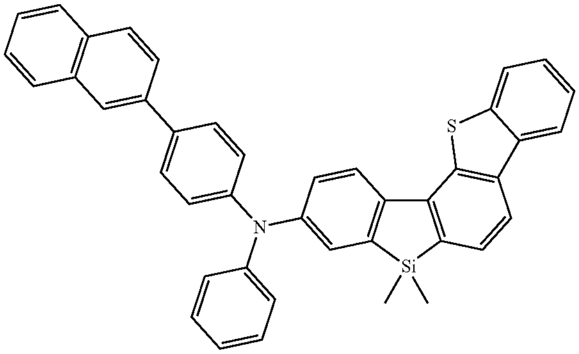
[2-188]
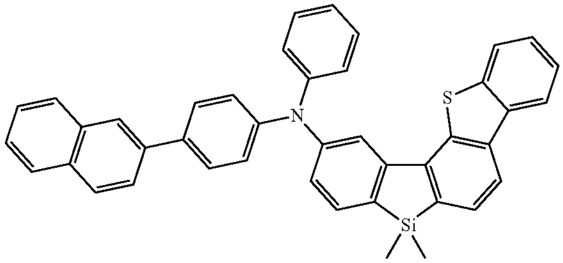
[2-189]
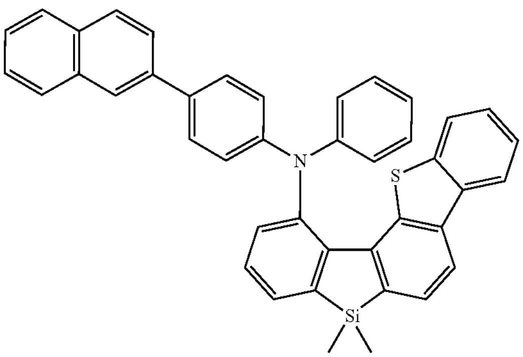
-continued
[2-190]
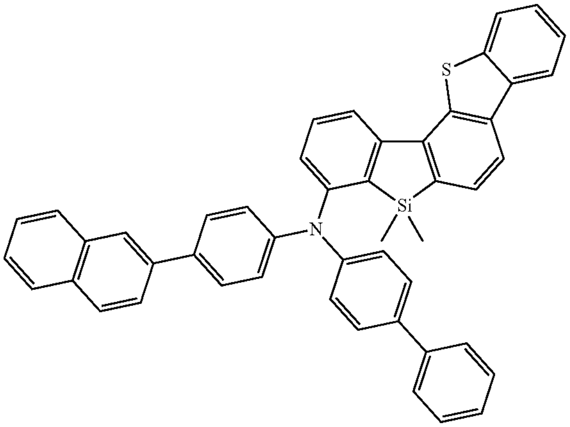
[2-191]
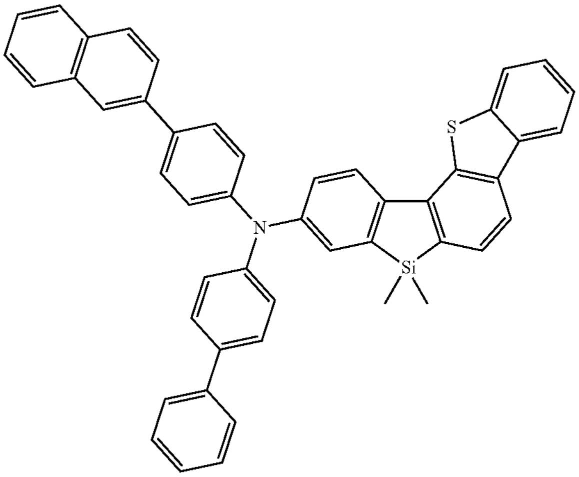
[2-192]
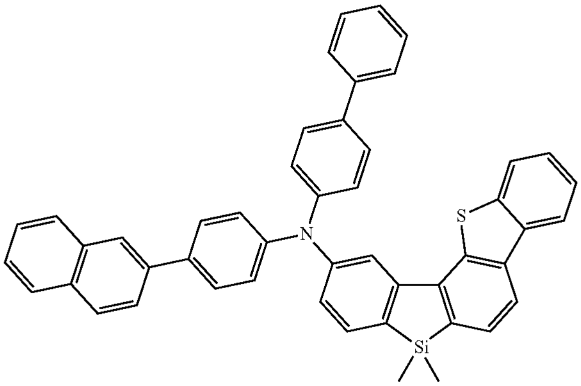

-continued
[2-193]
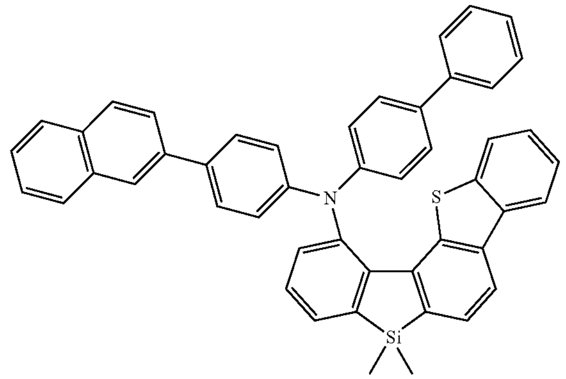
[2-194]
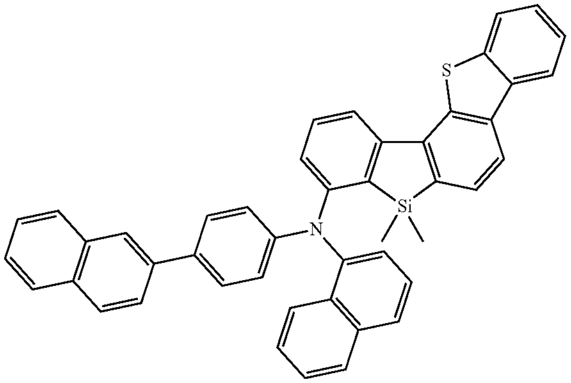
[2-195]
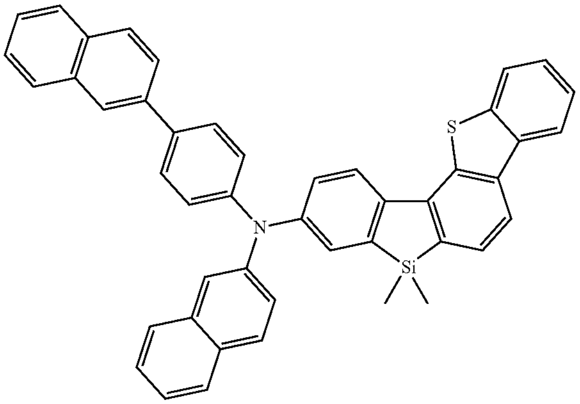
[2-196]
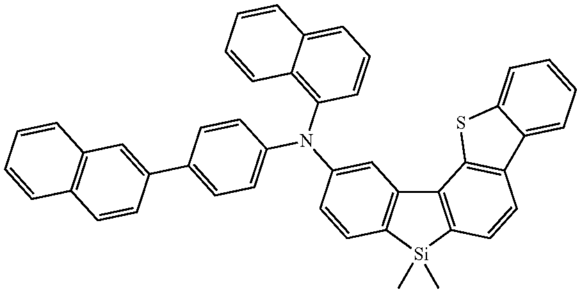
-continued
[2-197]
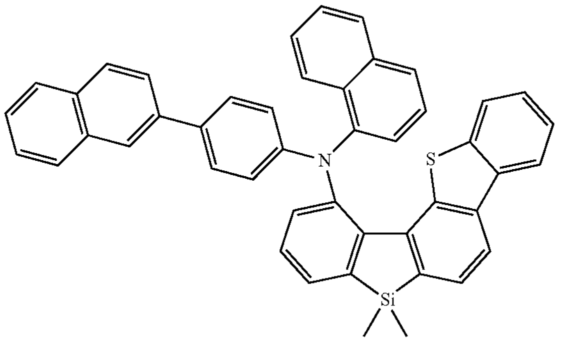
[2-198]
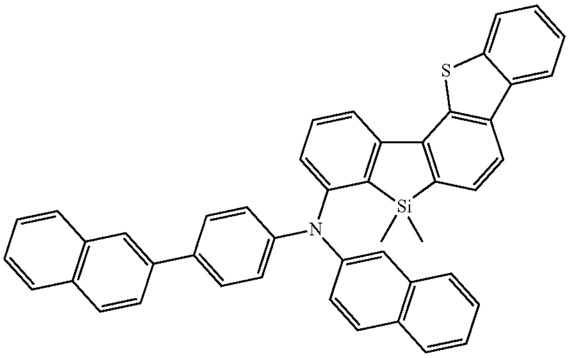
[2-199]
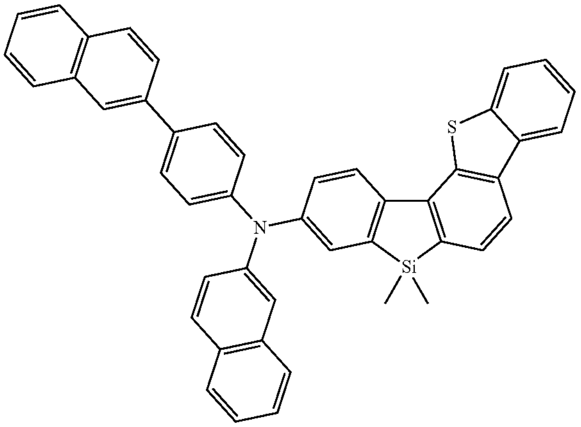
[2-200]
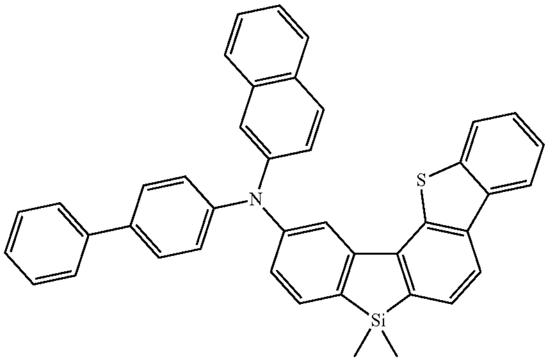

-continued
[2-201]
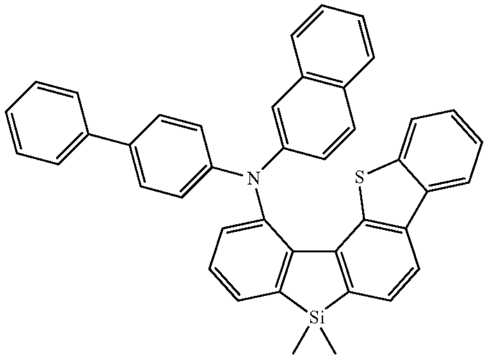
[2-202]
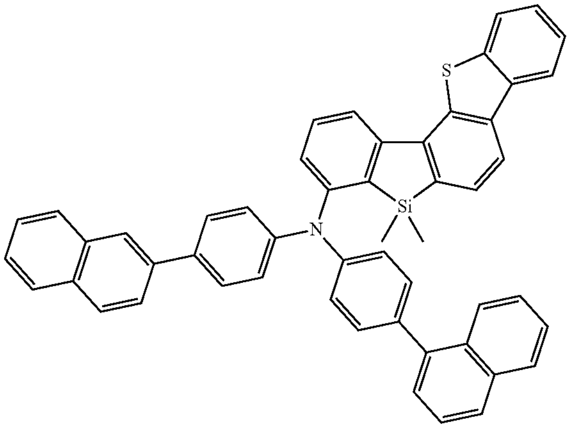
[2-203]
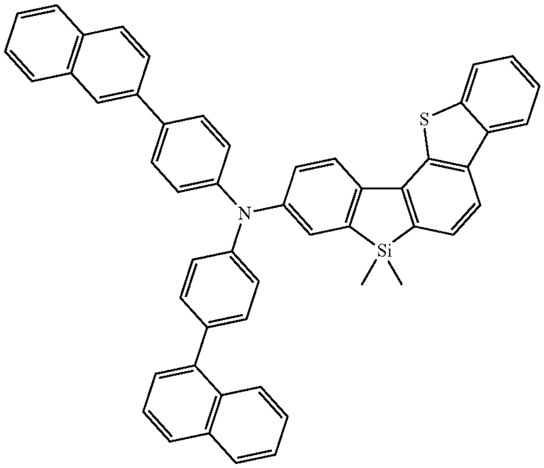
-continued
[2-204]
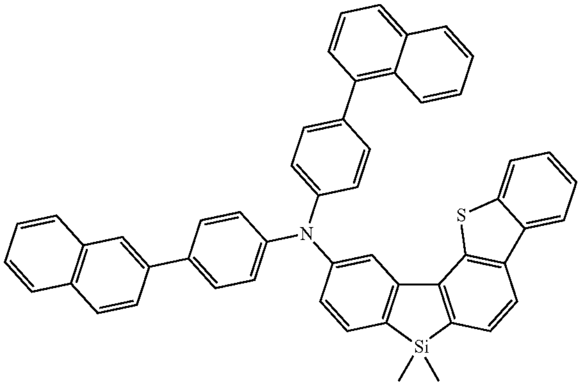
[2-205]
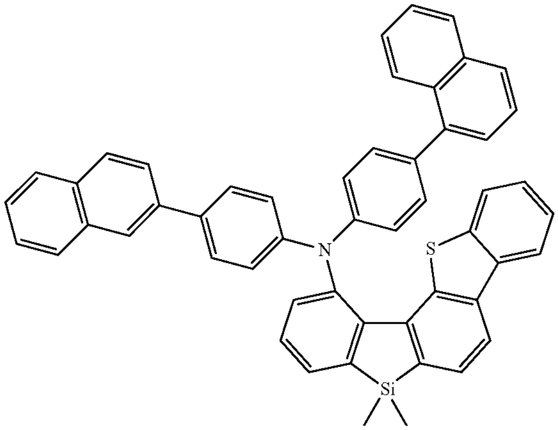
[2-206]
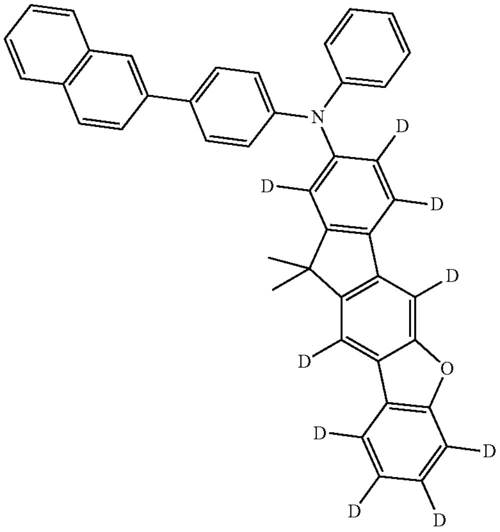

-continued

[2-207]

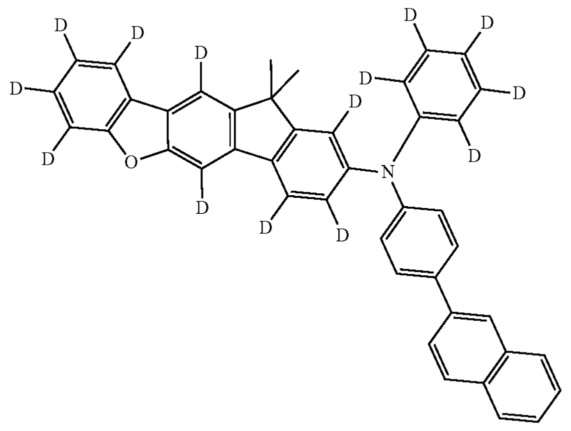

[2-208]

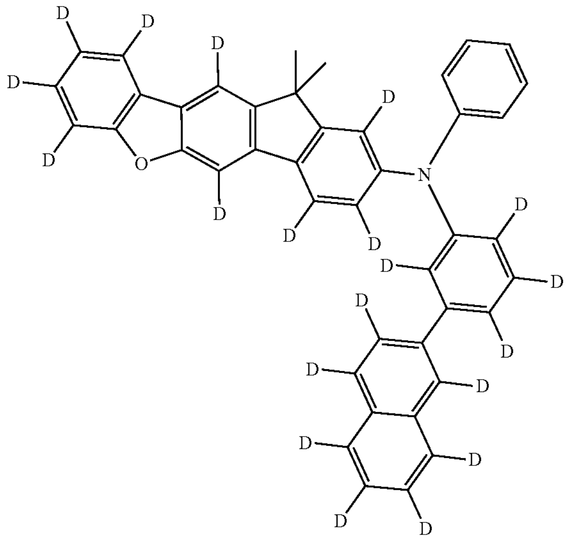

[2-209]

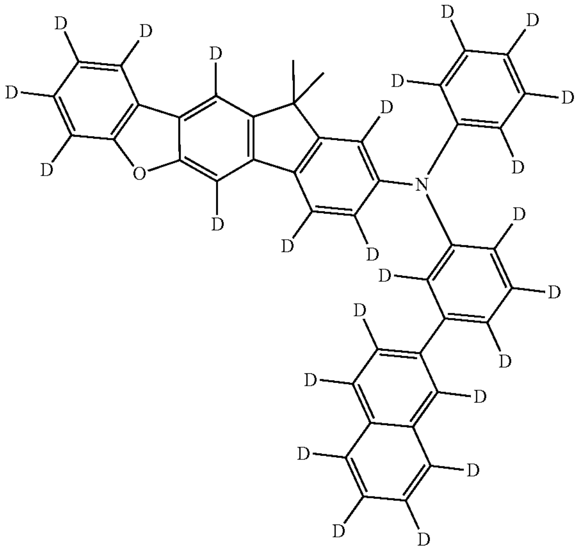

The first compound and the second compound may be included, e.g., mixed, in a weight ratio of, e.g., about 1:99 to about 99:1. Within the range, a desirable weight ratio may be adjusted using an electron transport capability of the first compound and a hole transport capability of the second compound to realize bipolar characteristics and thus to improve efficiency and life-span. Within the range, they may be, e.g., included in a weight ratio of about 10:90 to about 90:10, about 20:80 to about 80:20, about 20:80 to about 70:30, about 20:80 to about 60:40, and about 30:70 to about 60:40. In an implementation, they may be included in a weight ratio of, e.g., about 40:60, about 50:50, or about 60:40.

At least one compound may be further included in addition to the aforementioned first compound and second compound.

The aforementioned compound for the organic optoelectronic device or composition for the organic optoelectronic device may further include a dopant.

The dopant may be, e.g., a phosphorescent dopant, such as a red, green, or blue phosphorescent dopant, and may be, e.g., a red or green phosphorescent dopant.

The dopant is a material mixed with the compound or composition for an organic optoelectronic device in a small amount to cause light emission and may be generally a material such as a metal complex that emits light by multiple excitation into a triplet or more. The dopant may be, e.g., an inorganic, organic, or organic-inorganic compound, and one or more types thereof may be used.

Examples of the dopant may include a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by Chemical Formula Z.

$L^6MX^3$ [Chemical Formula Z]

In Chemical Formula Z, M may be, e.g., a metal, $L^6$ and $X^3$ may each independently be, e.g., ligands forming a complex compound with M.

The M may be, e.g., Ir, Pt, Os, Ti, Zr, Hf, Eu, Tb, Tm, Fe, Co, Ni, Ru, Rh, Pd, or a combination thereof, and $L^6$ and $X^3$ may be, e.g., a bidentate ligand.

Examples of the ligands represented by $L^6$ and $X^3$ may be ligands of Group A.

[Group A]

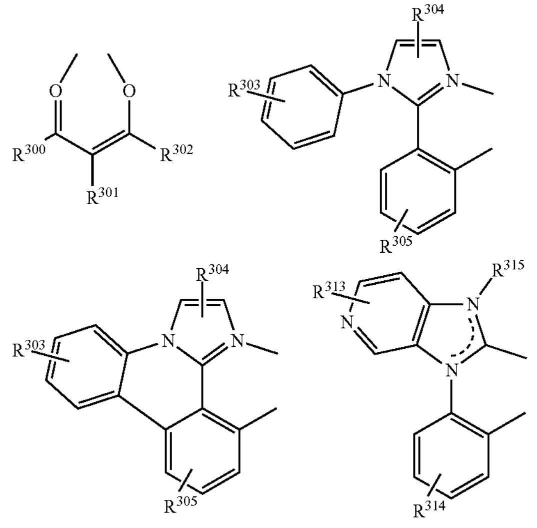

-continued
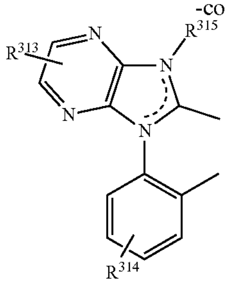
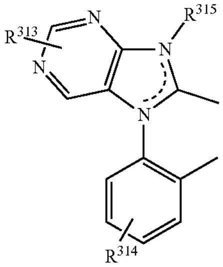
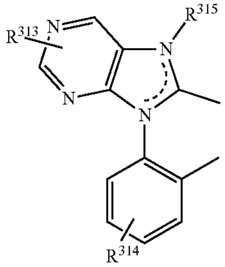
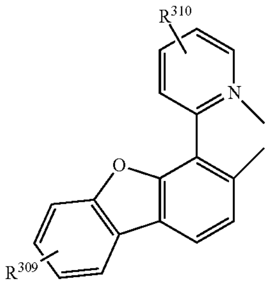
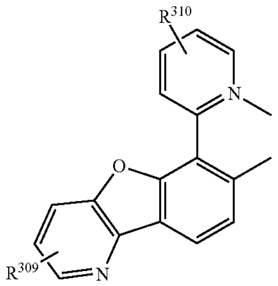
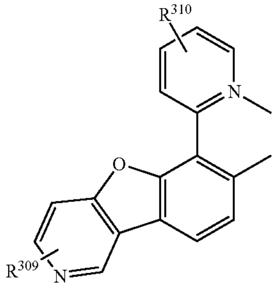
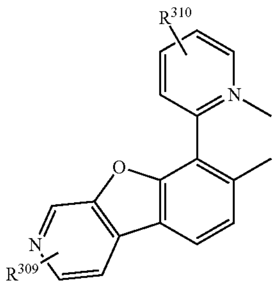
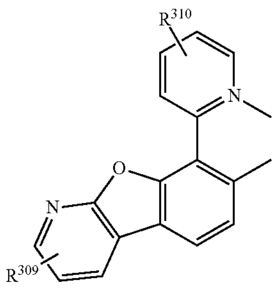
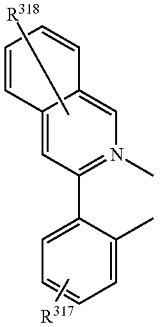
-continued
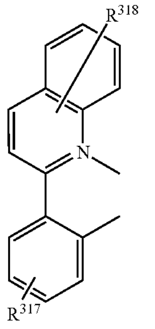
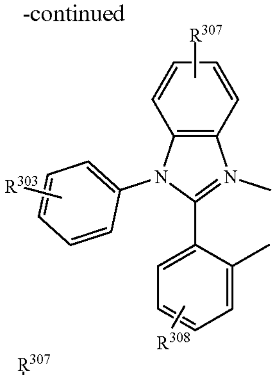
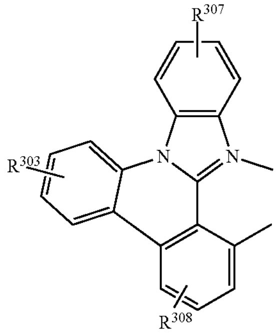
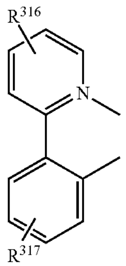
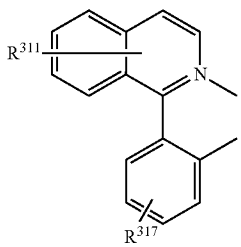
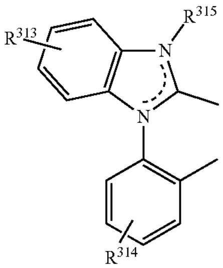
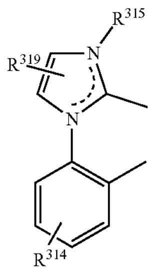
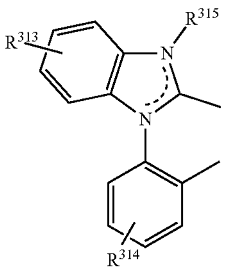
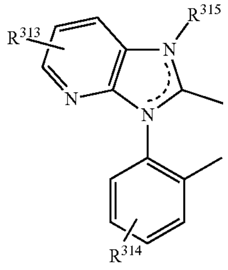
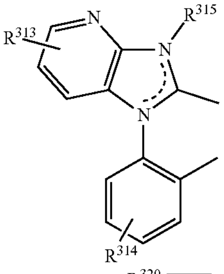
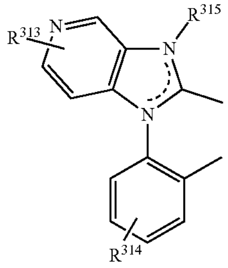
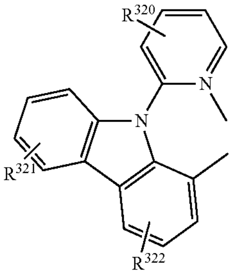

-continued

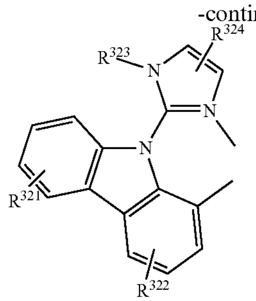

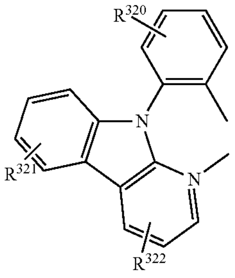

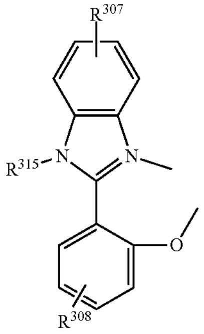

In Group A, $R^{300}$ to $R^{302}$ may each independently be, e.g., hydrogen, deuterium a C1 to C30 alkyl group that is substituted or unsubstituted with a halogen, a C6 to C30 aryl group that is substituted with a C1 to C30 alkyl, or halogen, and $R^{303}$ to $R^{324}$ may each independently be, e.g., hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C2 to C30 alkenyl group, a substituted or unsubstituted C6 to C30 aryl group, a substituted or unsubstituted C1 to C30 heteroaryl group, a substituted or unsubstituted C1 to C30 amino group, a substituted or unsubstituted C6 to C30 arylamino group, SFs, a trialkylsilyl group having a substituted or unsubstituted C1 to C30 alkyl group, a dialkylarylsilyl group having a substituted or unsubstituted C1 to C30 alkyl group and C6 to C30 aryl group, or a triarylsilyl group having a substituted or unsubstituted C6 to C30 aryl group.

In an implementation, a dopant represented by Chemical Formula I may be included.

[Chemical Formula I]

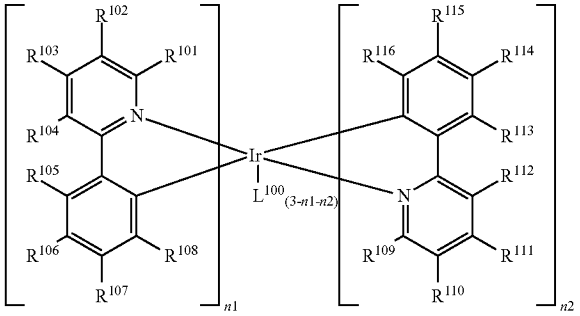

In Chemical Formula I, $R^{101}$ to $R^{116}$ may each independently be, e.g., hydrogen, deuterium, a substituted or unsubstituted C1 to C10 alkyl group, a substituted or unsubstituted C6 to C20 aryl group, or —$SiR^{132}R^{133}R^{134}$, $R^{132}$ to $R^{134}$ may each independently be, e.g., a C1 to C6 alkyl group, at least one of $R^{101}$ to $R^{116}$ may be a functional group represented by Chemical Formula I-1, $L^{100}$ may be, e.g., a bidentate ligand of a monovalent anion, and is a ligand that coordinates to iridium through a lone pair of carbons or heteroatoms, and n1 and n2 may each independently be, e.g., an integer of 0 to 3 and n1+n2 may be an integer of 1 to 3.

[Chemical Formula I-1]

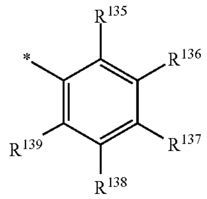

In Chemical Formula I-1, $R^{135}$ to $R^{139}$ may each independently be, e.g., hydrogen, deuterium, a substituted or unsubstituted C1 to C10 alkyl group, a substituted or unsubstituted C6 to C20 aryl group, or —$SiR^{132}R^{133}R^{134}$, $R^{132}$ to $R^{134}$ may each independently be, e.g., a C1 to C6 alkyl group, and

* indicates a portion linked to a carbon atom.

In an implementation, a dopant represented by Chemical Formula Z-1 may be included.

[Chemical Formula Z-1]

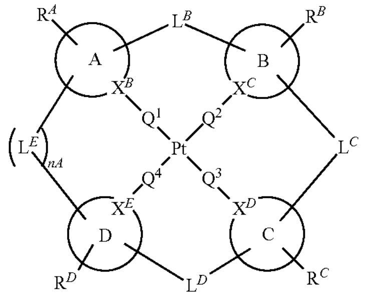

In Chemical Formula Z-1, rings A, B, C, and D may each independently be, e.g., a 5-membered or 6-membered carbocyclic or heterocyclic ring;

$R^A$, $R^B$, $R^C$, and $R^D$ may each independently be, e.g., mono-, di-, tri-, or tetra-substitution, or unsubstitution;

$L^B$, $L^C$, and $L^D$ may each independently be, e.g., a direct bond, BR, NR, PR, O, S, Se, C═O, S═O, $SO_2$, CRR', SiRR', GeRR', or a combination thereof, when nA is 1, $L^E$ is selected from a direct bond, BR, NR, PR, O, S, Se, C═O, S═O, $SO_2$, CRR', SiRR', GeRR', and a combination thereof, when nA is 0, $L^E$ does not exist; and $R^A$, $R^B$, $R^C$, $R^D$, R, and R' may each independently be, e.g., hydrogen, deuterium, a halogen, an alkyl group, a cycloalkyl group, a heteroalkyl group, an arylalkyl group, an alkoxy group, an aryloxy group, an amino group, a silyl group, an alkenyl group, a cycloalkenyl group, a heteroalkenyl group, an alkynyl group, an aryl group, a heteroaryl group, an acyl group, a carbonyl group, a carboxylic acid group, an ester group, a nitrile group, an isonitrile group, a sulfanyl group, a sulfinyl group, a sulfonyl group, a phosphino group, or a combination thereof, any adjacent $R^A$, $R^B$, $R^C$, $R^D$, R, and R' are optionally linked to each other to provide a ring; $X^B$, $X^C$, $X^D$, and $X^E$ are each independently selected from carbon and nitrogen; and $Q^1$, $Q^2$, $Q^3$, and $Q^4$ each represent oxygen or a direct bond.

The dopant according to an embodiment may be a platinum complex, and may be, e.g., represented by Chemical Formula II.

[Chemical Formula II]

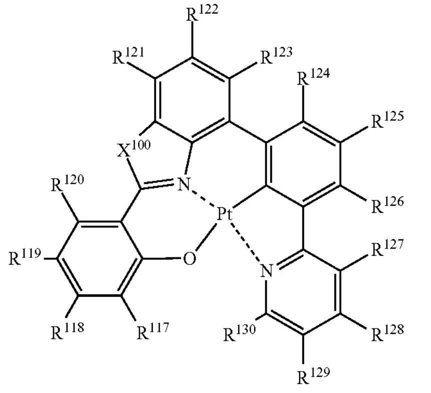

In Chemical Formula II, $X^{100}$ may be, e.g., O, S, or $NR^{131}$, $R^{117}$ to $R^{131}$ are each independently hydrogen, deuterium, a substituted or unsubstituted C1 to C10 alkyl group, a substituted or unsubstituted C6 to C20 aryl group, or $—SiR^{132}R^{133}R^{134}$, $R^{132}$ to $R^{134}$ may each independently be, e.g., a C1 to C6 alkyl group, and at least one of $R^{117}$ to $R^{131}$ may be, e.g., $—SiR^{132}R^{133}R^{134}$ or a tert-butyl group.

Hereinafter, an organic optoelectronic device including the aforementioned compound for an organic optoelectronic device or composition for an organic optoelectronic device is described.

The organic optoelectronic device may be a suitable device to convert electrical energy into photoenergy and vice versa, e.g., an organic photoelectric device, an organic light emitting diode, an organic solar cell, or an organic photoconductor drum.

Herein, an organic light emitting diode as one example of an organic optoelectronic device is described referring to drawings.

The FIGURE a cross-sectional view illustrating an organic light emitting diode according to an embodiment.

Referring to the FIGURE, an organic light emitting diode 100 according to an embodiment may include an anode 120 and a cathode 110 facing each other and an organic layer 105 disposed between the anode 120 and cathode 110.

The anode 120 may be made of a conductor having a large work function to help hole injection, and may be, e.g., a metal, a metal oxide, or a conductive polymer. The anode 120 may be, e.g., a metal such as nickel, platinum, vanadium, chromium, copper, zinc, gold, or the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; or a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to help electron injection, and may be, e.g., a metal, a metal oxide, or a conductive polymer. The cathode 110 may be, e.g., a metal such as magnesium, calcium, sodium, potassium, titanium, indium, yttrium, lithium, gadolinium, aluminum, silver, tin, lead, cesium, barium, or the like, or an alloy thereof; or a multi-layer structure material such as LiF/Al, $LiO_2$/Al, LiF/Ca, or $BaF_2$/Ca.

The organic layer 105 may include the aforementioned compound for an organic optoelectronic device or composition for an organic optoelectronic device.

The organic layer 105 may include a light emitting layer 130 and the light emitting layer 130 may include the aforementioned compound for an organic optoelectronic device or composition for an organic optoelectronic device.

The composition for an organic optoelectronic device further including the dopant may be, e.g., a red light emitting composition.

The light emitting layer 130 may include, e.g., the aforementioned first compound and second compound as a phosphorescent host.

The organic layer may further include a charge transport region in addition to the light emitting layer.

The charge transport region may be, e.g., the hole transport region 140.

The hole transport region 140 may help further increase hole injection and/or hole mobility between the anode 120 and the light emitting layer 130 and block electrons. In an implementation, the hole transport region 140 may include a hole transport layer between the anode 120 and the light emitting layer 130, and a hole transport auxiliary layer between the light emitting layer 130 and the hole transport layer, and a compound of Group B may be included in at least one of the hole transport layer and the hole transport auxiliary layer.

[Group B]

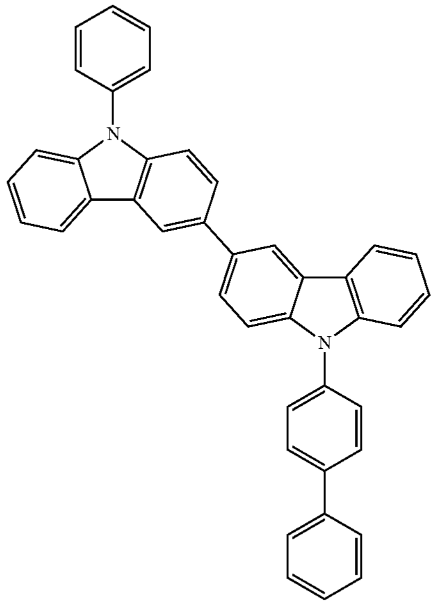

-continued
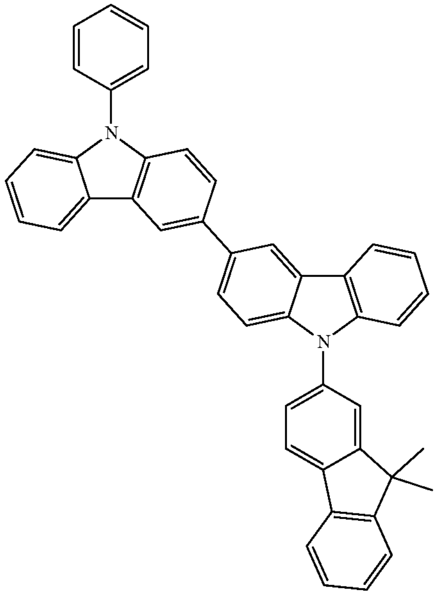
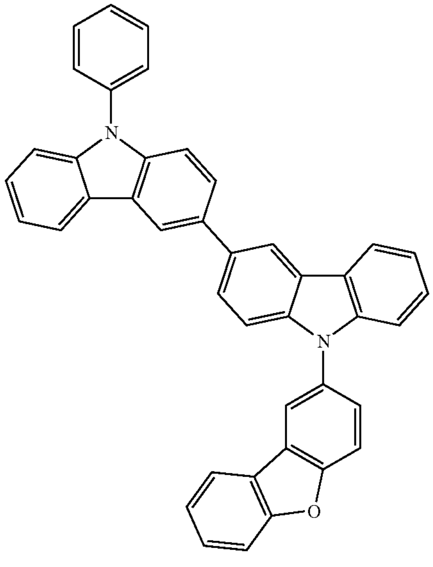
-continued
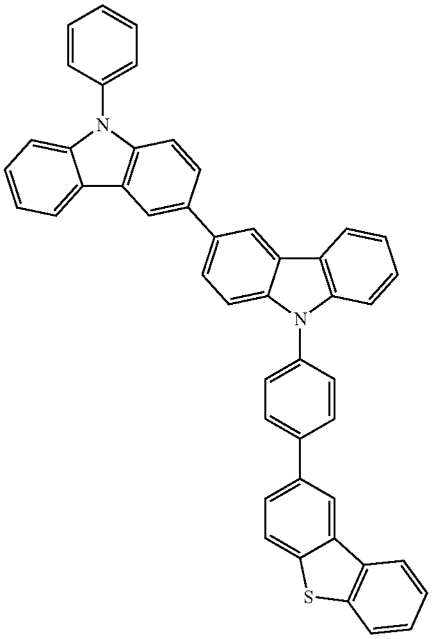
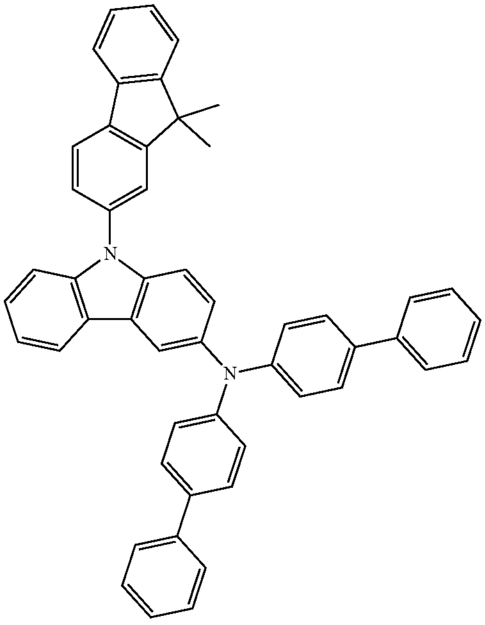

-continued
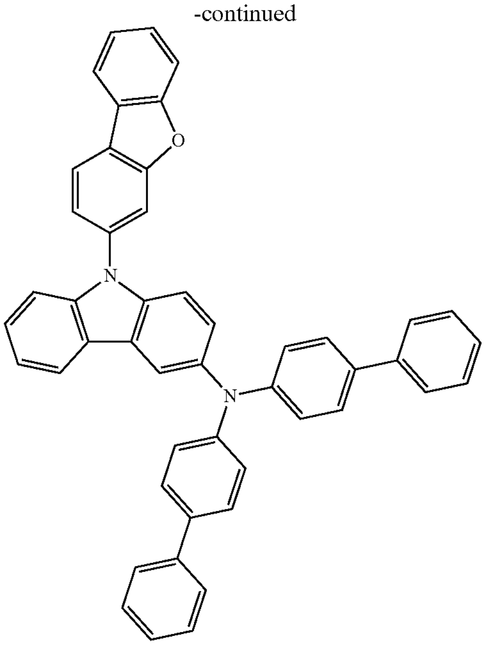
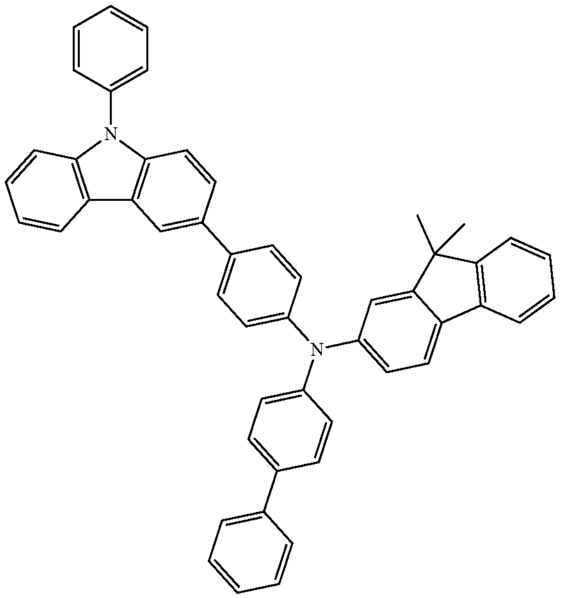
-continued
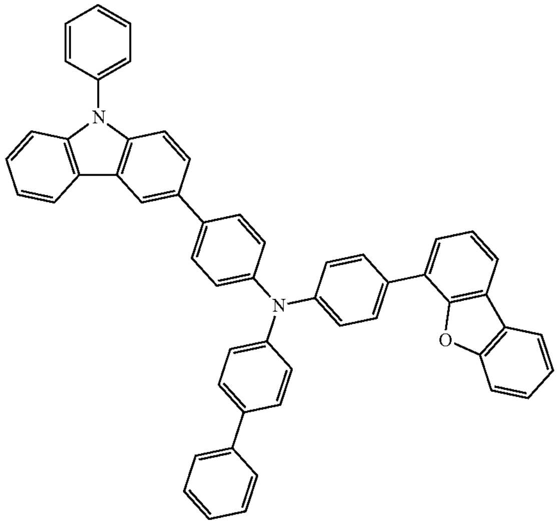
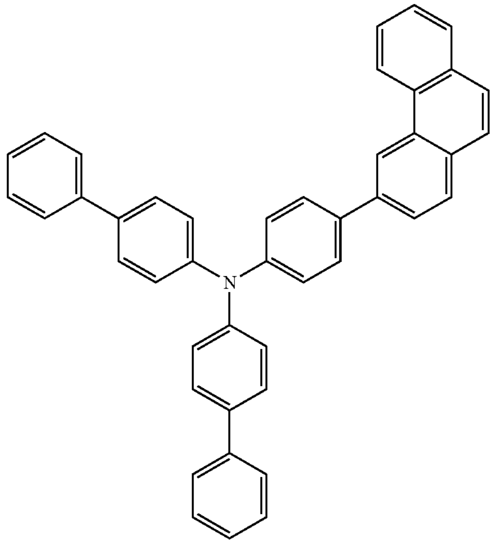
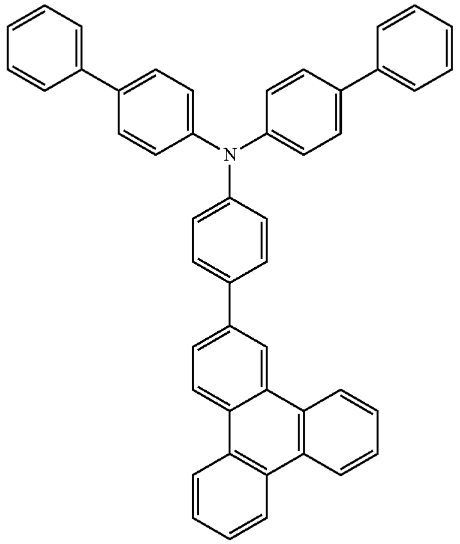

-continued
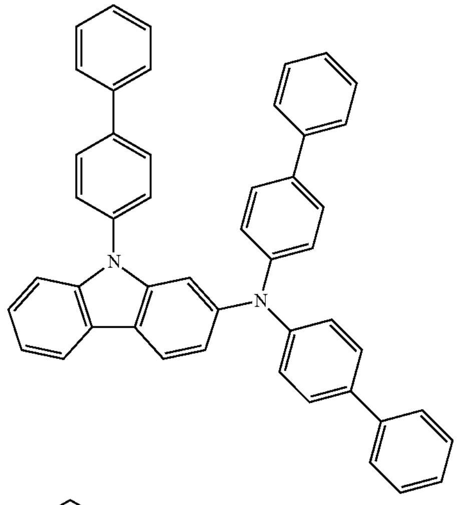
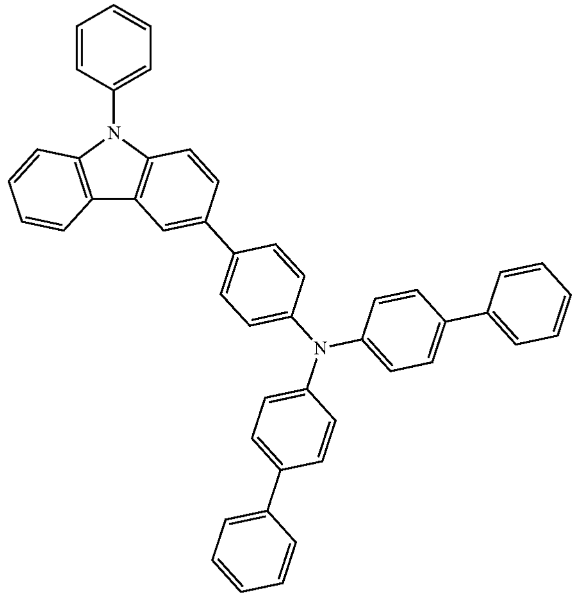
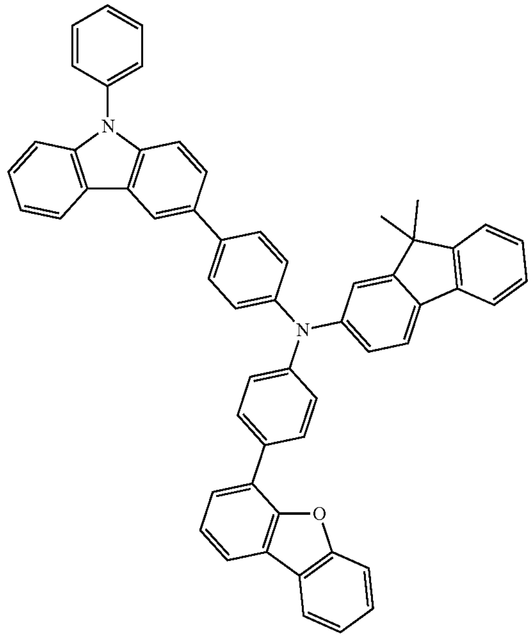
-continued
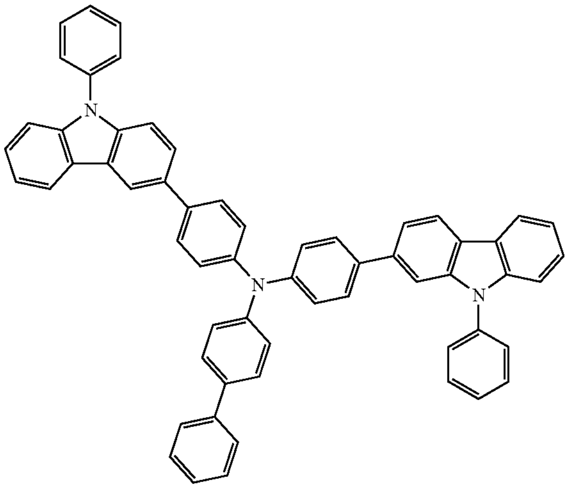
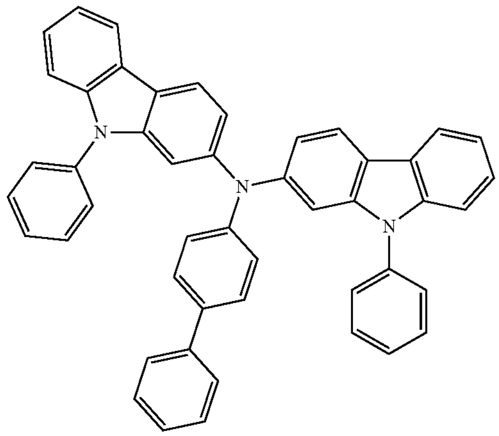
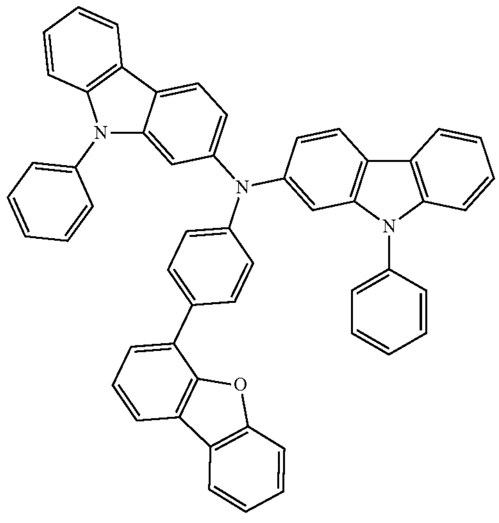

-continued
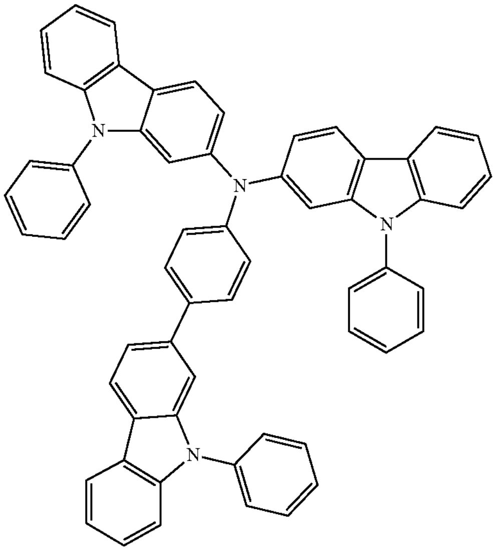
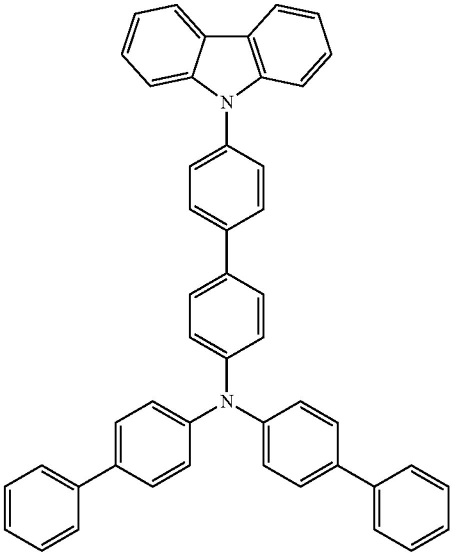
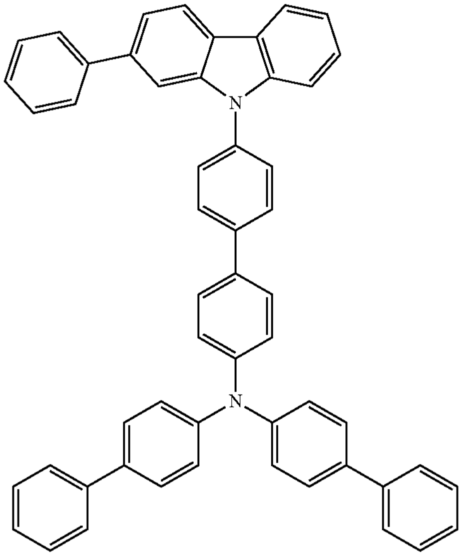
-continued
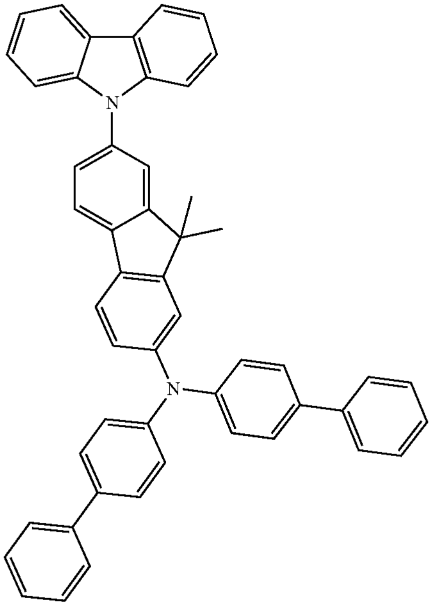
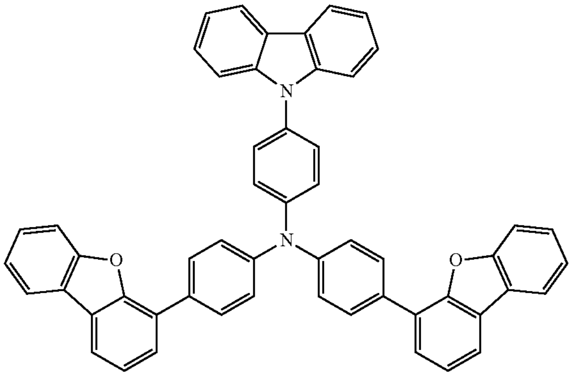
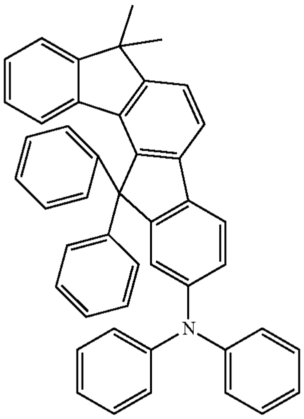

-continued
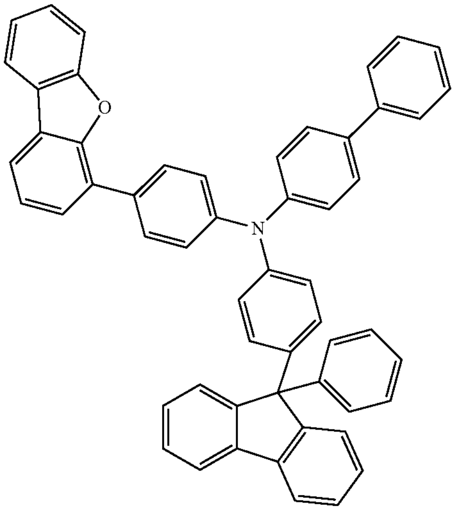
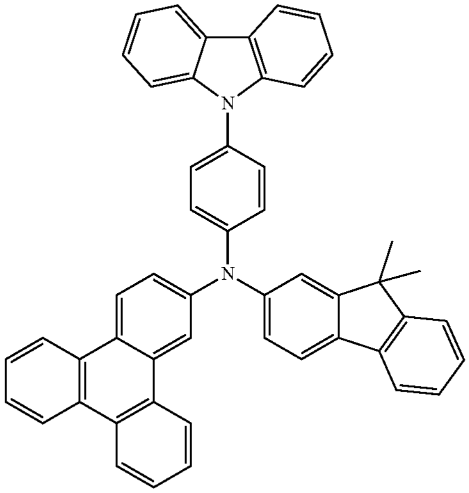
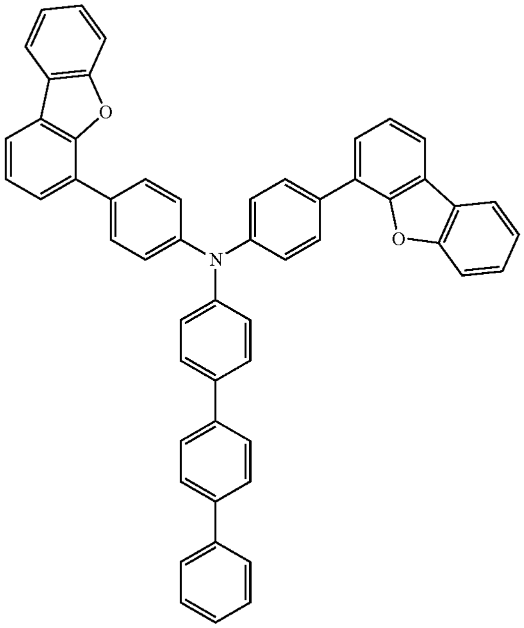
-continued
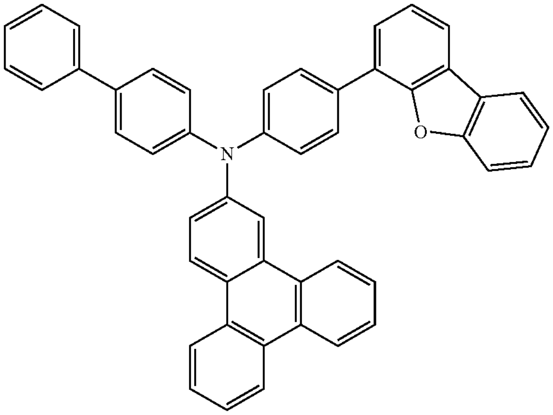
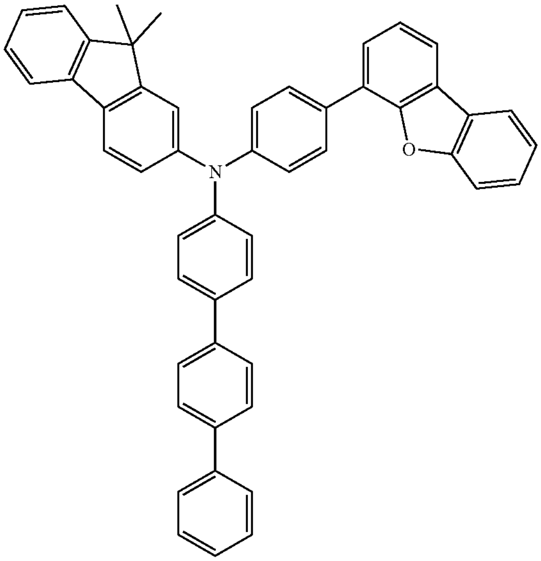
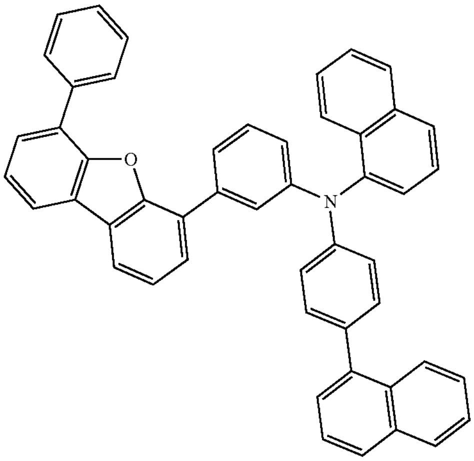

-continued
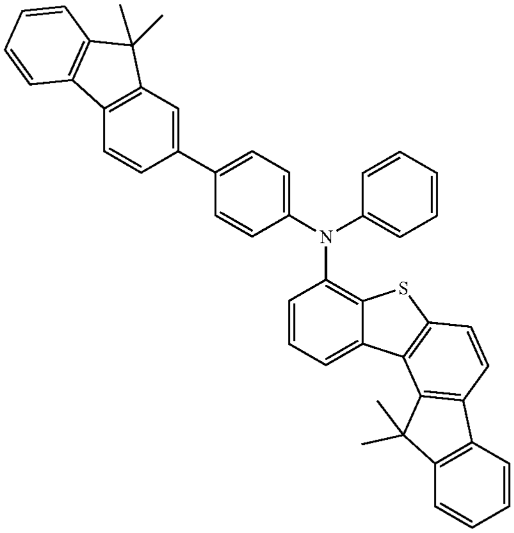
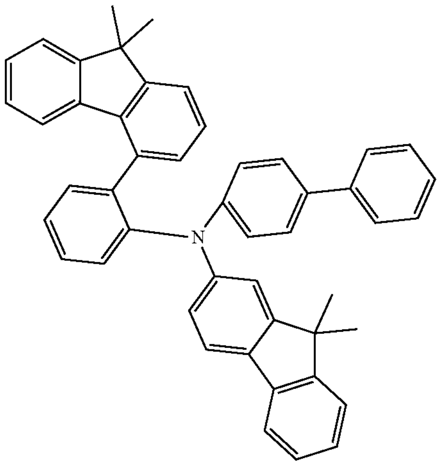
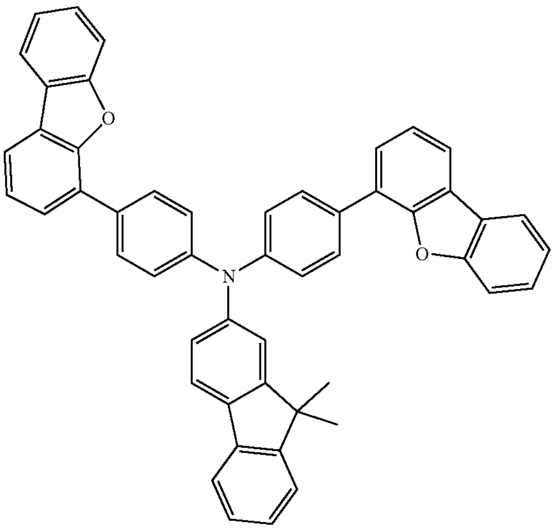
-continued
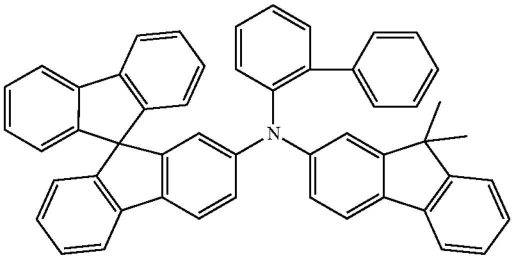
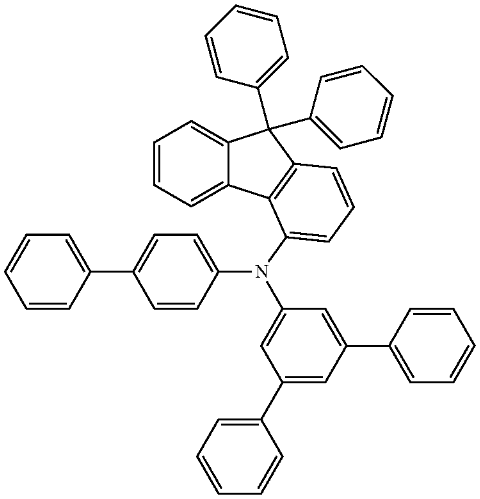
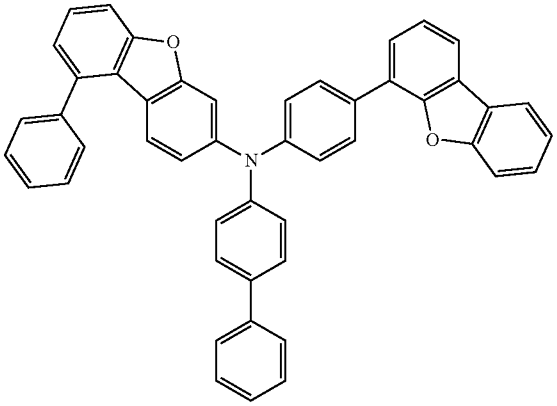
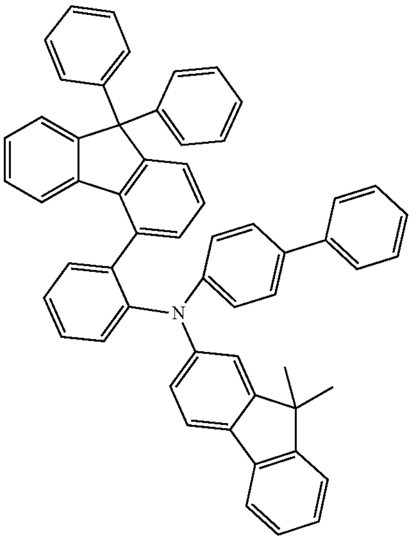

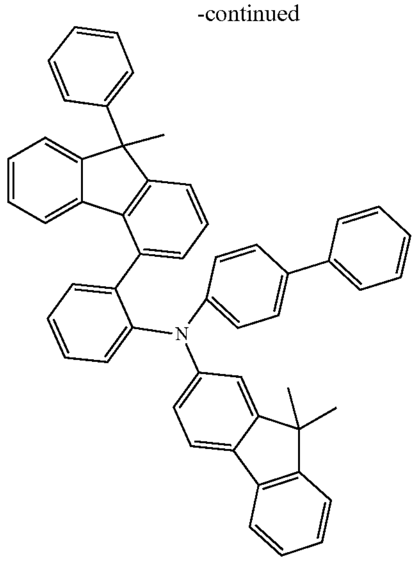
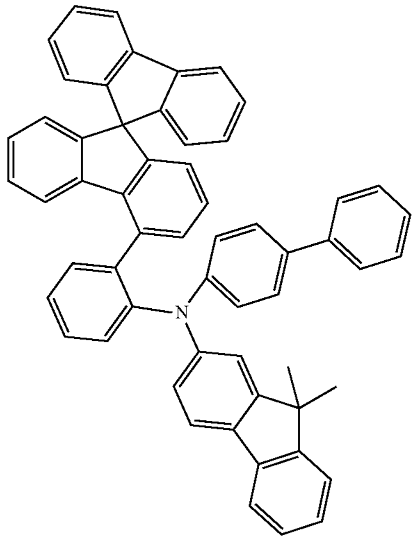
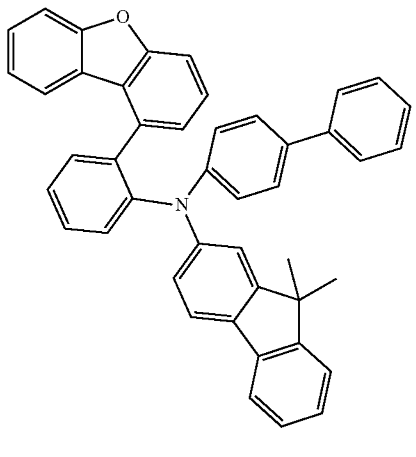
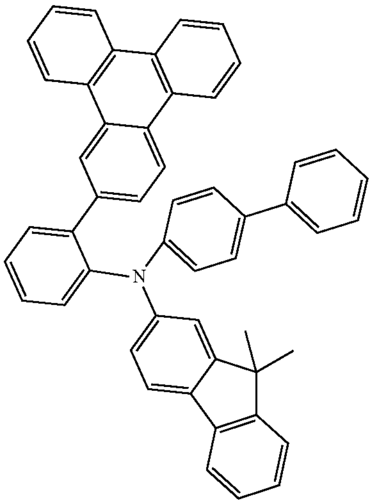
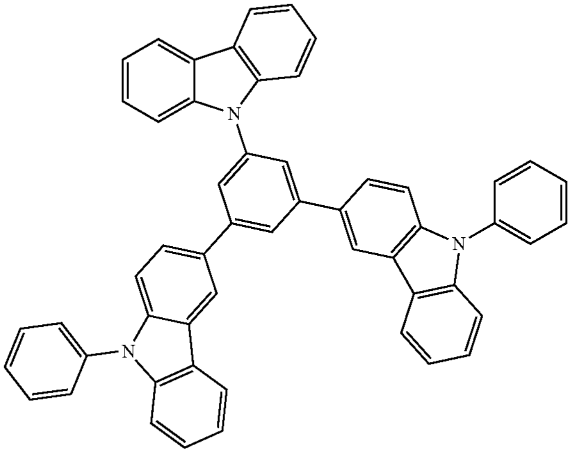
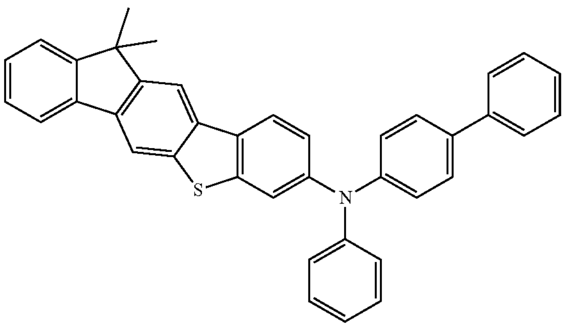

-continued
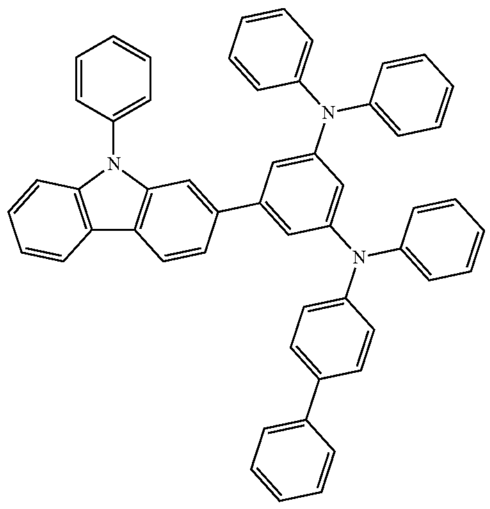
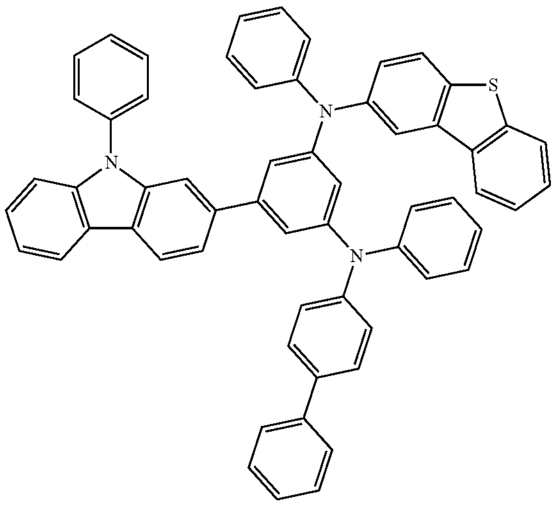
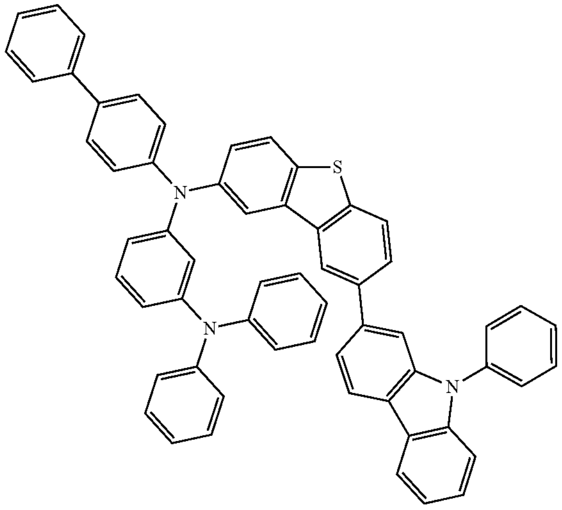
-continued
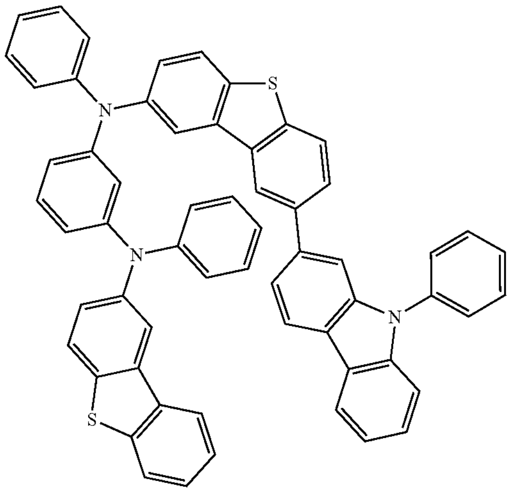
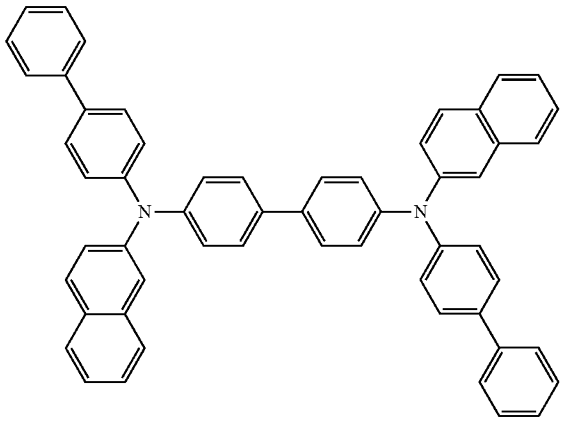
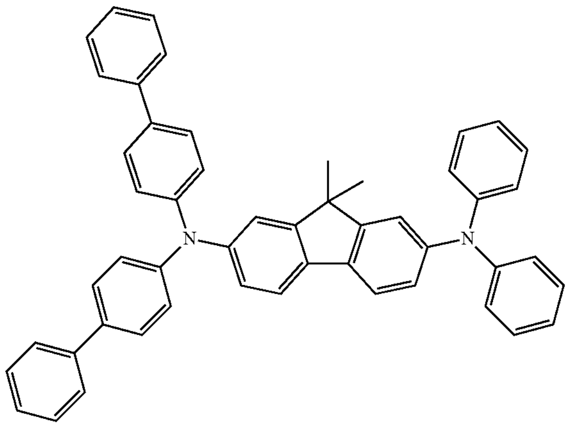

-continued
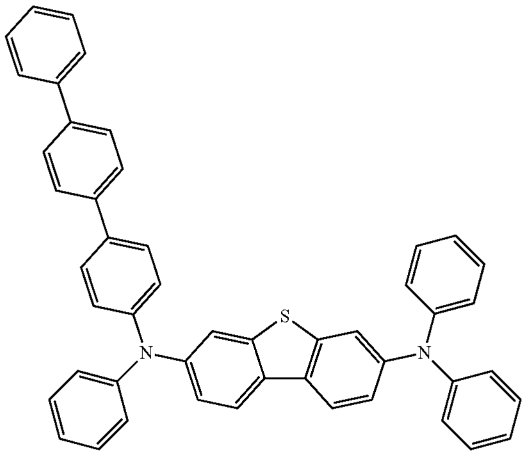
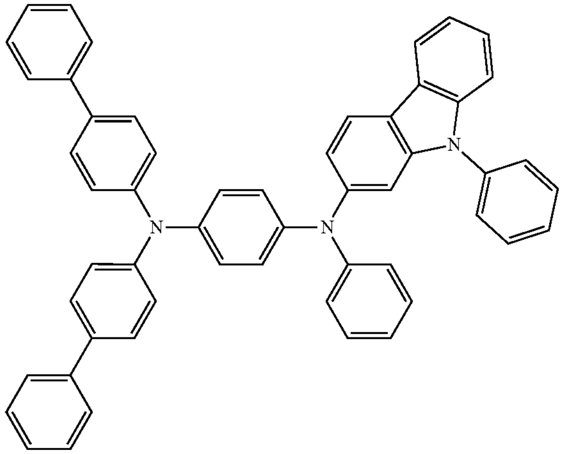
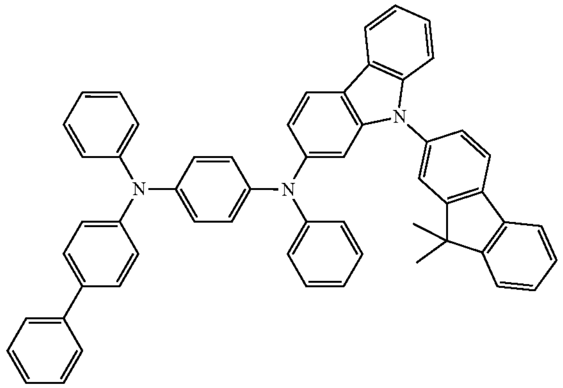
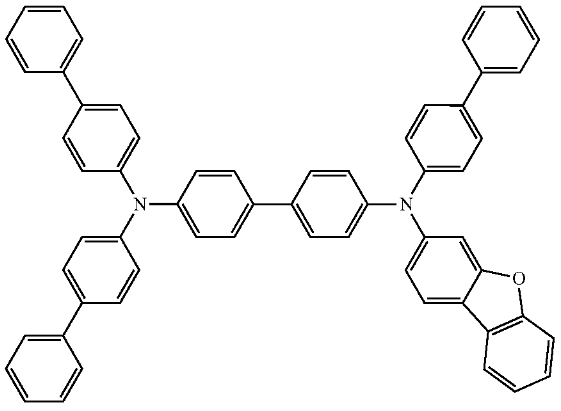
-continued
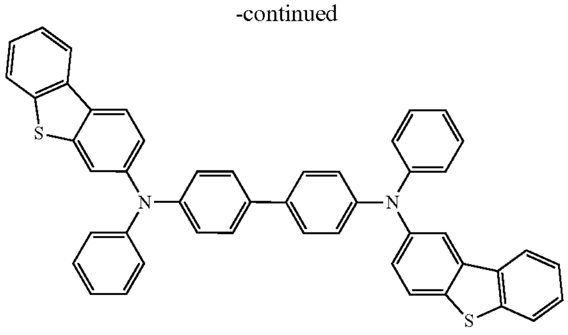
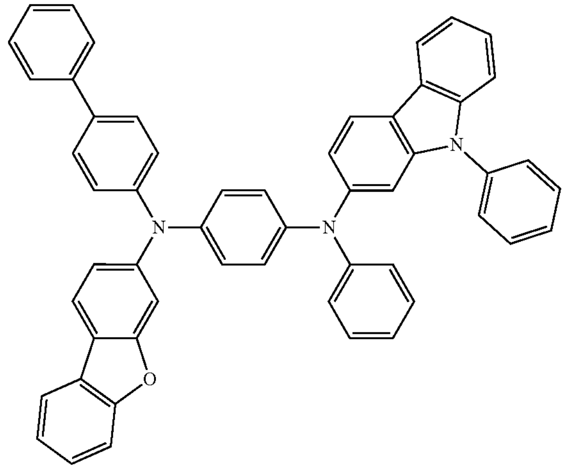
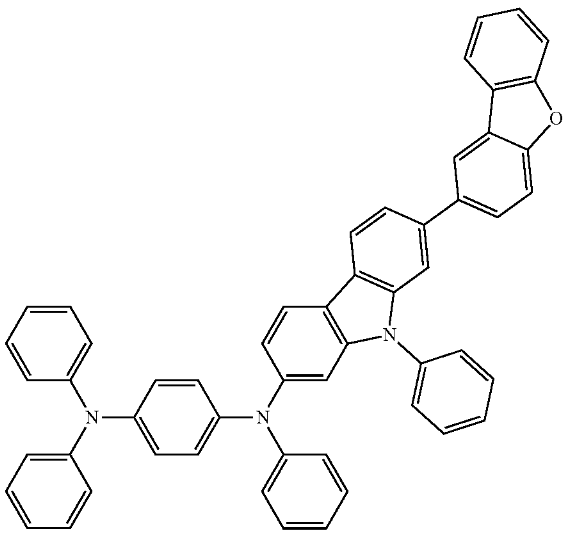

-continued
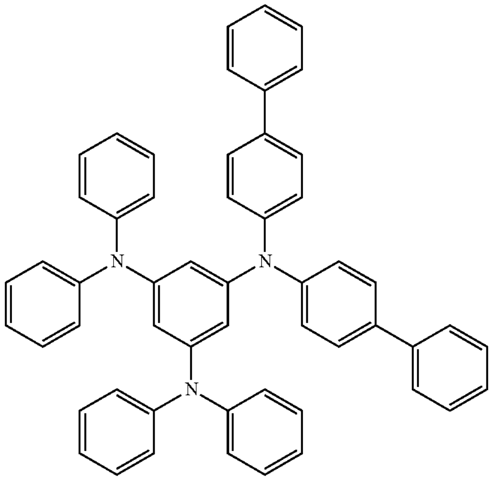
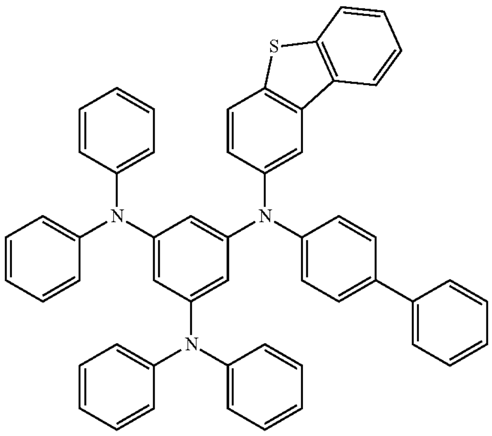
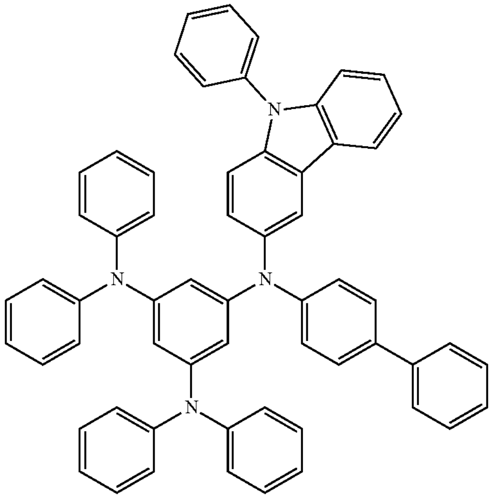
-continued
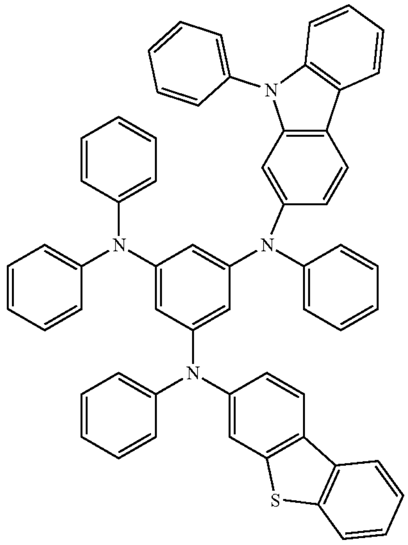
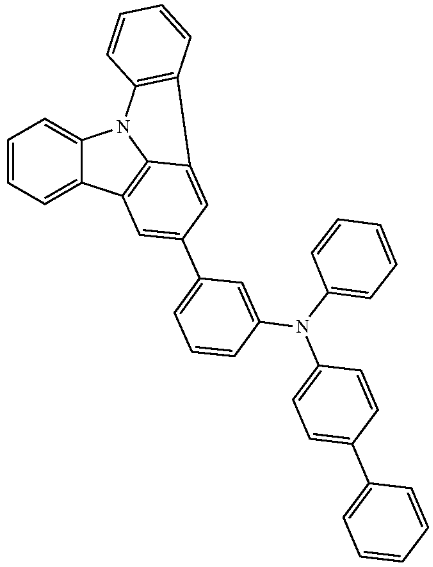
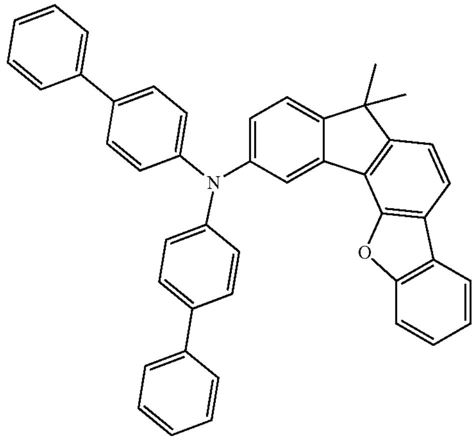

-continued
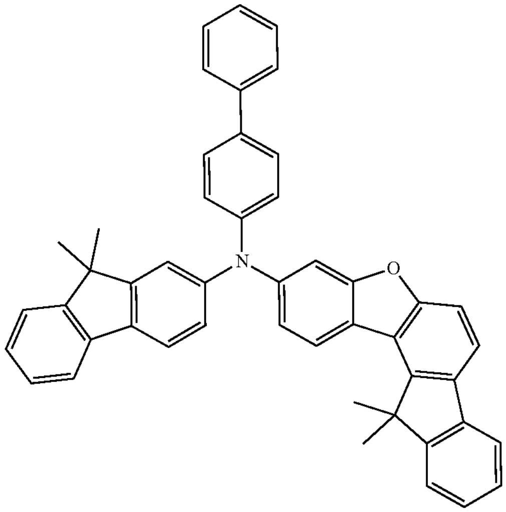
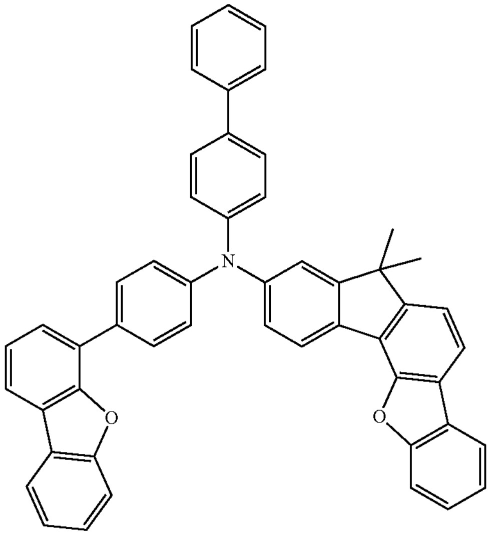
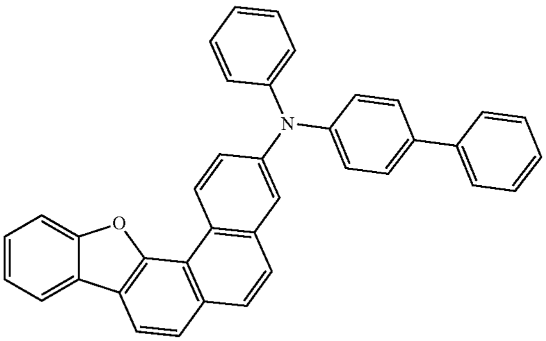
-continued
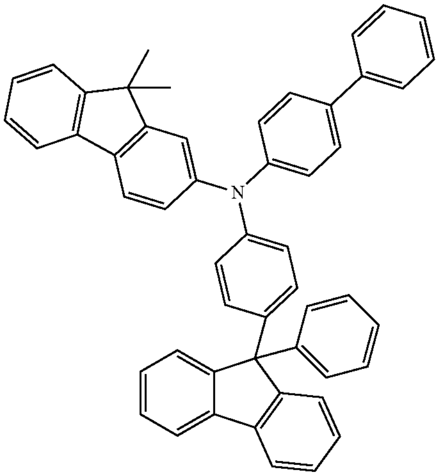
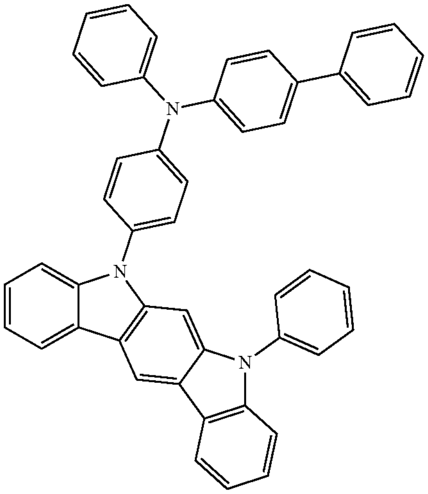
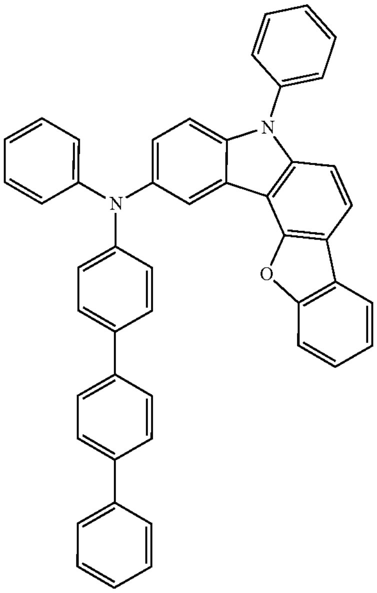

-continued
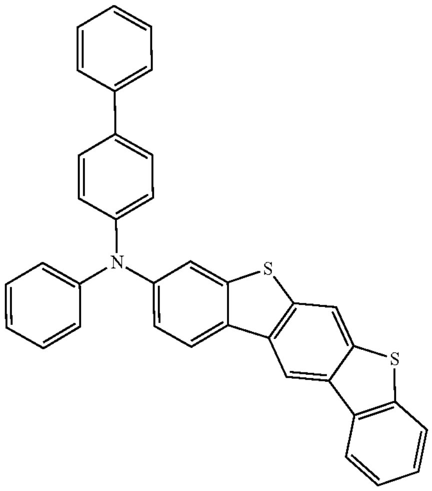
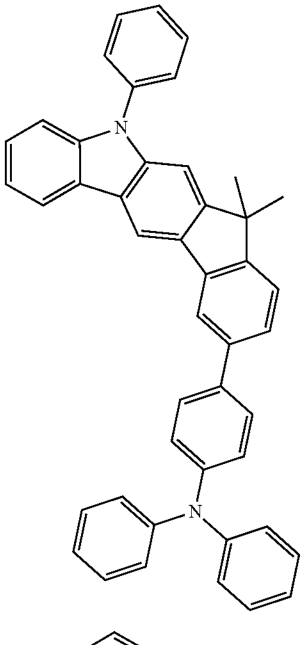
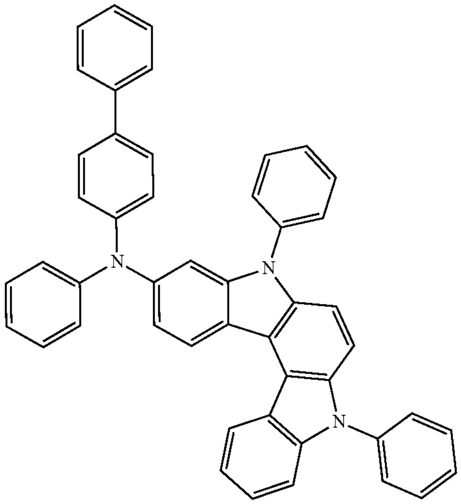
-continued
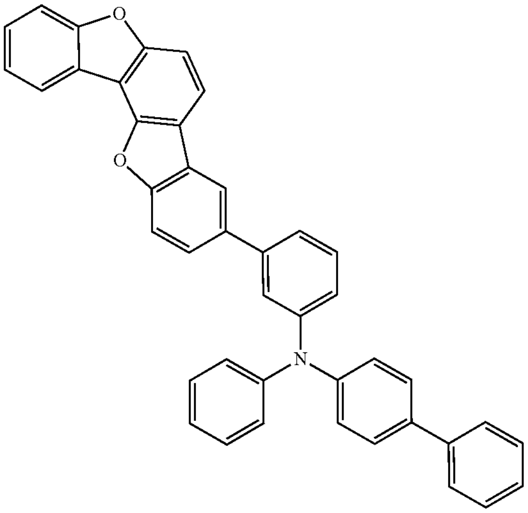
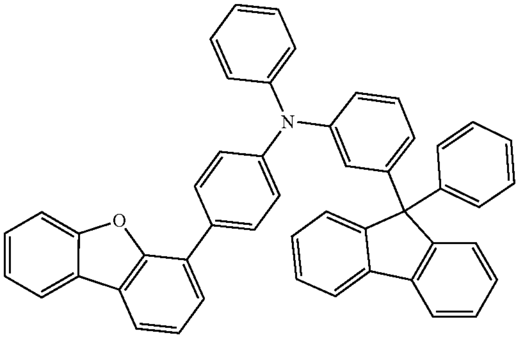
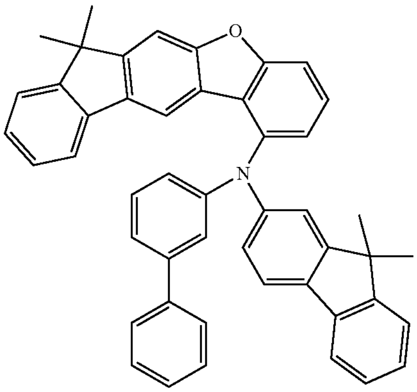
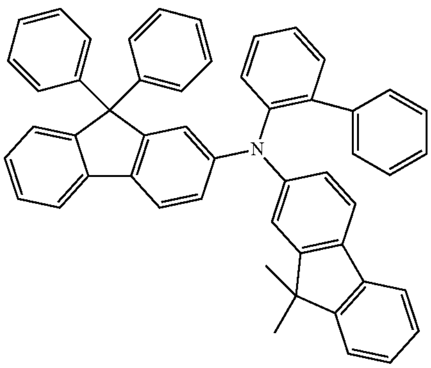

-continued
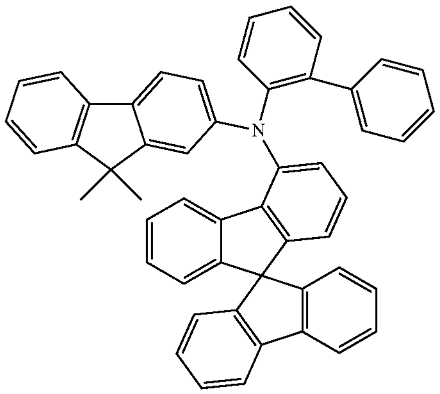
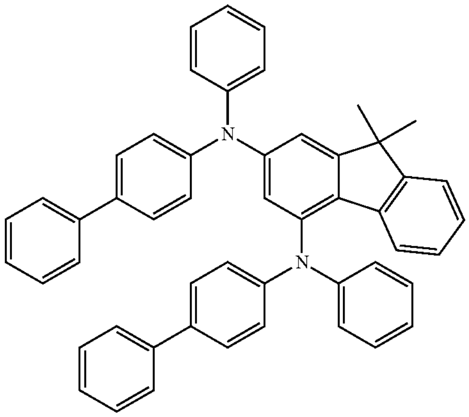
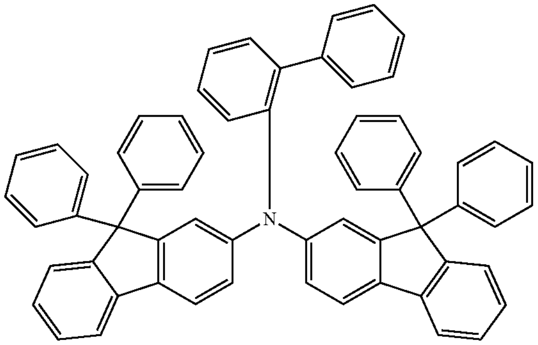
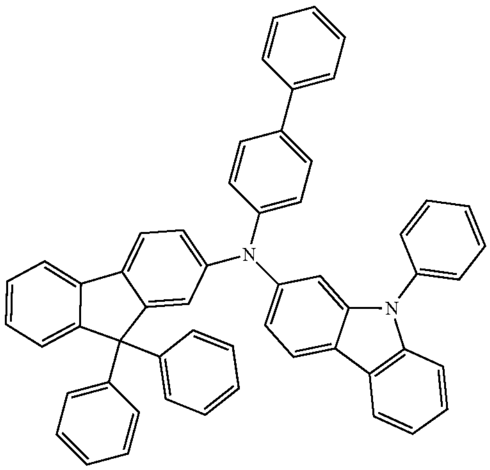
-continued
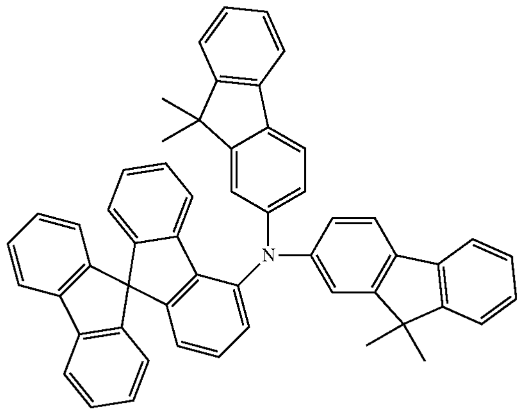
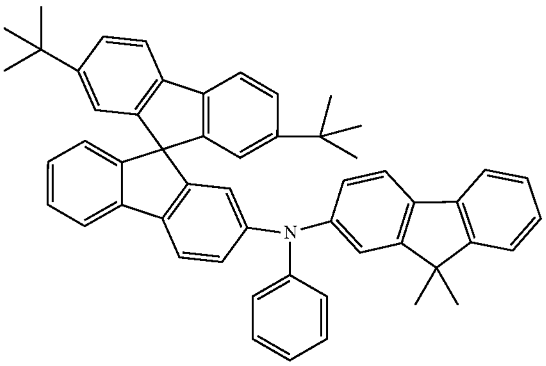
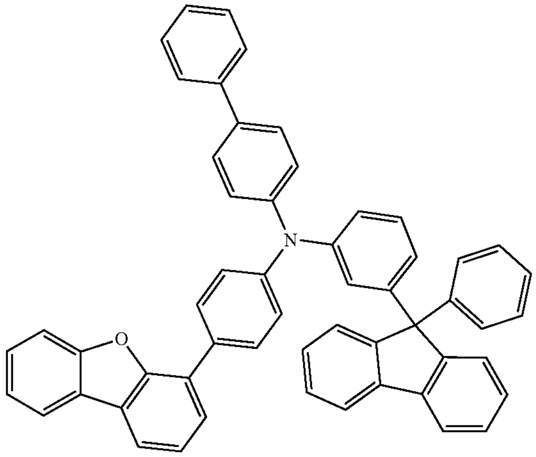
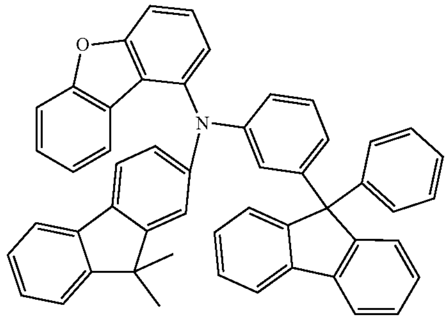

-continued
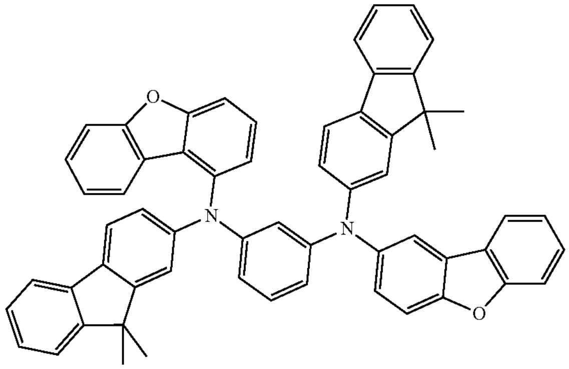
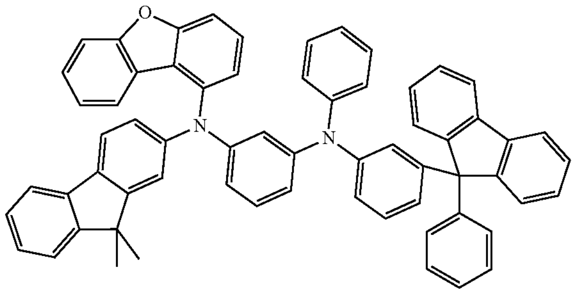
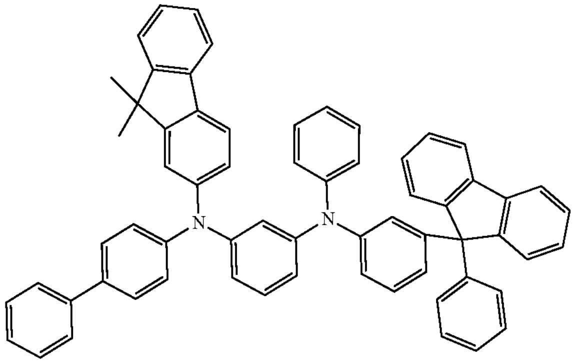
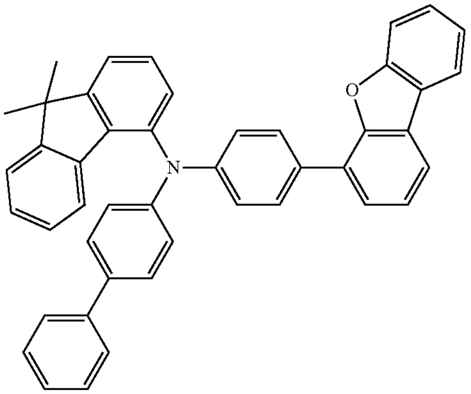
-continued
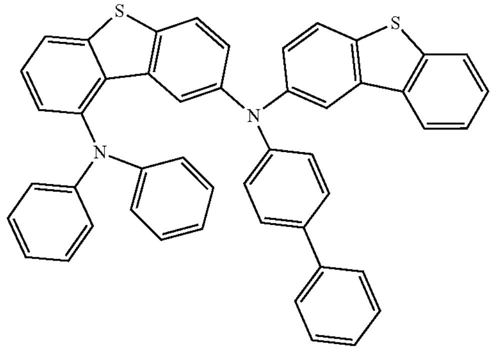
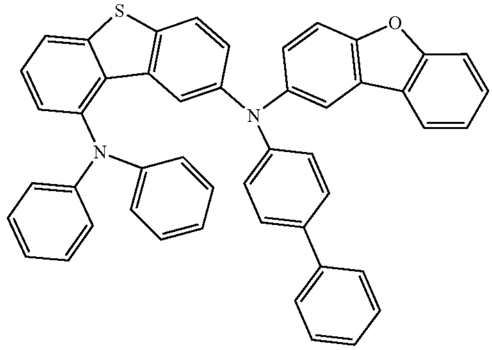
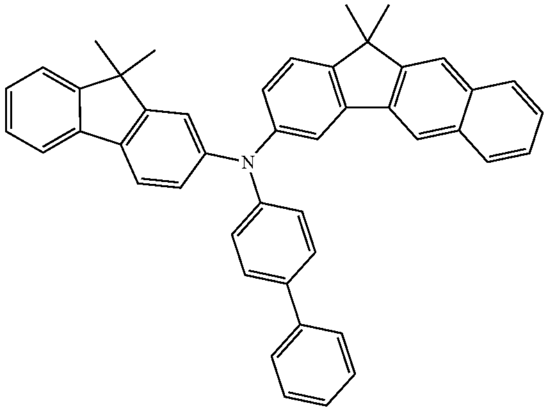
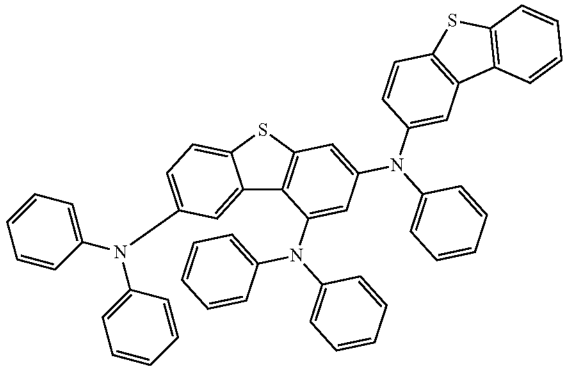

-continued

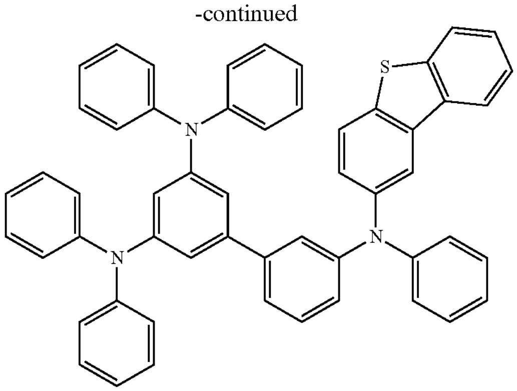

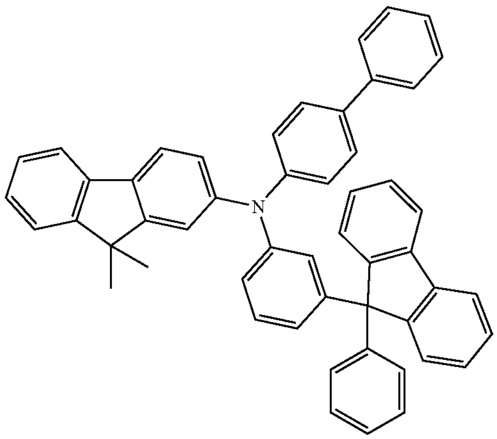

In the hole transport region 140, other suitable compounds may be used, in addition to the above compounds.

Also, the charge transport region may be, e.g., the electron transport region 150.

The electron transport region 150 may help further increase electron injection and/or electron mobility between the cathode 110 and the light emitting layer 130 and block holes.

In an implementation, the electron transport region 150 may include an electron transport layer between the cathode 110 and the light emitting layer 130, and an electron transport auxiliary layer between the light emitting layer 130 and the electron transport layer and a compound of Group C may be included in at least one layer of the electron transport layer and the electron transport auxiliary layer.

[Group C]

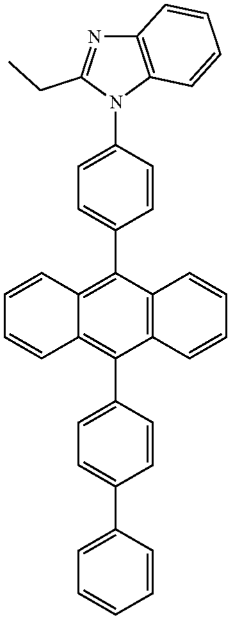

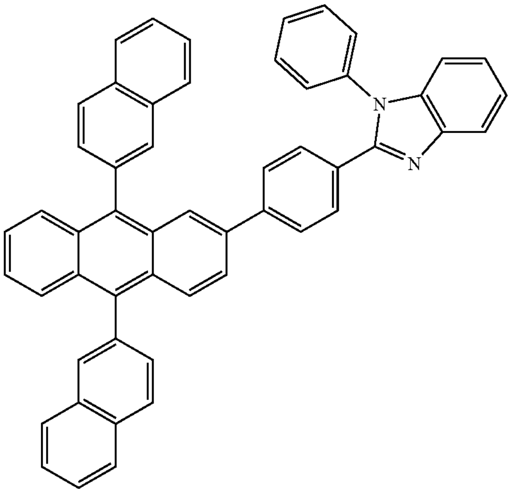

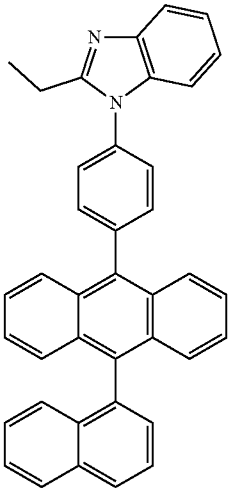

-continued
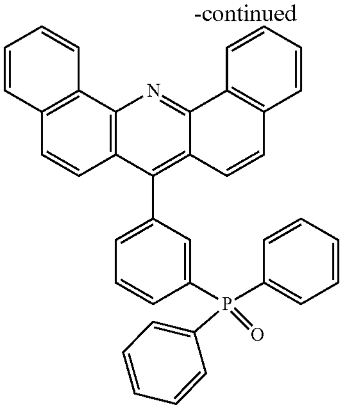
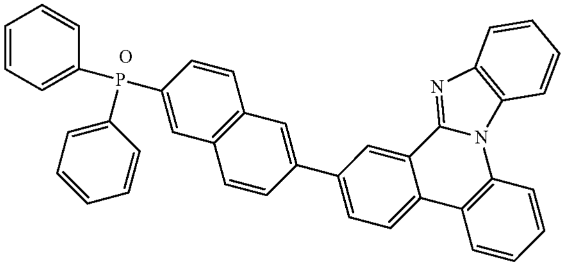
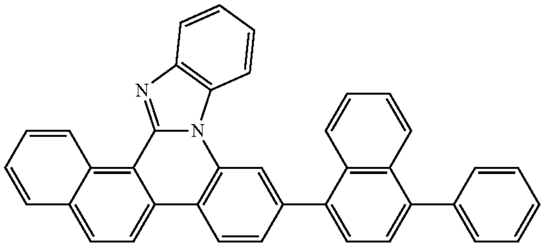
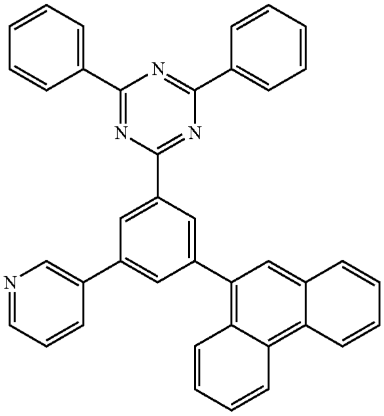
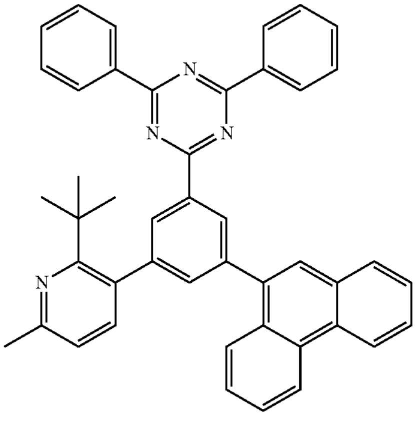
-continued
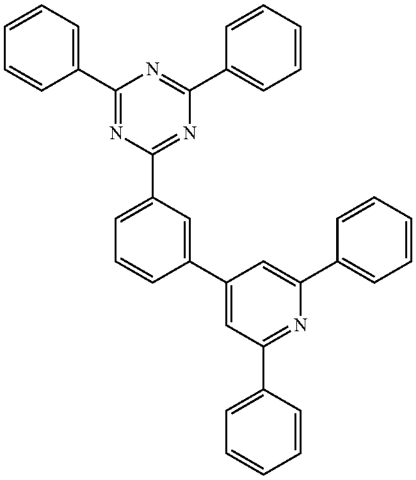
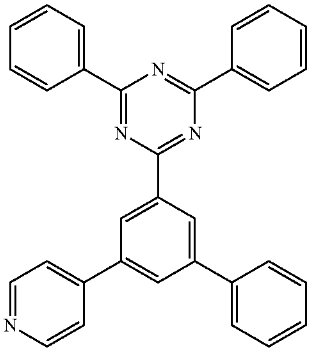
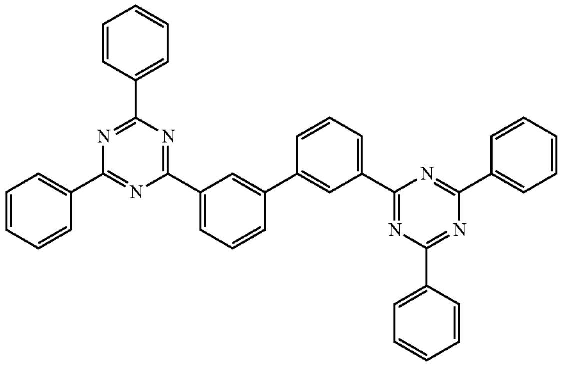
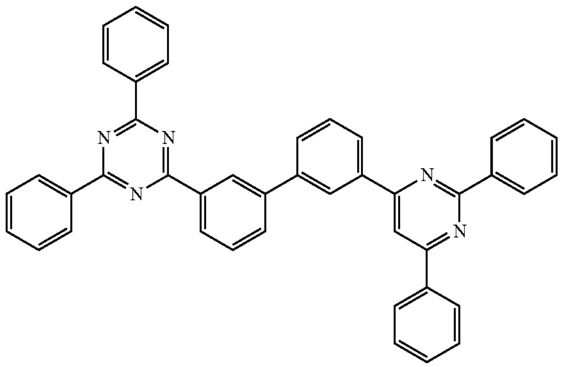

-continued
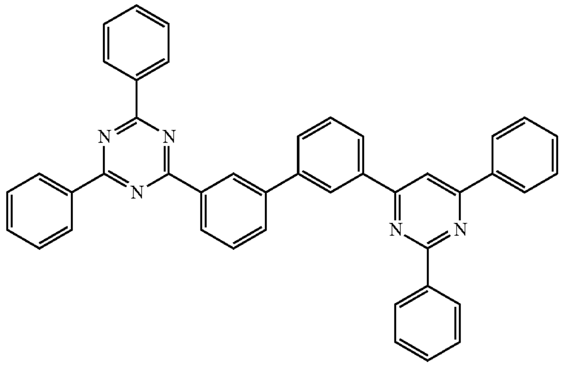
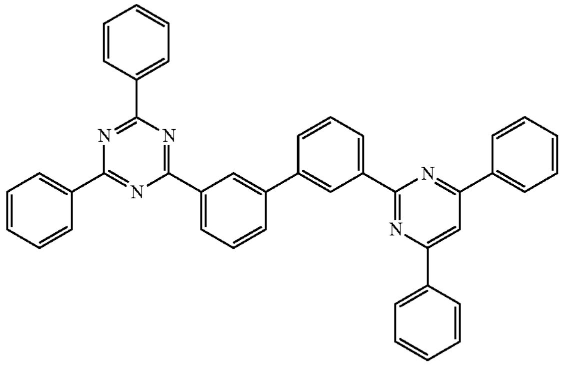
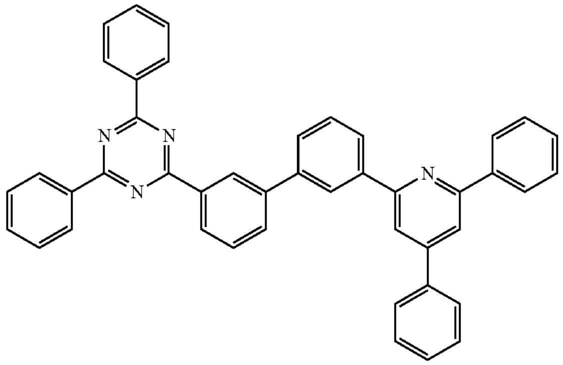
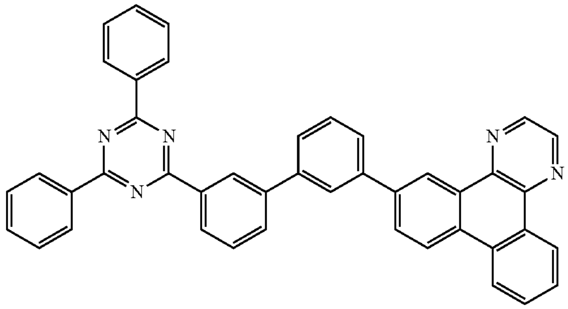
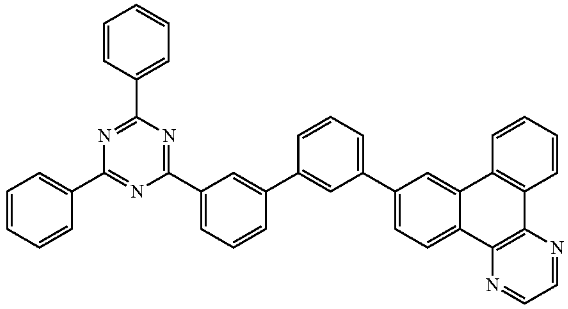
-continued
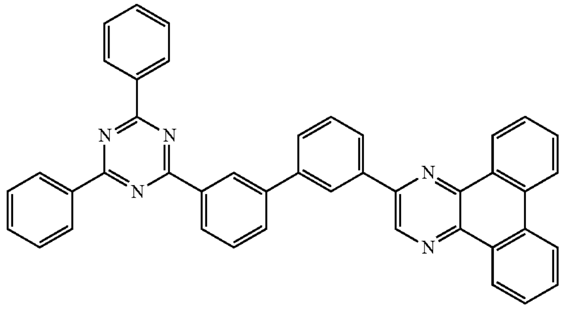
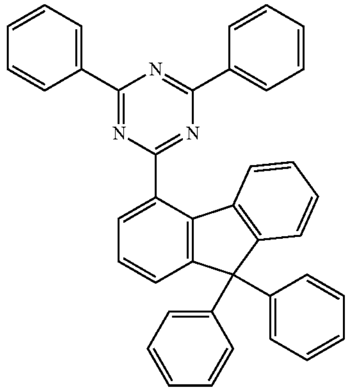
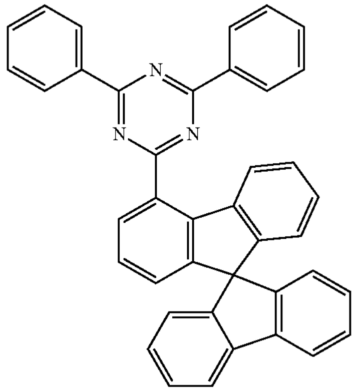
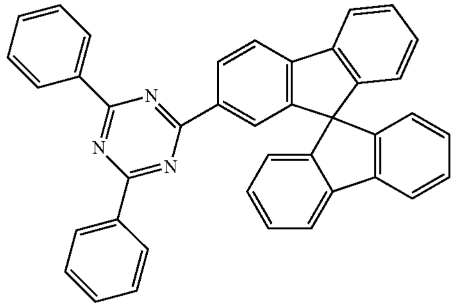

-continued
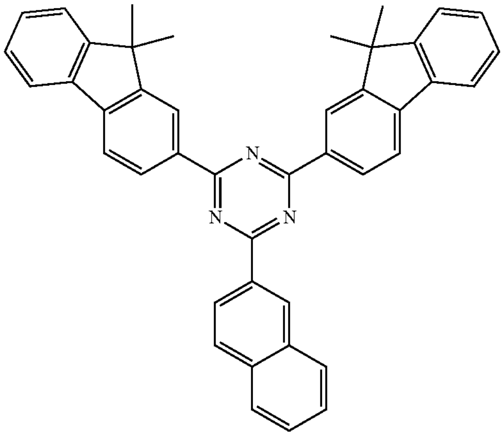
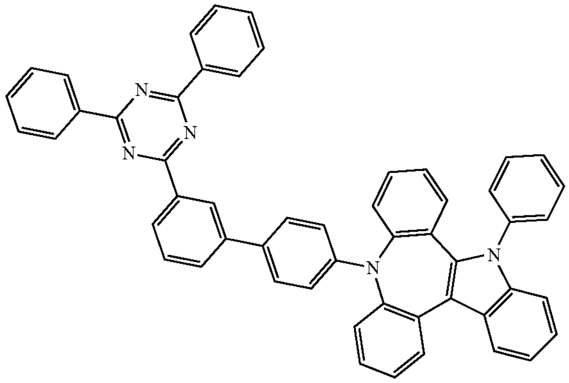
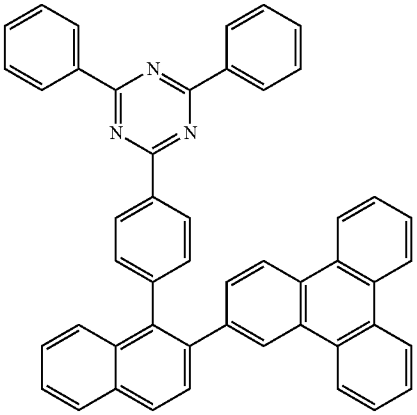
-continued
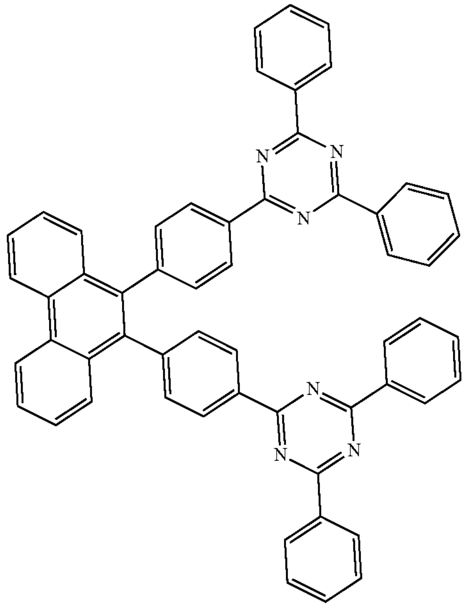
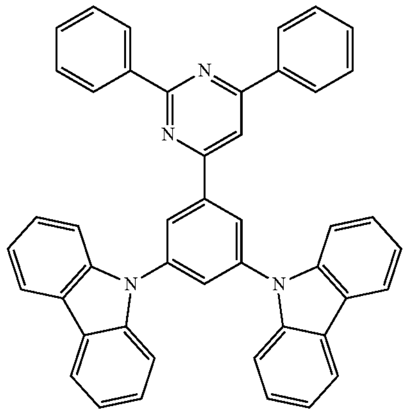
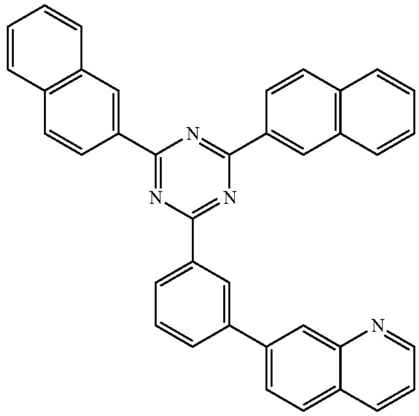
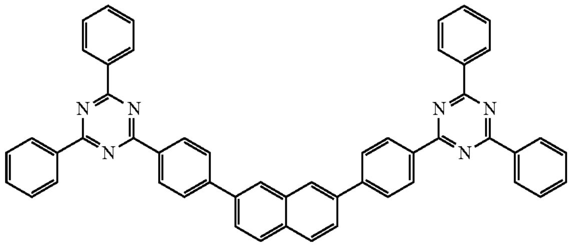

-continued
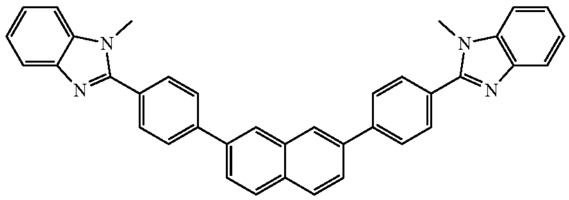
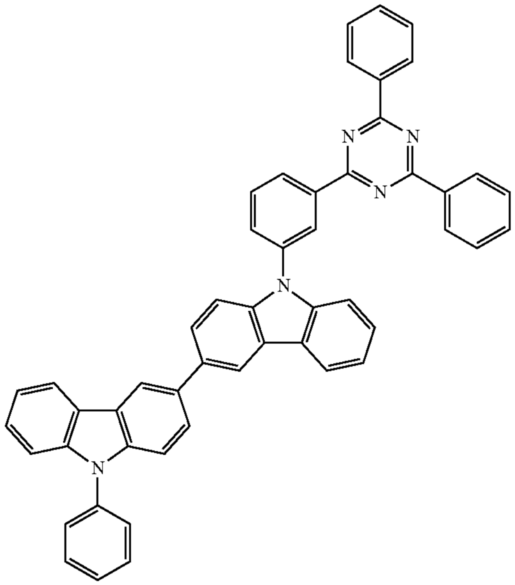
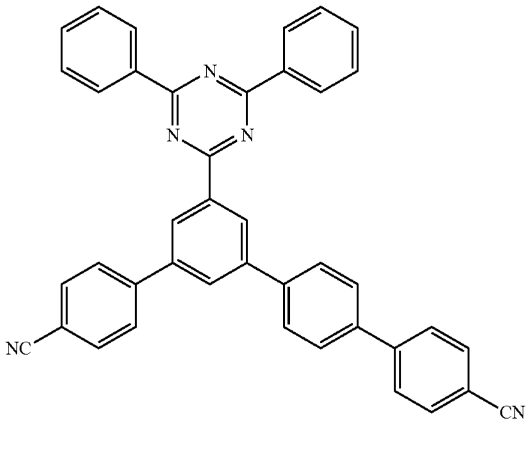
-continued
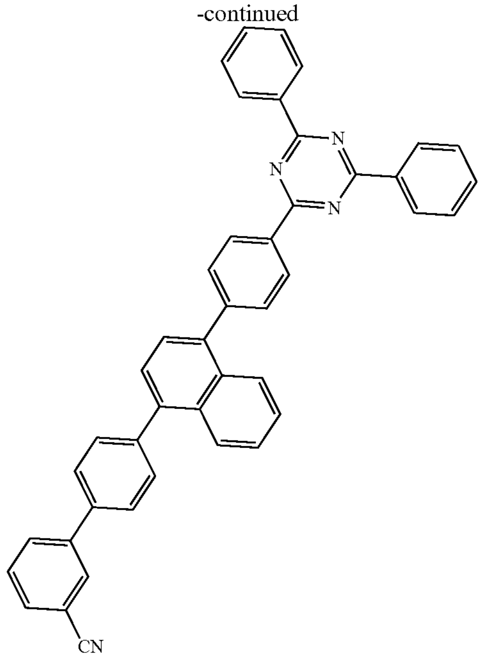
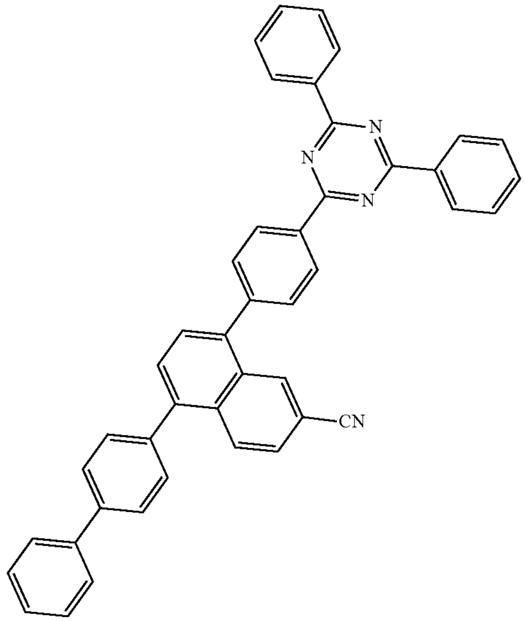

-continued
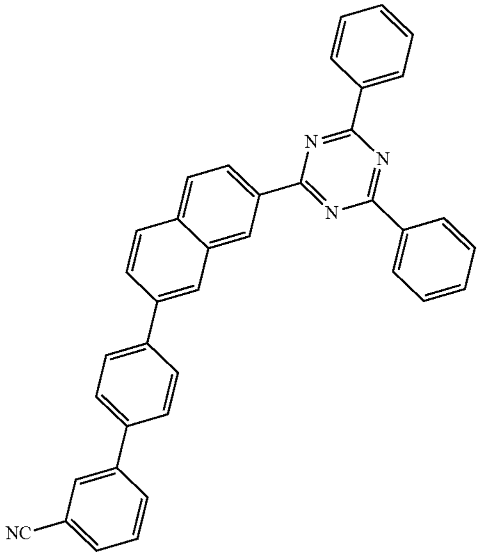
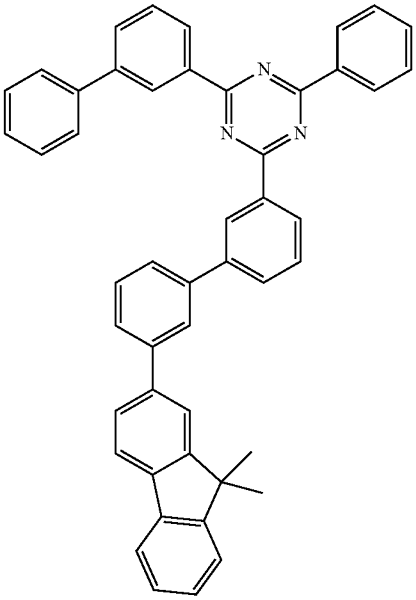
-continued
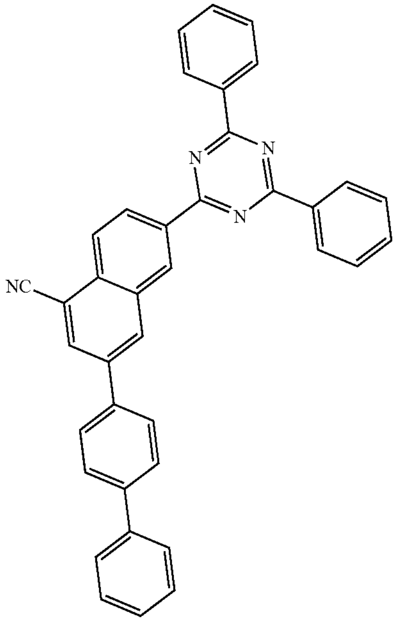
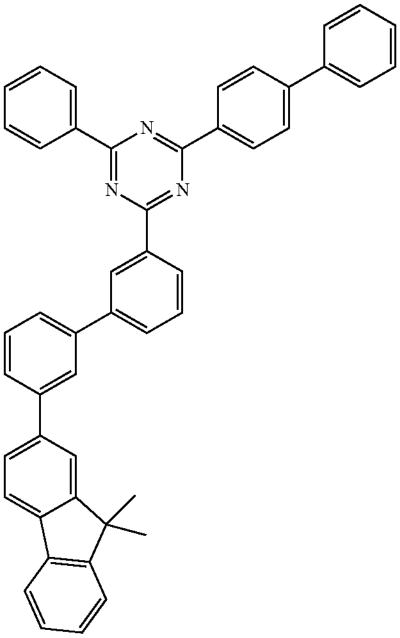

-continued
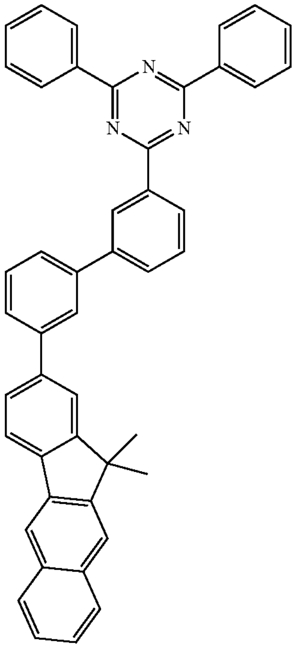
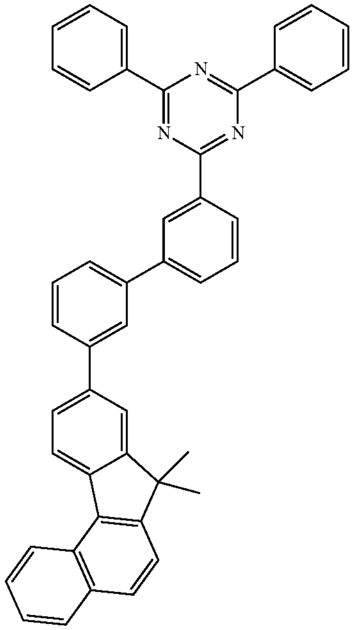
-continued
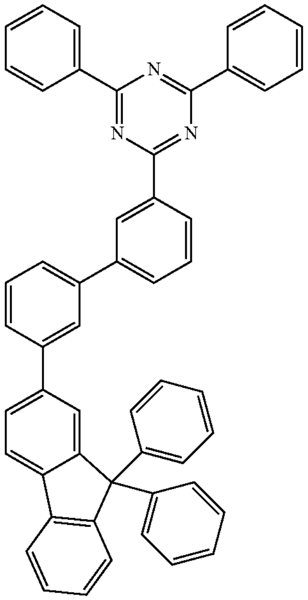
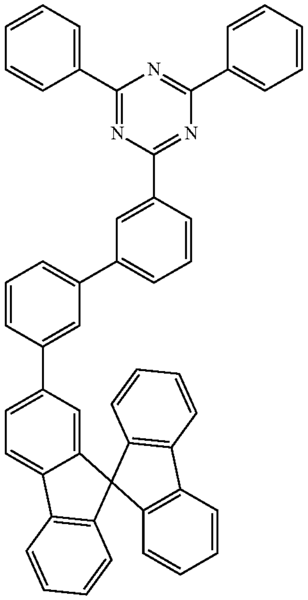
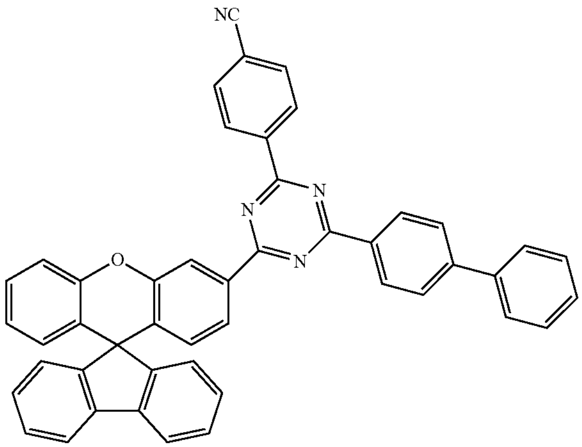

-continued
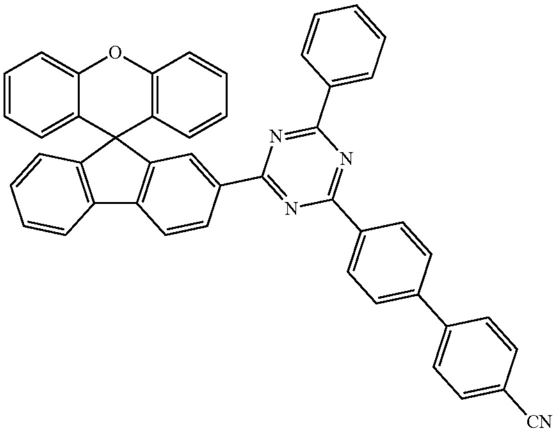
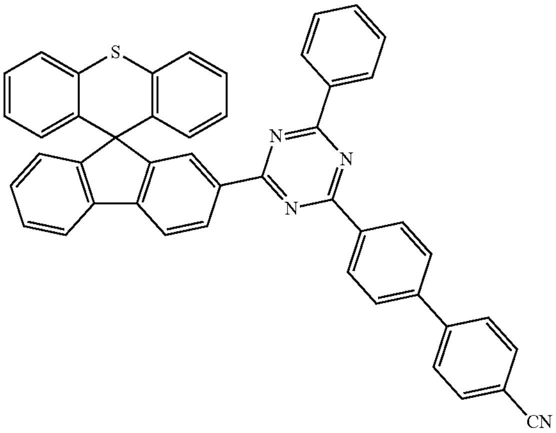
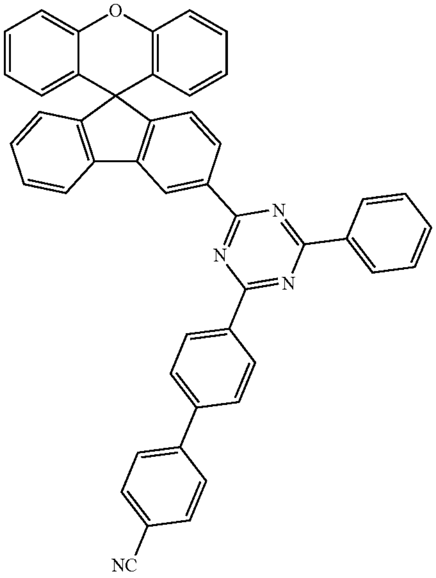
-continued
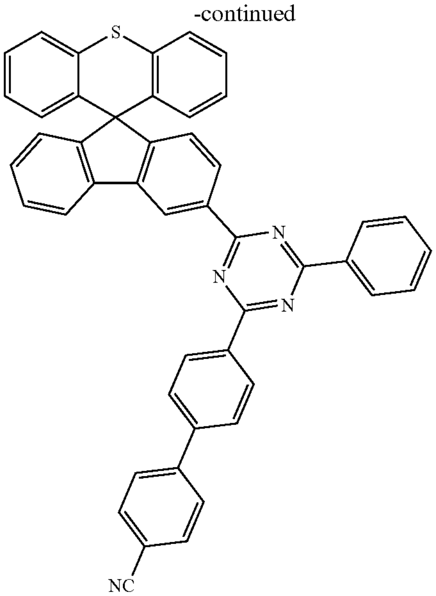
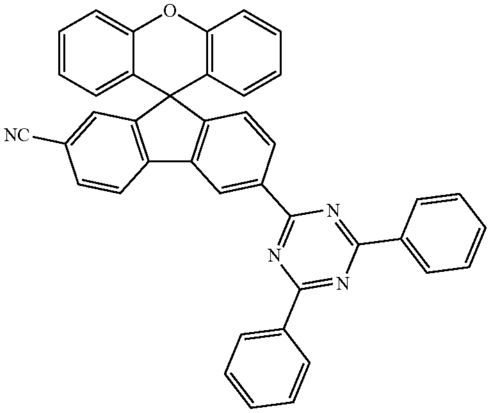
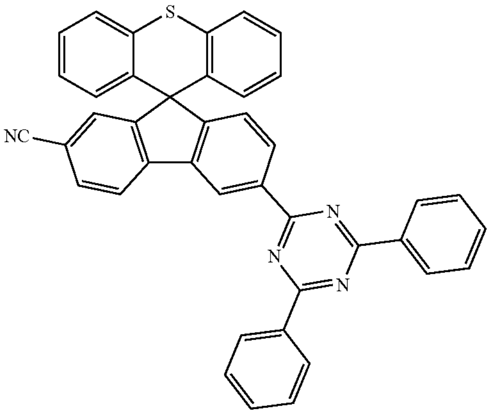

-continued
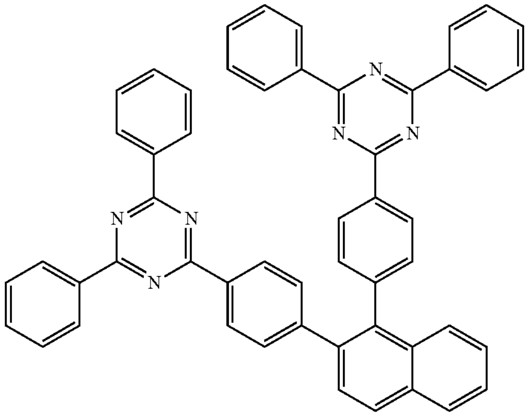
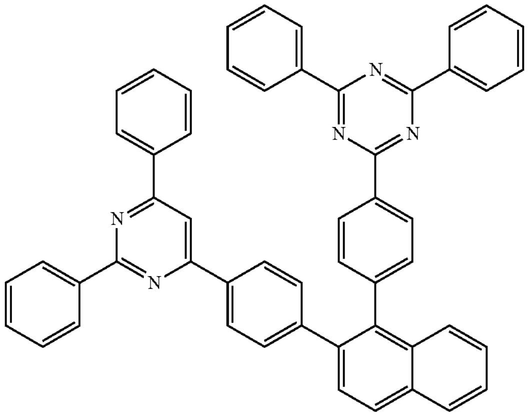
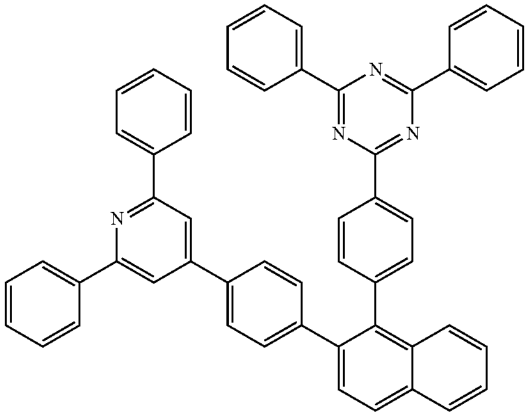
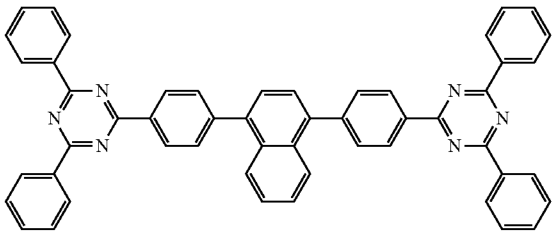
-continued
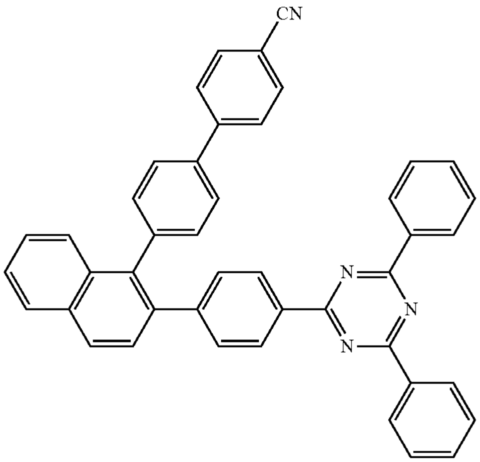
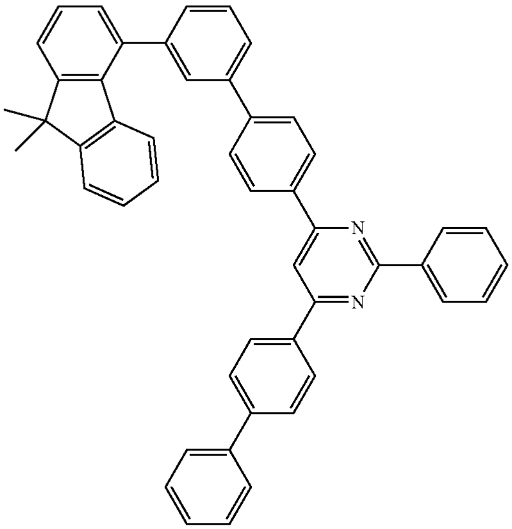
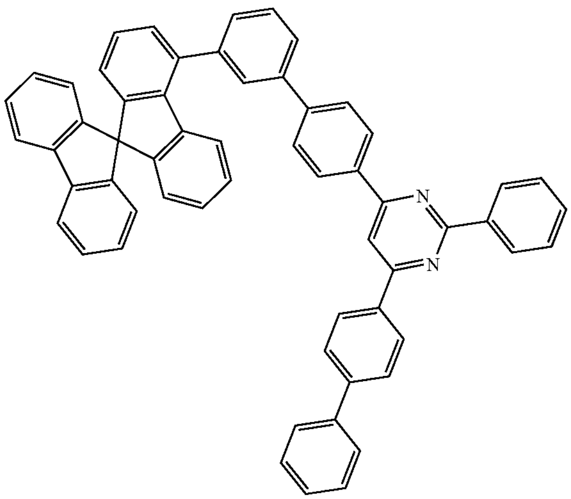

-continued

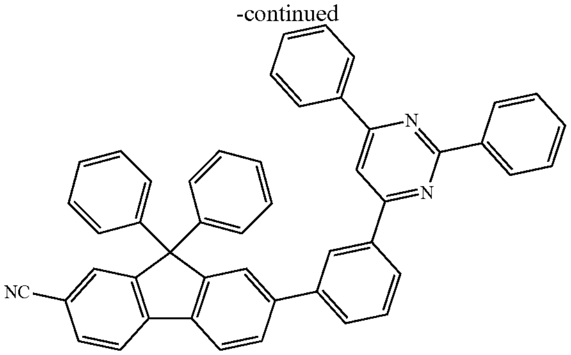

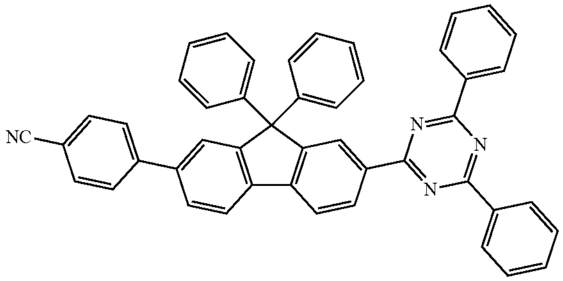

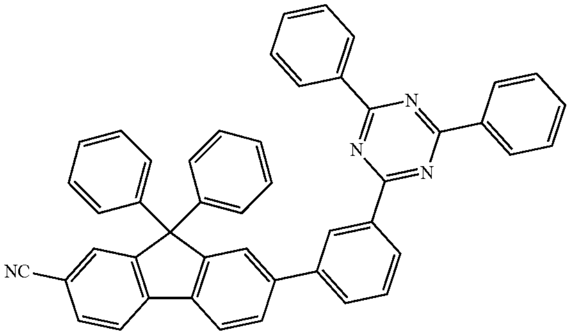

An embodiment may provide an organic light emitting diode including a light emitting layer as an organic layer.

Another embodiment may provide an organic light emitting diode including a light emitting layer and a hole transport region as an organic layer.

Another embodiment may provide an organic light emitting diode including a light emitting layer and an electron transport region as an organic layer.

The organic light emitting diode according to an embodiment of the present invention may include a hole transport region 140 and an electron transport region 150 in addition to the light emitting layer 130 as the organic layer 105, as shown in the FIGURE.

In an implementation, the organic light emitting diode may further include an electron injection layer, a hole injection layer, or the like, in addition to the light emitting layer as the aforementioned organic layer.

The organic light emitting diode 100 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

Hereinafter, the embodiments are illustrated in more detail with reference to examples. However, these examples are exemplary, and the present scope is not limited thereto.

Hereinafter, starting materials and reactants used in examples and synthesis examples were purchased from Sigma-Aldrich Co. Ltd., TCI Inc., Tokyo Chemical Industry, or P&H Tech, as far as there in no particular comment or were synthesized by suitable methods.

(Preparation of Compounds for Organic Optoelectronic Device)

Compounds were synthesized through the following steps.

Synthesis Example 1: Synthesis of Compound 1

[Reaction Scheme 1]

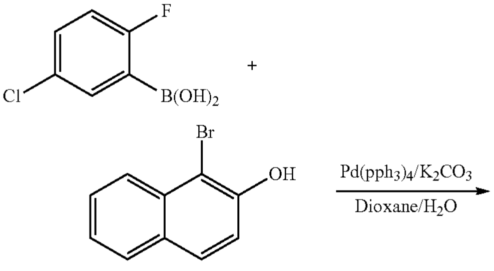

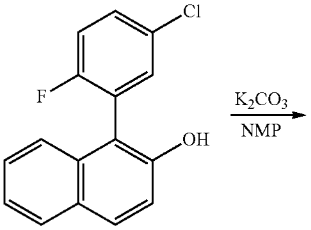

A-1

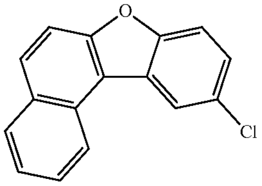

A-2

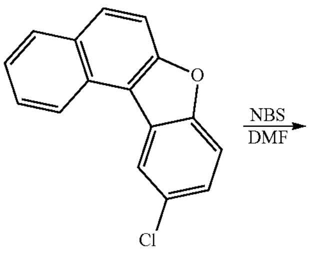

A-2

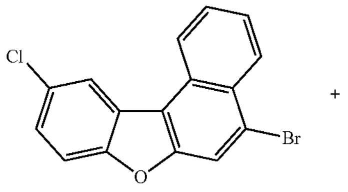

A-3

-continued

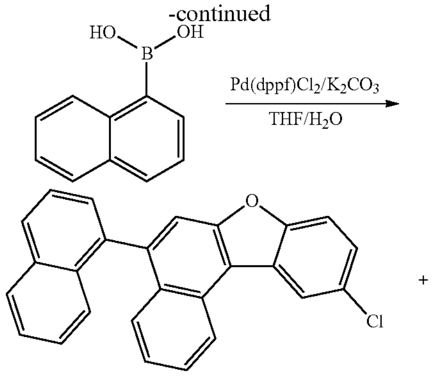

A-4

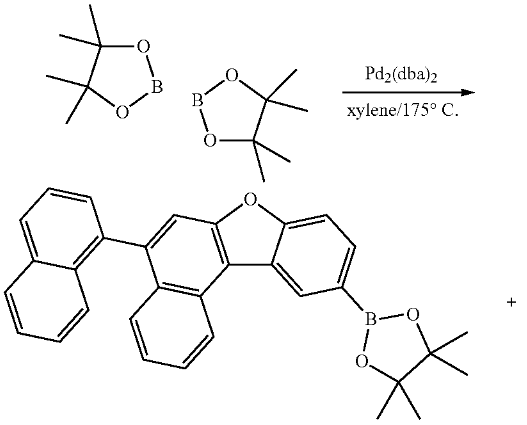

A

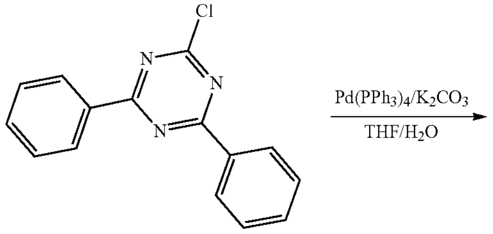

Int-1

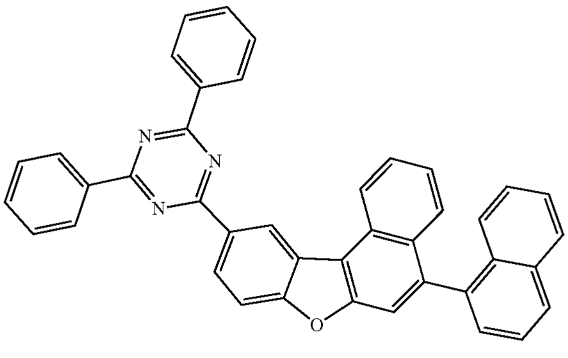

1

1st Step: Synthesis of Intermediate A-1

(5-chloro-2-fluorophenyl)boronic acid (30.0 g, 134.49 mmol), 1-bromonaphthalen-2-ol (28.14 g, 161.38 mmol), $Pd(PPh_3)_4$ (7.77 g, 6.72 mmol), and $K_2CO_3$ (55.76 g, 403.46 mmol) were dissolved in dioxane (300 ml) and $H_2O$ (150 ml) and then, heated under reflux under a nitrogen atmosphere. After 12 hours, the reaction solution was cooled, and after removing an aqueous layer, the solvents were removed with a rotary evaporator and then, extracted with methylene chloride. An organic layer obtained therefrom was columned with hexane:EA=4:1 (v/v), obtaining 15.0 g (Yield: 41%) of Intermediate A-1.

2nd Step: Synthesis of Intermediate A-2

Intermediate A-1 (15.00 g, 55.51 mmol) and $K_2CO_3$ (15.20 g, 110.01 mmol) were dissolved in NMP (200 ml) and then, heated under reflux at 130° C. for 3 hours. When a reaction was completed, after removing the solvent with a rotary evaporator, an organic layer extracted therefrom with methylene chloride was dried with $MgSO_4$ and concentrated and then, stirred with a small amount of methanol to obtain a solid, and the solid was recrystallized with 200 mL of toluene, obtaining 10.0 g (Yield: 72%) of Intermediate A-2.

3rd Step: Synthesis of Intermediate A-3

Intermediate A-2 (10.00 g, 39.57 mmol) and N-bromosuccinimide (NBS, 7.75 g, 43.53 mmol) were dissolved in DMF (200 ml) and then, stirred at 60° C. for 12 hours. When a reaction was completed, the reactant was cooled to ambient temperature, and a solid was obtained by adding methanol thereto and then, separated by filtering. The obtained solid was dried, obtaining 12 g (Yield: 91%) of Intermediate A-3.

4th Step: Synthesis of Intermediate A-4

In a round-bottomed flask, 12.0 g (36.19 mmol) of Intermediate A-3, 6.85 g (39.81 mmol) of naphthalene-1-boronic acid, 1.77 g (2.17 mmol) of Pd(dppf)$Cl_2$, and 12.50 g (90.47 mmol) of $K_2CO_3$ were dissolved in 100 mL of THF and 50 mL of distilled water and then, heated under reflux under a nitrogen atmosphere. After 12 hours, the reaction solution was cooled, and an organic layer obtained by removing an aqueous layer therefrom was dried under a reduced pressure. The obtained solid was washed with water and methanol and then, recrystallized with 100 mL of toluene, obtaining 11.0 g (Yield: 80%) of Intermediate A-4.

5th Step: Synthesis of Intermediate A 11.0 g (29.03 mmol) of Intermediate A-4, 8.11 g (31.94 mmol) of bis(pinacolato) diboron, 1.60 g (1.74 mmol) of $Pd_2(dba)_3$, 1.95 g (6.97 mmol) of $P(Cy)_3$, and 8.55 g (87.10 mmol) of KOAc were dissolved in 100 ml of xylene and then, stirred under reflux at 175° C. for 12 hours. After the reaction was completed, the reaction solvent was removed with a rotary evaporator, and an organic layer was extracted therefrom with methylene chloride and columned with hexane:EA=4:1 (v/v), obtaining 12.0 g (Yield: 88%) of Intermediate A. LC/MS calculated for: C32H27BO3 Exact Mass 470.38 found for 471.11 [M+H]

6th Step: Synthesis of Compound 1

In a round-bottomed flask, 12 g (25.59 mmol) of Intermediate A, 6.85 g (25.29 mmol) of 2-chloro-4,6-diphenyl-1,3,5-triazine (Int-1), 0.89 g (0.77 mmol) of $Pd(PPh_3)_4$, and 7.07 g (51.17 mmol) of $K_2CO_3$ were dissolved in 150 mL of THF and 70 mL of distilled water and then, heated under reflux under a nitrogen atmosphere. After 12 hours, the reaction solution was cooled, and after removing an aqueous layer, an organic layer therefrom was dried under a reduced pressure. A solid obtained therefrom was washed with water and methanol and recrystallized twice with 200 mL of toluene, obtaining 12.5 g (Yield: 85%) of Compound 1. LC/MS calculated for: C41H25N3O Exact Mass 575.67 found for 576.43 [M+H]

Synthesis Examples 2 to 5 and Comparative Synthesis Examples 1 to 5

In the 6th step of Synthesis Example 1, each reaction was performed in the same manner as in Synthesis Example 1,

TABLE 1

| Synthesis Examples | Int H | Int I | Final product | Amount (yield) | Property data of final products |
|---|---|---|---|---|---|
| Synthesis Example 2 | Interme-diate A | Int-2 | Compound 2 | 14.0 g (84%) | LC/MS calculated for: C47H29N3O Exact Mass: 651.77 found for 652.14 [M + H] |
| Synthesis Example 3 | Interme-diate A | Int-3 | Compound 5 | 13.0 g (81%) | LC/MS calculated for: C45H27N3O Exact Mass: 625.73 found for 625.89 [M + H] |
| Synthesis Example 4 | Interme-diate A | Int-4 | Compound 13 | 15.0 g (88%) | LC/MS calculated for: C47H27N3O2 Exact Mass: 665.75 found for 666.32 [M + H] |
| Synthesis Example 5 | Interme-diate A | Int-5 | Compound 32 | 19.0 g (77%) | LC/MS calculated for: C47H28N4O Exact Mass: 664.77 found for 664.83 [M + H] |
| Comparative Synthesis Example 1 | Interme-diate B | Int-2 | 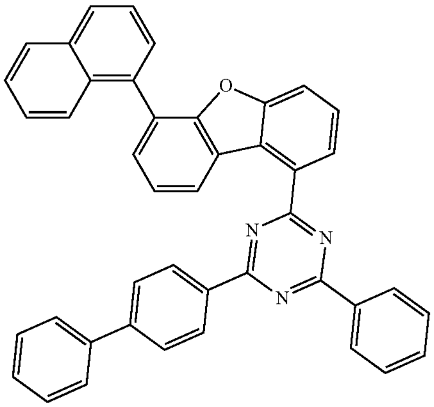 K1 | 18.0 g (89%) | LC/MS calculated for: C43H27N3O Exact Mass 601.71 found for 601.93 [M + H] |
| Comparative Synthesis Example 2 | Interme-diate C | Int-2 | 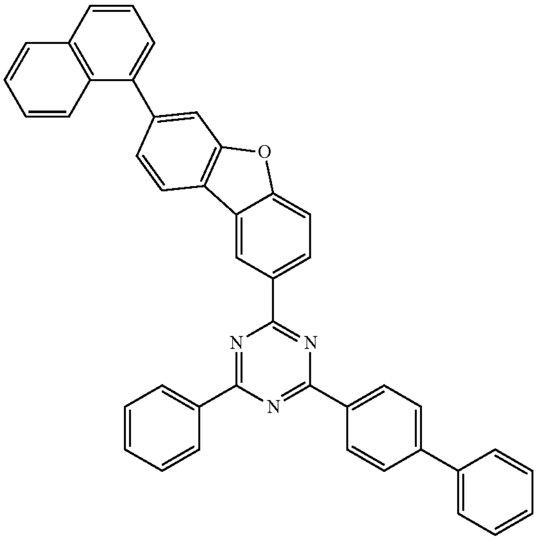 K2 | 17.4 g (86%) | LC/MS calculated for: C43H27N3O Exact Mass: 601.71 found for 601.99 [M + H] |

TABLE 1-continued
| Synthesis Examples | Int H | Int I | Final product | Amount (yield) | Property data of final products |
|---|---|---|---|---|---|
| Comparative Synthesis Example 3 | Interme-diate D | Int-2 | 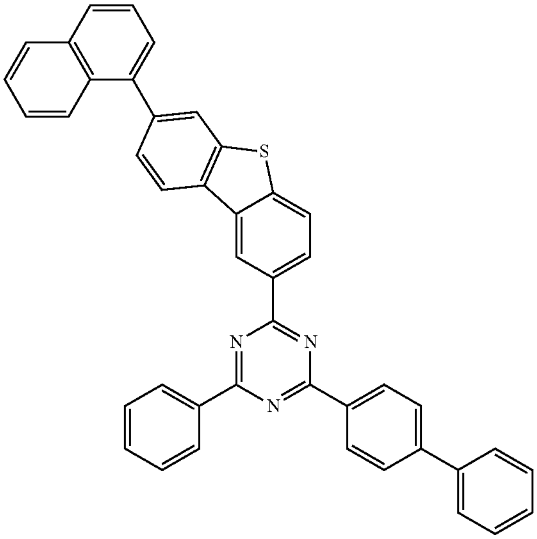 K3 | 15.8 g (83%) | LC/MS calculated for: C43H27N3S Exact Mass: 617.77 found for 618.13 [M + H] |
| Comparative Synthesis Example 4 | Interme-diate E | Int-2 | 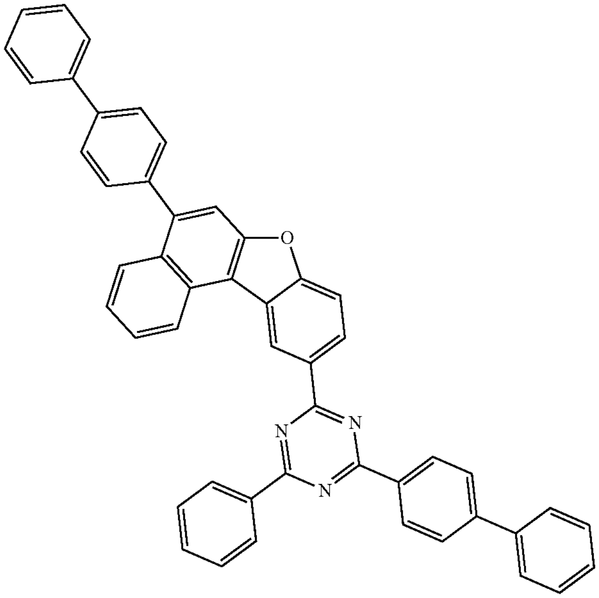 K4 | 15.0 g (85%) | LC/MS calculated for: C49H31N3O Exact Mass 677.81 found for 678.23 [M + H] |

TABLE 1-continued
| Synthesis Examples | Int H | Int I | Final product | Amount (yield) | Property data of final products |
| --- | --- | --- | --- | --- | --- |
| Comparative Synthesis Example 5 | Interme-diate F | Int-2 | 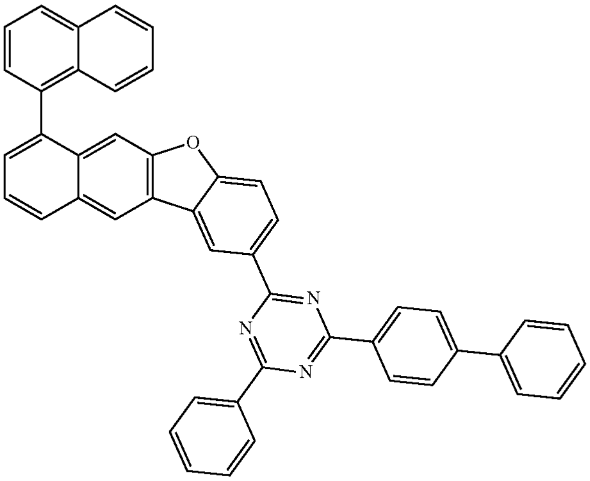 K5 | 13.0 g (86%) | LC/MS calculated for: C47H29N3O Exact Mass 651.77 found for 652.41 [M + H] |
<Int H>
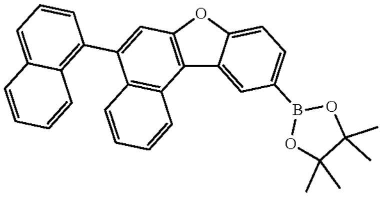
Intermediate A
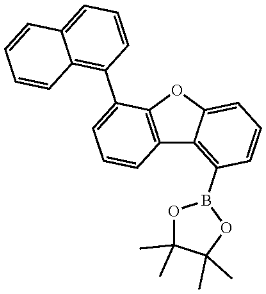
Intermediate B
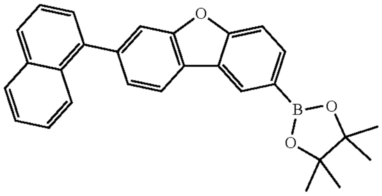
Intermediate C
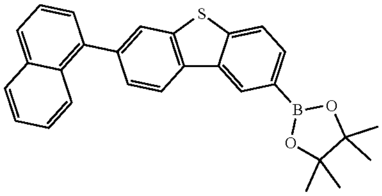
Intermediate D TABLE 1-continued
| Synthesis Examples | Int H | Int I | Final product | Amount (yield) | Property data of final products |
|---|---|---|---|---|---|
| 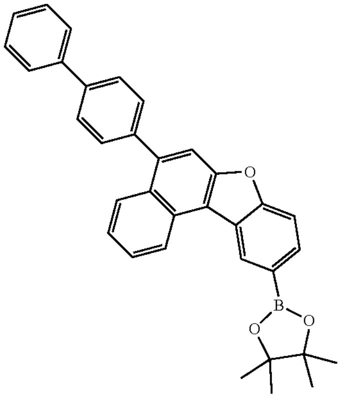 Intermediate E | | | | | |
| 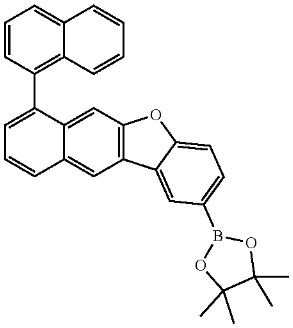 Intermediate F | | | | | |
| <Int I> | | | | | |
| 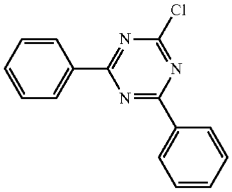 Int-1 | | | | | |
| 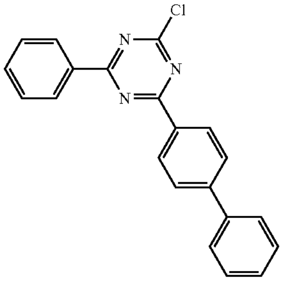 Int-2 | | | | | |
| 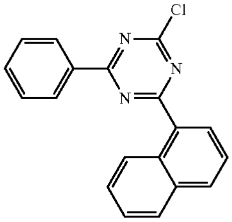 Int-3 | | | | | |

TABLE 1-continued
| Synthesis Examples | Int H | Int I | Final product | Amount (yield) | Property data of final products |
|---|---|---|---|---|---|
| 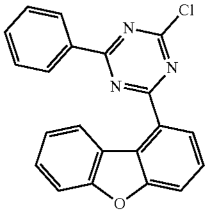 Int-4 | | | | | |
| 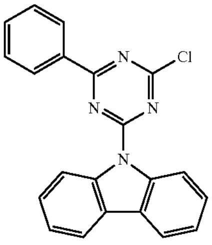 Int-5 | | | | | |
Specific synthesis methods of each of intermediates and compounds according to comparative synthesis examples were as follows.
Comparative Synthesis Example 1: Synthesis of Compound K1
[Reaction Scheme 2]
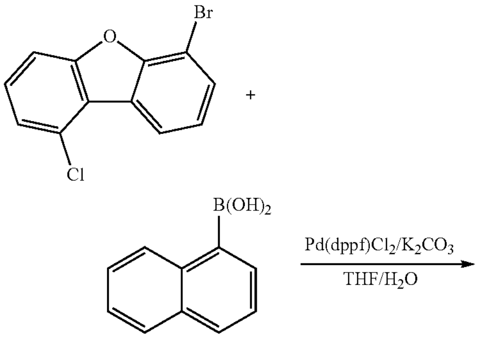
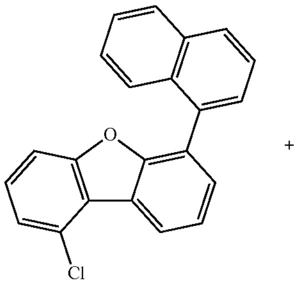
B-1
-continued
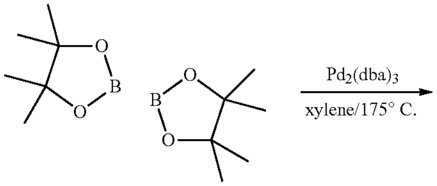
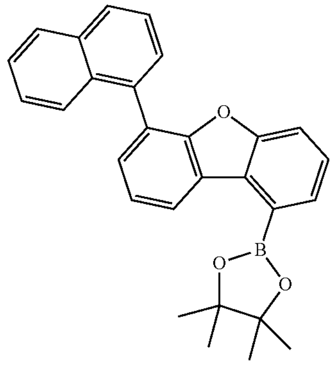
B
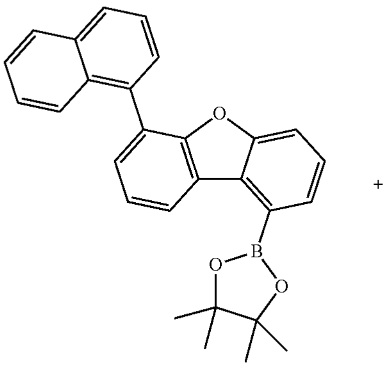
B -continued

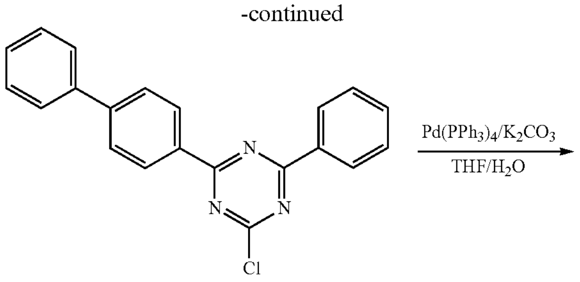

Int-2

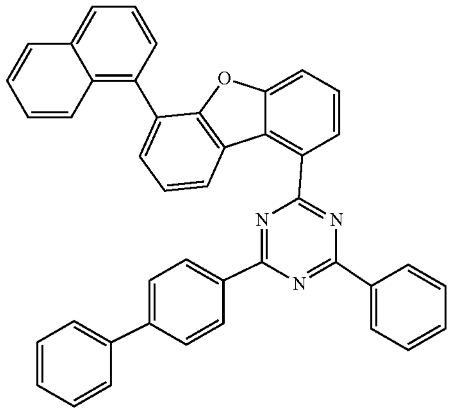

K1

1st Step: Synthesis of Intermediate B-1

In a round-bottomed flask, 15.0 g (53.28 mmol) of 6-bromo-1-chlorodibenzo[b,d]furan, 10.08 g (58.61 mmol) of 1-naphthaleneboronic acid, 2.61 g (3.20 mmol) of Pd(dppf)$Cl_2$, and 18.41 g (133.20 mmol) of $K_2CO_3$ were dissolved in 150 mL of THE and 70 mL of distilled water and then, heated under reflux under a nitrogen atmosphere. After 12 hours, the reaction solution was cooled, and an organic layer obtained therefrom by removing an aqueous layer was dried under a reduced pressure. The obtained solid was washed with water and methanol and then, recrystallized with 100 mL of toluene, obtaining 13.0 g (Yield: 74%) of Intermediate B-1.

2nd Step: Synthesis of Intermediate B 13.0 g (39.54 mmol) of Intermediate B-1, 11.01 g (43.49 mmol) of bis(pinacolato) diboron, 2.17 g (0.06 mmol) of $Pd_2(dba)_3$, 2.66 g (9.49 mmol) of $P(Cy)_3$, and 11.64 g (118.61 mmol) of KOAc were dissolved in 100 ml of xylene and then, stirred under reflux at 175° C. for 12 hours. After the reaction was completed, the reaction solvent was removed with a rotary evaporator, and an organic layer extracted therefrom with methylene chloride was columned with hexane:EA=4:1 (v/v), obtaining 14.0 g (Yield: 84%) of Intermediate B. LC/MS calculated for: C28H25BO3 Exact Mass 420.32 found for 420.87 [M+H]

3rd Step: Synthesis of Compound K1

In a round-bottomed flask, 14 g (33.62 mmol) of Intermediate B, 9.0 g (33.62 mmol) of 2-([1,1'-biphenyl]-4-yl)-4-chloro-6-phenyl-1,3,5-triazine (Int-2), 1.17 g (1.01 mmol) of $Pd(PPh_3)_4$, and 9.29 g (67.23 mmol) of $K_2CO_3$ were dissolved in 200 mL of THE and 100 mL of distilled water and then, heated under reflux under a nitrogen atmosphere. After 12 hours, the reaction solution was cooled, and an organic layer obtained by removing an aqueous layer was dried under a reduced pressure. The obtained solid was washed with water and methanol and then, twice recrystallized with 200 mL of toluene, obtaining 18.0 g (Yield: 89%) of Compound K1. LC/MS calculated for: C43H27N3O Exact Mass 601.71 found for 601.93 [M+H]

Comparative Synthesis Example 2 and 3: Synthesis of Compound K2 and Compound K3

Compound K2 and Compound K3 were synthesized in the same manner as in Comparative Synthesis Example 1 except that Intermediate C or Intermediate D was used instead of Intermediate B.

Intermediate C and Intermediate D were synthesized in the following method.

Synthesis of Intermediate C

[Reaction Scheme 3]

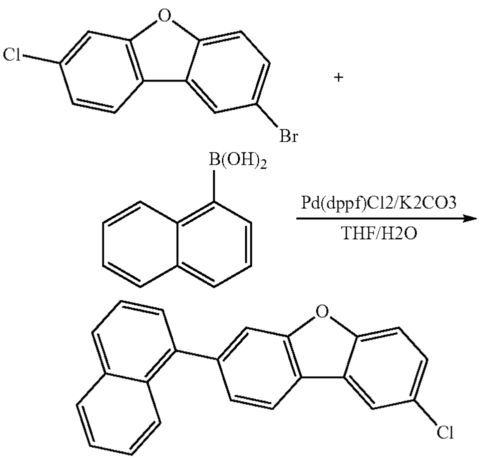

C-1

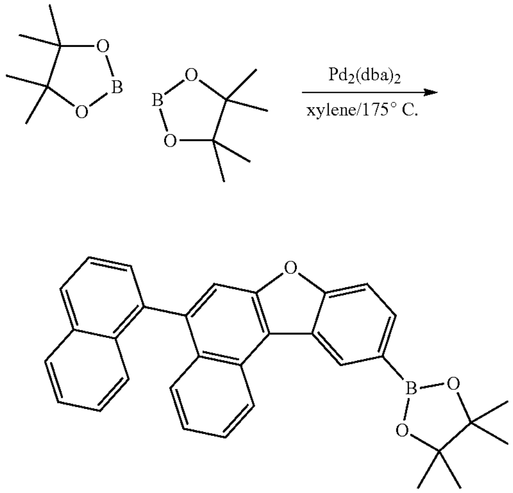

C 14.2 g (Yield: 85%) of Intermediate C was obtained through Intermediate C-1 in the same manner as in the 1st and 2nd steps of Comparative Synthesis Example 1 except that 15 g of 2-bromo-7-chloro dibenzo [b,d]furan was used instead of the 6-bromo-1-chlorodibenzo[b,d]furan. LC/MS calculated for: C28H25BO3 Exact Mass 420.32 found for 420.54 [M+H]

Synthesis of Intermediate D

[Reaction Scheme 4]

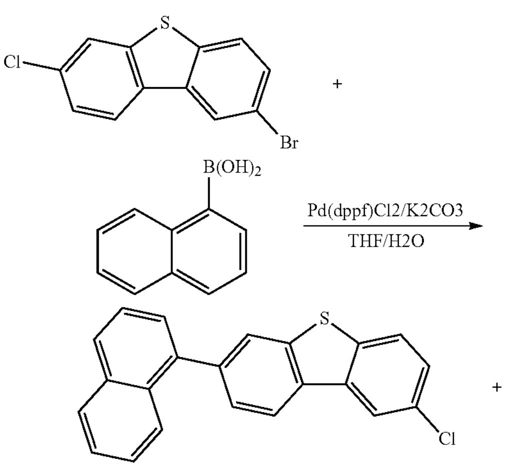

D-1

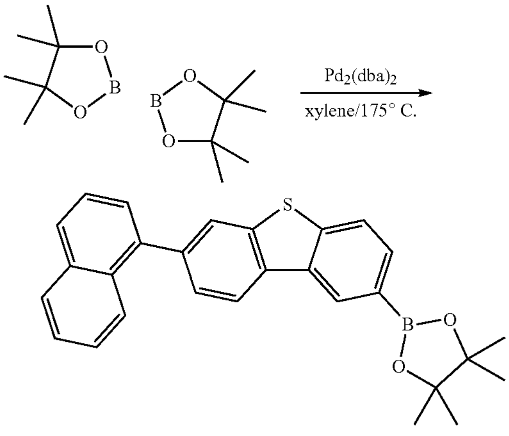

D 13.8 g (Yield: 79%) of Intermediate D was obtained through Intermediate D-1 in the same manner as in the 1st and 2nd steps of Comparative Synthesis Example 1 except that 15 g of 2-bromo-7-chlorodibenzo[b,d]thiophene was used instead of the 6-bromo-1-chlorodibenzo[b,d]furan. LC/MS calculated for: C28H25BO2S Exact Mass 436.38 found for 436.84 [M+H]

Comparative Synthesis Example 4: Synthesis of Compound K4

[Reaction Scheme 5]

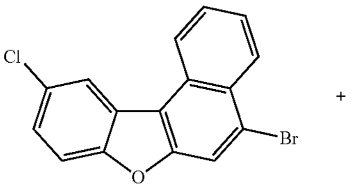

A-3

-continued

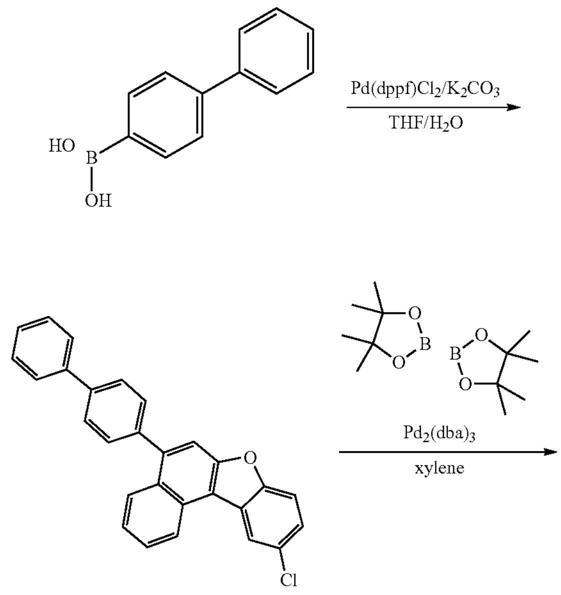

E-1

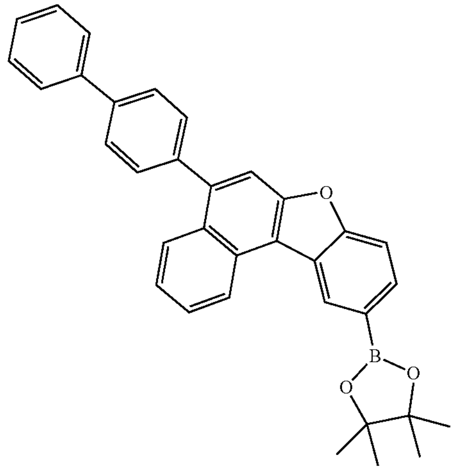

E

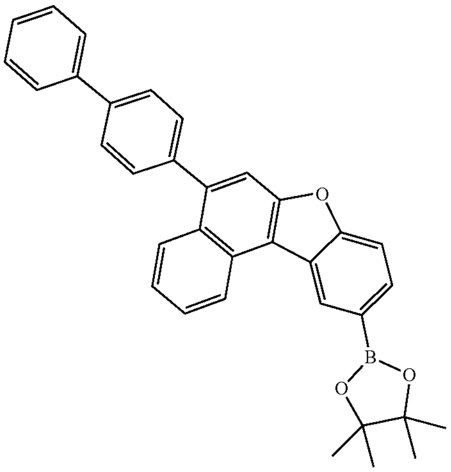

E

-continued

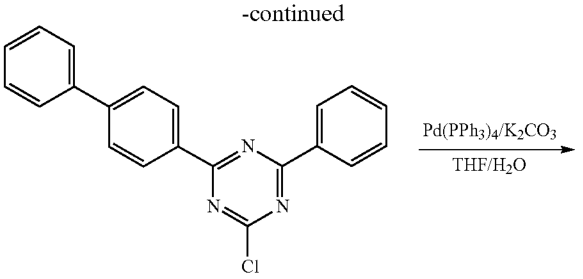

Int-2

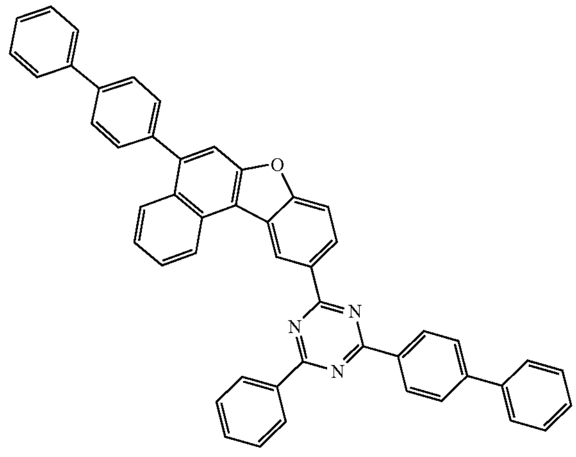

K4

1st Step: Synthesis of Intermediate E-1

In a round-bottomed flask, 15.0 g (45.24 mmol) of Intermediate A-3, 9.85 g (49.76 mmol) of [1,1'-biphenyl]-4-ylboronic acid, 2.22 g (2.71 mmol) of $Pd(dppf)Cl_2$, and 15.63 g (113.09 mmol) of $K_2CO_3$ were dissolved in 120 mL of THF and 60 mL of distilled water and then, heated under reflux under a nitrogen atmosphere. After 12 hours, the reaction solution was cooled, and an organic layer obtained by removing an aqueous layer was dried under a reduced pressure. The obtained solid was washed with water and methanol and then, recrystallized with 100 mL of toluene, obtaining 15.0 g (Yield: 82%) of Intermediate E-1.

2nd Step: Synthesis of Intermediate E 13.5 g (Yield: 76%) of Intermediate E was obtained in the same manner as in the 2nd step of Comparative Synthesis Example 1 except that 15 g (37.05 mmol) of Intermediate E-1 was used instead of the 6-bromo-1-chlorodibenzo[b,d]furan. LC/MS calculated for: C33H26BO3 Exact Mass 481.38 found for 481.77 [M+H]

3rd Step: Synthesis of Compound K4

15.0 g (Yield: 85%) of Compound K4 was obtained in the same manner as in the 3rd step of Comparative Synthesis Example 1 except that Intermediate E was used instead of Intermediate B. LC/MS calculated for: C49H31N3O Exact Mass 677.81 found for 678.23 [M+H]

Comparative Synthesis Example 5: Synthesis of Compound K5

[Reaction Scheme 6]

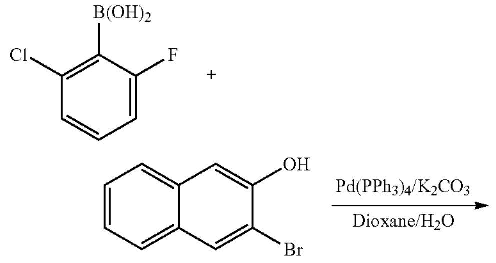

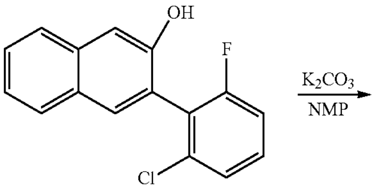

F-1

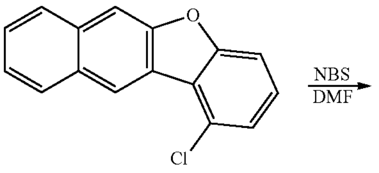

F-2

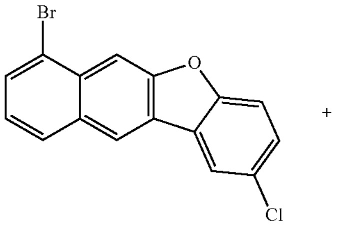

F-3

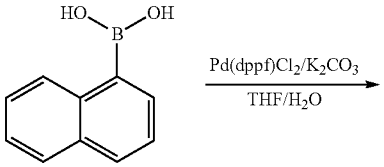

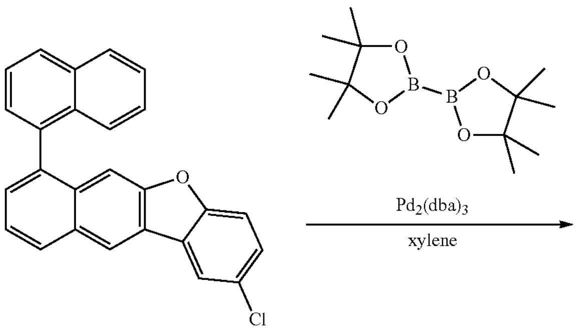

F-4

-continued

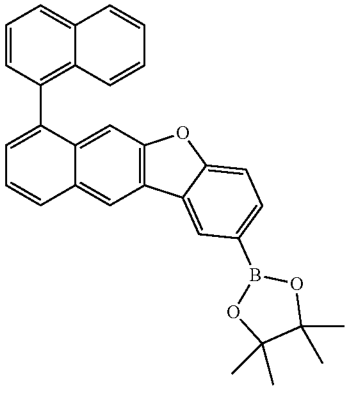

F

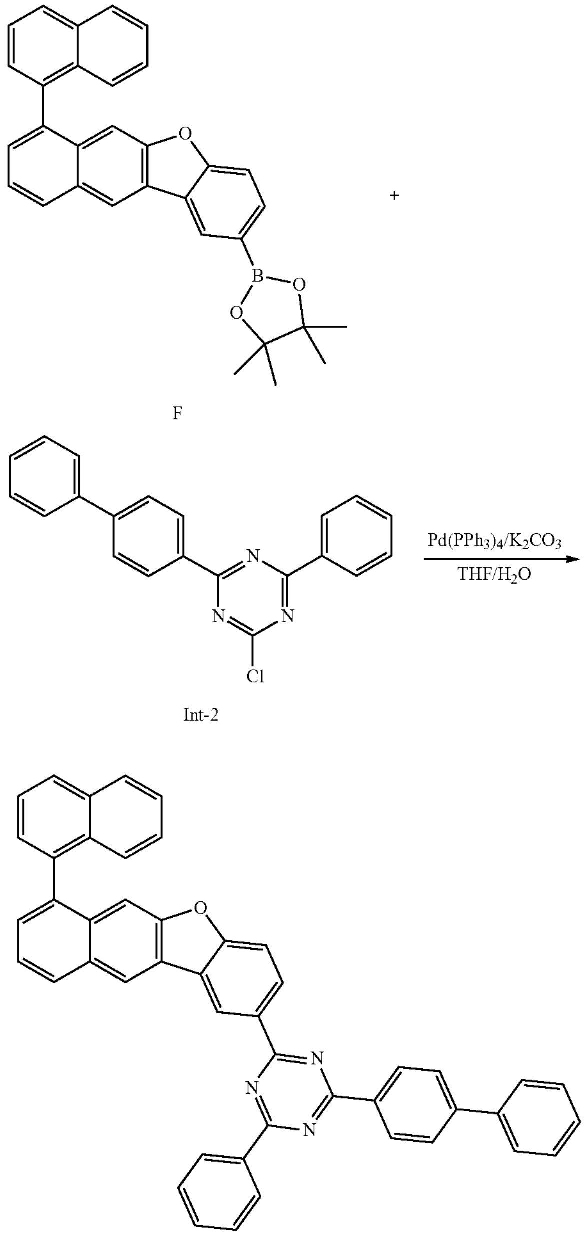

F

\+

Int-2

K5

1st Step: Synthesis of Intermediate F-1

(2-chloro-6-fluorophenyl)boronic acid (30.0 g, 134.49 mmol), 3-bromonaphthalen-2-ol (28.14 g, 161.38 mmol), $Pd(PPh_3)_4$ (7.77 g, 6.72 mmol), and $K_2CO_3$ (55.76 g, 403.46 mmol) were dissolved in dioxane (300 ml) and $H_2O$ (150 ml) and then, heated under reflux under a nitrogen atmosphere. After 12 hours, the reaction solution was cooled, and after removing an aqueous layer and then, removing the solvent with a rotary evaporator, the residue was extracted with methylene chloride. The obtained organic layer was columned with hexane:EA=4:1 (v/v), obtaining 17.0 g (Yield: 46%) of Intermediate F-1.

2nd Step: Synthesis of Intermediate F-2

Intermediate F-1 (17.00 g, 62.34 mmol) and $K_2CO_3$ (17.23 g, 124.68 mmol) were dissolved in NMP (210 ml) and then, heated under reflux at 130° C. for 3 hours. When a reaction was completed, after removing the solvent with a rotary evaporator, an organic layer extracted therefrom with methylene chloride was dried with $MgSO_4$ and concentrated and then, stirred with a small amount of methanol and recrystallized with 200 mL of toluene, obtaining 12.0 g (Yield: 76%) of Intermediate F-2.

3rd Step: Synthesis of Intermediate F-3

Intermediate F-2 (12.00 g, 47.49 mmol) and N-bromosuccinimide (8.45 g, 47.49 mmol) were dissolved in DMF (200 ml) and then, stirred at 60° C. for 12 hours. When a reaction was completed, the reactant was cooled to ambient temperature, and a solid obtained by adding methanol thereto was separated by filtering. The obtained solid was dried, obtaining 13 g (Yield: 83%) of Intermediate F-3.

4th Step: Synthesis of Intermediate F-4

In a round-bottomed flask, 11.0 g (33.17 mmol) of Intermediate F-3, 6.28 g (36.49 mmol) of 1-naphthaleneboronic acid, 1.63 g (1.99 mmol) of $Pd(dppf)Cl_2$, and 11.46 g (82.93 mmol) of $K_2CO_3$ were dissolved in 100 mL of THF and 50 mL of distilled water and then, heated under reflux under a nitrogen atmosphere. After 12 hours, the reaction solution was cooled, and an organic layer obtained by removing an aqueous layer was dried under a reduced pressure. The obtained solid was washed with water and methanol and then, recrystallized with 100 mL of toluene, obtaining 10.4 g (Yield: 83%) of Intermediate F-4.

5th Step: Synthesis of Intermediate F 10.4 g (27.45 mmol) of Intermediate F-4, 7.67 g (30.20 mmol) of bis(pinacolato) diboron, 1.51 g (1.65 mmol) of $Pd_2(dba)_3$, 1.85 g (6.59 mmol) of $P(Cy)_3$, and 8.08 g (82.35 mmol) of KOAc were dissolved in 90 ml of xylene and then, stirred under reflux for 12 hours. When the reaction was completed, after removing the reaction solvent with a rotary evaporator, an organic layer extracted with methylene chloride was columned with hexane:EA=4:1 (v/v), obtaining 11.0 g (Yield: 85%) of Intermediate F. LC/MS calculated for: C32H27BO3 Exact Mass 470.38 found for 470.84 [M+H]

6th Step: Synthesis of Compound K5

13.0 g (Yield: 86%) of Compound K5 was obtained in the same manner as in in the 3rd step of Comparative Synthesis Example 1 except that Intermediate F was used instead of Intermediate B. LC/MS calculated for: C47H29N3O Exact Mass 651.77 found for 652.41 [M+H]

Comparative Synthesis Example 6: Synthesis of Compound K6

[Reaction Scheme 7]

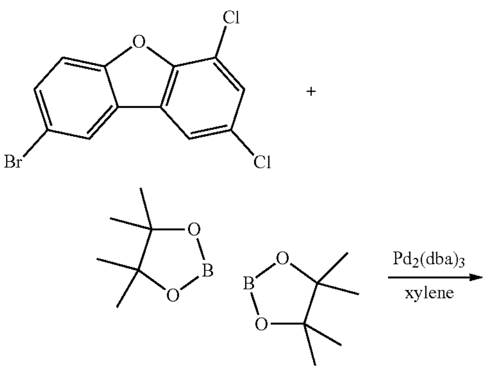

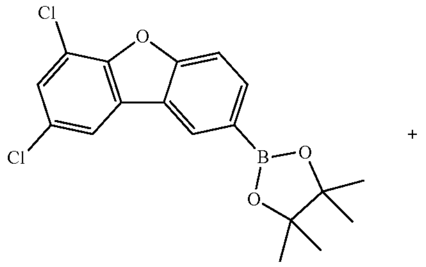

G-1

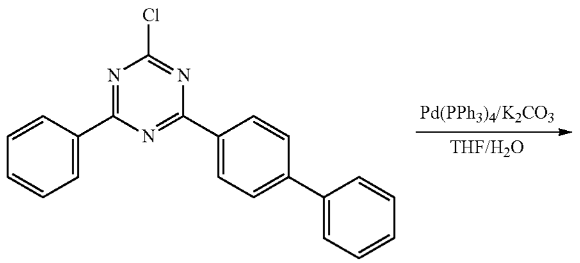

Int-2

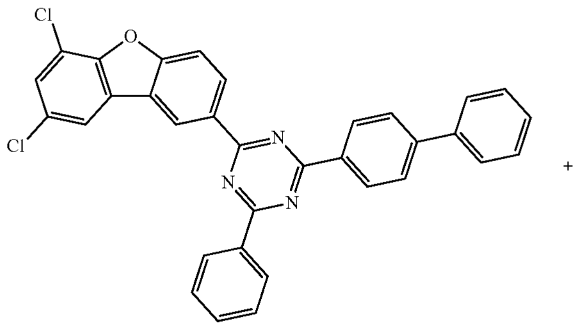

G

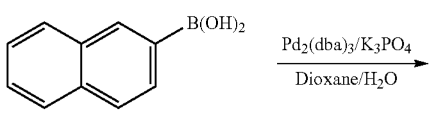

-continued

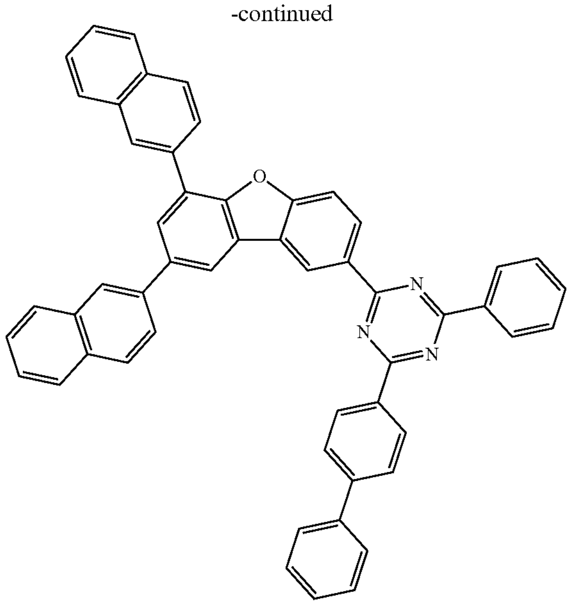

K6

1st Step: Synthesis of Intermediate G-1

15.0 g (47.47 mmol) of 8-bromo-2,4-dichlorodibenzo[b,d]furan, 12.66 g (49.84 mmol) of bis(pinacolato) diboron, 2.61 g (2.85 mmol) of $Pd_2(dba)_3$, 3.19 g (11.39 mmol) of $P(Cy)_3$, and 13.98 g (142.41 mmol) of KOAc were dissolved in 150 ml of xylene and then, stirred under reflux for 12 hours. When the reaction was completed, after removing the reaction solvent with a rotary evaporator, an organic layer extracted with methylene chloride was columned with hexane:EA=4:1 (v/v), obtaining 14.0 g (Yield: 81%) of Intermediate G-1.

2nd Step: Synthesis of Intermediate G

In a round-bottomed flask, 14 g (32.12 mmol) of Intermediate G-1, 8.60 g (32.12 mmol) of 2-([1,1'-biphenyl]-4-yl)-4-chloro-6-phenyl-1,3,5-triazine (Int-2), 1.11 g (0.96 mmol) of $Pd(PPh_3)_4$, and 8.88 g (64.25 mmol) of $K_2CO_3$ were dissolved in 200 mL of THE and 100 mL of distilled water and then, heated under reflux under a nitrogen atmosphere. After 12 hours, the reaction solution was cooled, and an organic layer obtained by removing an aqueous layer was dried under a reduced pressure. The obtained solid was washed with water and methanol and then, twice recrystallized with 200 mL of toluene, obtaining 14.0 g (Yield: 80%) of Intermediate G. LC/MS calculated for: C33H19C12N3O Exact Mass 544.44 found for 544.72 [M+H]

3rd Step: Synthesis of Compound K6

In a round-bottomed flask, 14.0 g (25.71 mmol) of Intermediate G, 8.85 g (51.43 mmol) of naphthalen-2-ylboronic acid, 2.83 g (3.09 mmol) of $Pd_2(dba)_3$, and 21.83 g (102.86 mmol) of $K_3PO_4$ were dissolved in 60 mL of dioxane and 30 mL of distilled water and then, heated under reflux under a nitrogen atmosphere. After 12 hours, the reaction solution was cooled, an organic layer obtained by removing an aqueous layer was dried under a reduced pressure. The obtained solid was washed with water and methanol and recrystallized with 100 mL of toluene, obtaining 15.0 g (Yield: 80%) of Compound K6. LC/MS calculated for: C53H33N3O Exact Mass 727.87 found for 728.26 [M+H]

Synthesis Example 6: Synthesis of Compound A-84

[Reaction Scheme 8]

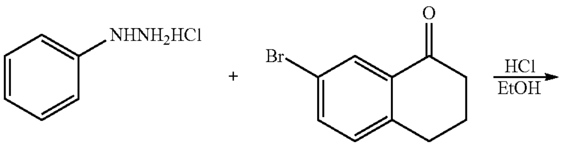

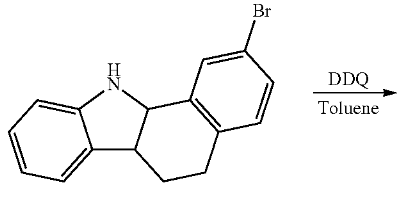

2-1a

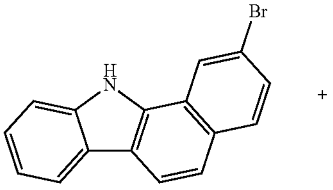

2-1b

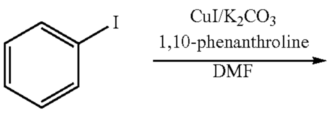

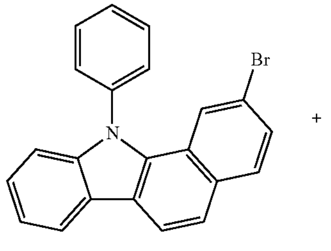

2-1c

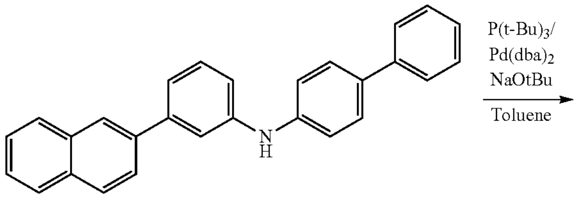

21-d

-continued

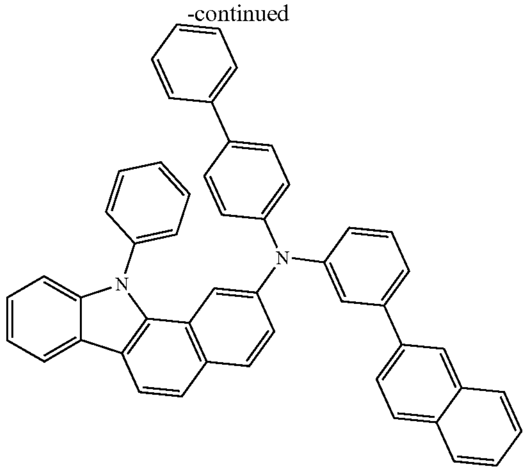

A-84

1st Step: Synthesis of Intermediate 2-1a

Phenylhydrazine hydrochloride (70.0 g, 484.1 mmol) and 7-bromo-3,4-dihydro-2H-naphthalen-1-one (108.9 g, 484.1 mmol) were put in a round-bottomed flask and dissolved in ethanol (1,200 ml). Subsequently, 60 mL of hydrochloric acid was slowly added thereto in a dropwise fashion at ambient temperature and then, stirred at 90° C. for 12 hours. When a reaction was completed, after removing the solvent under a reduced pressure, an excessive amount of EA was used for extraction. After removing an organic solvent under a reduced pressure, the residue was stirred in a small amount of methanol and then, filtered, obtaining 95.2 g (66%) of Intermediate 2-1a.

2nd Step: Synthesis of Intermediate 2-1b

Intermediate 2-1a (95.2 g, 319.3 mmol) and 2,3-dichloro-5,6-dicyano-1,4-benzoquinone (108.7 g, 478.9 mmol) were put in a round-bottomed flask and dissolved in 600 ml of toluene. The solution was stirred at 80° C. for 12 hours. When a reaction was completed, after removing the reaction solvent, the residue was treated through column chromatography, obtaining 41.3 g (44%) of Intermediate 2-1b.

3rd Step: Synthesis of Intermediate 2-1c

Intermediate 2-1b (41.3 g, 139.0 mmol), iodobenzene (199.2 g, 976.0 mmol), CuI (5.31 g, 28.0 mmol), $K_2CO_3$ (28.9 g, 209.0 mmol), and 1,10-phenanthroline (5.03 g, 28.0 mmol) were dissolved in 500 ml of DMF in a round-bottomed flask. The solution was stirred at 180° C. for 12 hours. When a reaction was completed, after removing the reaction solvent under a reduced pressure, a product therefrom was dissolved in dichloromethane and then, silica gel-filtered. The product was concentrated with dichloromethane and recrystallized with hexane, obtaining 39.0 g (75%) of Intermediate 2-1c.

4th Step: Synthesis of Compound A-84

5.0 g (13.46 mmol) of Intermediate 2-1c, 4.41 g (13.46 mmol) of an amine intermediate 2-1d, 1.94 g (20.19 mmol) of sodium t-butoxide, and 0.54 g (1.35 mmol) of tri-tert-butylphosphine were dissolved in 100 ml of toluene, and 0.37 g (0.4 mmol) of Pd(dba)$_2$ was added thereto and then, stirred under reflux at nitrogen atmosphere for 12 hours. After the reaction was completed, an organic layer was extracted therefrom with toluene and distilled water, dried with anhydrous magnesium sulfate, filtered, and the filtrate was concentrated under reduced pressure. A product therefrom was purified by silica gel column chromatography with normal hexane/dichloromethane (a volume ratio of 2:1) to obtain 6.4 g (Yield: 82.0%) of Compound A-84.

Synthesis Example 7: Synthesis of Compound 2-92

[Reaction Scheme 9]

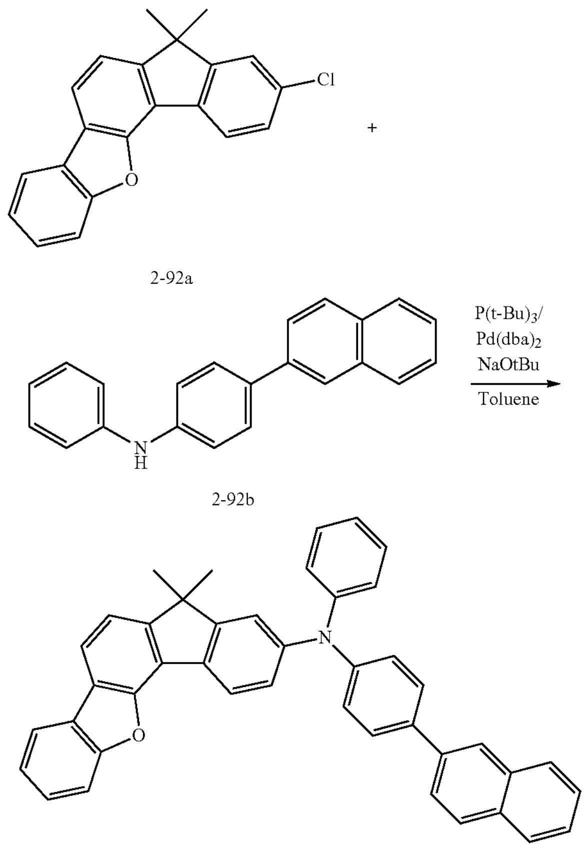

2-92a 2-92b 2-92

1st Step: Synthesis of Intermediate 2-92a

It was synthesized with as described in Korean Patent No. KR10-1423173 B1.

2nd Step: Synthesis of Compound 2-92

5.0 g (16.93 mmol) of Intermediate 2-92a, 5.4 g (16.93 mmol) of an amine intermediate 2-92b, 2.44 g (25.39 mmol) of sodium t-butoxide, and 0.68 g (1.69 mmol) of tri-tert-butylphosphine were dissolved in 100 ml of toluene, and 0.47 g (0.51 mmol) of $Pd(dba)_2$ was added thereto and then, stirred under reflux for 12 hours under a nitrogen atmosphere. After the reaction was completed, extraction was performed with toluene and distilled water, the organic layer was dried with anhydrous magnesium sulfate, filtered, and the filtrate was concentrated under reduced pressure. The product was purified by silica gel column chromatography with normal hexane/dichloromethane (volume ratio of 2:1) to obtain 8.2 g (yield 84.0%) of the target compound 2-92.

Manufacture of Organic Light Emitting Diode

Example 1

The glass substrate coated with ITO (Indium tin oxide) was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This prepared ITO transparent electrode was used as an anode, Compound A doped with 3% NDP-9 (Novaled GmbH) was vacuum-deposited on the ITO substrate to form a 100 Å-thick hole injection layer, and Compound A is deposited on the hole injection layer to a thickness of 1,300 Å to form a hole transport layer. Compound B was deposited on the hole transport layer to a thickness of 700 Å to form a hole transport auxiliary layer. On the hole transport auxiliary layer, Compound 1 obtained in Synthesis Example 1 was used as a host and 2 wt % of $[Ir(piq)_2acac]$ was used as a dopant to form a 400 Å-thick light emitting layer by vacuum deposition. In the case of the following Examples and Comparative Examples, ratios were separately described. Subsequently, Compound C was deposited at a thickness of 50 Å on the light emitting layer to form an electron transport auxiliary layer, and Compound D and LiQ were simultaneously vacuum-deposited at a weight ratio of 1:1 to form a 300 Å-thick electron transport layer. On the electron transport layer, LiQ and Al were sequentially vacuum-deposited to be 15 Å-thick and 1,200 Å-thick, manufacturing an organic light emitting diode.

The organic light emitting device has a structure having a five-layered organic layer, specifically as follows.

ITO/Compound A (3% NDP-9 doping, 100 Å)/Compound A (1,300 Å)/Compound B (700 Å)/EML [Compound 1: $[Ir(piq)_2acac]$=98:2 (wt %/wt %)](400 Å)/Compound C (50 Å)/Compound D: LiQ (300 Å)/LiQ (15 Å)/Al (1,200 Å)

Compound A: N-(biphenyl-4-yl)-9,9-dimethyl-N-(4-(9-phenyl-9H-carbazol-3-yl)phenyl)-9H-fluoren-2-amine Compound B: N,N-di([1,1'-biphenyl]-4-yl)-7,7-dimethyl-7H-fluoreno[4,3-b]benzofuran-10-amine Compound C: 2-(3-(3-(9,9-dimethyl-9H-fluoren-2-yl)phenyl)phenyl)-4,6-diphenyl-1,3,5-triazine Compound D: 8-(4-(4,6-di(naphthalen-2-yl)-1,3,5-triazin-2-yl)phenyl)quinoline Examples 2 to 5 and Comparative Examples 1 to 6

Diodes of Examples 2 to 5 and Comparative Examples 1 to 6 were manufactured in the same manner as in Example 1, except that the host was changed as shown in Table 2.

Example 6 to 15 and Comparative Example 7 to 12

Diodes of Examples 6 to 15 and Comparative Examples 7 to 12 were manufactured in the same manner as in Example 1, except that the host was changed as shown in Table 3, and the first host and the second host were mixed in a weight ratio of 5:5.

Evaluation

The luminous efficiency and life-span characteristics of the organic light emitting diodes according to Examples 1 to 15 and Comparative Examples 1 to 12 were evaluated. Specific measurement methods are as follows, and the results are shown in Tables 2 and 3.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Luminous efficiency (cd/A) at the same current density (10 $mA/cm^2$) were calculated by using the luminance and current density from the items (1) and (2), and a voltage.

The relative values based on the luminous efficiency of Comparative Example 1 and Comparative Example 7 were calculated and shown in Tables 2 and 3.

(4) Measurement of Life-Span

T95 life-spans of the organic light emitting diodes according to Examples 6 to 15 and Comparative Examples 7 to 12 were measured as a time when their luminance decreased down to 95% relative to the initial luminance after emitting light with 6,000 $cd/m^2$ as the initial luminance ($cd/m^2$) and measuring their luminance decrease depending on a time with a Polanonix life-span measurement system.

The relative values based on the T95 life-span of Comparative Example 7 were calculated and shown in Table 3.

(5) Measurement of Driving Voltage

A driving voltage of each diode was measured using a current-voltage meter (Keithley 2400) at 15 $mA/cm^2$.

The relative values based on the driving voltages of Comparative Example 1 and Comparative Example 7 were calculated and shown in Tables 2 and 3.

TABLE 2

| | Single host | Driving voltage (%) | Luminous efficiency (%) |
|---|---|---|---|
| Example 1 | 1 | 60 | 150 |
| Example 2 | 2 | 60 | 170 |
| Example 3 | 5 | 80 | 165 |
| Example 4 | 13 | 50 | 180 |
| Example 5 | 32 | 55 | 175 |
| Comparative Example 1 | K1 | 100 | 100 |
| Comparative Example 2 | K2 | 95 | 90 |
| Comparative Example 3 | K3 | 110 | 95 |
| Comparative Example 4 | K4 | 90 | 120 |
| Comparative Example 5 | K5 | 95 | 125 |
| Comparative Example 6 | K6 | 150 | 110 |

TABLE 3

| | Host | | T95 | Driving | Luminous |
|---|---|---|---|---|---|
| | First host | Second host | life-span (%) | voltage (%) | efficiency (%) |
| Example 6 | 1 | A-84 | 150 | 60 | 160 |
| Example 7 | 2 | A-84 | 160 | 70 | 180 |
| Example 8 | 5 | A-84 | 120 | 80 | 175 |
| Example 9 | 13 | A-84 | 190 | 50 | 190 |
| Example 10 | 32 | A-84 | 200 | 55 | 180 |
| Example 11 | 1 | 2-92 | 140 | 65 | 155 |
| Example 12 | 2 | 2-92 | 150 | 70 | 175 |
| Example 13 | 5 | 2-92 | 120 | 85 | 180 |
| Example 14 | 13 | 2-92 | 180 | 55 | 190 |
| Example 15 | 32 | 2-92 | 185 | 70 | 180 |
| Comparative Example 7 | K1 | A-84 | 100 | 100 | 100 |
| Comparative Example 8 | K2 | A-84 | 110 | 95 | 80 |
| Comparative Example 9 | K3 | A-84 | 80 | 110 | 90 |
| Comparative Example 10 | K4 | A-84 | 120 | 90 | 120 |
| Comparative Example 11 | K5 | A-84 | 110 | 95 | 125 |
| Comparative Example 12 | K6 | A-84 | 50 | 150 | 110 |

Referring to Tables 2 and 3, when the compound according to an embodiment was used as a single host or a mixed host in combination with a second host, the driving voltages, efficiencies, and/or life-spans were significantly improved, compared to those using the comparative compounds.

One or more embodiments may provide a compound for an organic optoelectronic device capable of implementing a high efficiency and long life-span organic optoelectronic device.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composition for an organic optoelectronic device, the composition comprising:

a first compound; and a second compound, wherein:

the first compound is represented by Chemical Formula 1, and the second compound is represented by Chemical Formula 2:

[Chemical Formula 1]

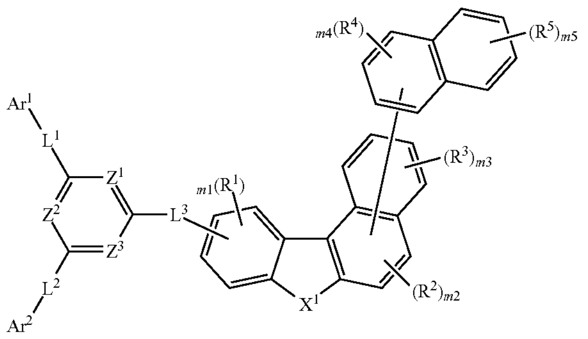

wherein, in Chemical Formula 1, $X^1$ is O or S, $Z^1$ to $Z^3$ are each independently N or $CR^a$, at least two of $Z^1$ to $Z^3$ being N, $L^1$ and $L^2$ are each independently a single bond, a substituted or unsubstituted C6 to C30 arylene group, or a substituted or unsubstituted C2 to C30 heterocyclic group, $L^3$ is a single bond, a substituted or unsubstituted C6 to C30 arylene group, or a substituted or unsubstituted C2 to C30 heterocyclic group, $Ar^1$ and $Ar^2$ are each independently a substituted or unsubstituted C6 to C30 aryl group or a substituted or unsubstituted C2 to C30 heterocyclic group, $R^a$ and $R^1$ to $R^5$ are each independently hydrogen, deuterium, a substituted or unsubstituted C1 to C20 alkyl group, or a substituted or unsubstituted C6 to C20 aryl group, m1 and m4 are each independently an integer of 1 to 3, m2 is 1 or 2, and m3 and m5 are each independently an integer of 1 to 4,

[Chemical Formula 2]

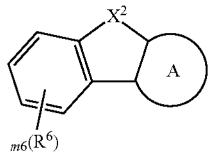

in Chemical Formula 2, $X^2$ is O, S, $NR^b$, $CR^cR^d$, or $SiR^eR^f$, $R^b$, $R^c$, $R^d$, $R^e$, $R^f$ and $R^6$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, m6 is an integer of 1 to 4, and ring A is a ring of Group II,

[Group II]

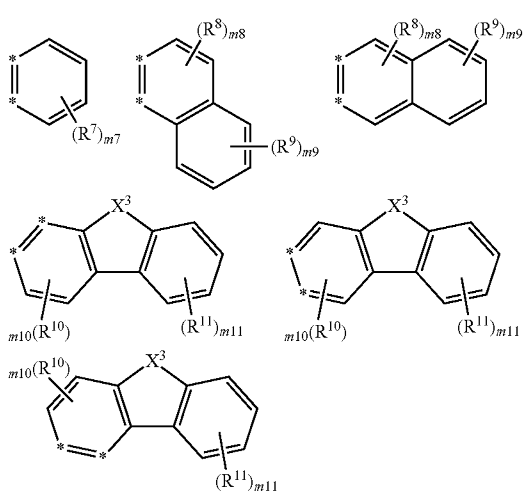

in Group II,

* is a linking point, $X^3$ is O, S, $NR^g$, $CR^hR^i$, or $SiR^jR^k$, $R^g$, $R^h$, $R^i$, $R^j$, $R^k$, and $R^7$ to $R^{11}$ are each independently hydrogen, deuterium, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, m7, m9, and m11 are each independently an integer of 1 to 4, m8 and m10 are each independently 1 or 2, and at least one of $R^6$ to $R^{11}$ is a group represented by Chemical Formula a,

[Chemical Formula a]

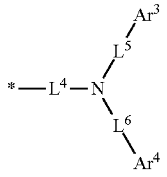

in Chemical Formula a, $L^4$ to $L^6$ are each independently a single bond or a substituted or unsubstituted C6 to C30 arylene group, $Ar^3$ and $Ar^4$ are each independently a substituted or unsubstituted amine group, a substituted or unsubstituted C6 to C30 aryl group, or a substituted or unsubstituted C2 to C30 heterocyclic group, and

* is a linking point.

2. The composition as claimed in claim 1, wherein:

Chemical Formula 1 is represented by Chemical Formula 1A-1 or Chemical Formula 1A-2:

[Chemical Formula 1A-1]

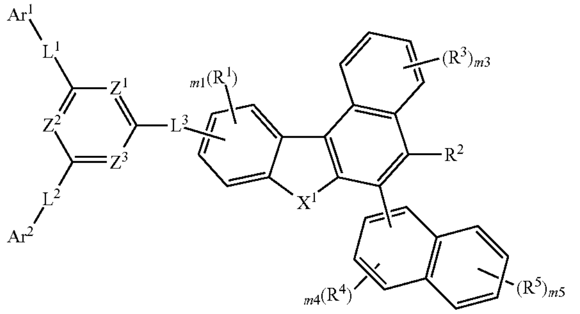

[Chemical Formula 1A-2]

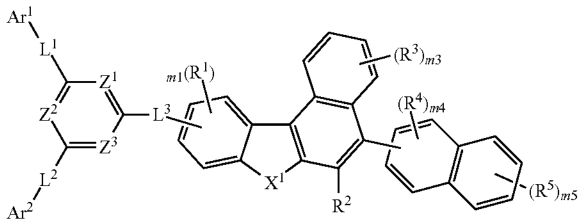

in Chemical Formula 1A-1 and Chemical Formula 1A-2, $X^1$, $Z^1$ to $Z^3$, $L^1$ to $L^3$, $Ar^1$, $Ar^2$, $R^1$ to $R^5$, m1, and m3 to m5 are defined the same as those of Chemical Formula 1.

3. The composition as claimed in claim 1, wherein:

Chemical Formula 1 is represented by Chemical Formula 1A-1-1, Chemical Formula 1A-1-2, Chemical Formula 1A-2-1, or Chemical Formula 1A-2-2:

[Chemical Formula 1A-1-1]

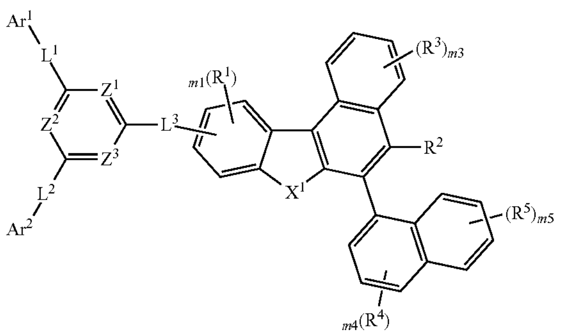

[Chemical Formula 1A-1-2]

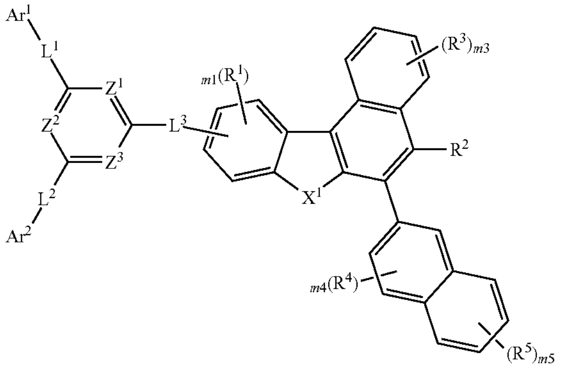

[Chemical Formula 1A-2-1]

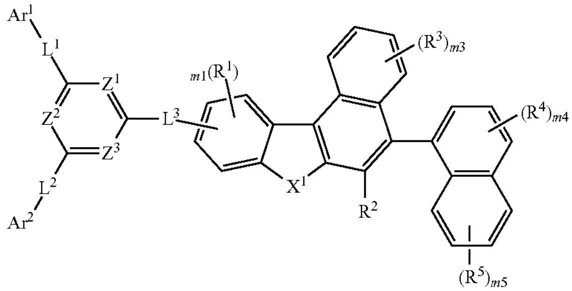

[Chemical Formula 1A-2-2]

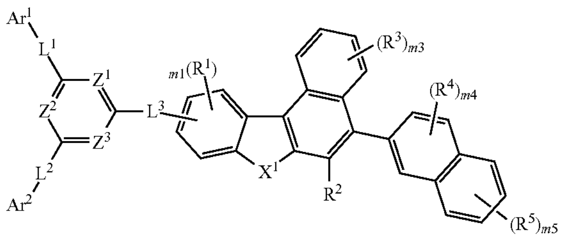

in Chemical Formula 1A-1-1, Chemical Formula 1A-1-2, Chemical Formula 1A-2-1, and Chemical Formula 1A-2-2, $X^1$, $Z^1$ to $Z^3$, $L^1$ to $L^3$, $Ar^1$, $Ar^2$, $R^1$ to $R^5$, m1, and m3 to m5 are defined the same as those of Chemical Formula 1.

4. The composition as claimed in claim 1, wherein:

Chemical Formula 1 is represented by one of Chemical Formula 1B-1 to Chemical Formula 1B-4:

[Chemical Formula 1B-1]

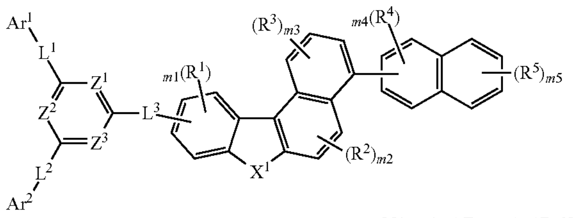

[Chemical Formula 1B-2]

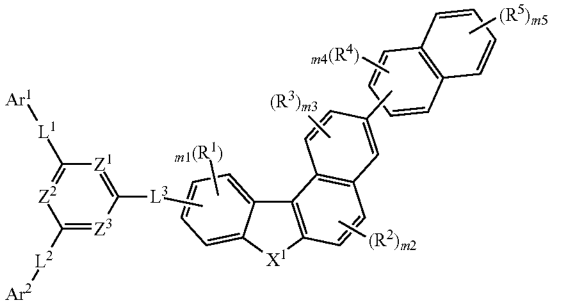

[Chemical Formula 1B-3]

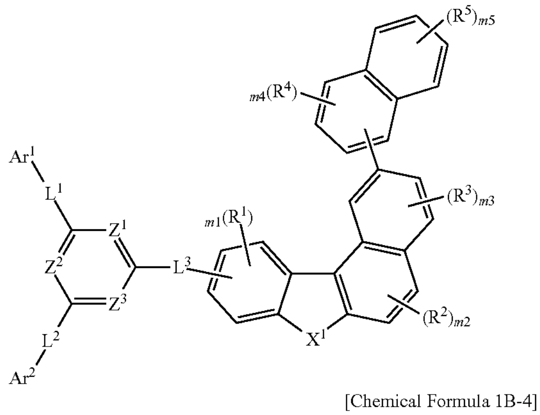

[Chemical Formula 1B-4]

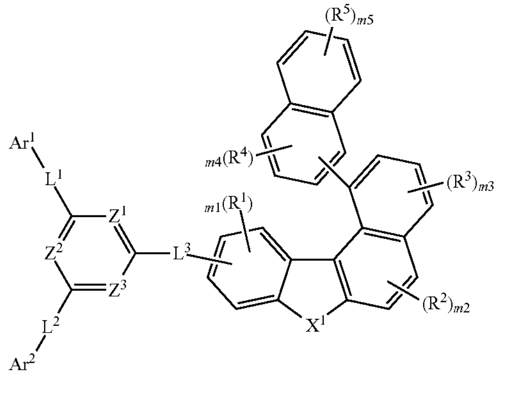

in Chemical Formula 1B-1 to Chemical Formula 1B-4, $X^1$, $Z^1$ to $Z^3$, $L^1$ to $L^3$, $Ar^1$, $Ar^2$, $R^1$ to $R^5$, m1, m2, m4, and m5 are defined the same as those of Chemical Formula 1, and m3 is an integer of 1 to 3.

5. The composition as claimed in claim 1, wherein:

Chemical Formula 1 is represented by Chemical Formula 1B-1-1, Chemical Formula 1B-1-2, Chemical Formula 1B-2-1, Chemical Formula 1B-2-2, Chemical Formula 1B-3-1, Chemical Formula 1B-3-2, Chemical Formula 1B-4-1, or Chemical Formula 1B-4-2:
[Chemical Formula 1B-1-1]
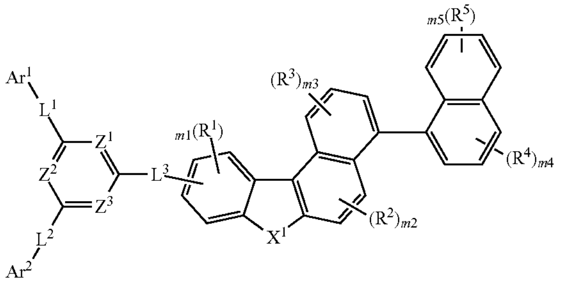
[Chemical Formula 1B-1-2]
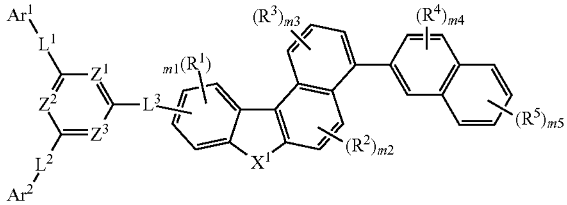
[Chemical Formula 1B-2-1]
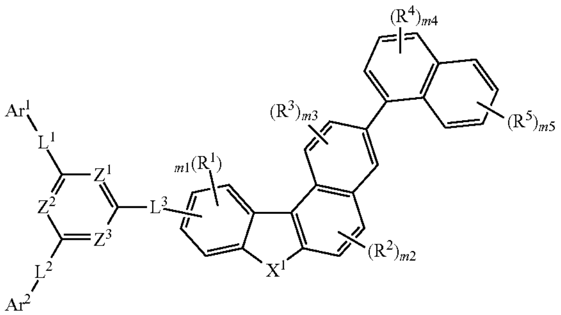
[Chemical Formula 1B-2-2]
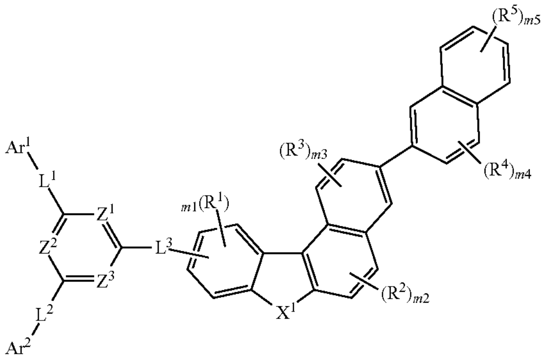
-continued
[Chemical Formula 1B-3-1]
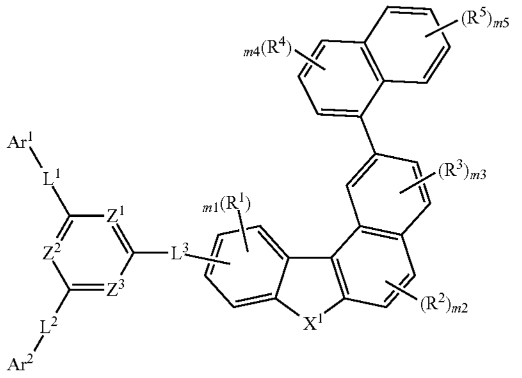
[Chemical Formula 1B-3-2]
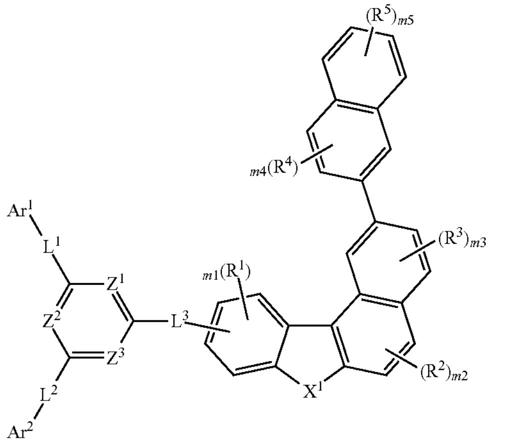
[Chemical Formula 1B-4-1]
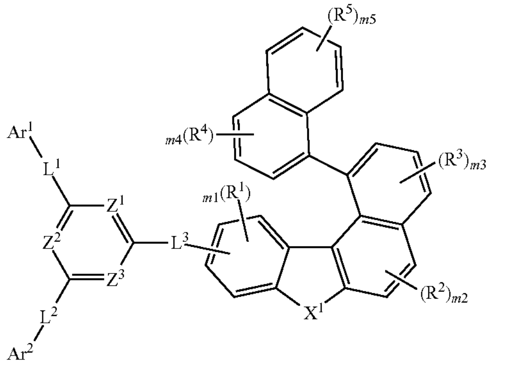
[Chemical Formula 1B-4-2]
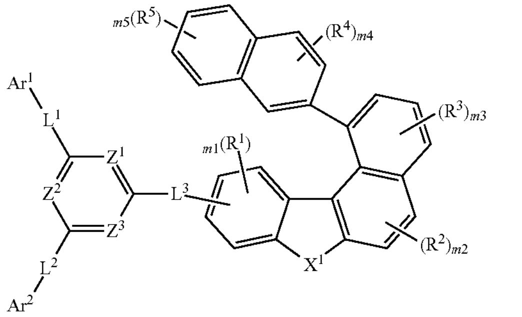
in Chemical Formula 1B-1-1, Chemical Formula 1B-1-2, Chemical Formula 1B-2-1, Chemical Formula 1B-2-2, Chemical Formula 1B-3-1, Chemical Formula 1B-3-2, Chemical Formula 1B-4-1, and Chemical Formula 1B-4-2, $X^1$, $Z^1$ to $Z^3$, $L^1$ to $L^3$, $Ar^1$, $Ar^2$, $R^1$ to $R^5$, m1, m2, m4, and m5 are defined the same as those of Chemical Formula 1, and m3 is an integer of 1 to 3.

6. The composition as claimed in claim 1, wherein $Ar^1$ and $Ar^2$ are each independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted chrysenyl group, a substituted or unsubstituted benzophenanthrenyl group, a substituted or unsubstituted acridinyl group, a substituted or unsubstituted xanthenyl group, substituted or unsubstituted 10-phenyl-10H-spiro [acridine-9,9'-fluorenyl group], a substituted or unsubstituted 10H-spiro[acridine-9,9'-fluorenyl group], a substituted or unsubstituted spiro[fluorene-9,9'-xanthenyl group], a substituted or unsubstituted dibenzosilolyl group, a substituted or unsubstituted dibenzofuranyl group, a substituted or unsubstituted dibenzothiophenyl group, a substituted or unsubstituted benzonaphthofuranyl group, a substituted or unsubstituted benzonaphthothiophenyl group, a substituted or unsubstituted carbazolyl group, a substituted or unsubstituted benzocarbazolyl group, a substituted or unsubstituted dibenzocarbazolyl group, a substituted or unsubstituted dinaphthofuranyl group, a substituted or unsubstituted dinaphthothiophenyl group, a substituted or unsubstituted benzofuranofluorenyl group, a substituted or unsubstituted benzothiophenofluorenyl group, a substituted or unsubstituted phenoxazinyl group, a substituted or unsubstituted thiophenoxazinyl group, a substituted or unsubstituted benzophenoxazinyl group, or a substituted or unsubstituted benzothiophenoxazinyl group.

7. The composition as claimed in claim 1, wherein:

$L^1$ and $L^2$ are each independently a single bond, a substituted or unsubstituted phenylene group, or a substituted or unsubstituted naphthylene group, and $L^3$ is a single bond, a substituted or unsubstituted phenylene group, a substituted or unsubstituted naphthylene group, a substituted or unsubstituted anthracenylene group, a substituted or unsubstituted phenanthrenylene group, a substituted or unsubstituted dibenzofuranylene group, or a substituted or unsubstituted dibenzothiophenylene group.

8. The composition as claimed in claim 1, wherein:

moieties *-$L^1$-$Ar^1$ and *-$L^2$-$Ar^2$ are each independently a moiety of Group I:

[Group I]

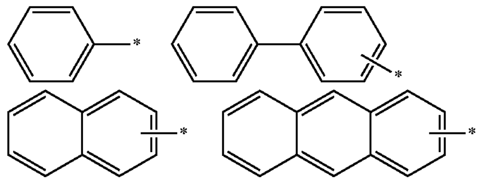

-continued

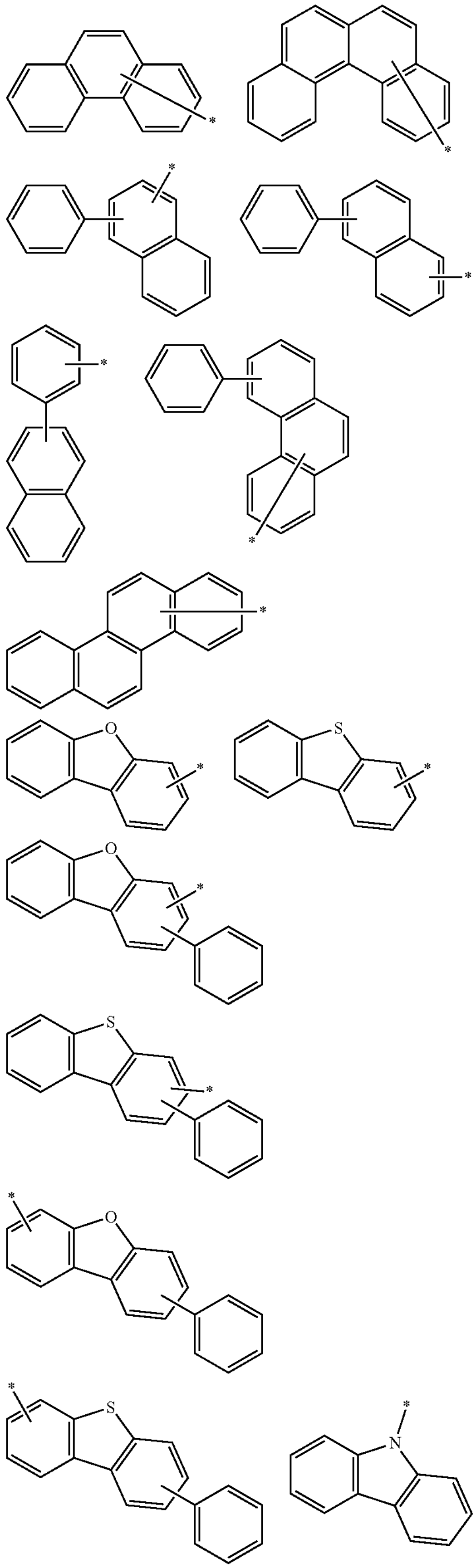

-continued
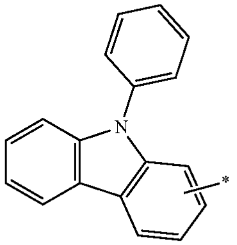
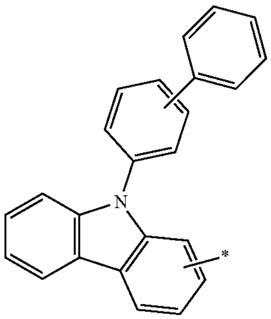
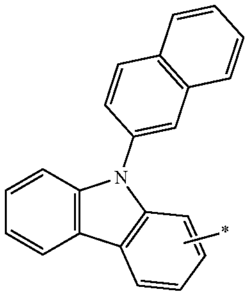
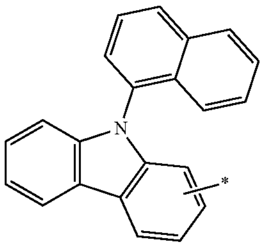
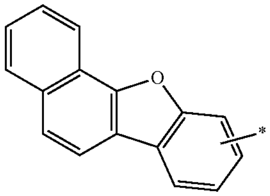
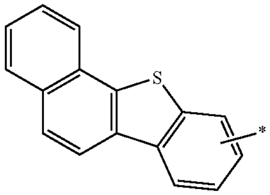
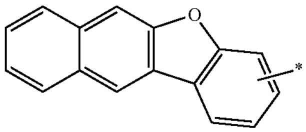
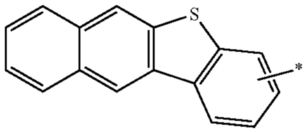
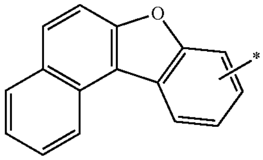
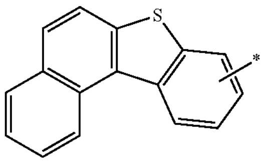
-continued
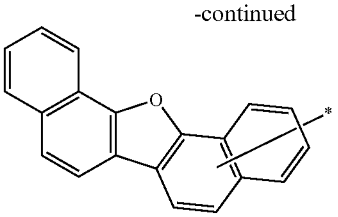
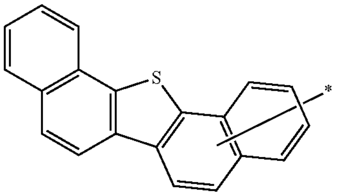
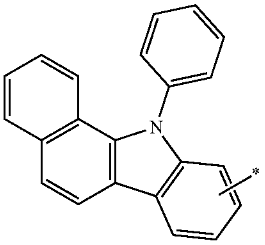
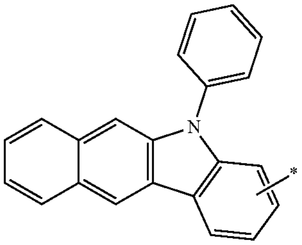
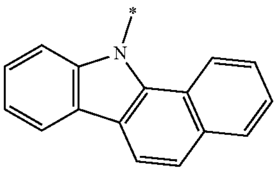
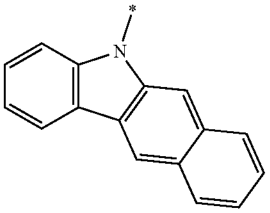
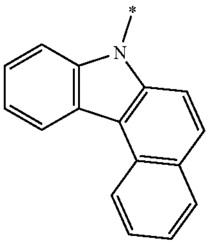
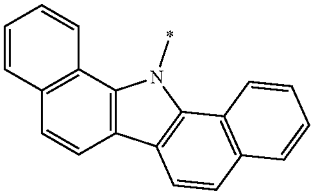
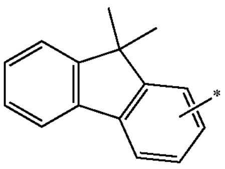
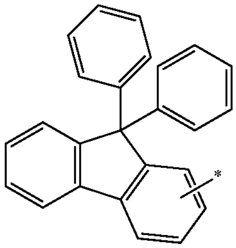

-continued
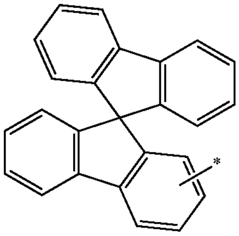
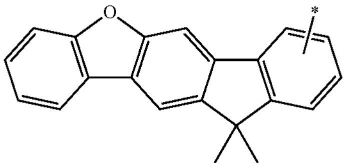
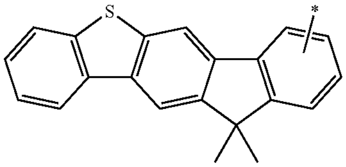
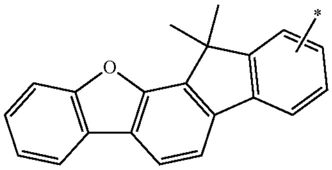
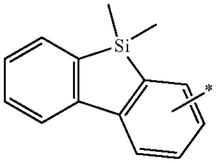
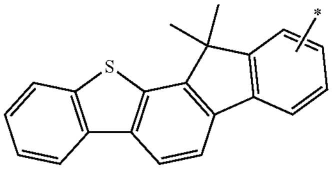
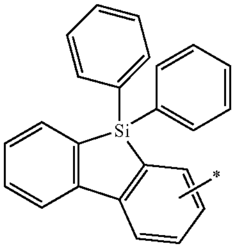
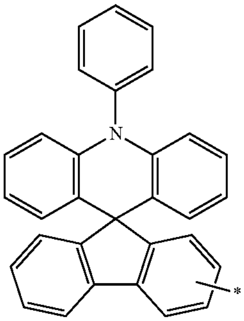
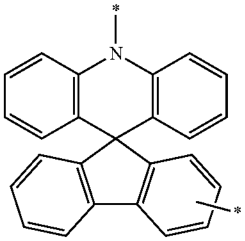
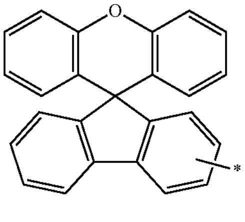
-continued
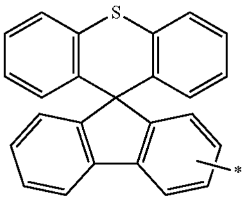
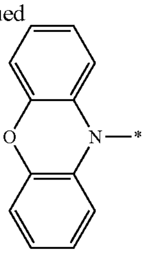
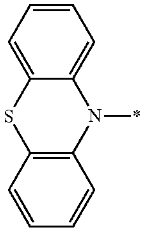
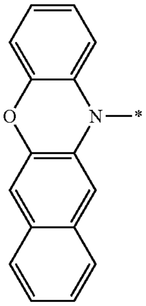
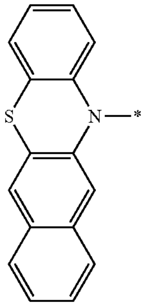
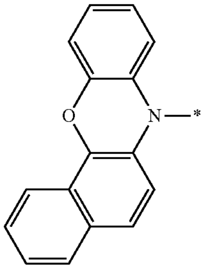
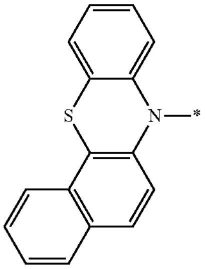
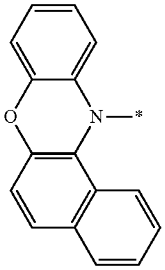
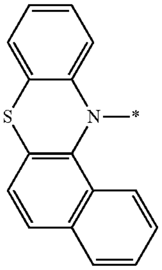
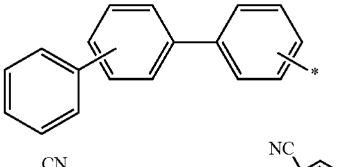
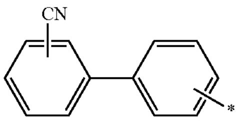
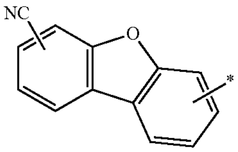
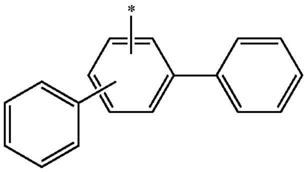
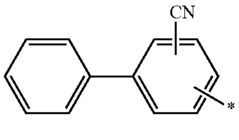
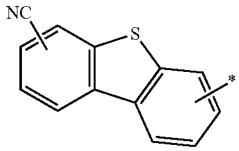
in Group I, * is a linking point.

9. The composition as claimed in claim 1, wherein the first compound is a compound of Group 1:
[Group 1]
[1]
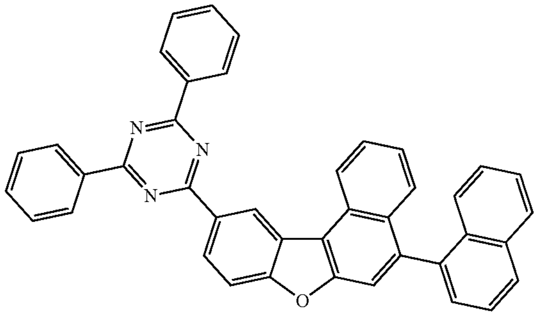
[2]
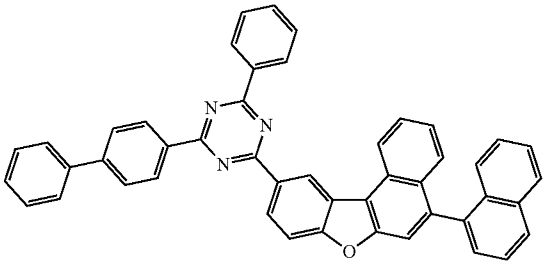
[3]
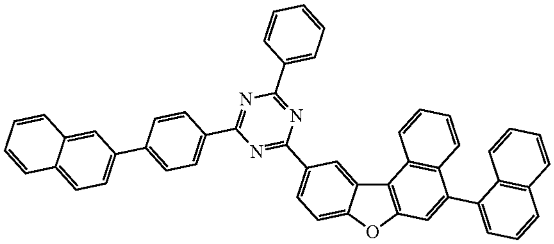
[4]
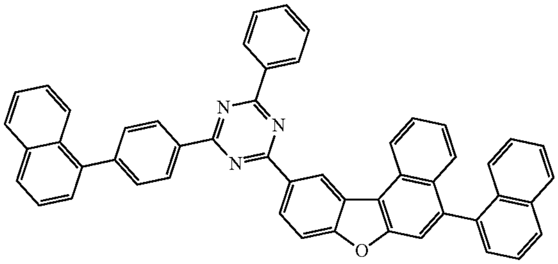
[5]
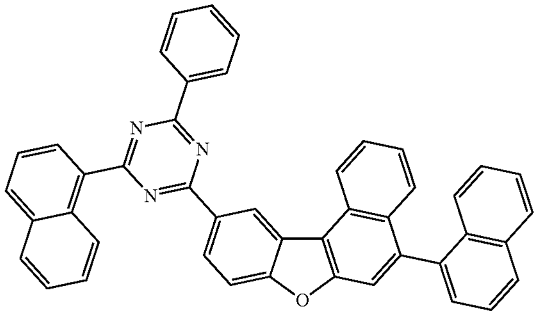
[6]
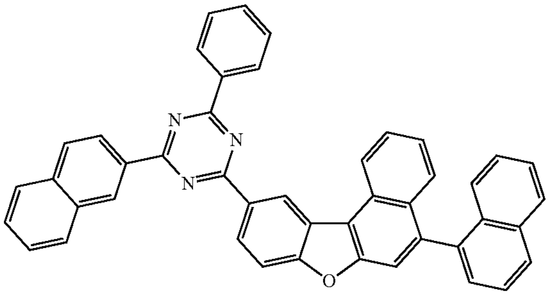
[7]
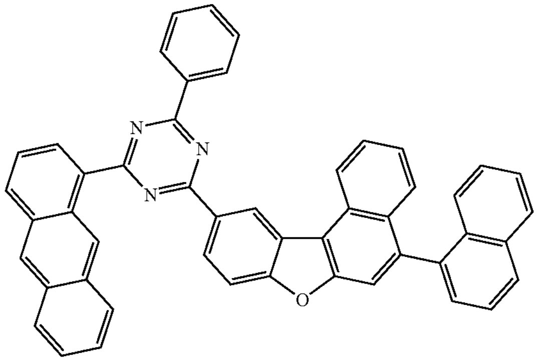
[8]
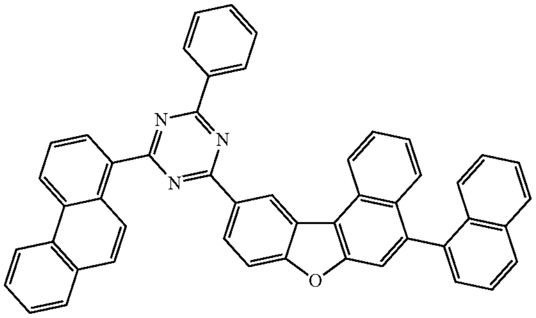

-continued
[9]
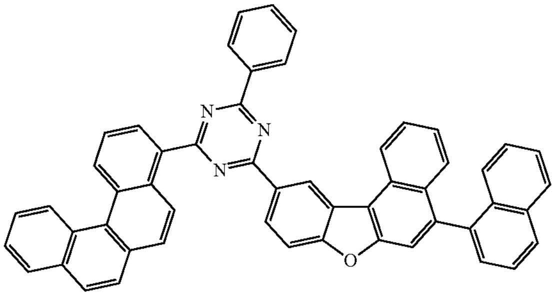
[10]
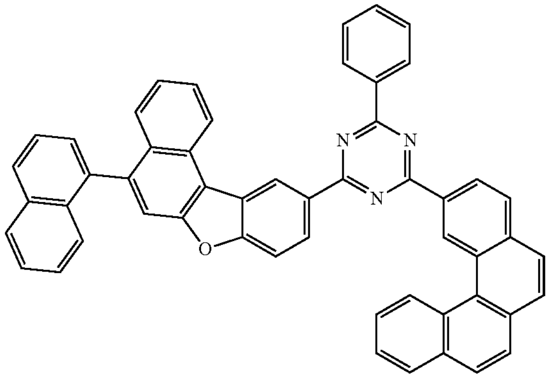
[11]
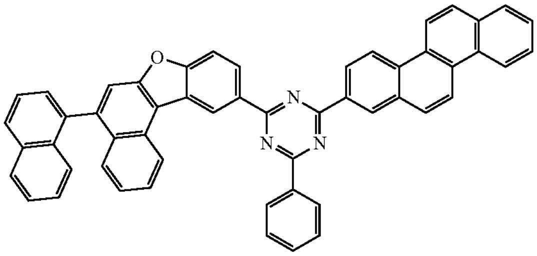
[12]
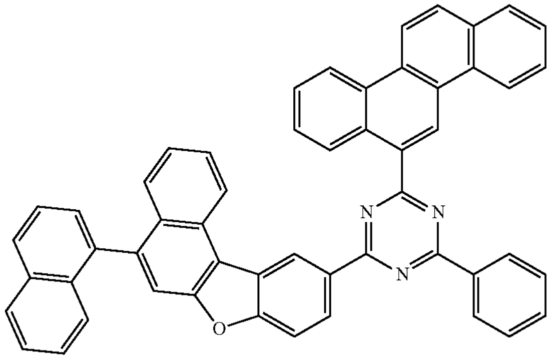
[13]
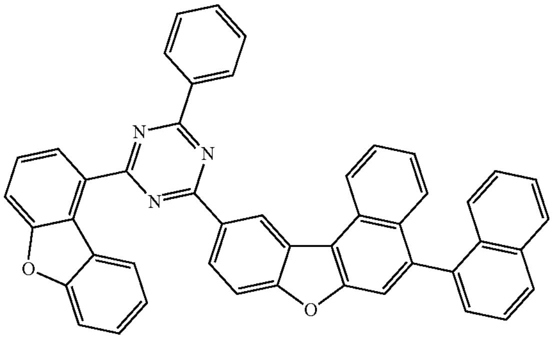
[14]
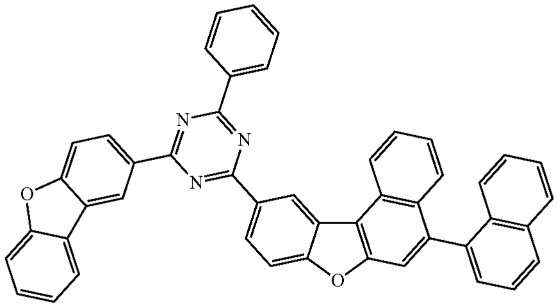
[15]
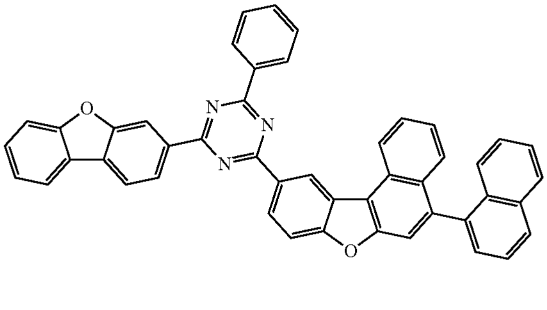
[16]
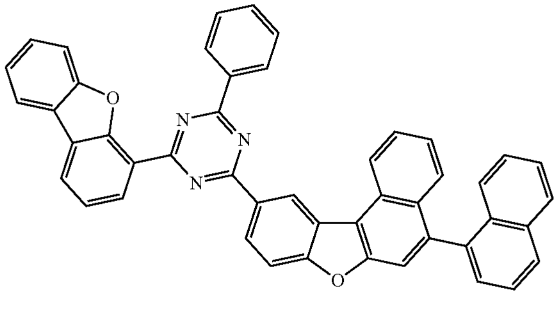

-continued
[17]
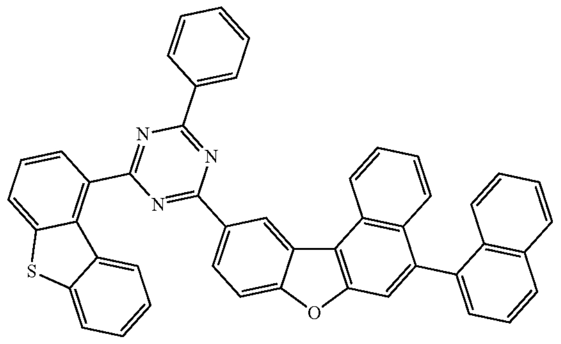
[18]
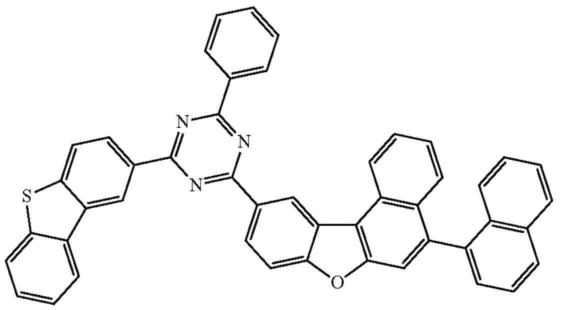
[19]
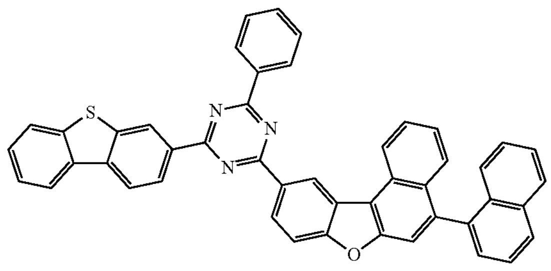
[20]
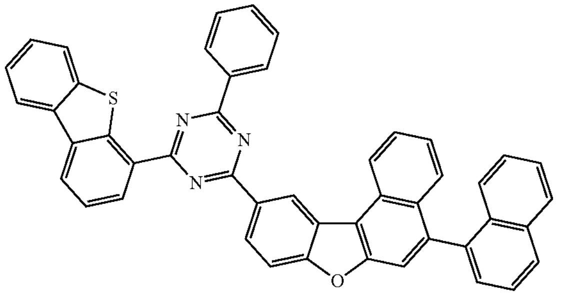
[21]
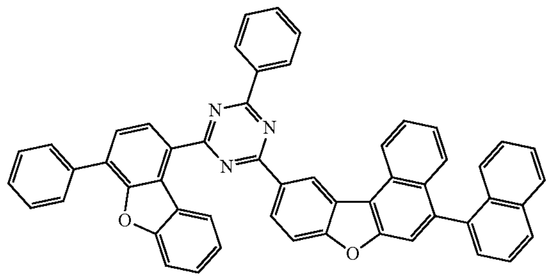
[22]
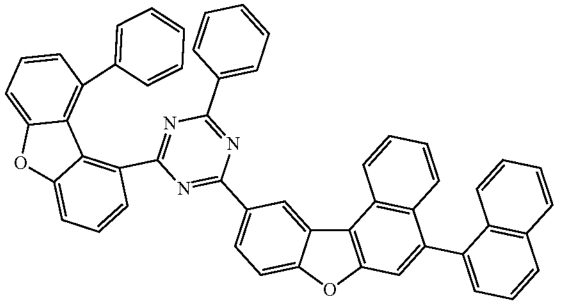
[23]
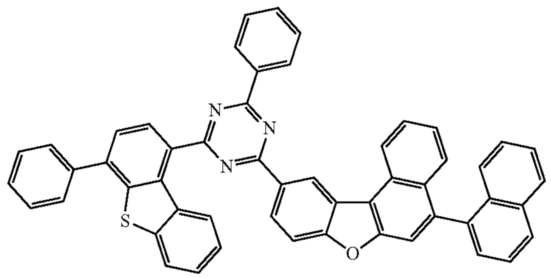
[24]
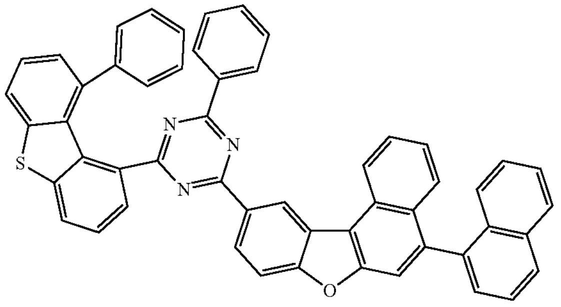

-continued
[25]
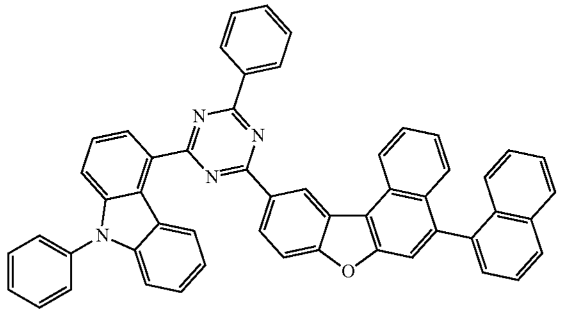
[26]
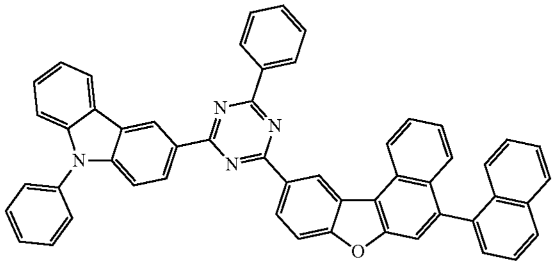
[27]
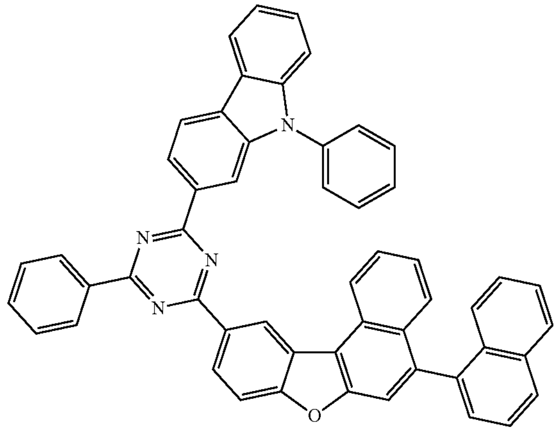
[28]
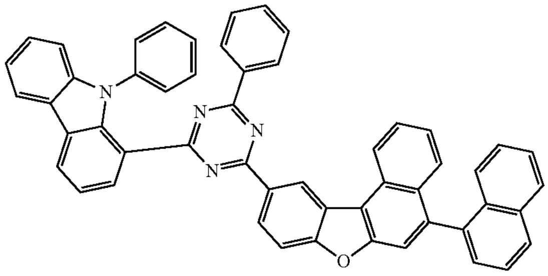
[29]
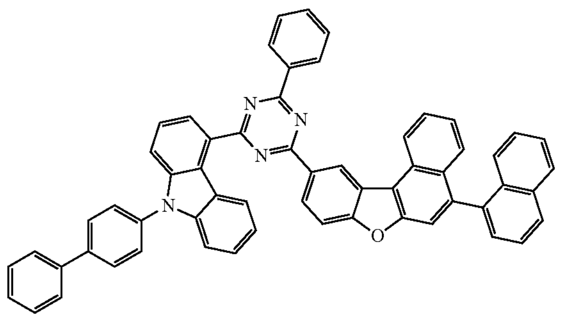
[30]
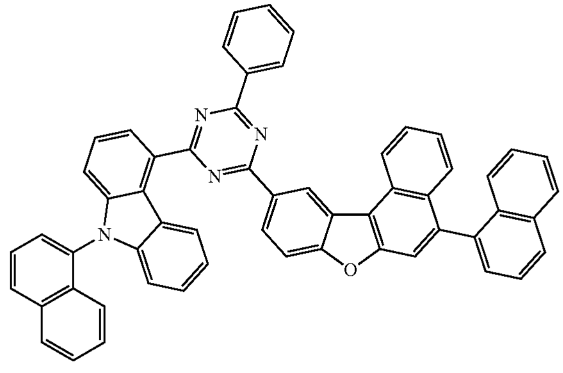
[31]
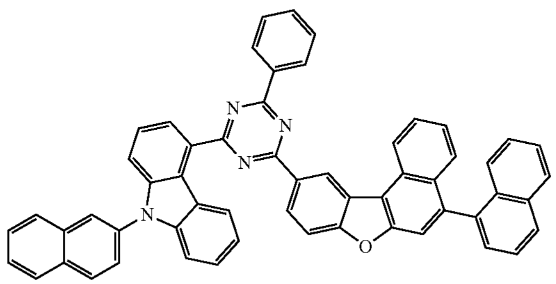
[32]
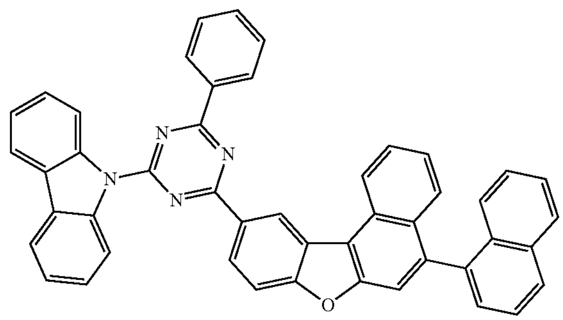

-continued
[33]
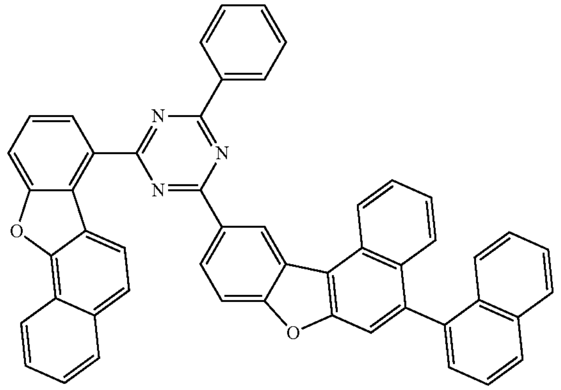
[34]
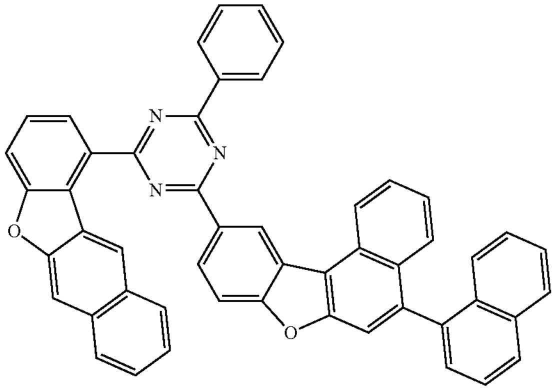
[35]
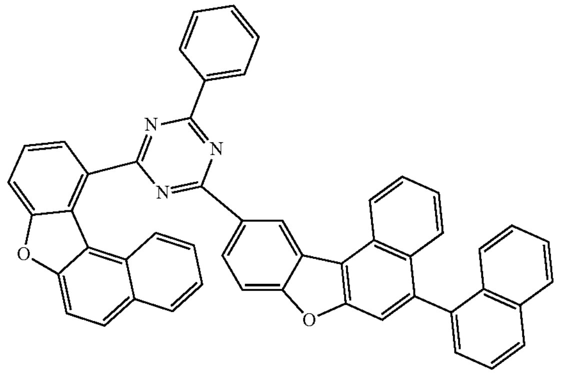
[36]
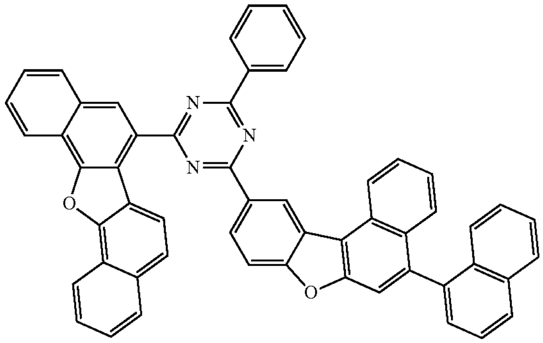
[37]
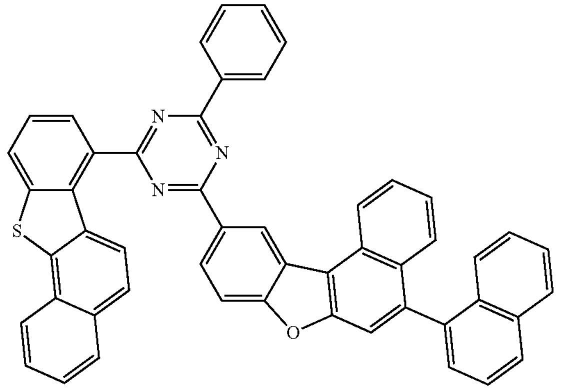
[38]
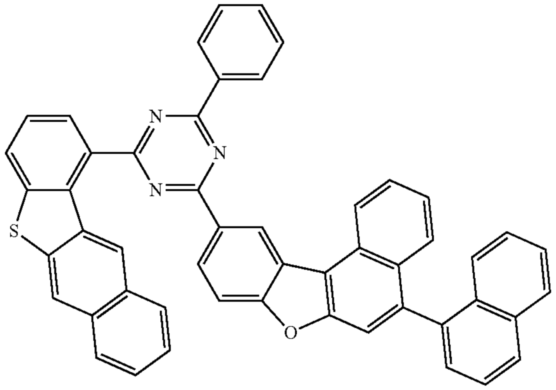
[39]
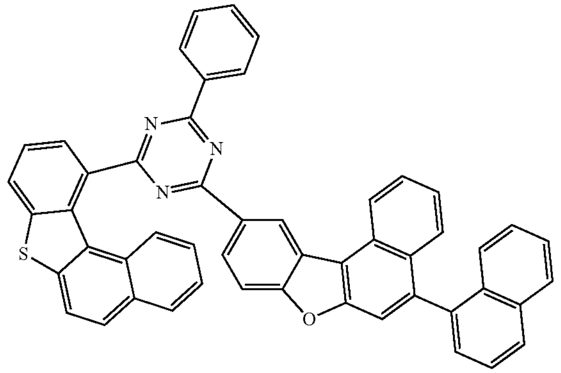
[40]
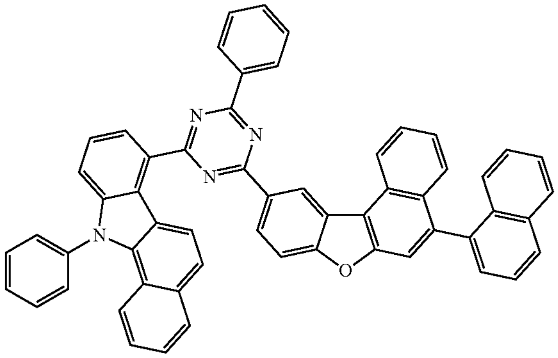

-continued
[41]
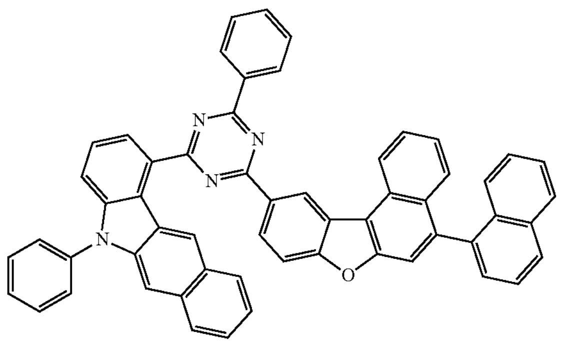
[42]
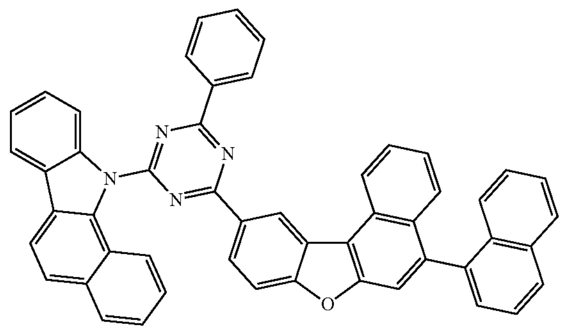
[43]
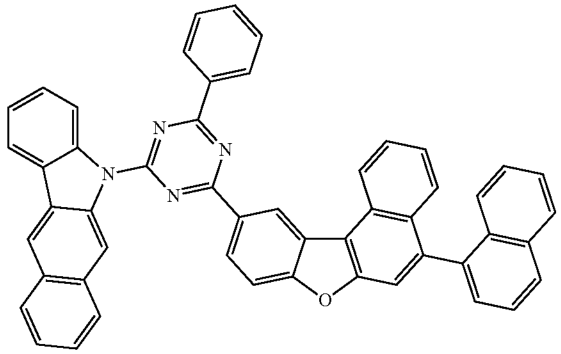
[44]
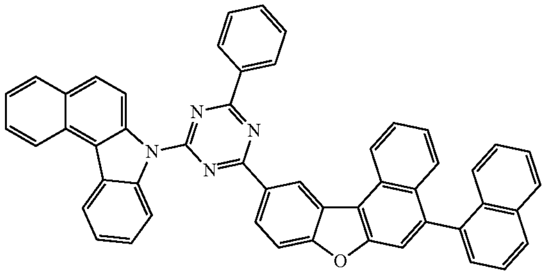
[45]
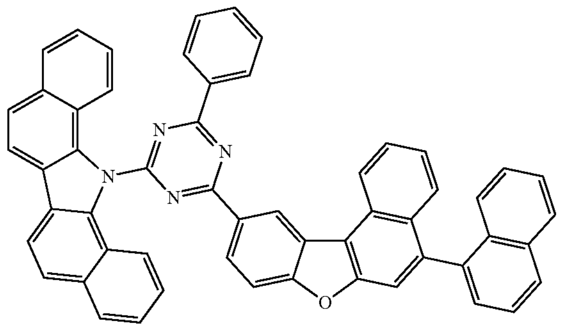
[46]
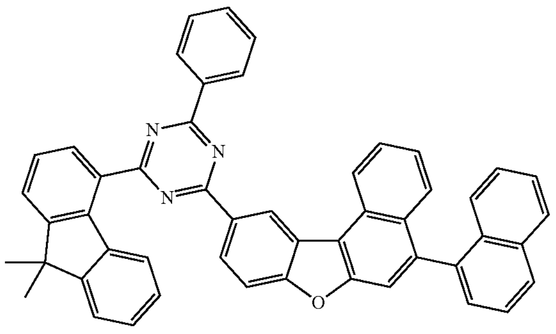
[47]
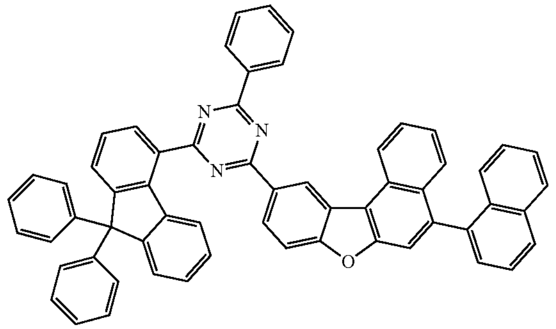
[48]
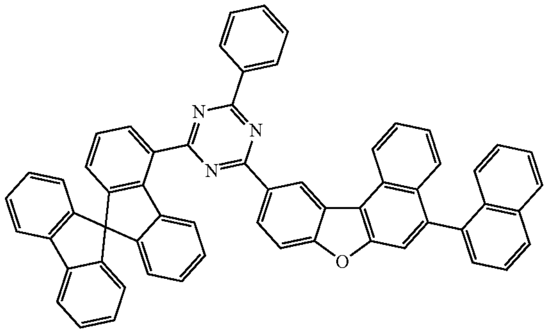

-continued
[49]
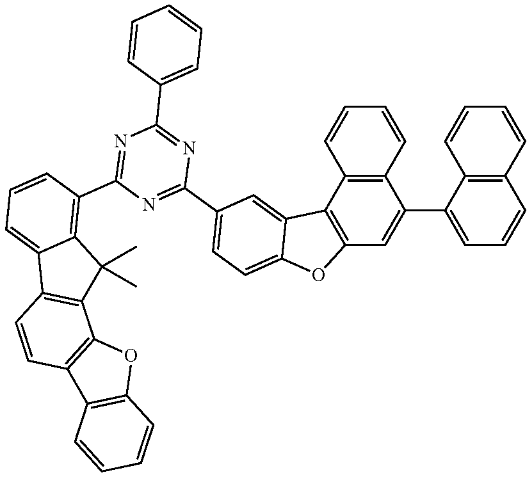
[50]
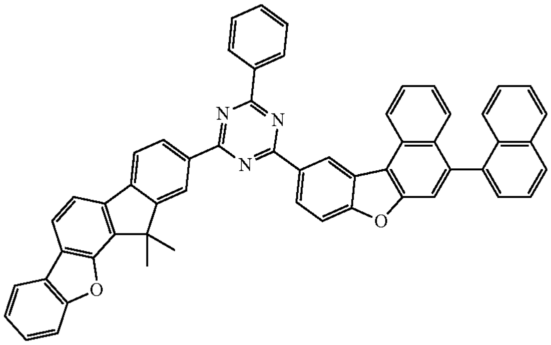
[51]
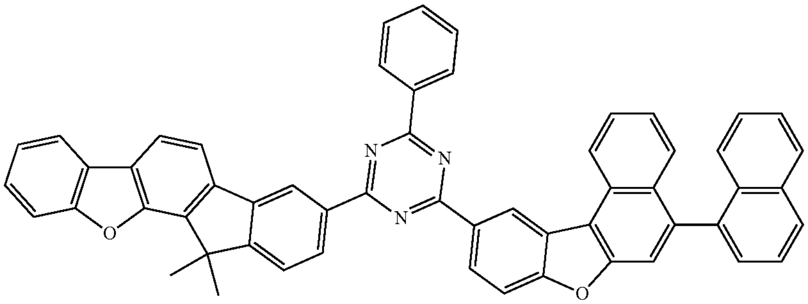
[52]
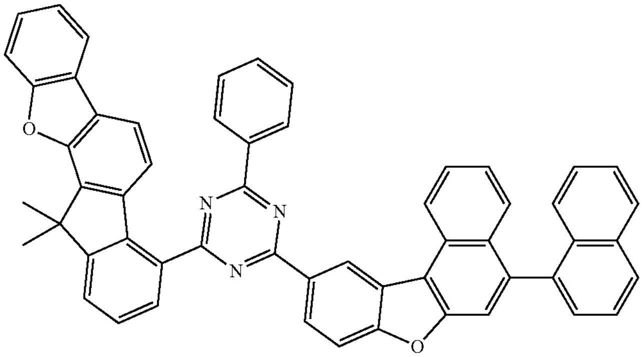
[53]
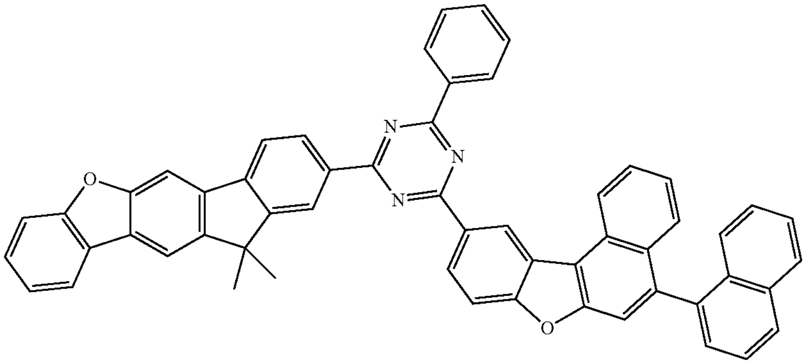

-continued
[54]
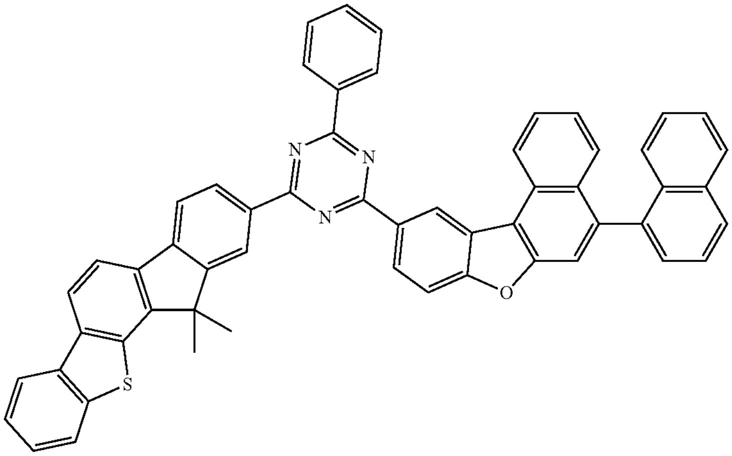
[55]
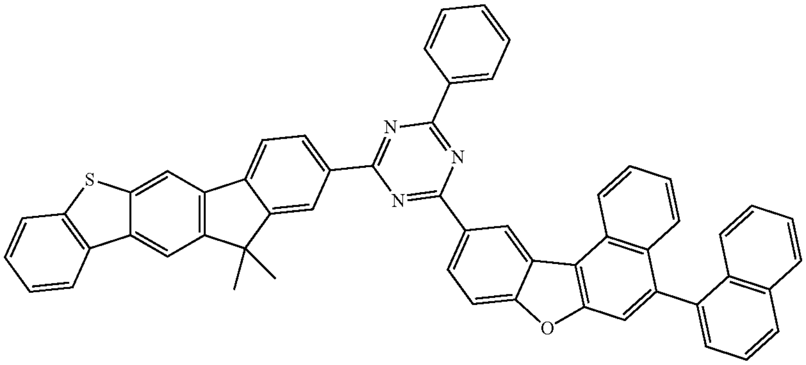
[56]
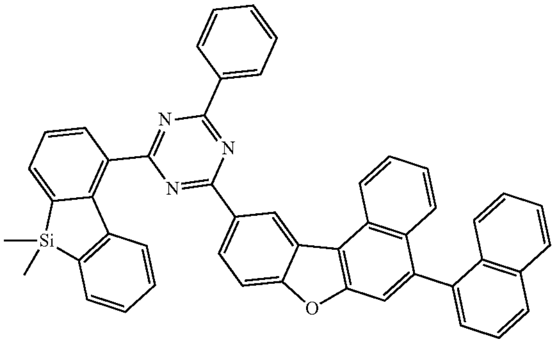
[57]
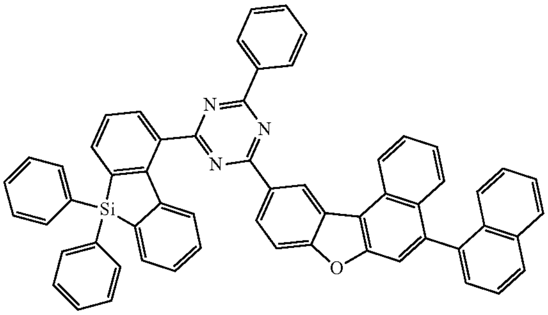
[58]
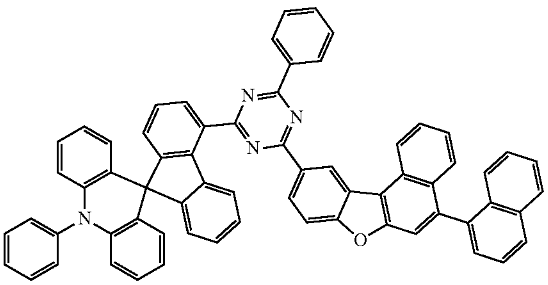
[59]
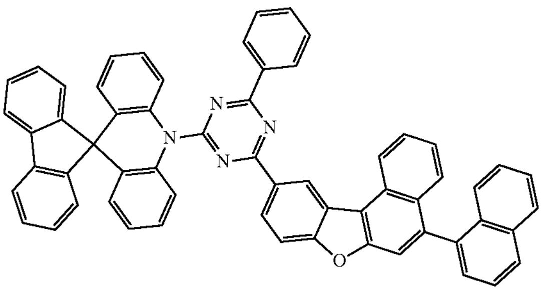

-continued
[60]
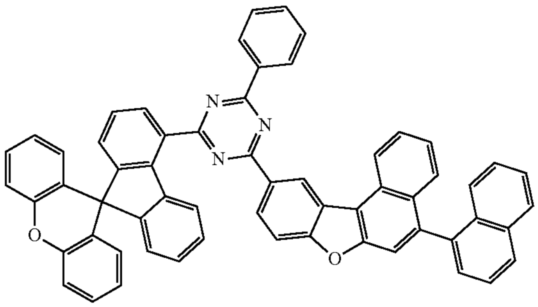
[61]
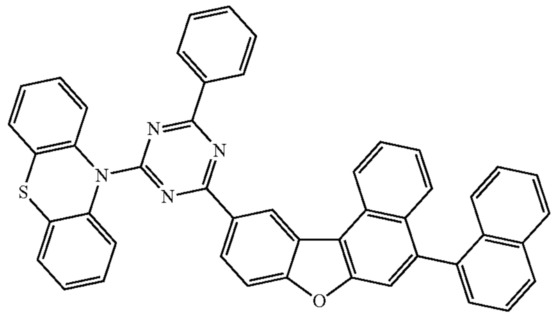
[62]
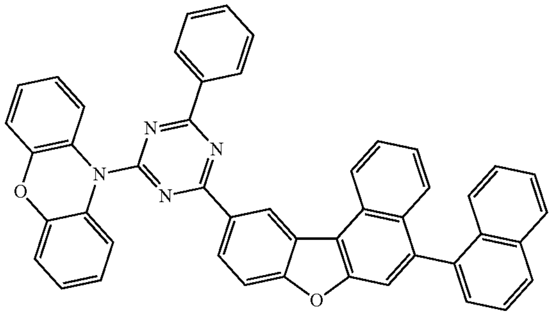
[63]
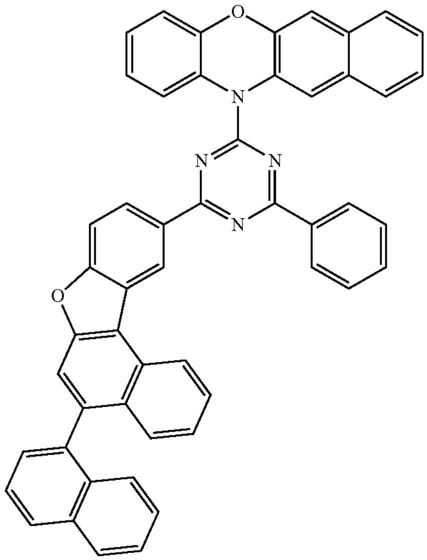
[64]
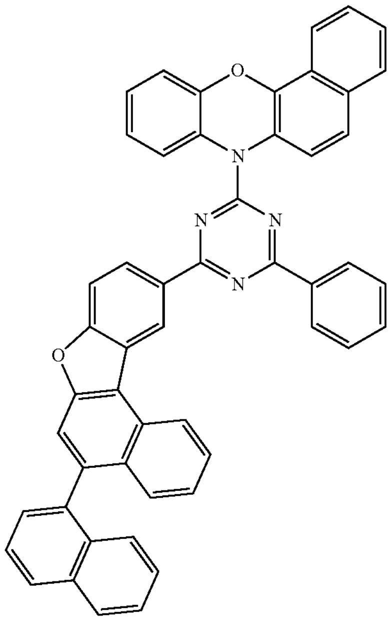
[65]
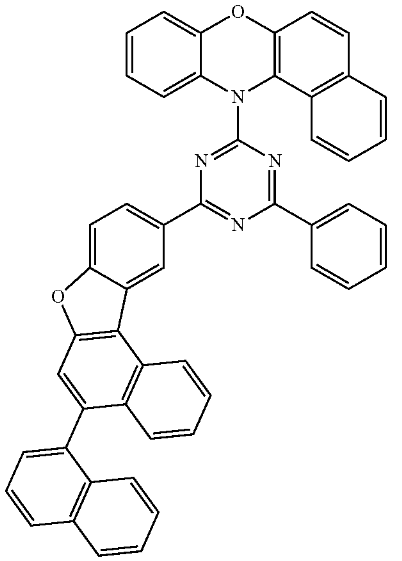

-continued
[66]
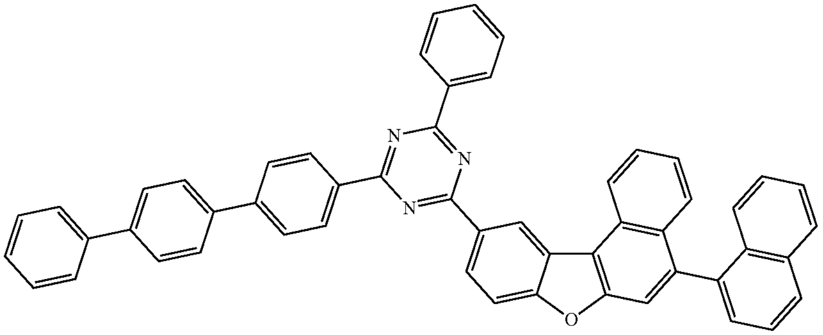
[67]
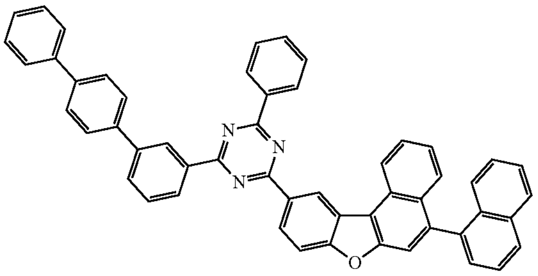
[68]
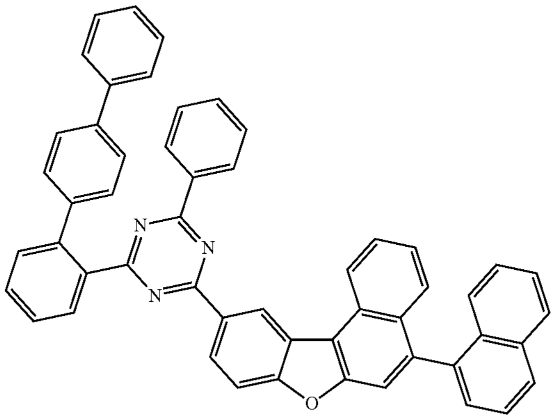
[69]
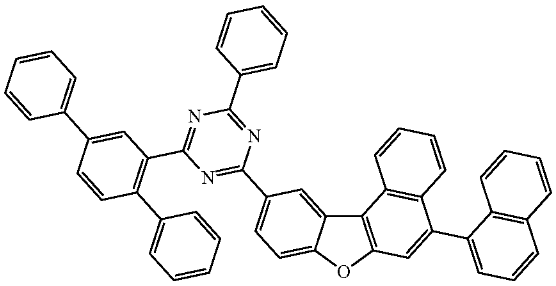
[70]
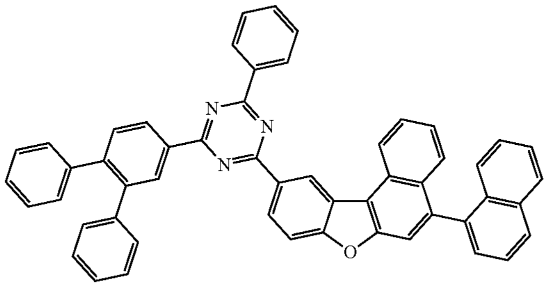
[71]
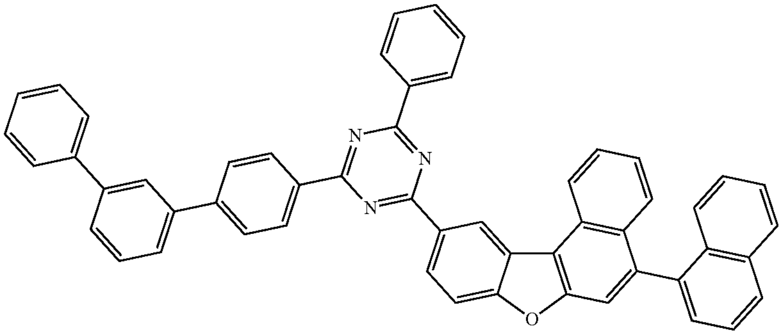

-continued
[72]
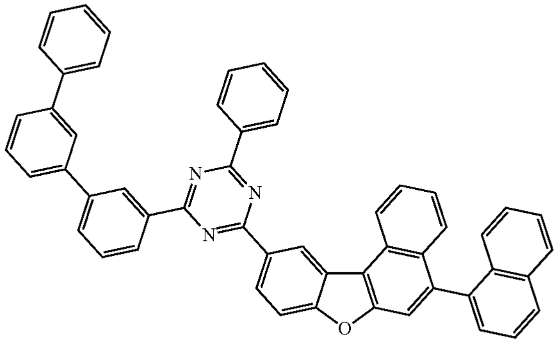
[73]
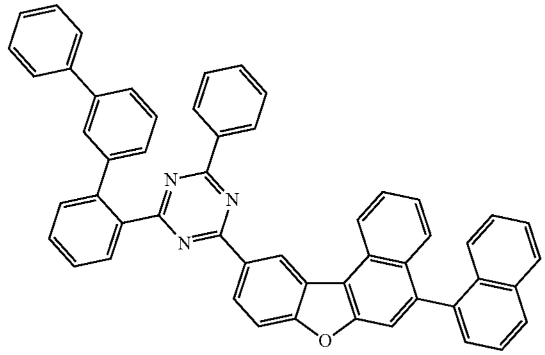
[74]
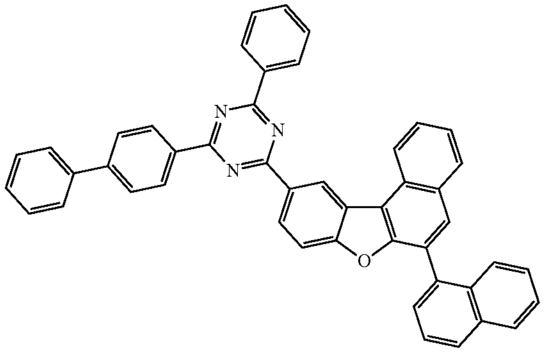
[75]
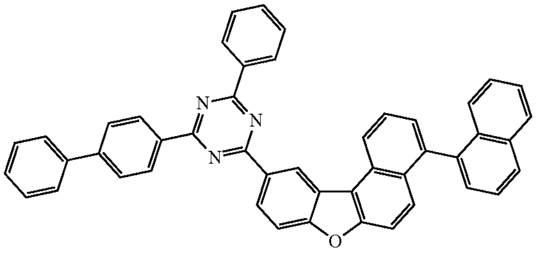
[76]
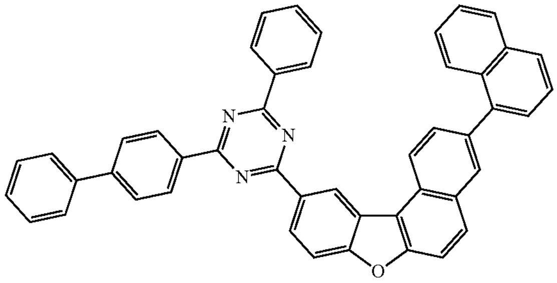
[77]
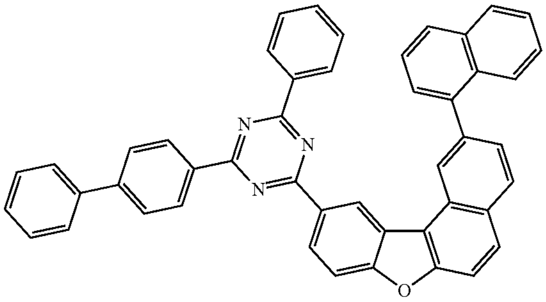
[78]
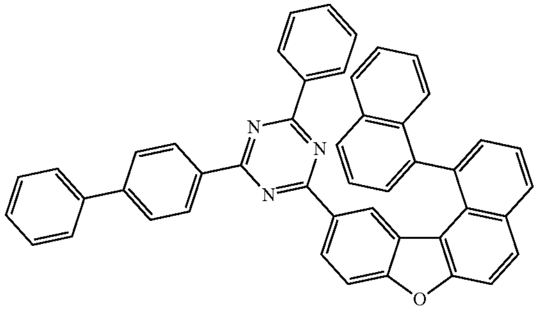
[79]
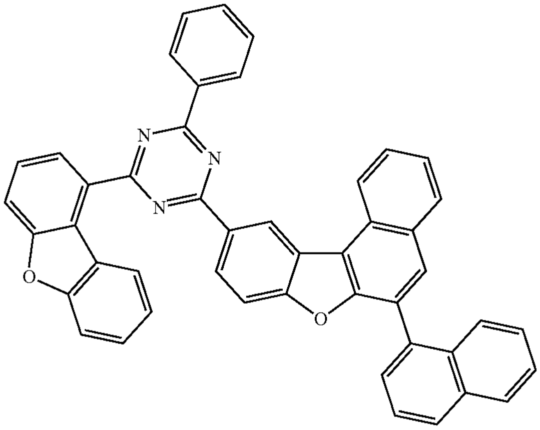

-continued
[80]
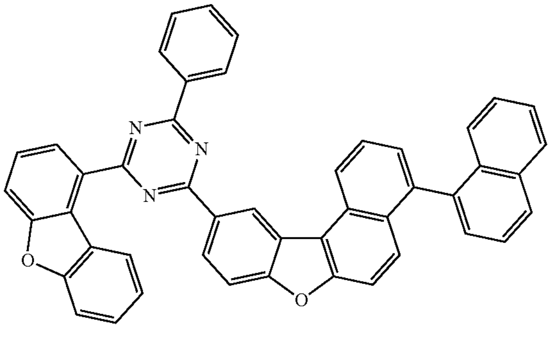
[81]
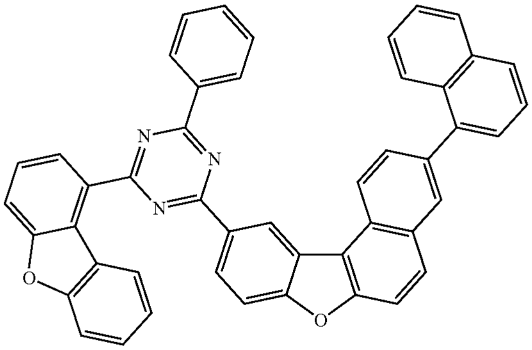
[82]
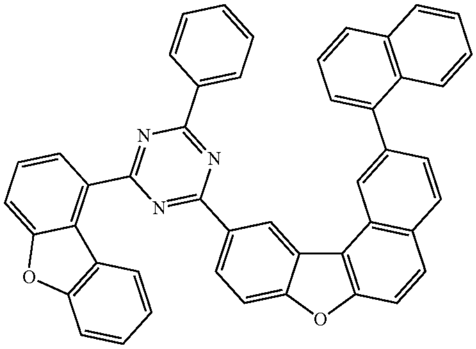
[83]
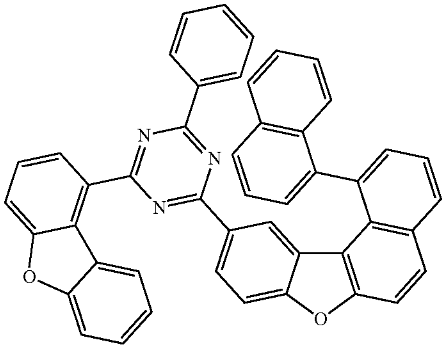
[84]
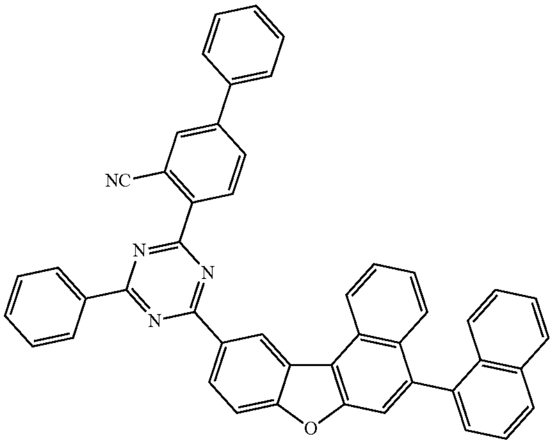
[85]
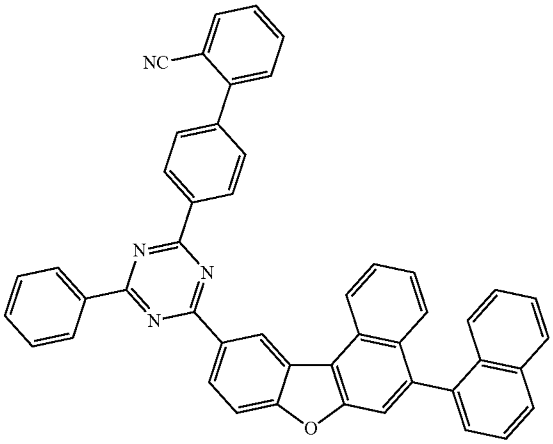
[86]
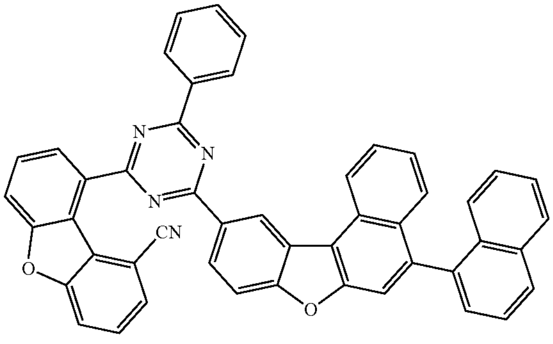
[87]
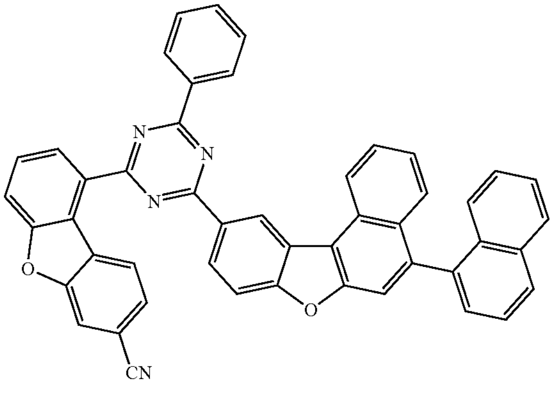

-continued
[88]
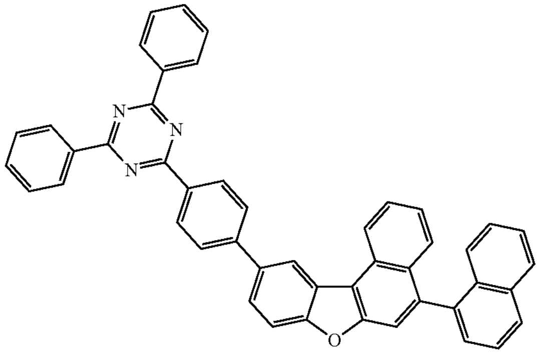
[89]
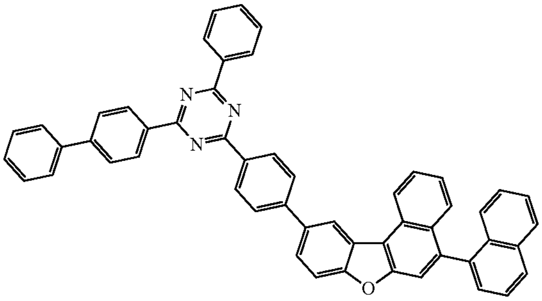
[90]
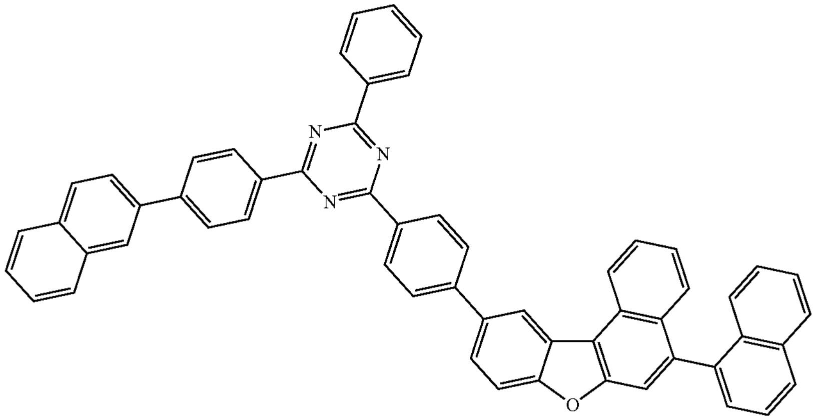
[91]
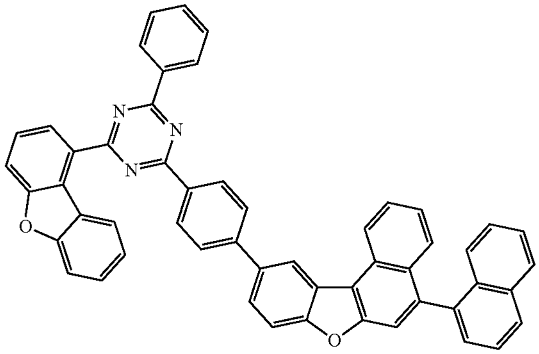
[92]
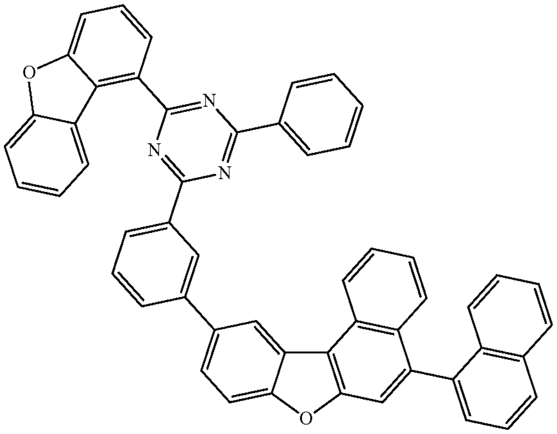
[93]
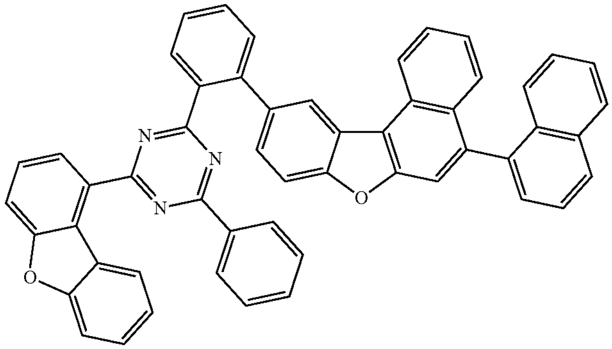

-continued
[94]
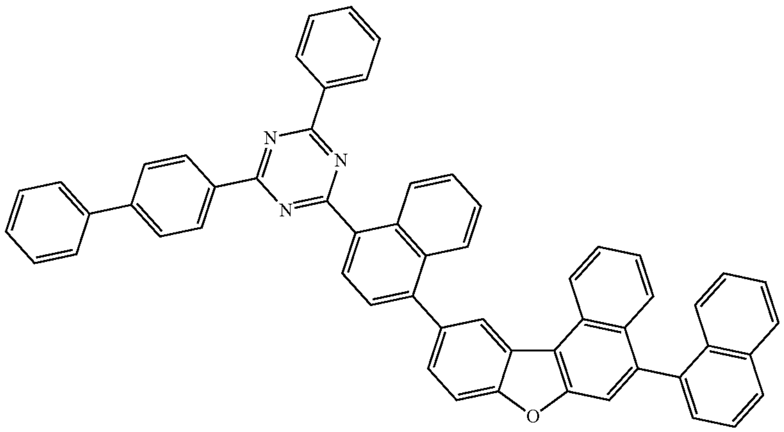
[95]
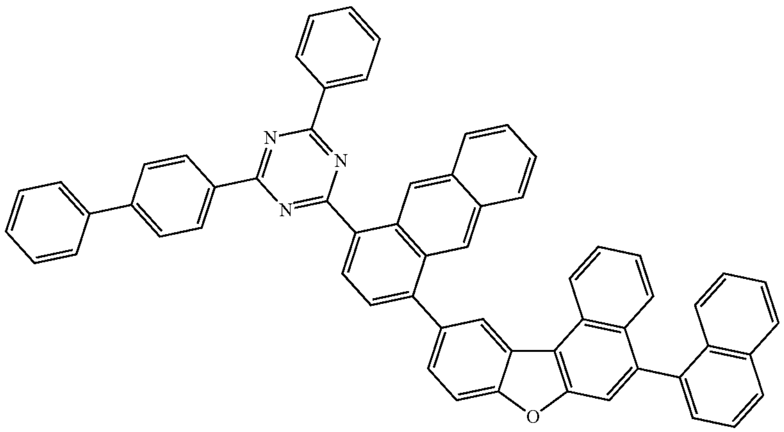
[96]
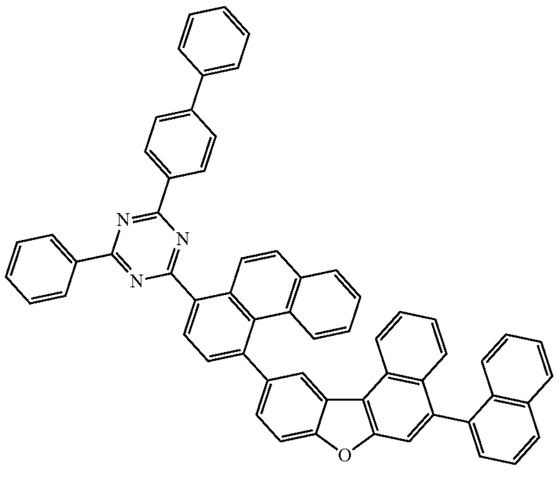
[97]
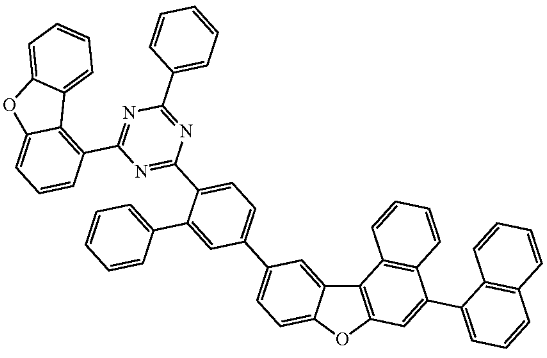

-continued
[98]
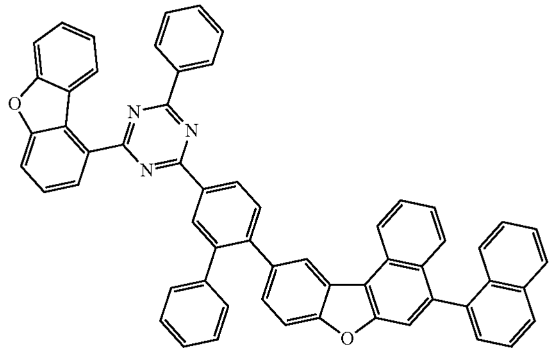
[99]
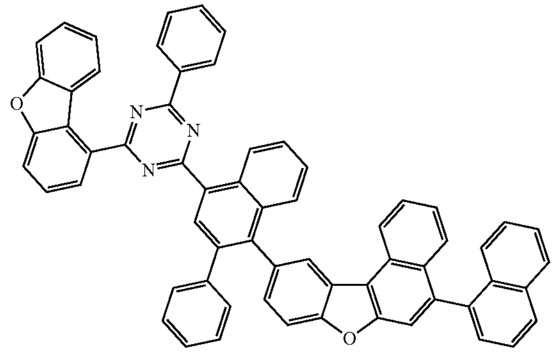
[100]
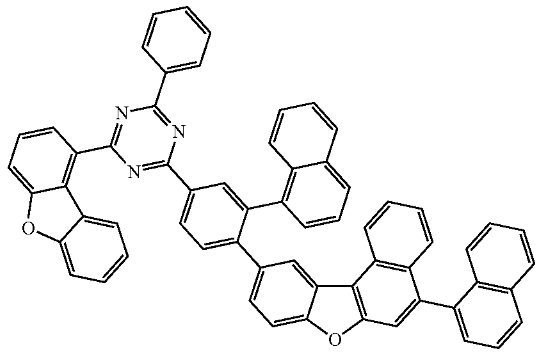
[101]
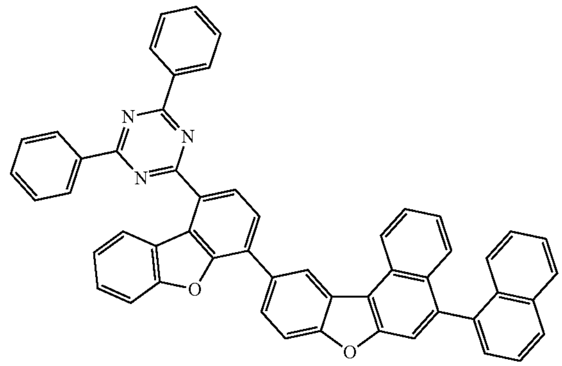
[102]
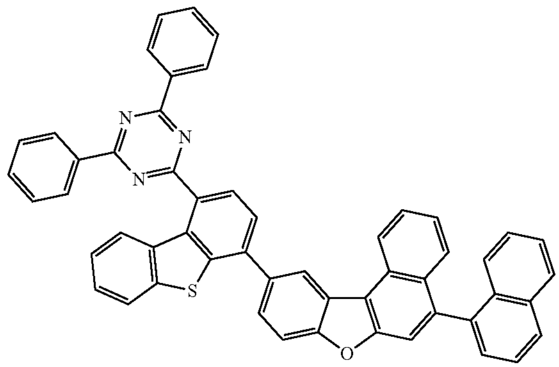
[103]
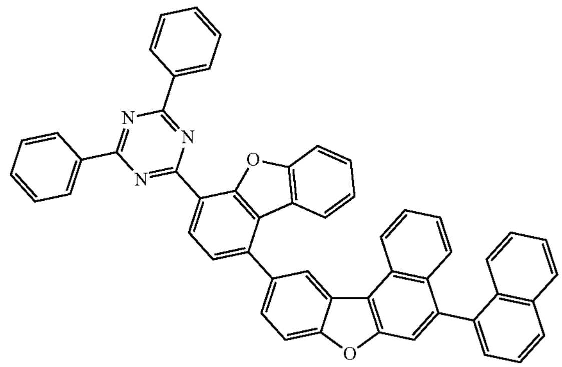
[104]
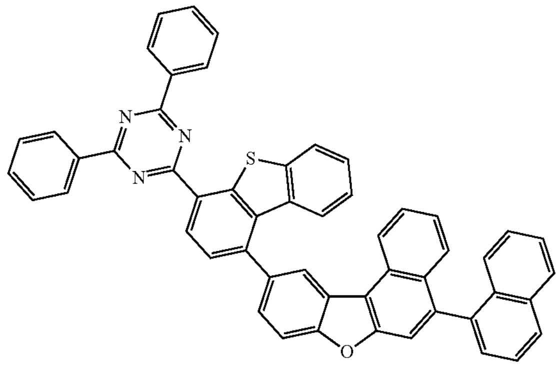
[105]
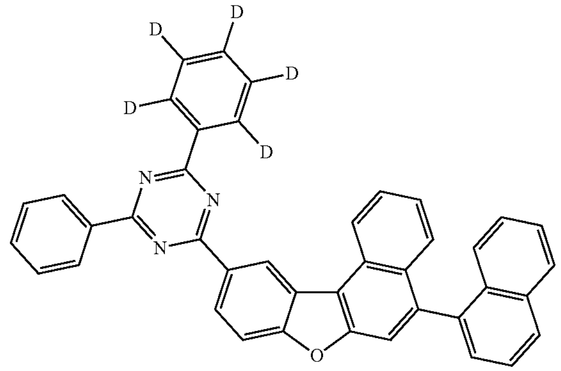

-continued
[106]
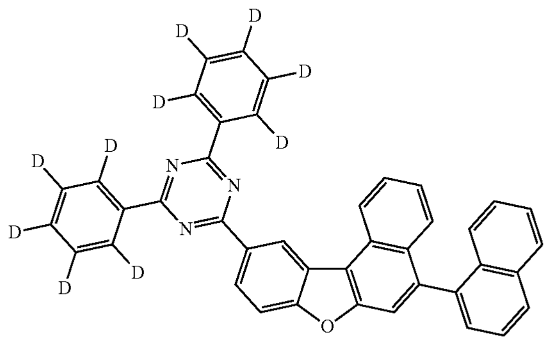
[107]
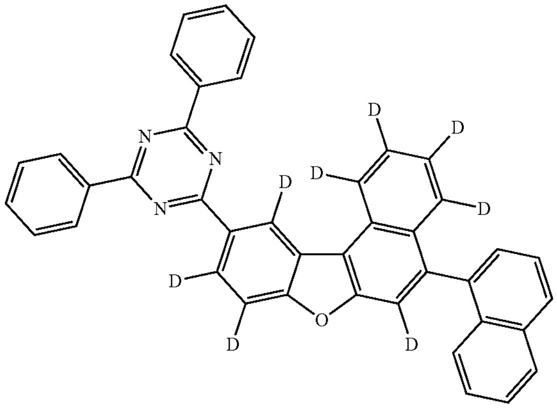
[108]
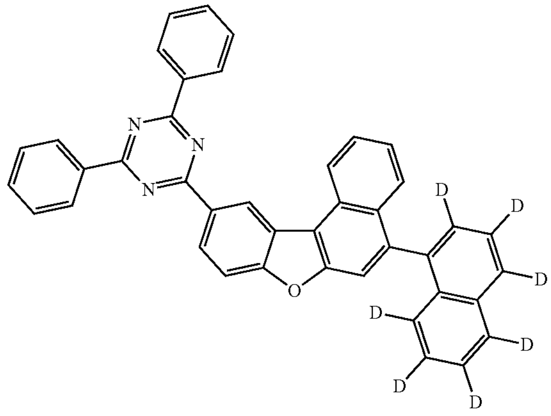
[109]
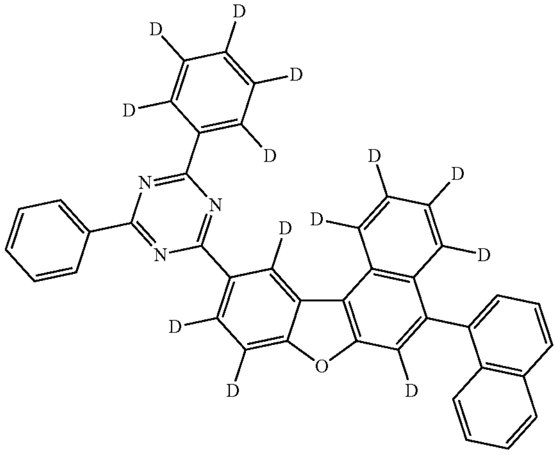
[110]
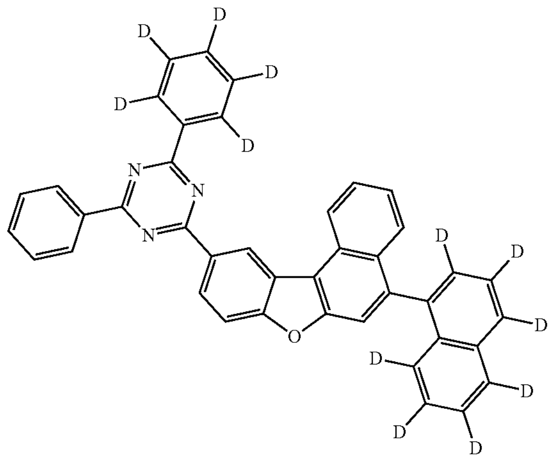
[111]
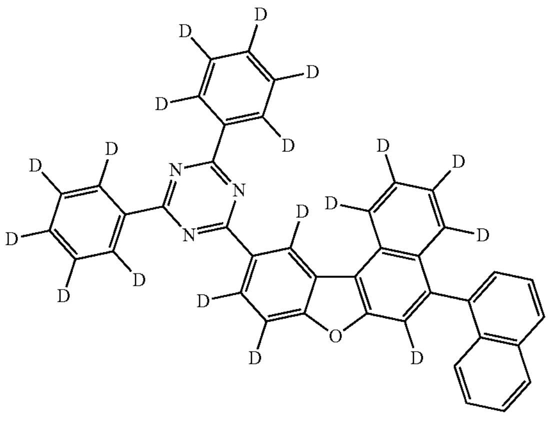

-continued
[112]
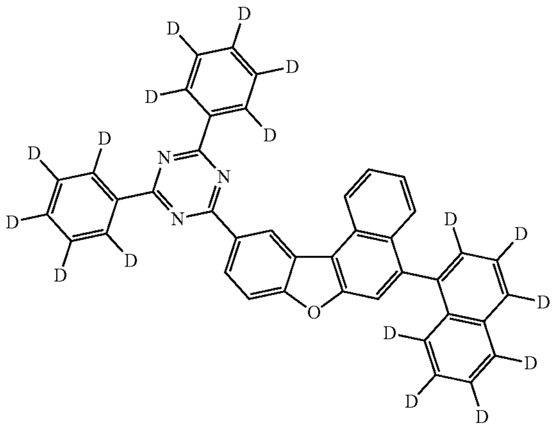
[113]
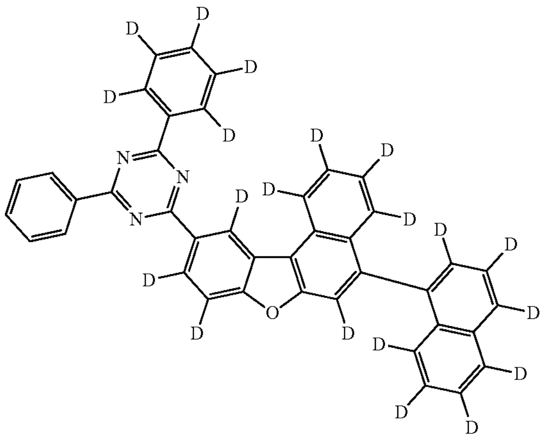
[114]
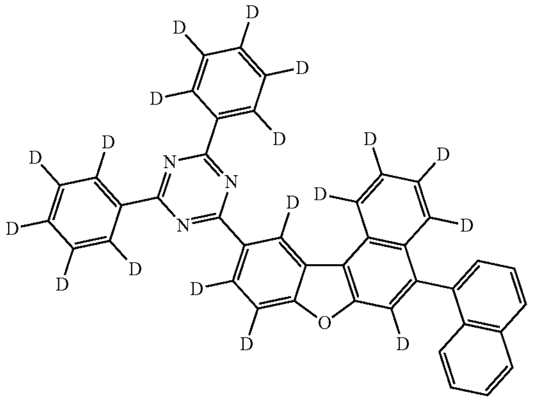
[115]
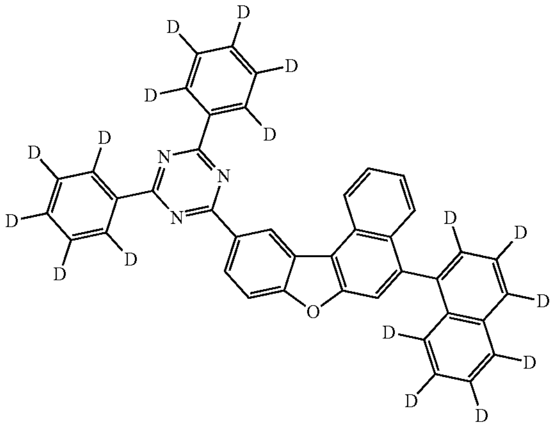
[116]
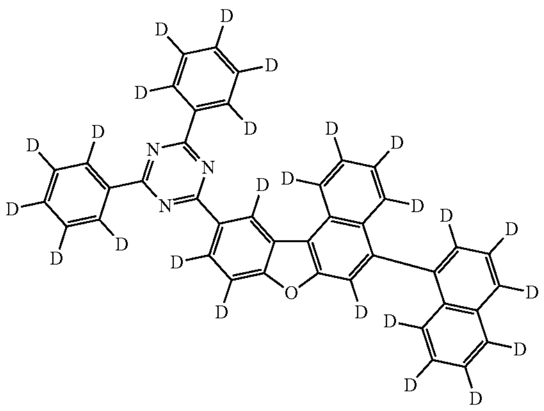
[117]
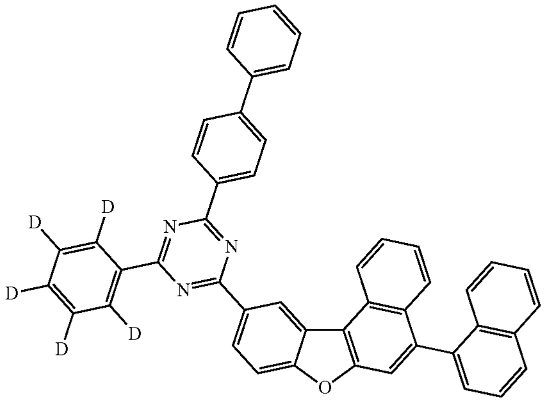

-continued
[118]
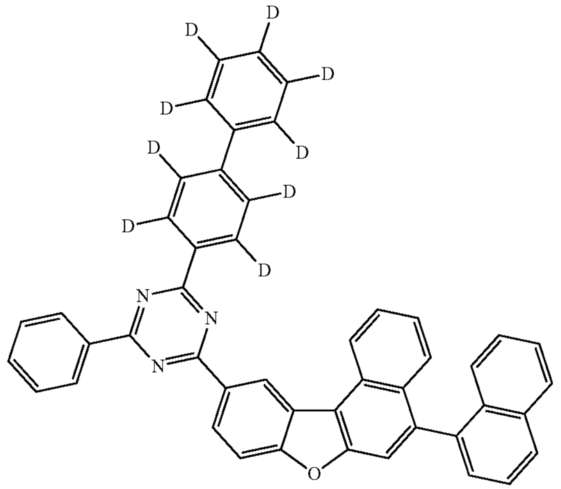
[119]
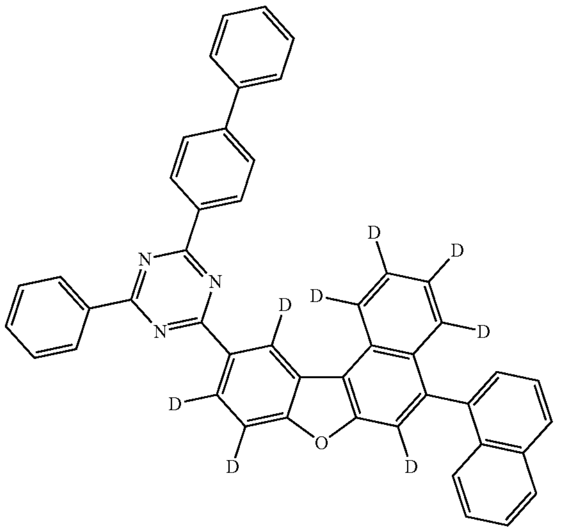
[120]
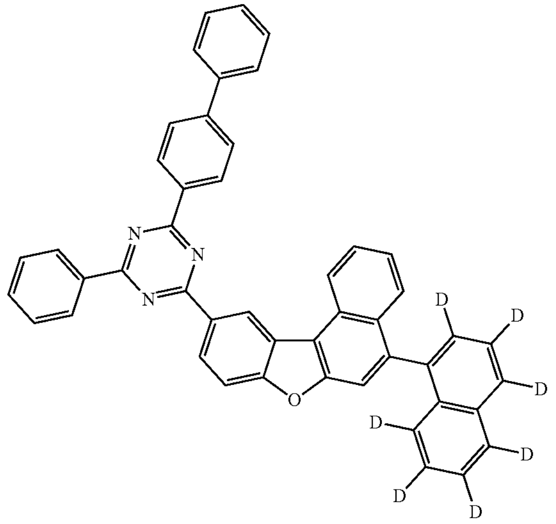
[121]
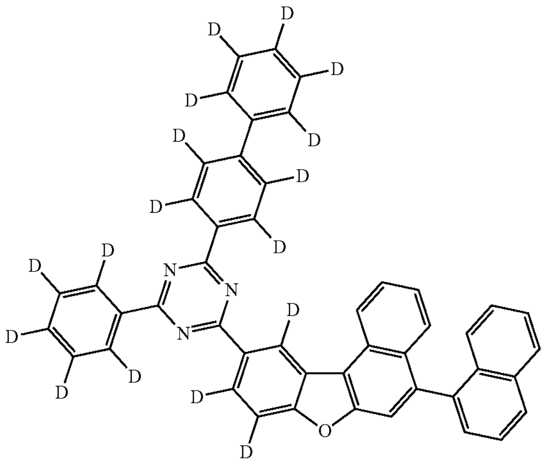
[122]
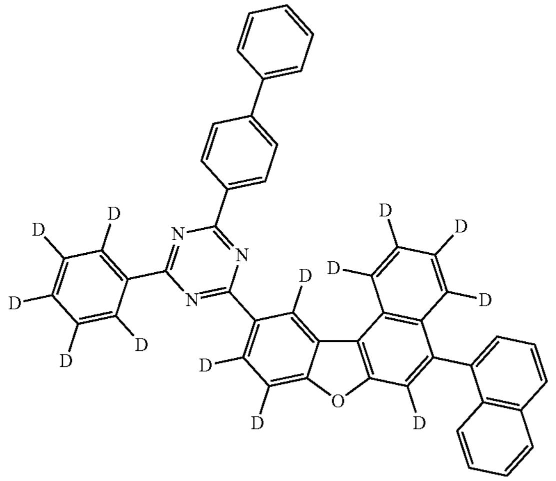
[123]
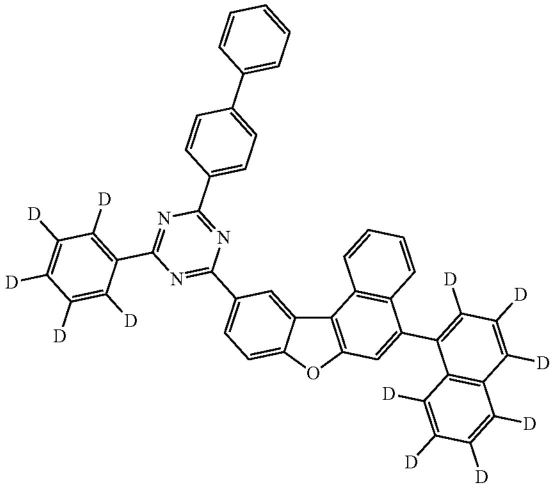

-continued
[124]
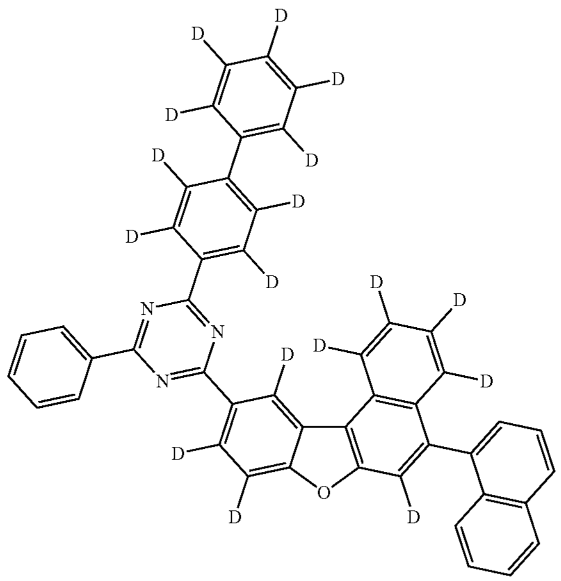
[125]
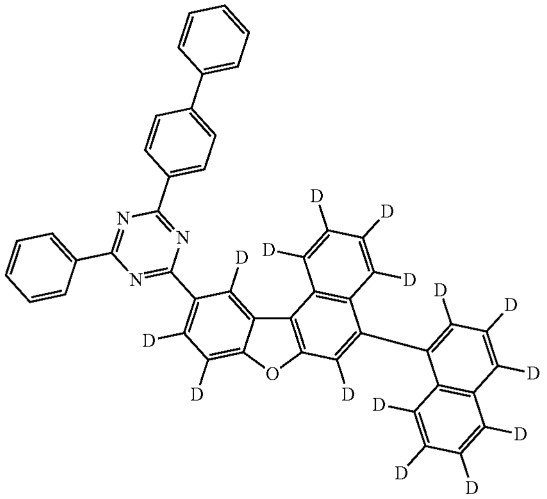
[126]
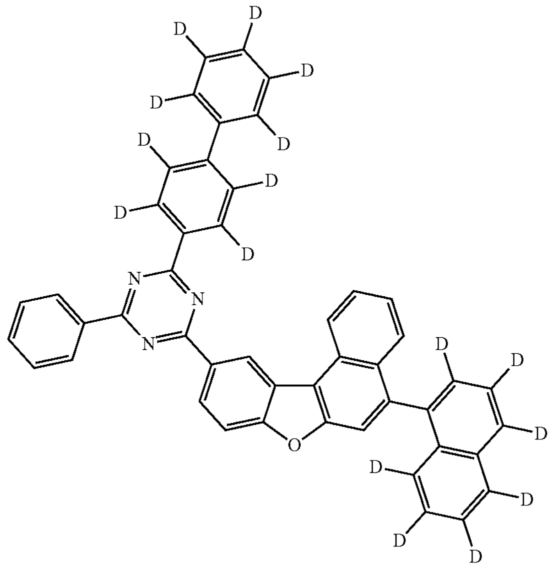
[127]
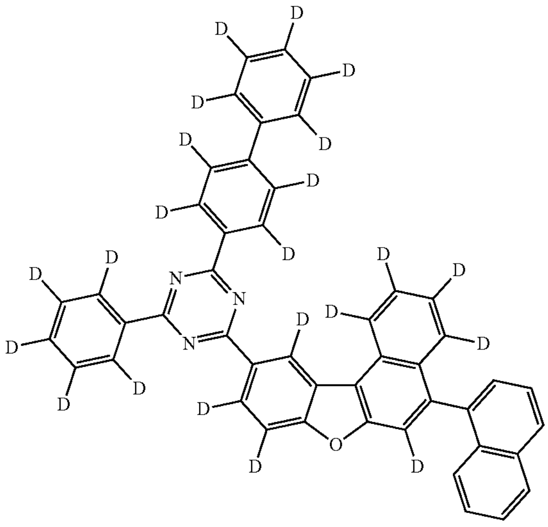

-continued
[128]
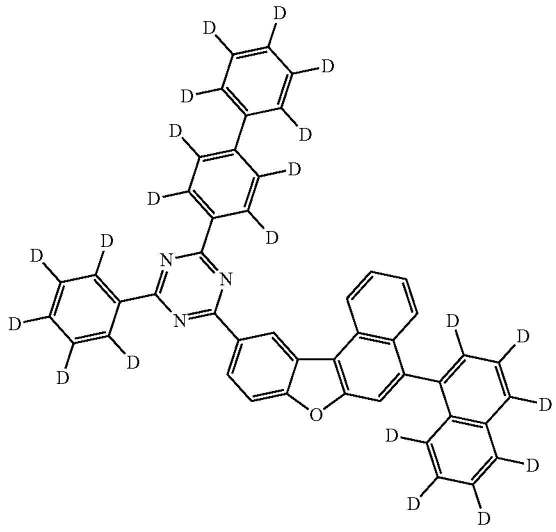
[129]
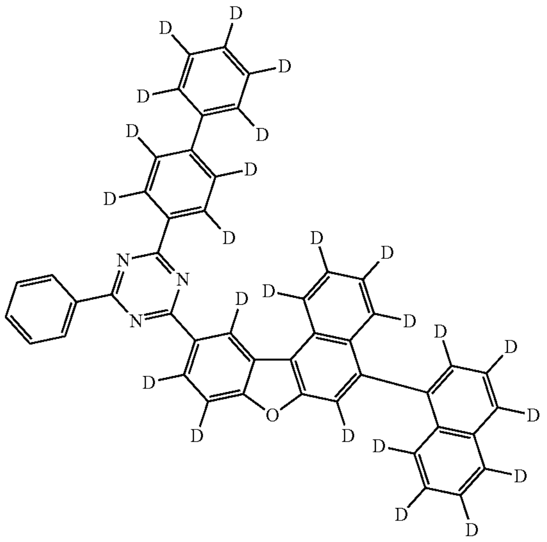
[130]
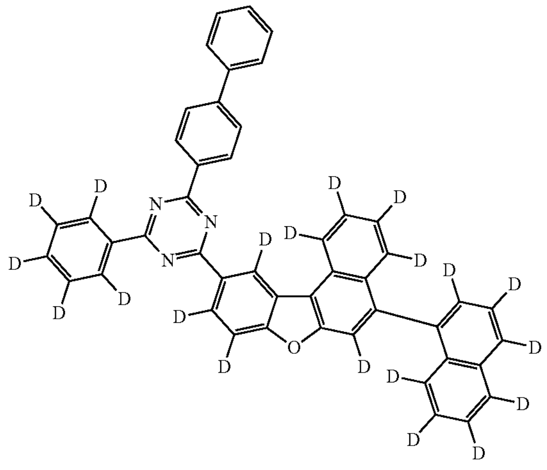
[131]
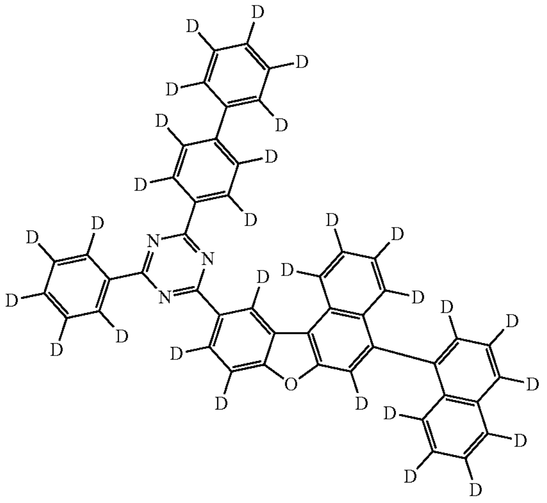
[132]
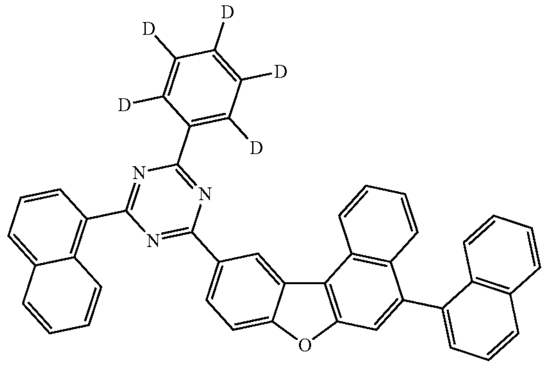
[133]
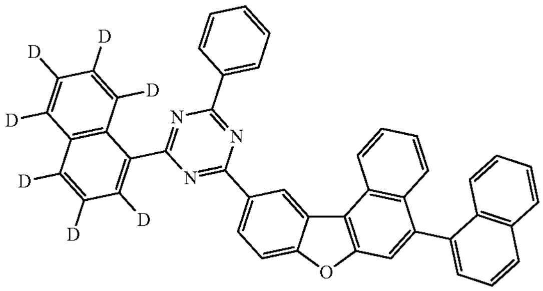

-continued
[134]
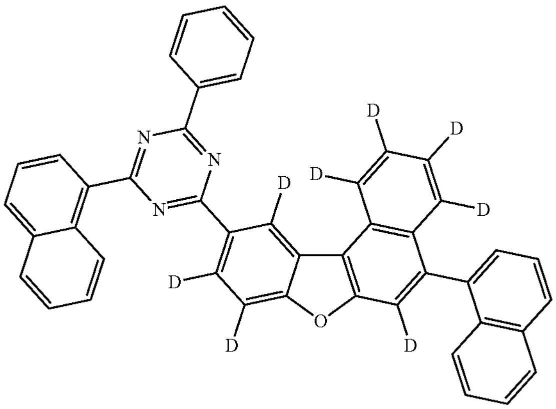
[135]
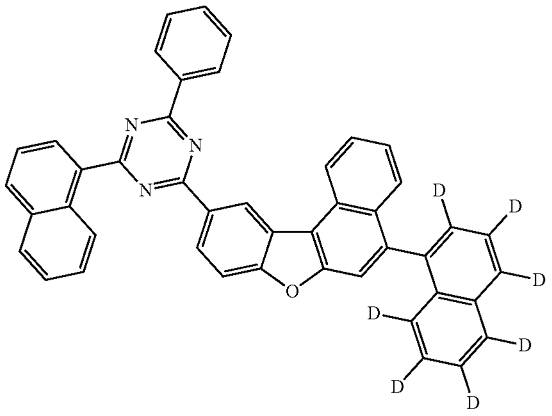
[136]
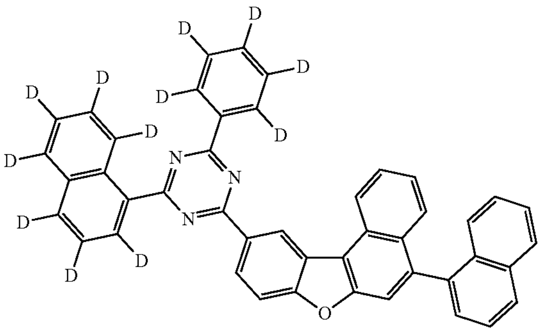
[137]
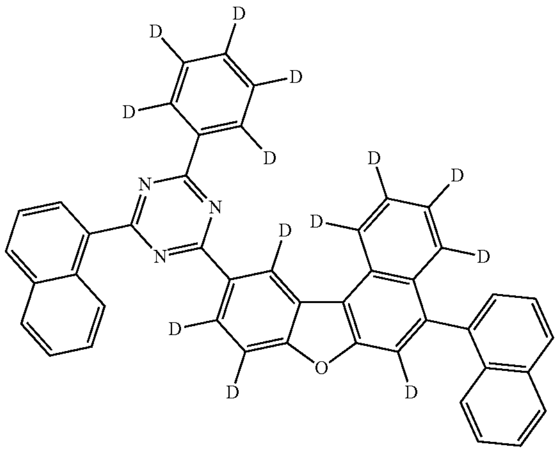
[138]
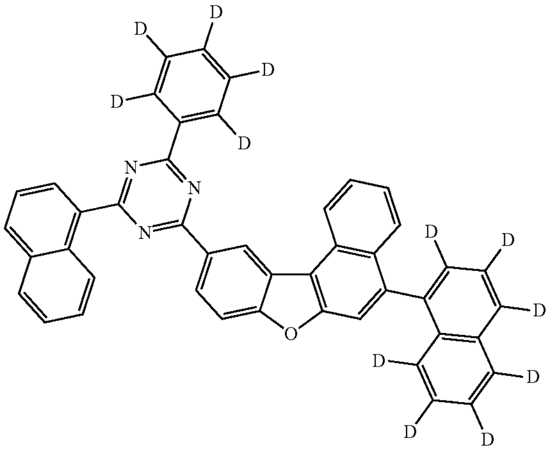
[139]
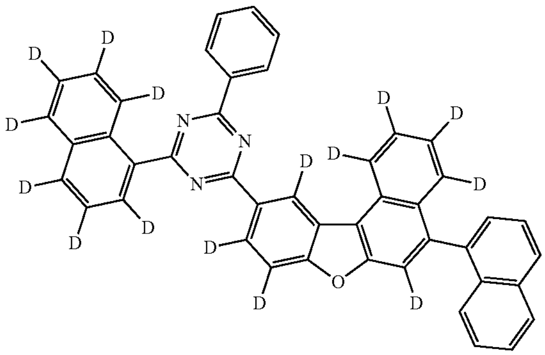

-continued
[140]
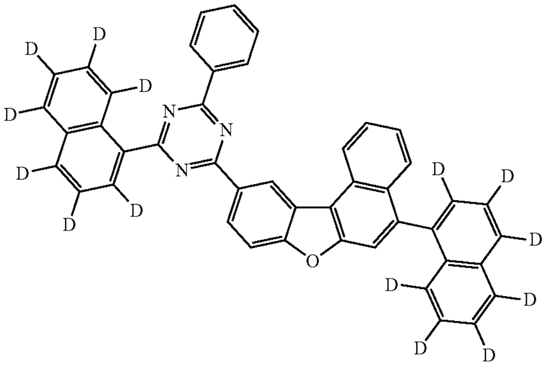
[141]
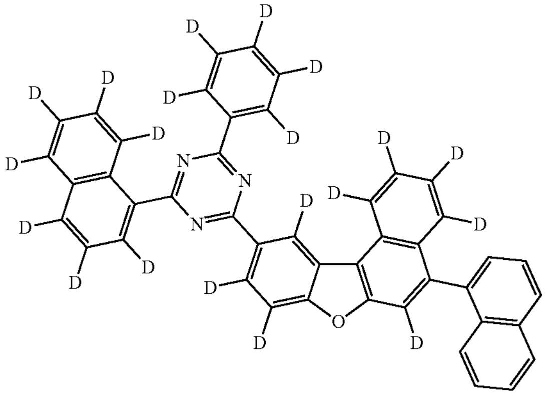
[142]
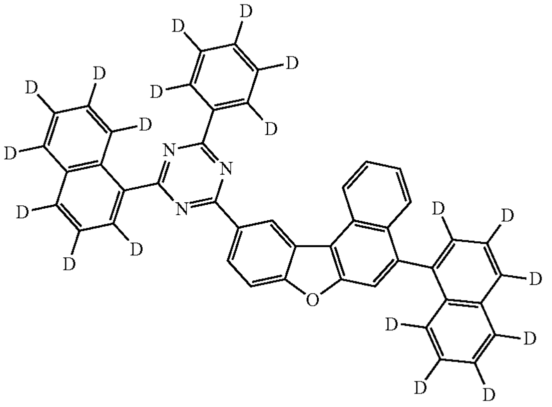
[143]
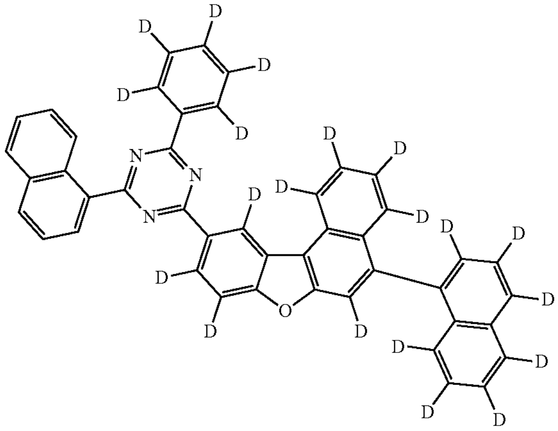
[144]
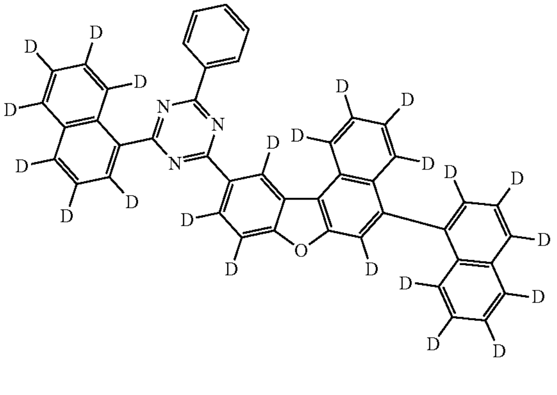
[145]
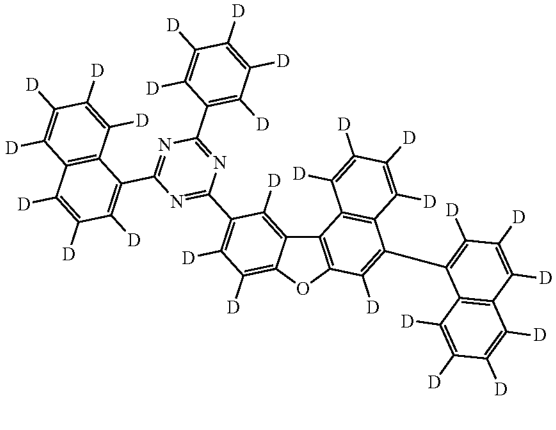

-continued
[146]
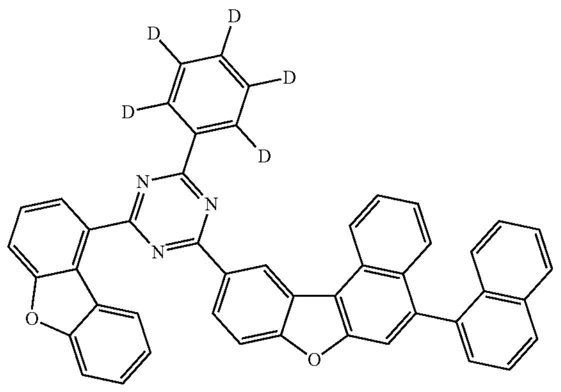
[147]
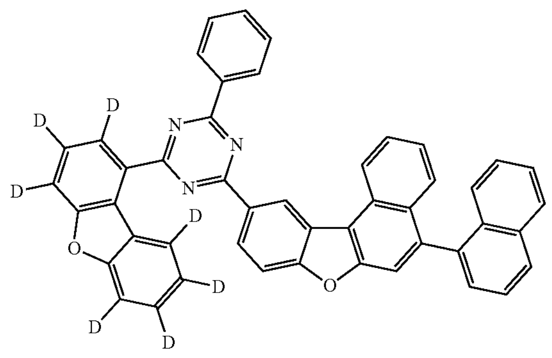
[148]
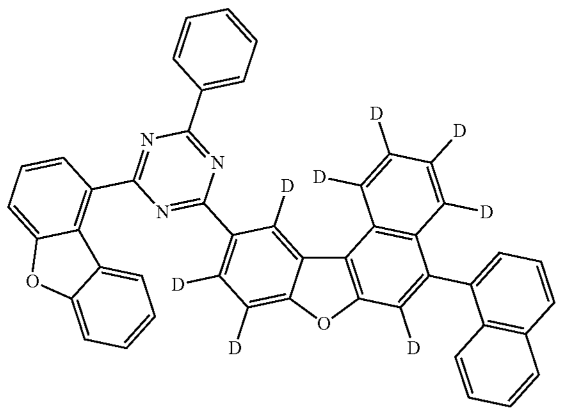
[149]
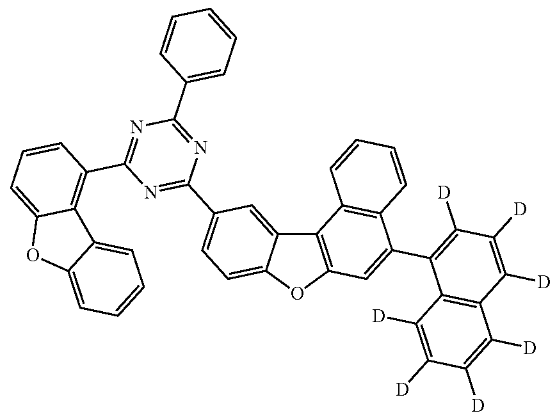
[150]
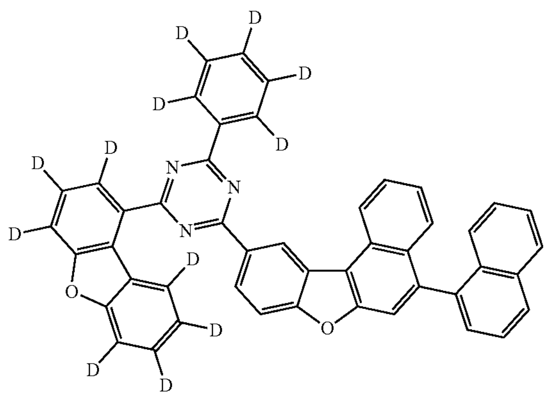
[151]
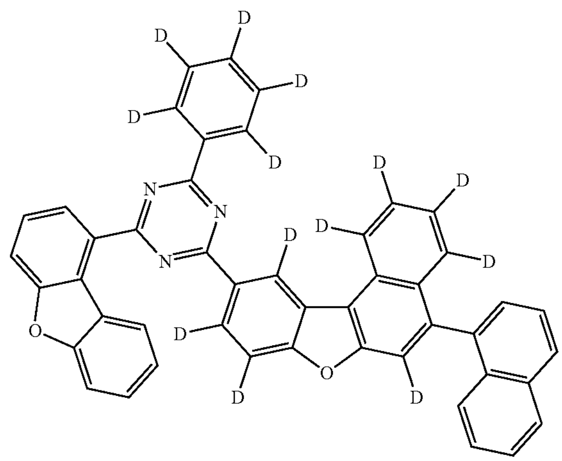

-continued
[152]
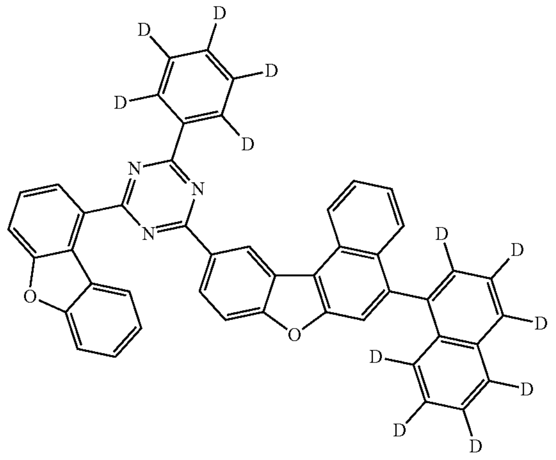
[153]
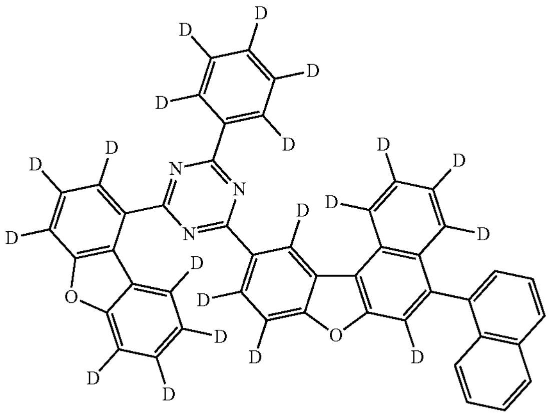
[154]
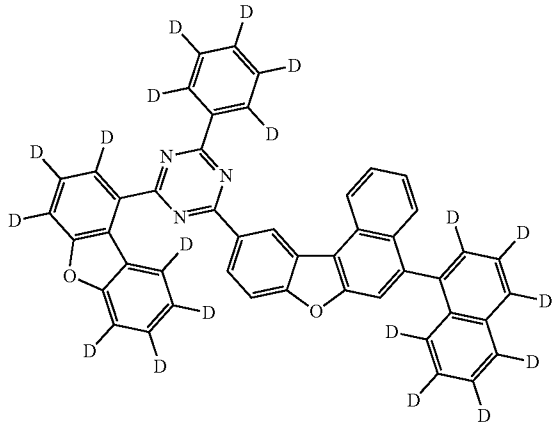
[155]
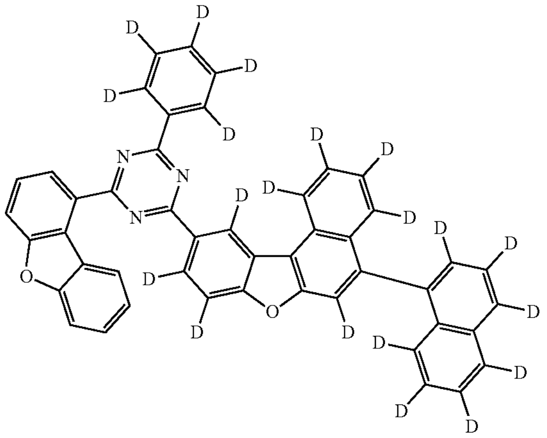
[156]
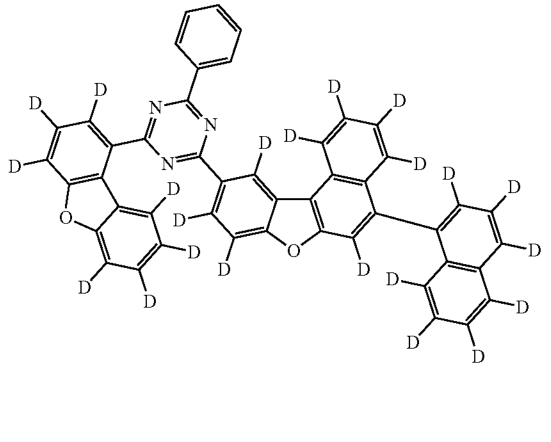
[157]
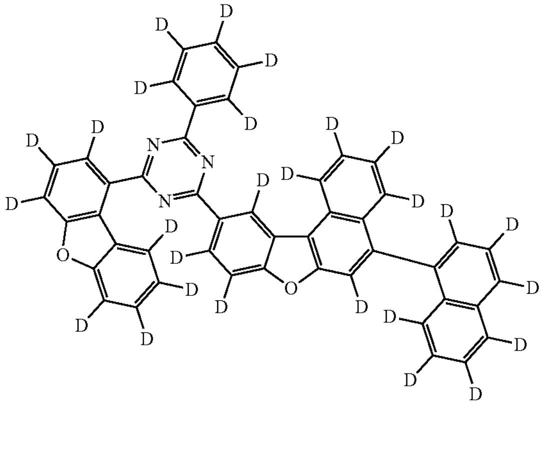

-continued
[158]
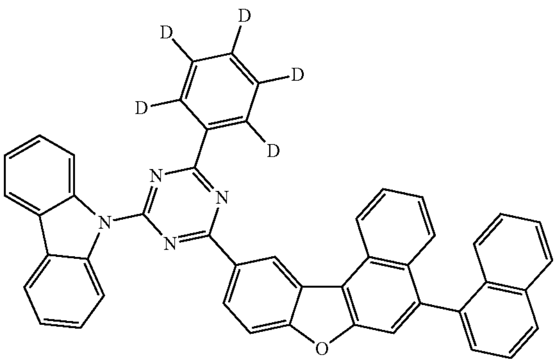
[159]
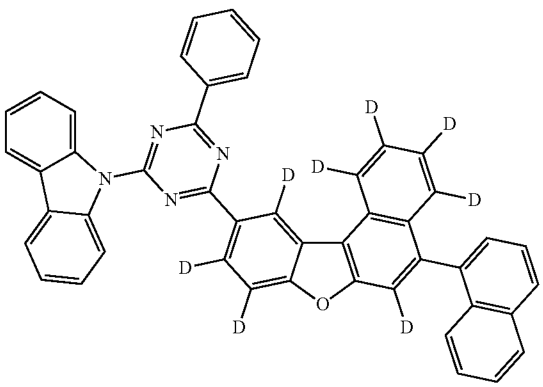
[160]
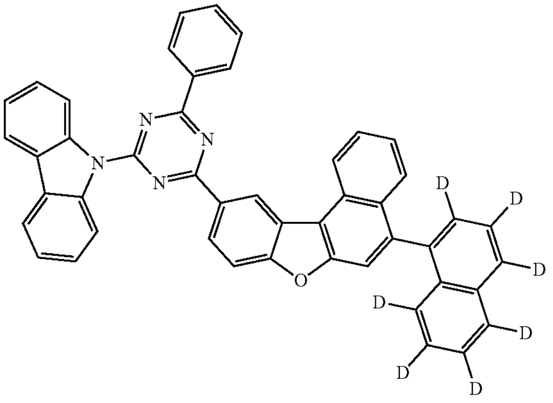
[161]
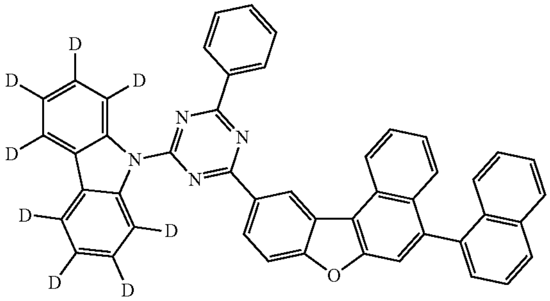
[162]
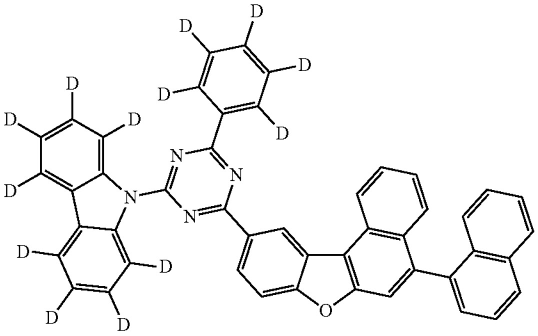
[163]
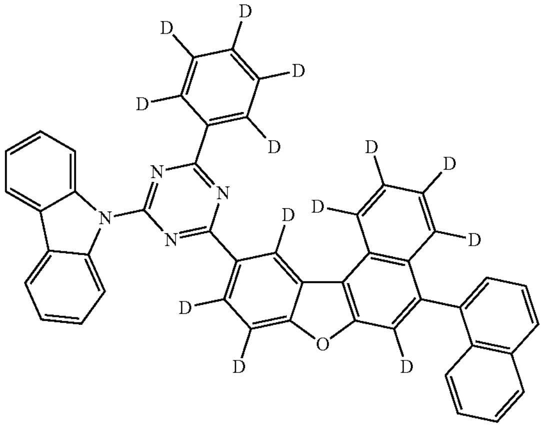

-continued
[164]
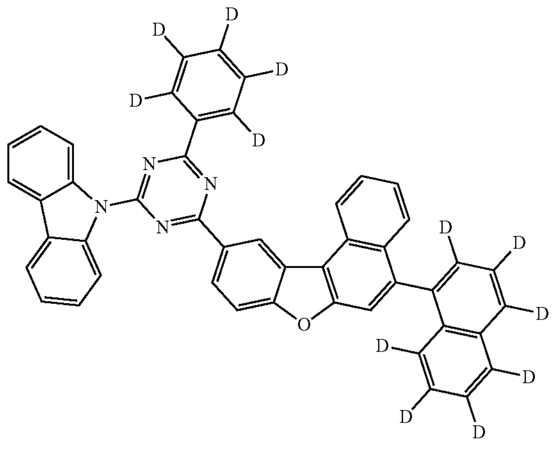
[165]
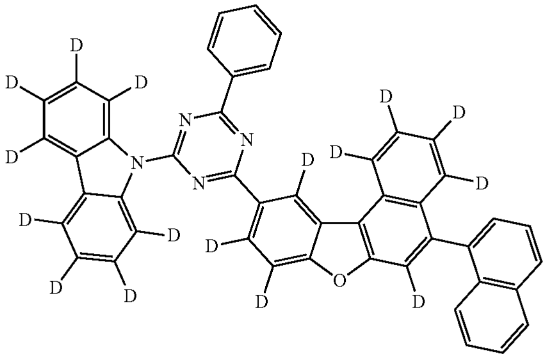
[166]
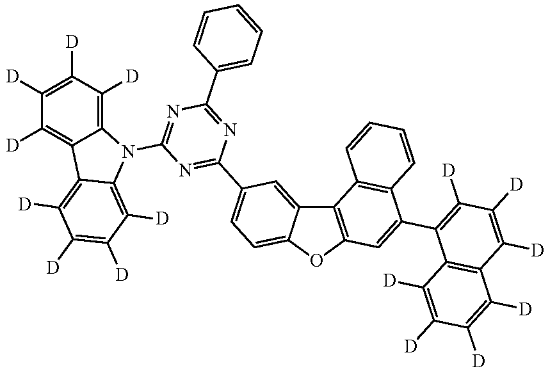
[167]
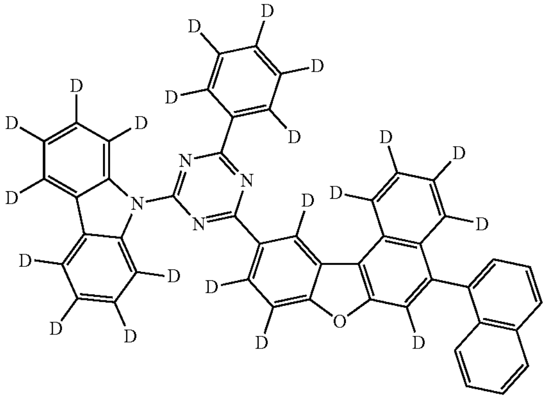
[168]
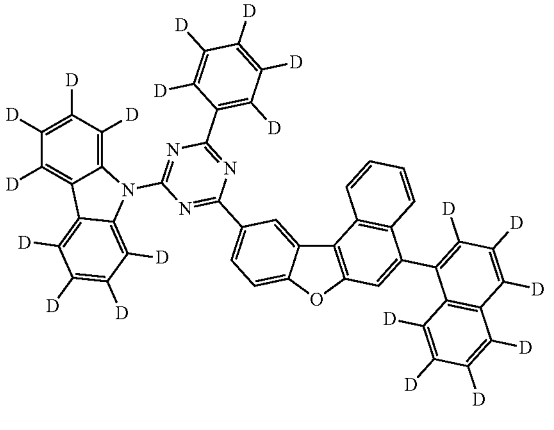
[169]
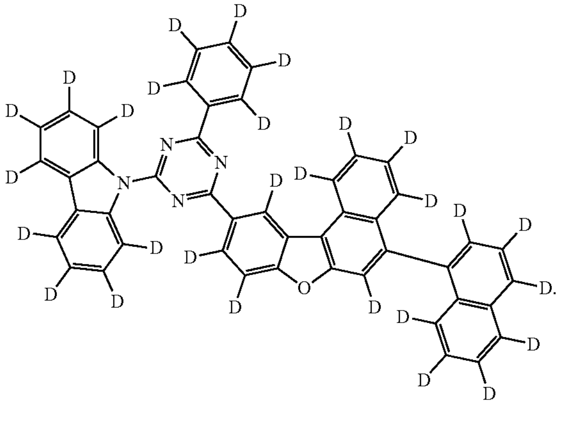
10. The composition as claimed in claim 1 wherein: Chemical Formula 2 is represented by one of Chemical Formula 2-I to Chemical Formula 2-IX:
[Chemical Formula 2-I]
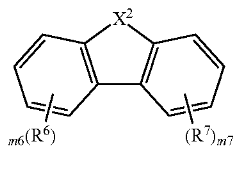
-continued
[Chemical Formula 2-II]
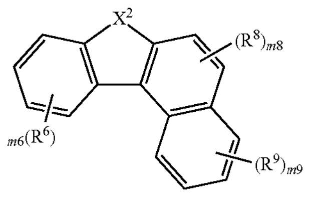

-continued

[Chemical Formula 2-III]

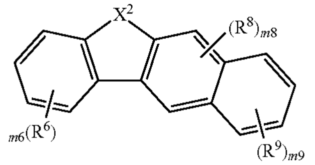

[Chemical Formula 2-IV]

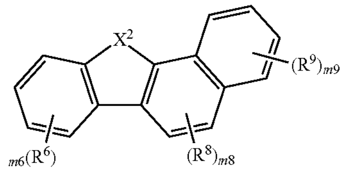

[Chemical Formula 2-V]

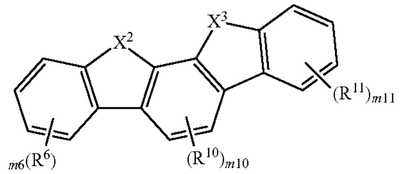

[Chemical Formula 2-VI]

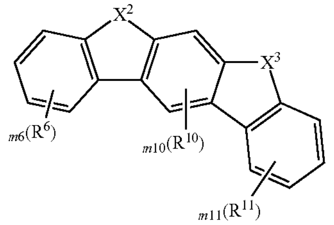

[Chemical Formula 2-VII]

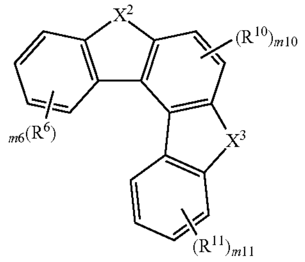

[Chemical Formula 2-VIII]

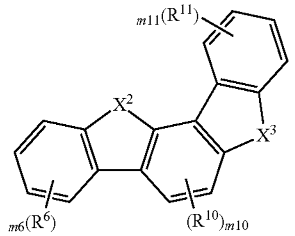

[Chemical Formula 2-IX]

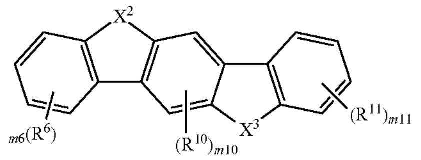

in Chemical Formula 2-I to Chemical Formula 2-IX, $X^2$, $X^3$, m6 to m11, and $R^6$ to $R^{11}$ are defined the same as those of Chemical Formula 2.

11. The composition as claimed in claim 10, wherein:

the second compound is represented by one of Chemical Formula 2-IA to Chemical Formula 2-IXA, Chemical Formula 2-IB to Chemical Formula 2-IXB, and Chemical Formula 2-IIC to Chemical Formula 2-IVC:

[Chemical Formula 2-IA]

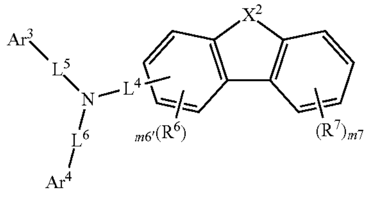

[Chemical Formula 2-IIA]

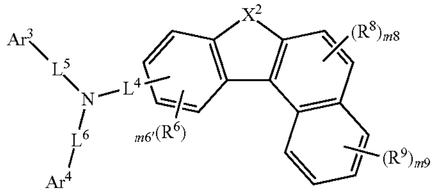

[Chemical Formula 2-IIIA]

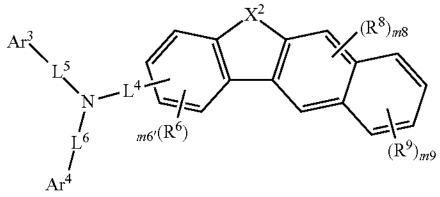

[Chemical Formula 2-IVA]

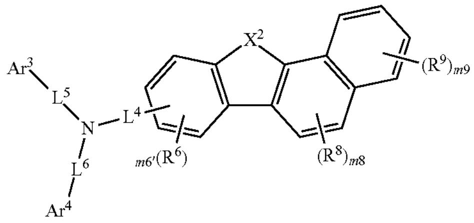

[Chemical Formula 2-VA]

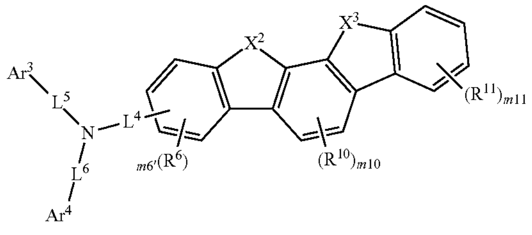

[Chemical Formula 2-VIA]

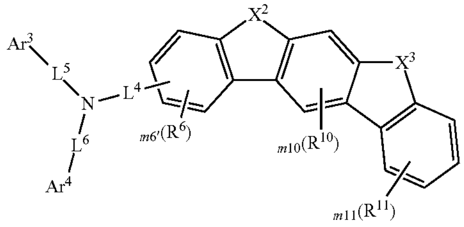

-continued
[Chemical Formula 2-VIIA]
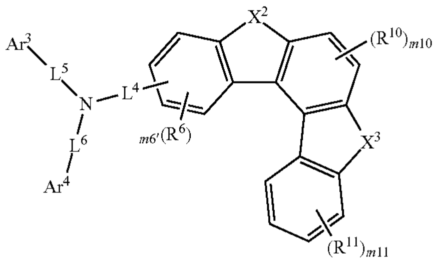
[Chemical Formula 2-VIIIA]
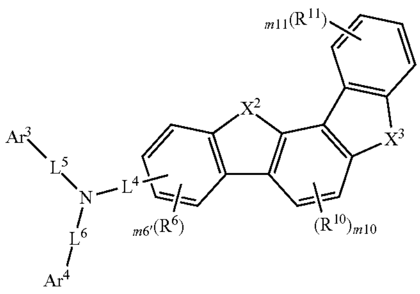
[Chemical Formula 2-IXA]
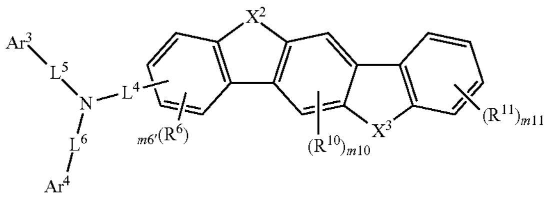
[Chemical Formula 2-IB]
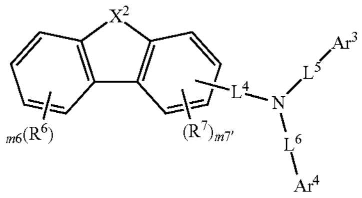
[Chemical Formula 2-IIB]
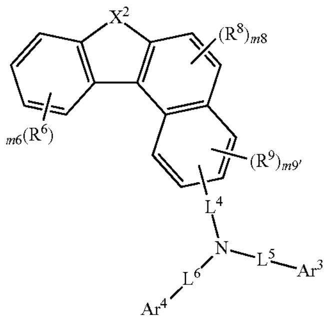
[Chemical Formula 2-IIIB]
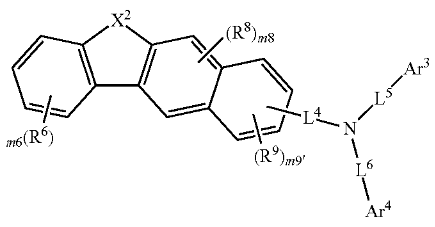
-continued
[Chemical Formula 2-IVB]
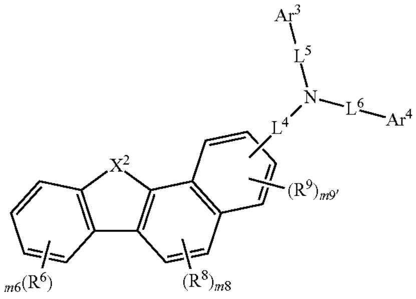
[Chemical Formula 2-VB]
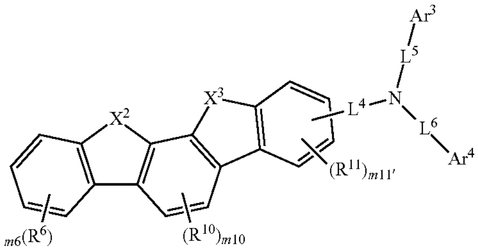
[Chemical Formula 2-VIB]
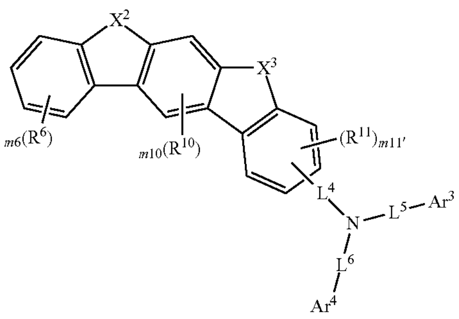
[Chemical Formula 2-VIIB]
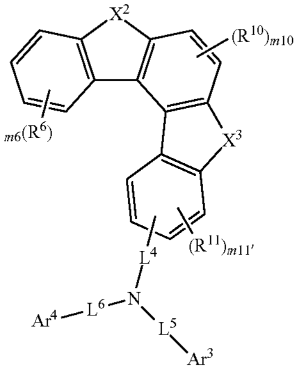

-continued

[Chemical Formula 2-VIIIB]

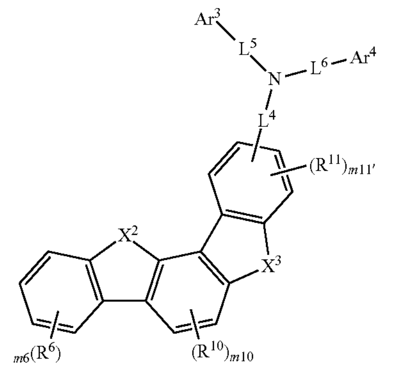

[Chemical Formula 2-IXB]

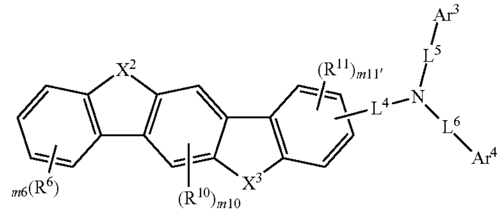

[Chemical Formula 2-IIC]

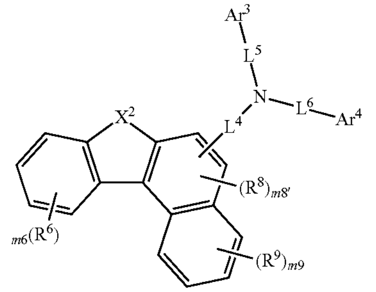

[Chemical Formula 2-IIIC]

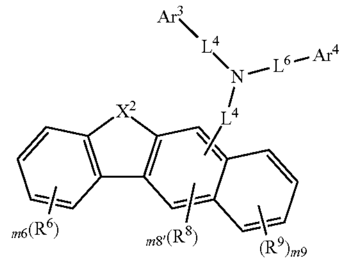

[Chemical Formula 2-IVC]

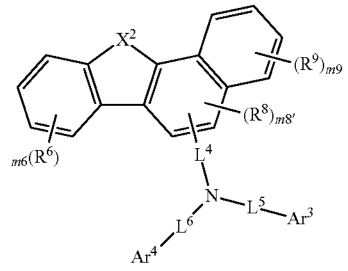

in Chemical Formula 2-IA to Chemical Formula 2-IXA, Chemical Formula 2-IB to Chemical Formula 2-IXB, and Chemical Formula 2-IIC to Chemical Formula 2-IVC, $X^2$, $X^3$, $L^4$ to $L^6$, m6 to m11, $Ar^3$ and $Ar^4$ are defined the same as those of Chemical Formula 2, $R^6$ to $R^{11}$ are each independently hydrogen, deuterium, a substituted or unsubstituted C1 to C30 alkyl group, or a substituted or unsubstituted C6 to C30 aryl group, m6', m7', m9', and m11' are each independently an integer of 1 to 3, and m8' is 1.

12. The composition as claimed in claim 10, wherein:

the second compound is represented by Chemical Formula 2-IVB-2 or Chemical Formula 2-VIIIB-2:

[Chemical Formula 2-IVB-2]

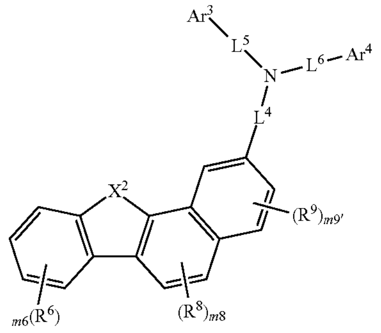

[Chemical Formula 2-VIIIB-2]

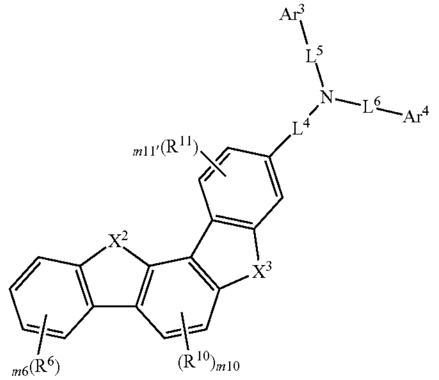

0 in Chemical Formula 2-IVB-2 and Chemical Formula 2-VIIIB-2, $L^4$ to $L^6$ are each independently a single bond or a substituted or unsubstituted phenylene group, $Ar^3$ and $Ar^4$ are each independently a substituted or unsubstituted phenyl group, a substituted or unsubstituted biphenyl group, or a substituted or unsubstituted naphthyl group, $X^2$ is $NR^b$, O, or S, $X^3$ is $CR^hR^i$ or $SiR^jR^k$, $R^b$, $R^h$, $R^i$, $R^j$, and $R^k$ are each independently a substituted or unsubstituted C1 to C10 alkyl group, or a substituted or unsubstituted C6 to C20 aryl group, $R^6$, $R^8$, $R^9$, $R^{10}$, and $R^{11}$ are each independently hydrogen, deuterium, a substituted or unsubstituted C1 to C30 alkyl group, or a substituted or unsubstituted C6 to C30 aryl group, m6 is an integer of 1 to 4, m8 and m10 are each independently 1 or 2, and m9' and m11' are each independently an integer of 1 to 3.

13. An organic optoelectronic device, comprising:

an anode and a cathode facing each other, and at least one organic layer between the anode and the cathode, wherein:

the at least one organic layer includes a light emitting layer, and the light emitting layer includes the composition for the organic optoelectronic device as claimed in claim 1.

14. The organic optoelectronic device as claimed in claim 13, wherein the composition for the organic optoelectronic device is a host of the light emitting layer.

15. A display device comprising the organic optoelectronic device as claimed in claim 13.

16. A compound for an organic optoelectronic device, wherein the compound is a compound of Group 1:

[Group 1]

[1]

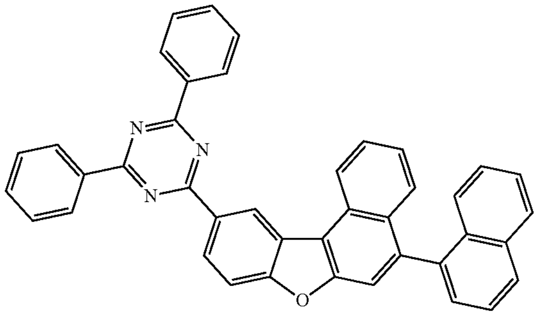

[2]

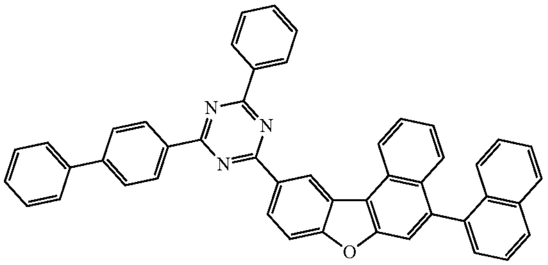

[3]

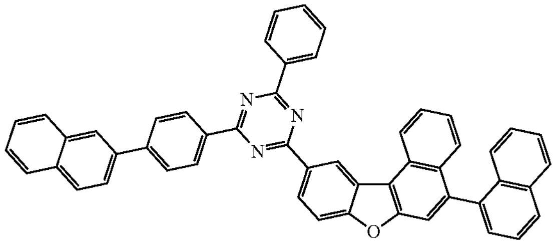

[4]

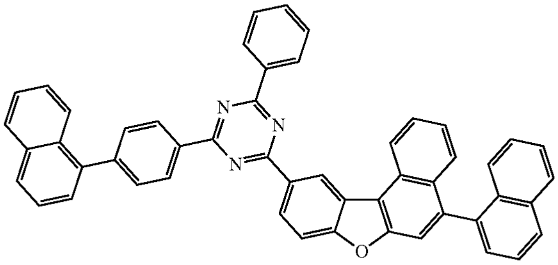

[5]

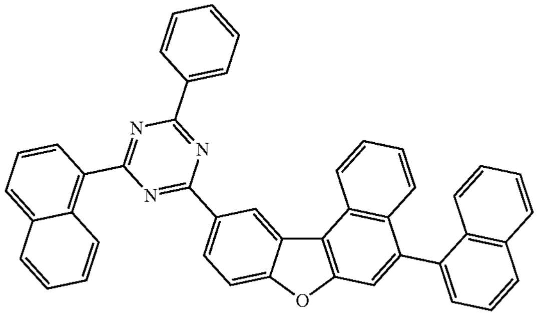

[6]

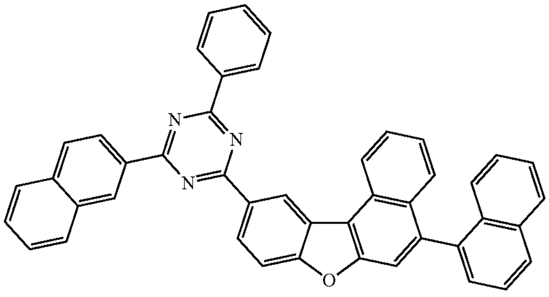

[7]

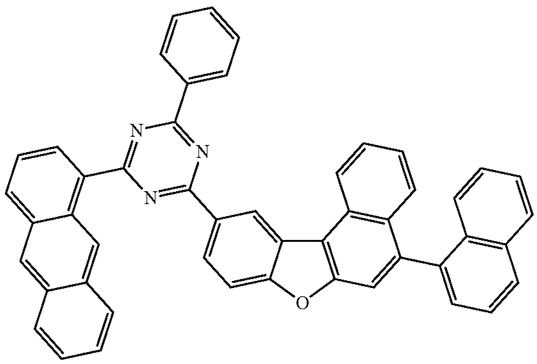

[8]

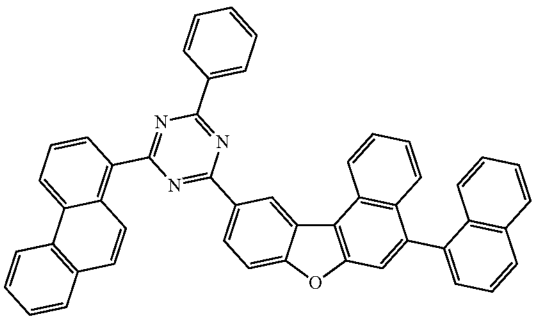

-continued
[9]
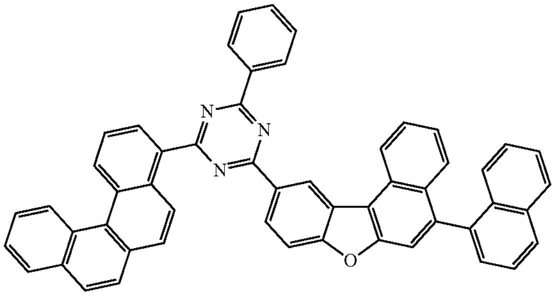
[10]
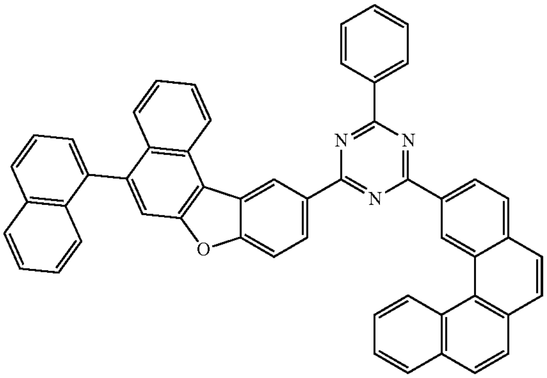
[11]
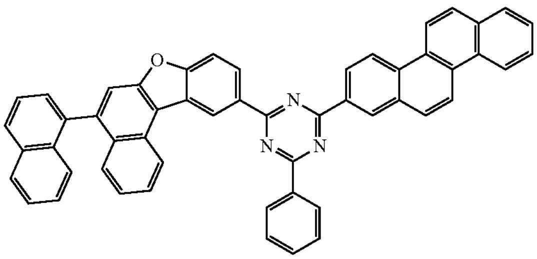
[12]
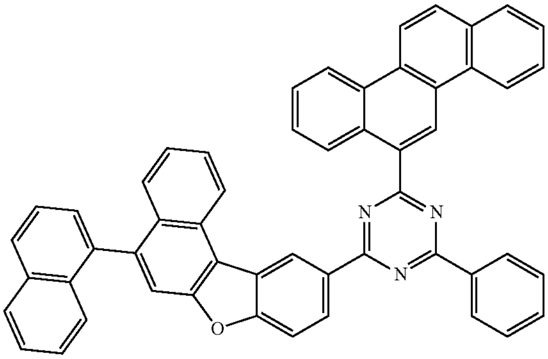
[13]
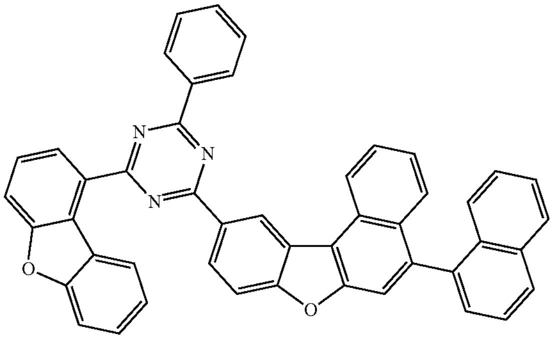
[14]
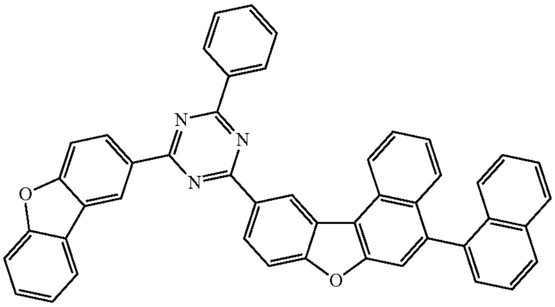
[15]
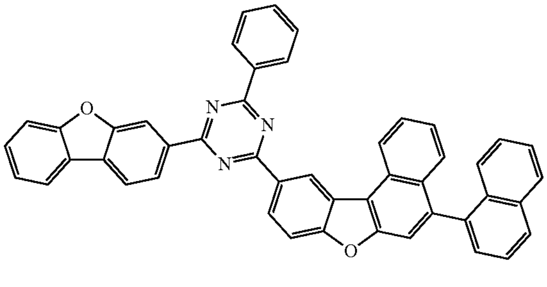
[16]
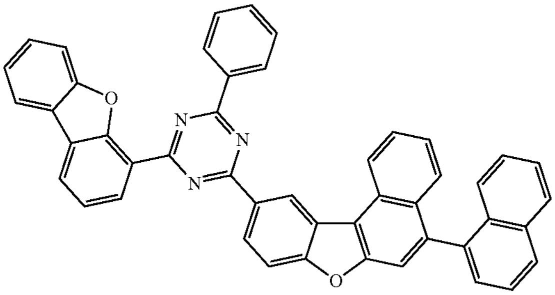

-continued
[17]
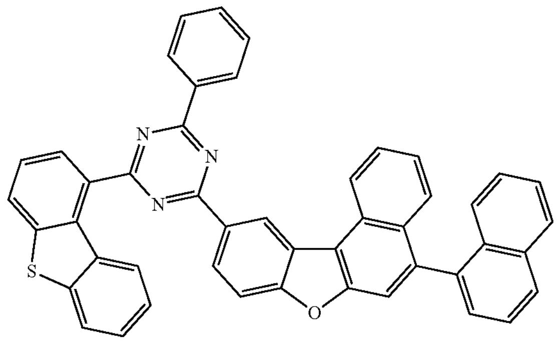
[18]
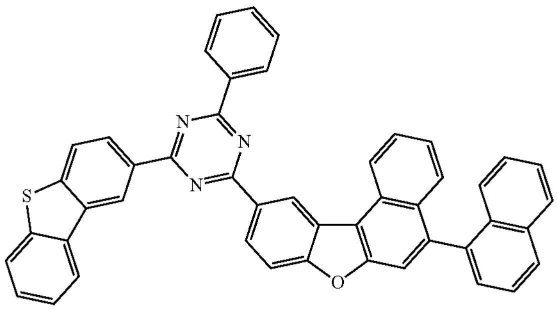
[19]
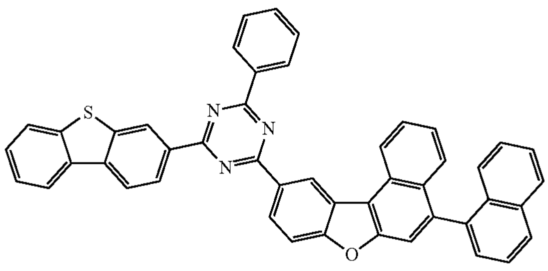
[20]
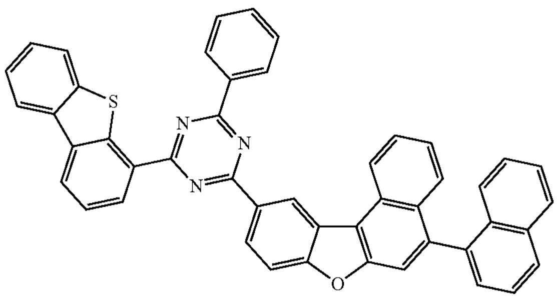
[21]
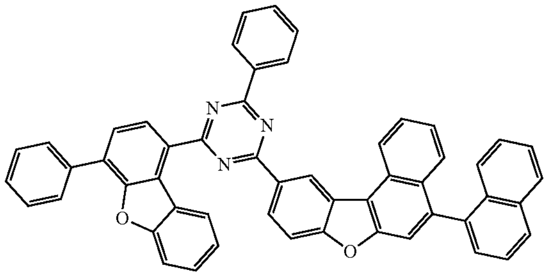
[22]
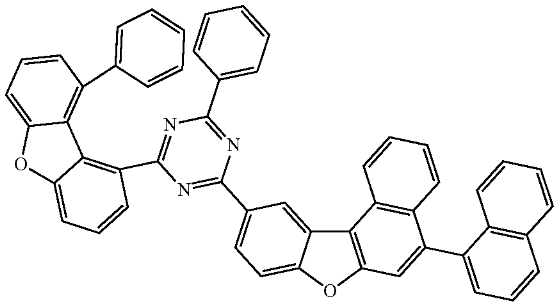
[23]
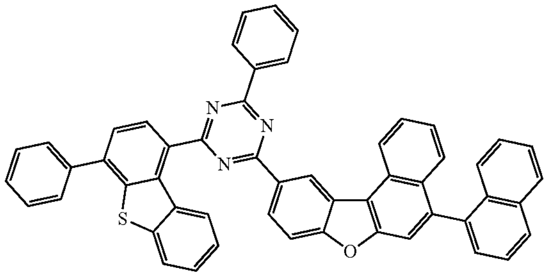
[24]
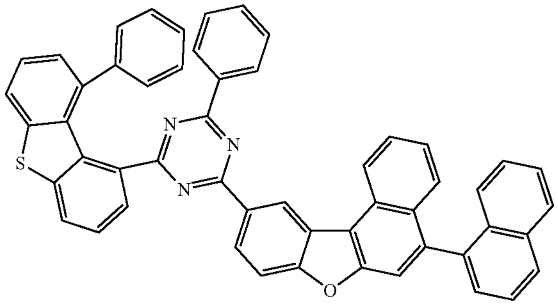

-continued
[25]
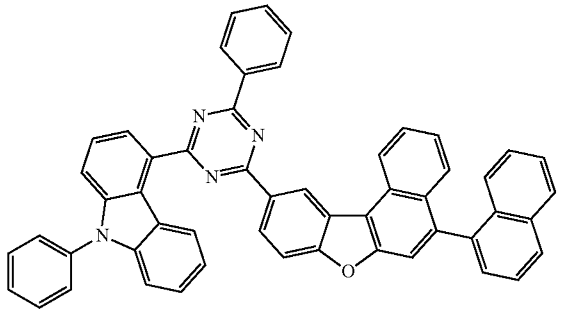
[26]
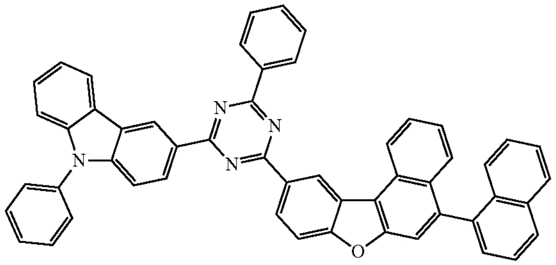
[27]
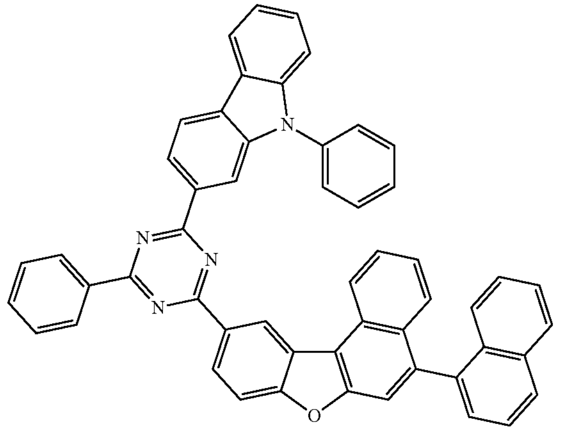
[28]
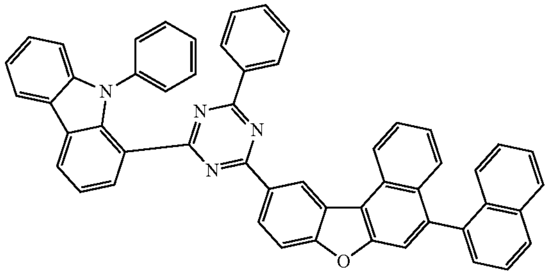
[29]
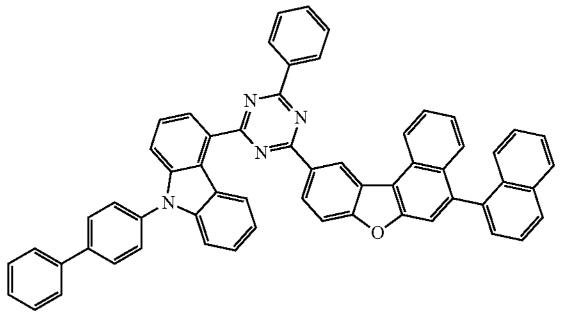
[30]
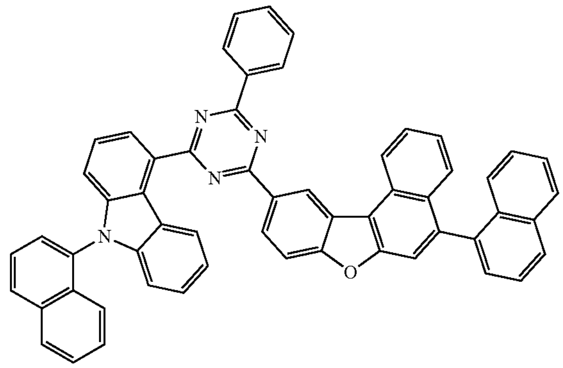
[31]
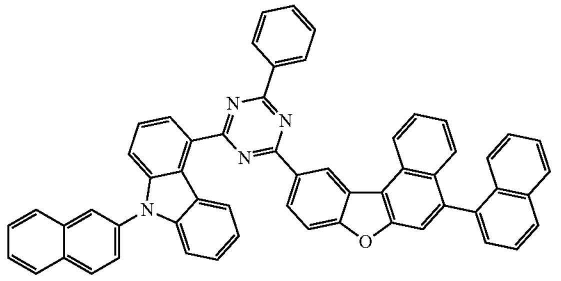
[32]
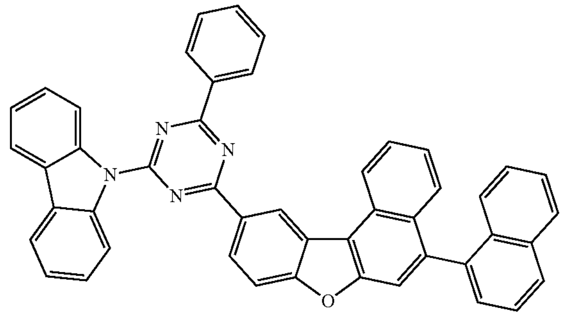

-continued
[33]
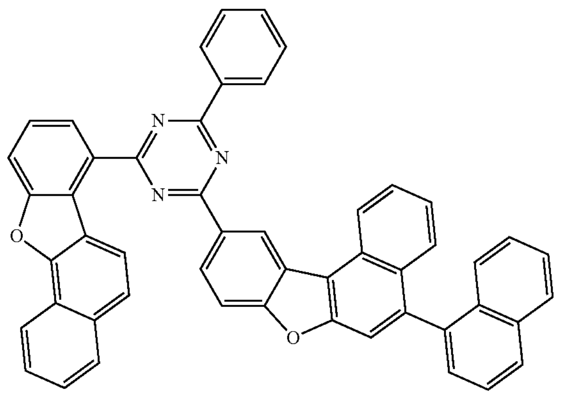
[34]
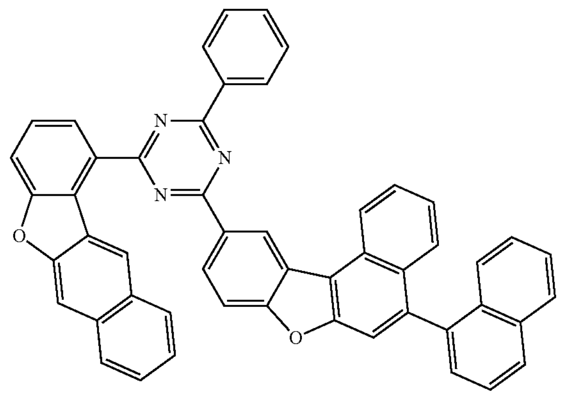
[35]
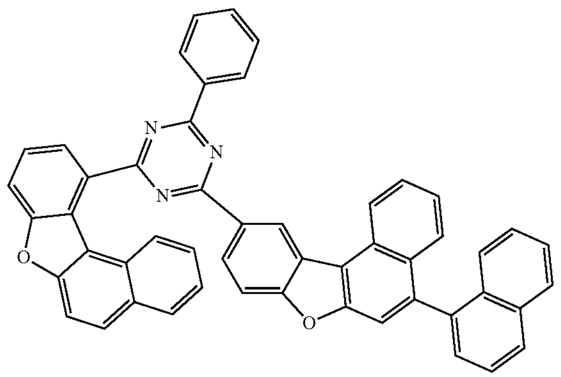
[36]
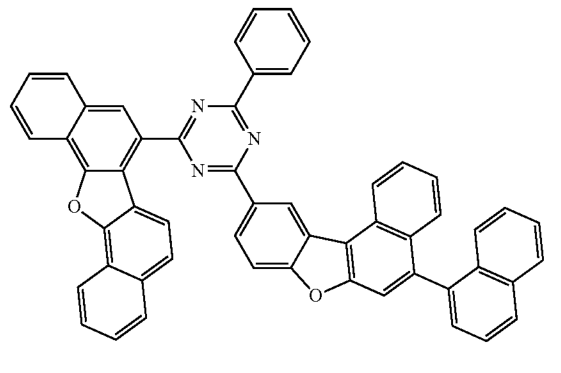
[37]
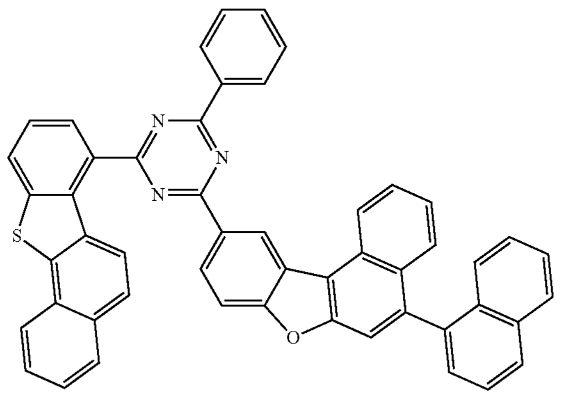
[38]
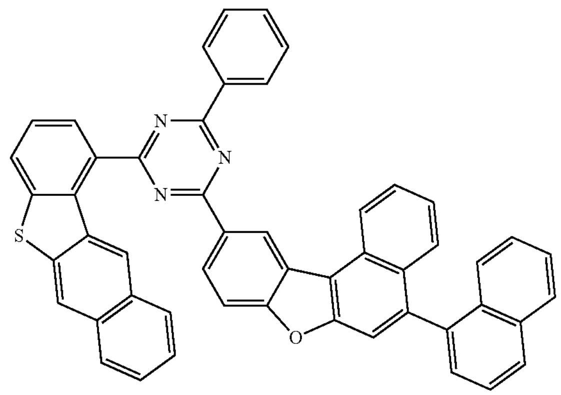
[39]
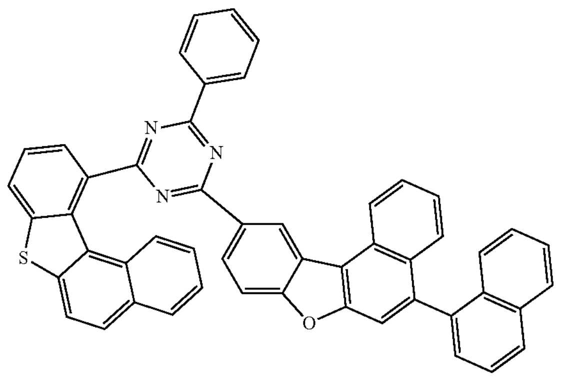
[40]
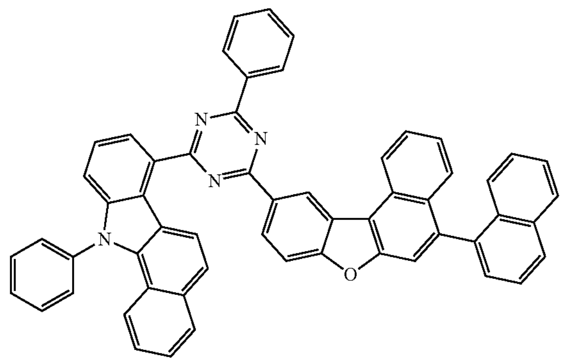

-continued
[41]
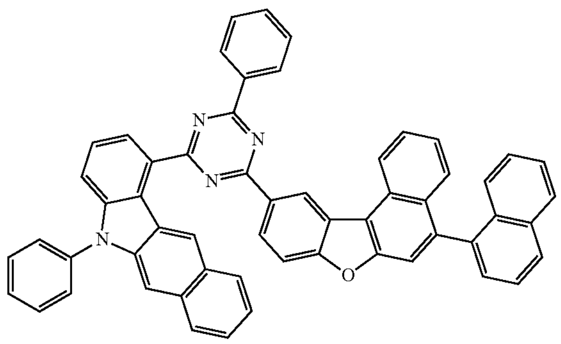
[42]
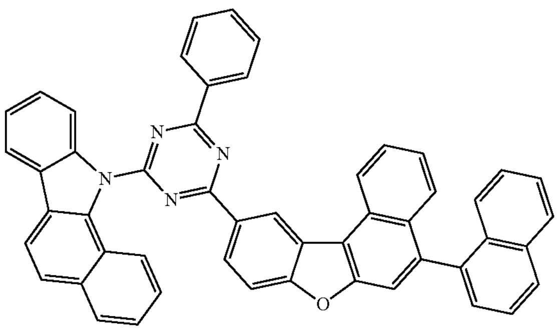
[43]
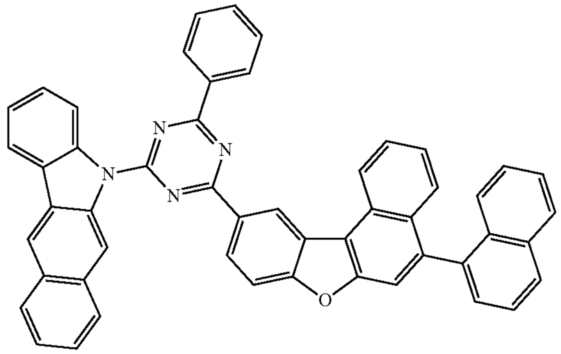
[44]
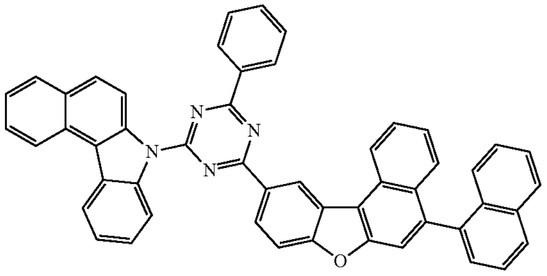
[45]
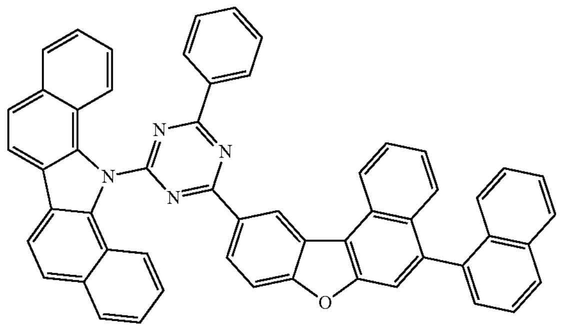
[46]
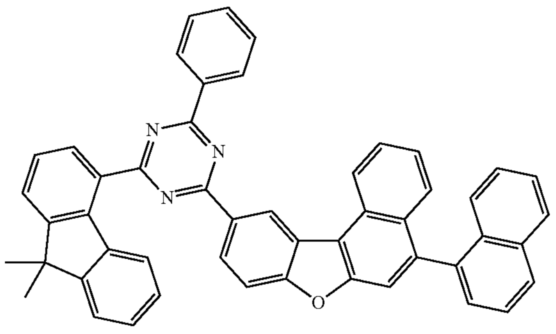
[47]
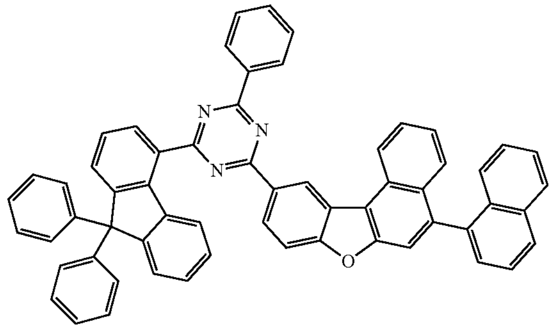
[48]
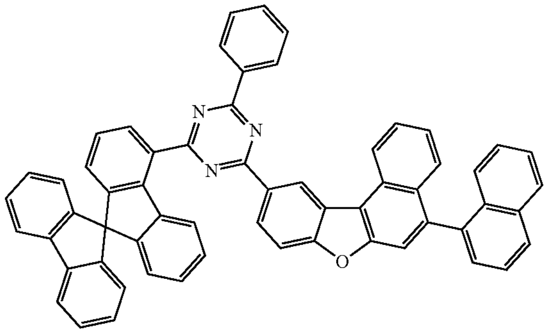

-continued
[49]
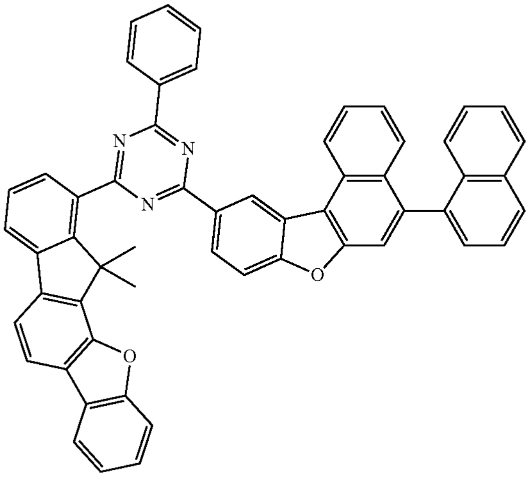
[50]
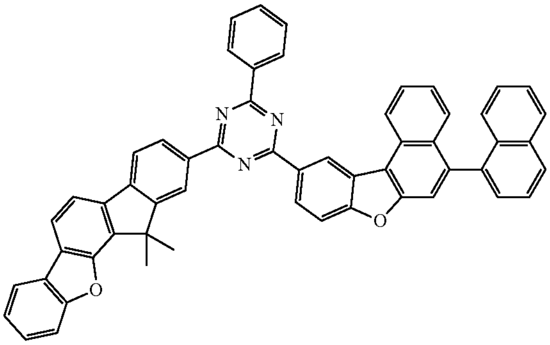
[51]
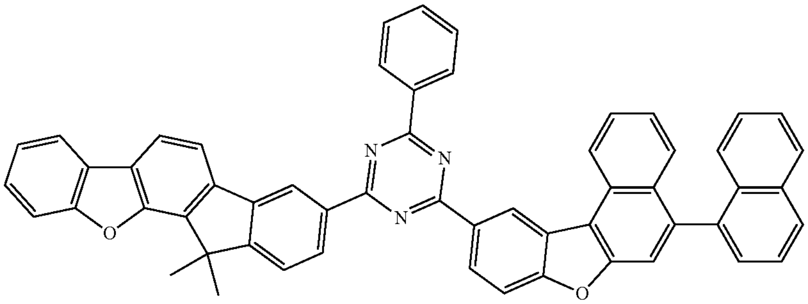
[52]
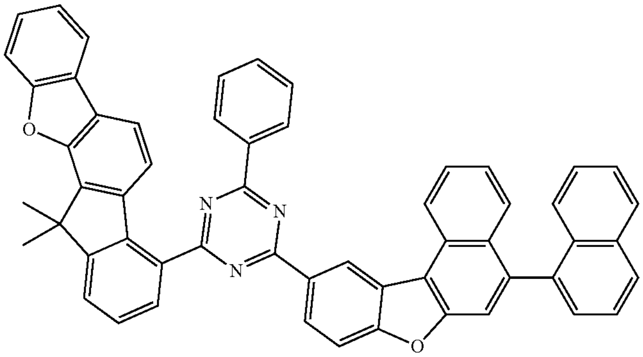
[53]
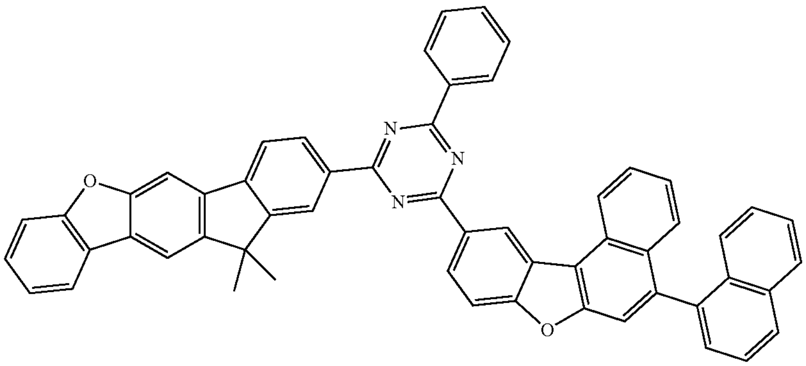

-continued
[54]
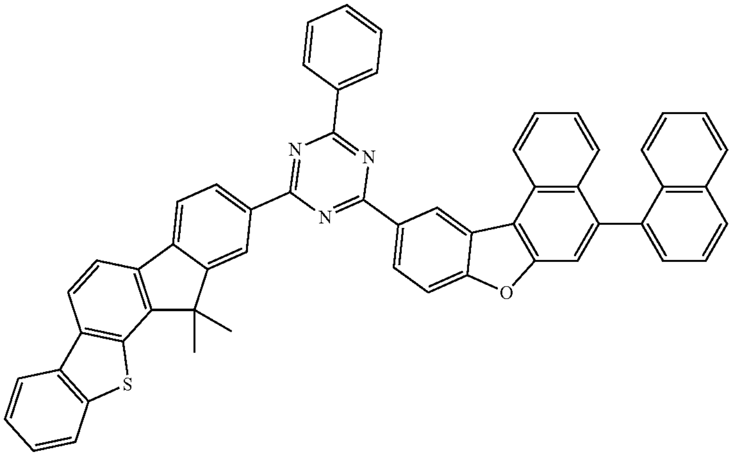
[55]
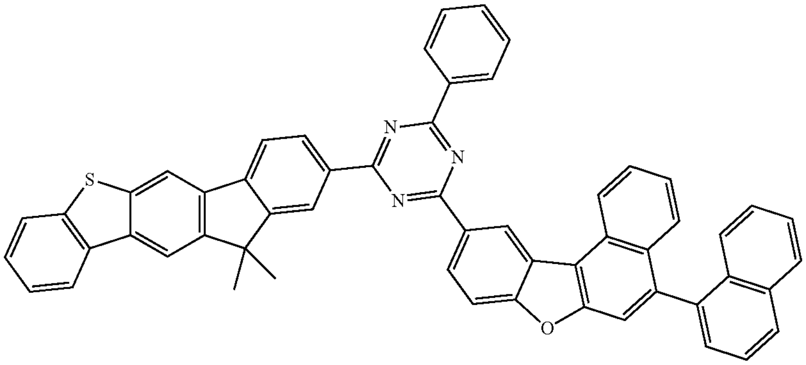
[56]
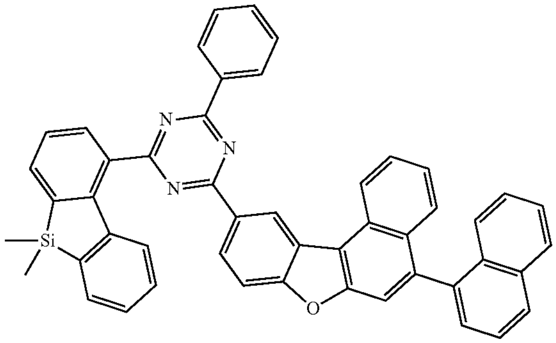
[57]
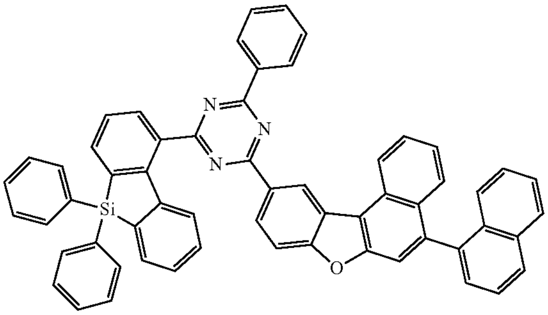
[58]
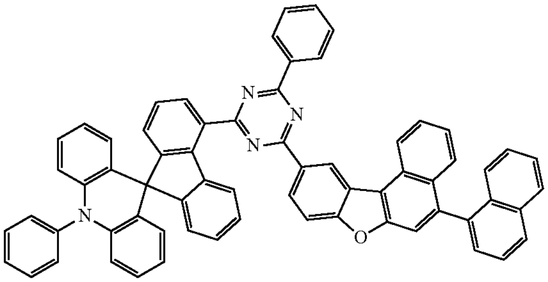
[59]
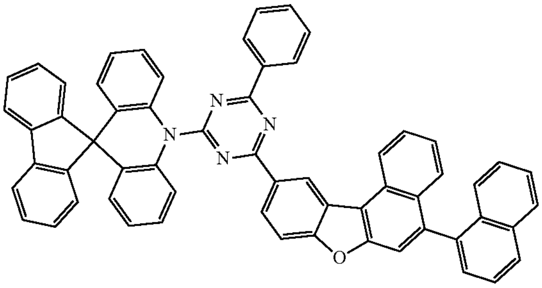

-continued
[60]
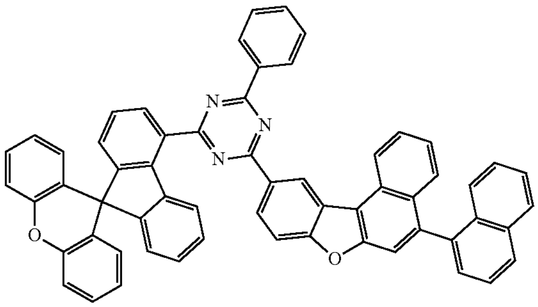
[61]
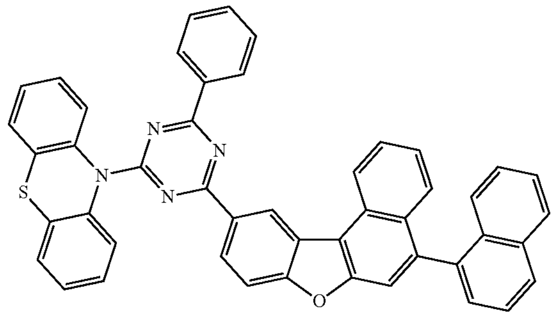
[62]
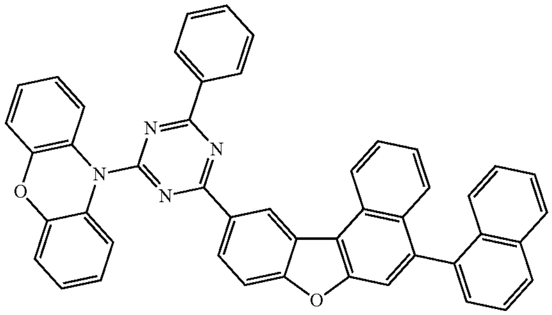
[63]
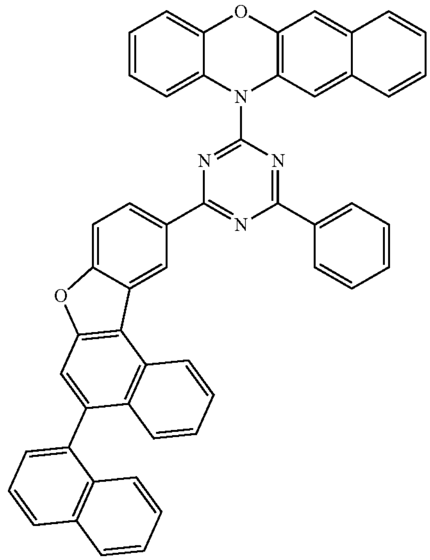
[64]
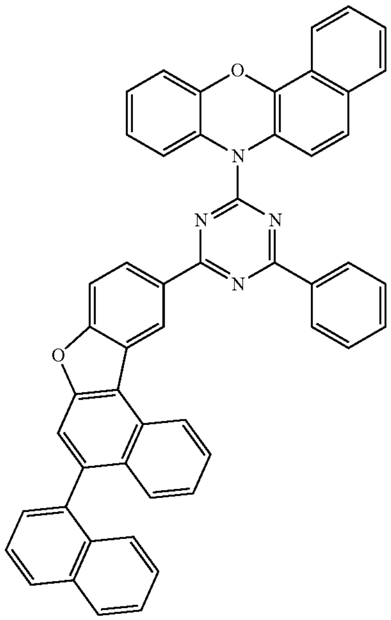
[65]
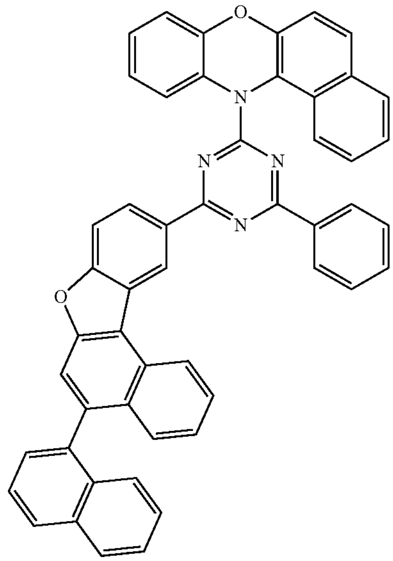

-continued
[66]
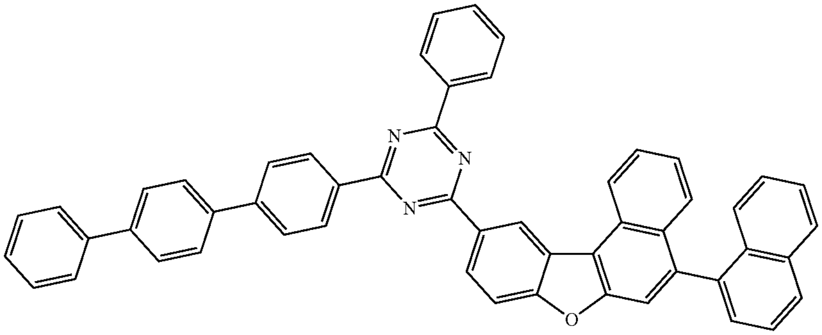
[67]
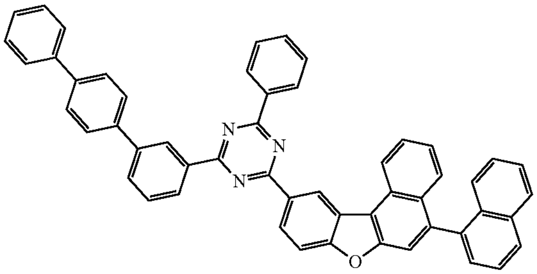
[68]
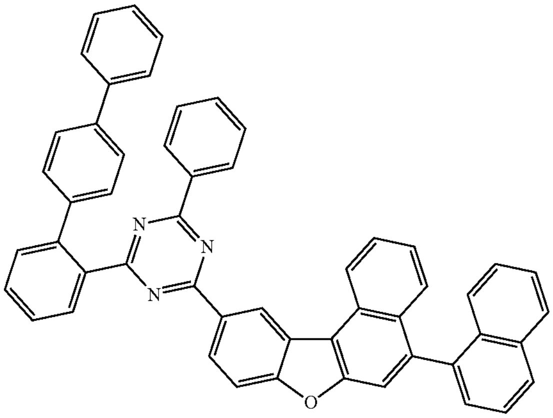
[69]
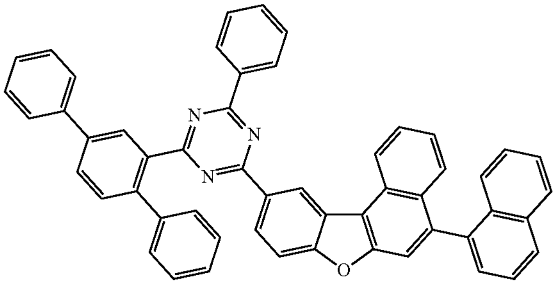
[70]
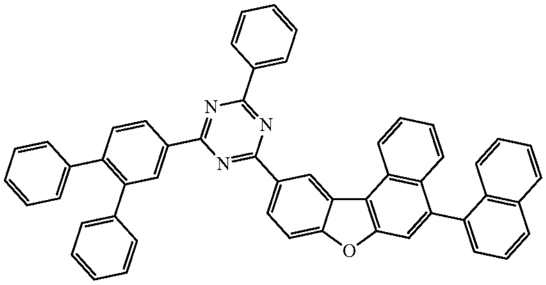
[71]
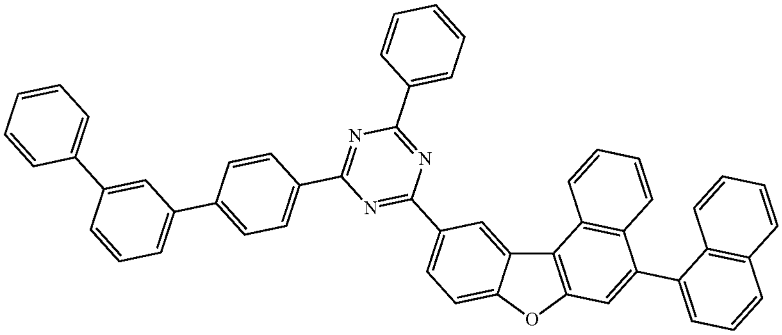

-continued
[72]
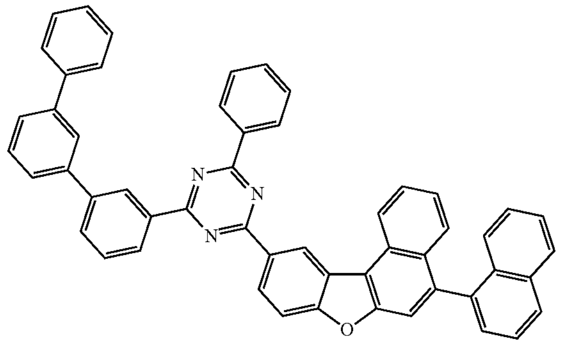
[73]
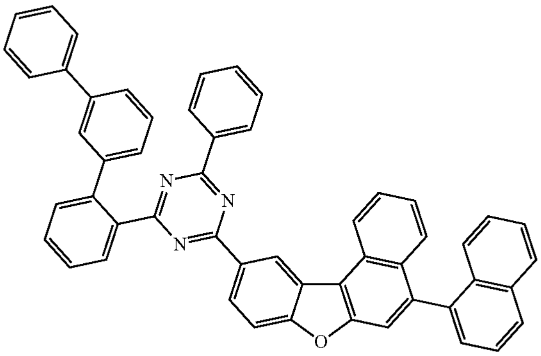
[74]
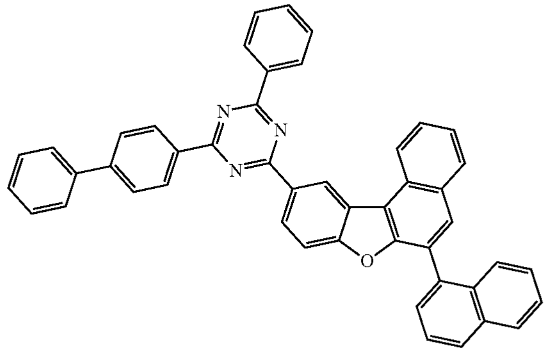
[75]
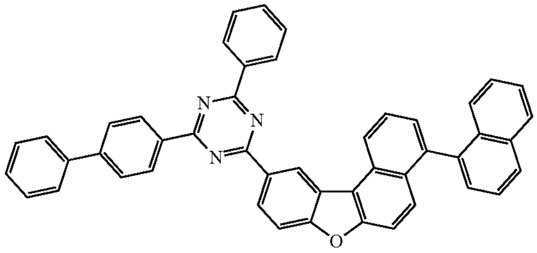
[76]
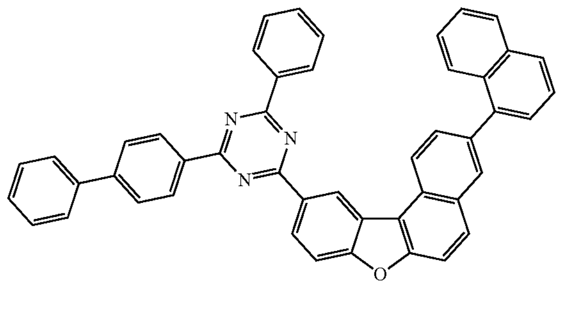
[77]
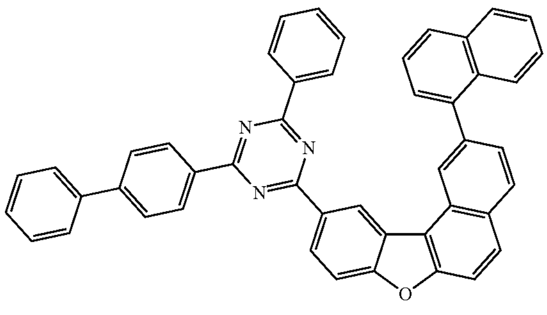
[78]
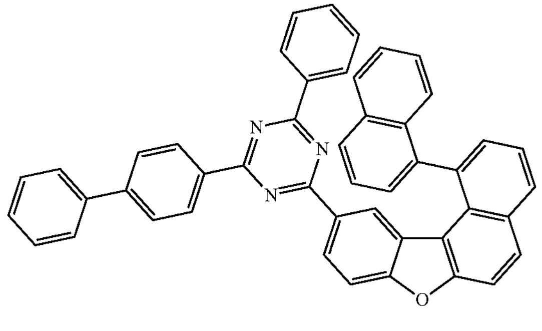
[79]
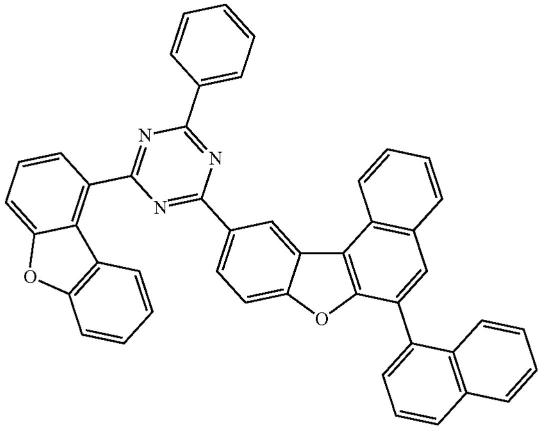

-continued
[80]
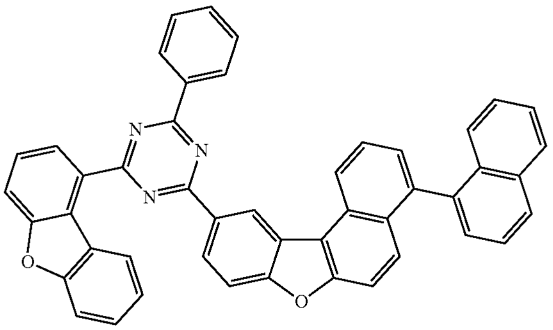
[81]
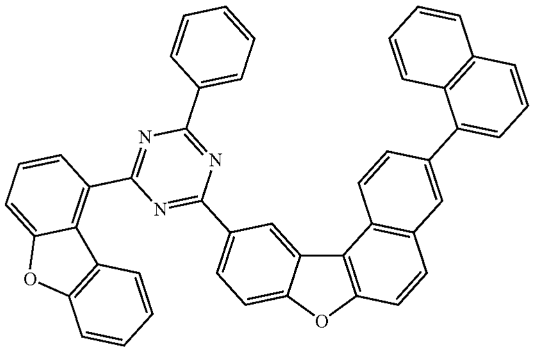
[82]
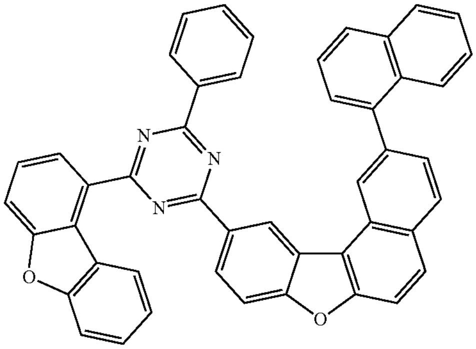
[83]
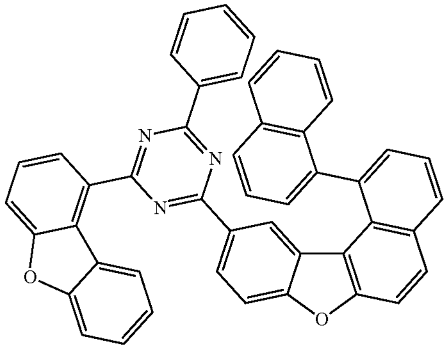
[84]
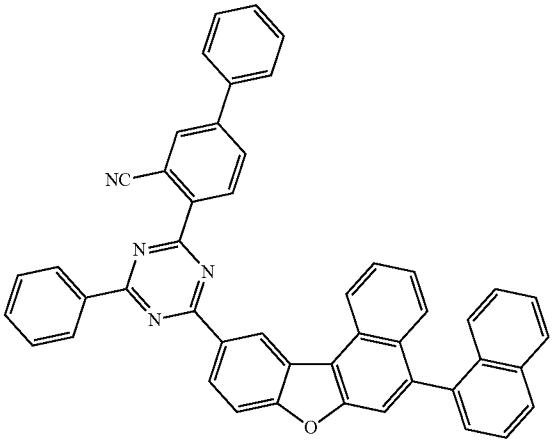
[85]
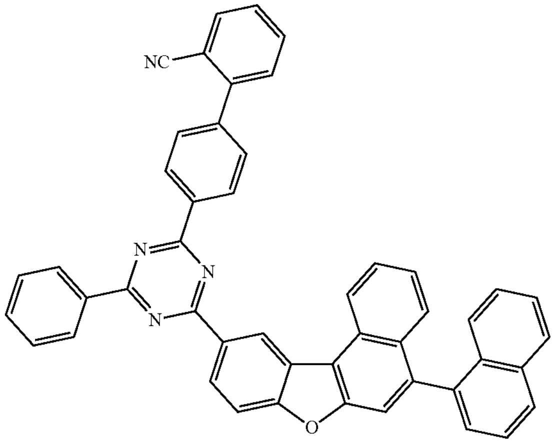
[86]
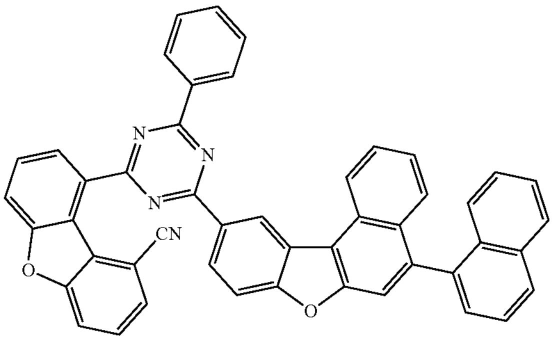
[87]
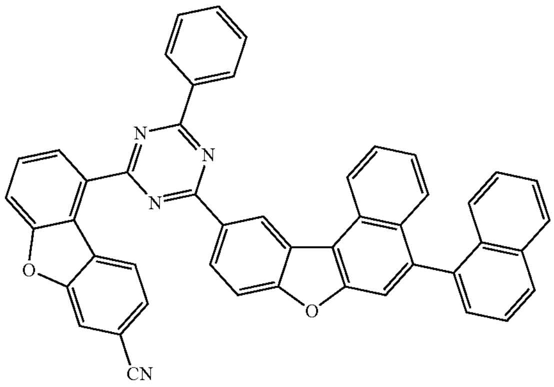

-continued
[88]
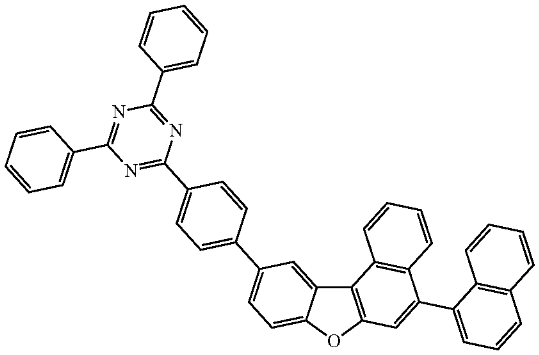
[89]
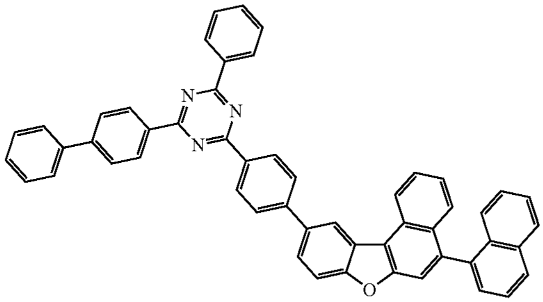
[90]
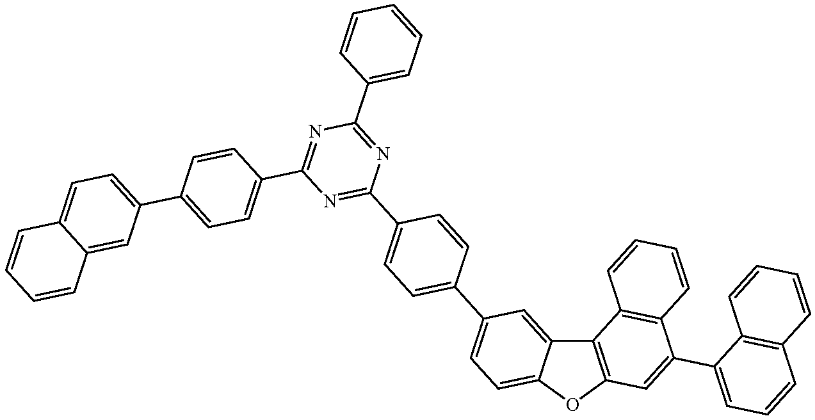
[91]
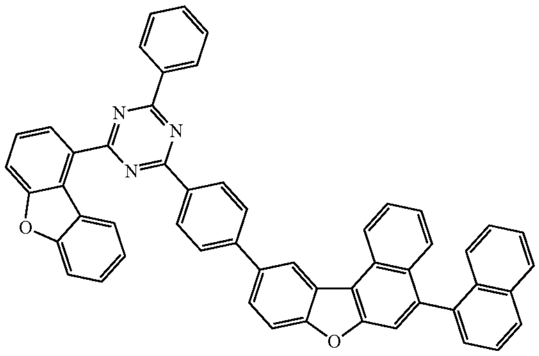
[92]
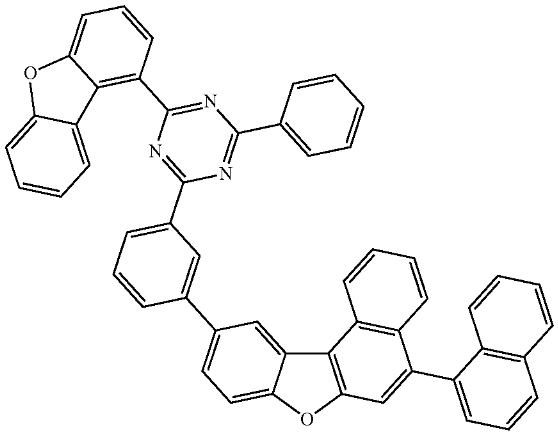
[93]
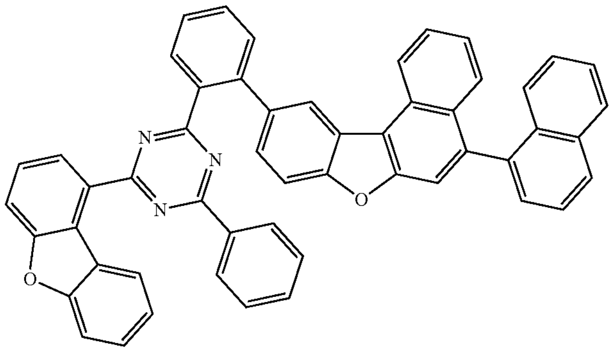

-continued
[94]
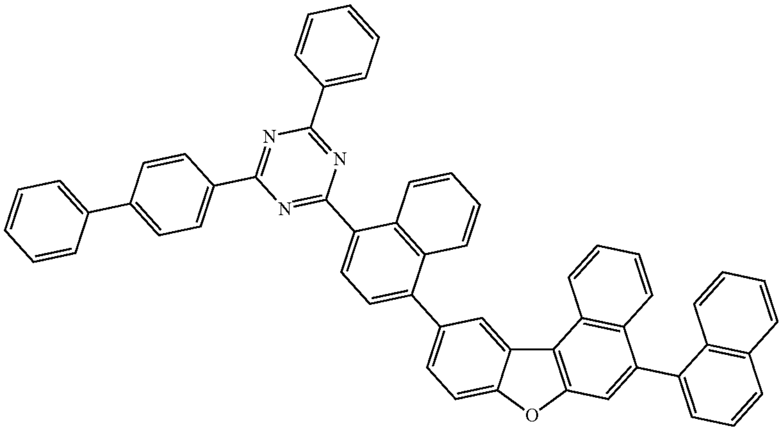
[95]
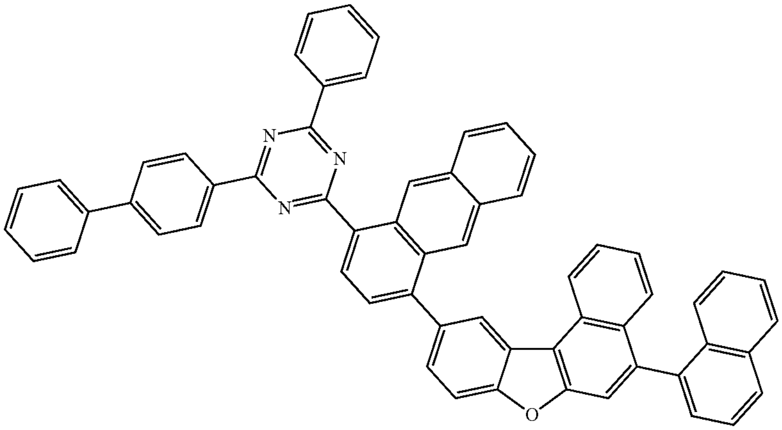
[96]
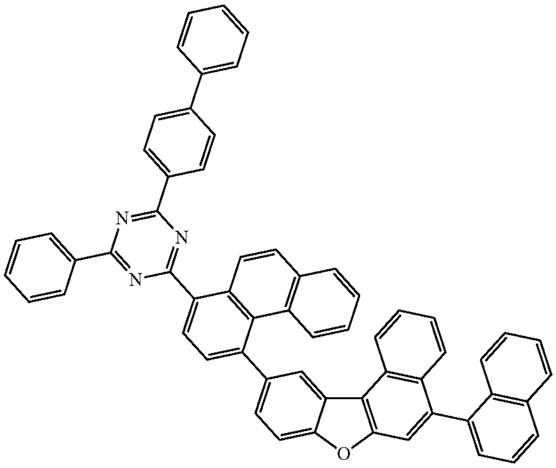
[97]
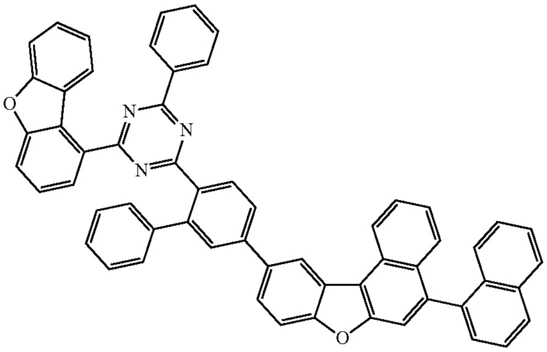

-continued
[98]
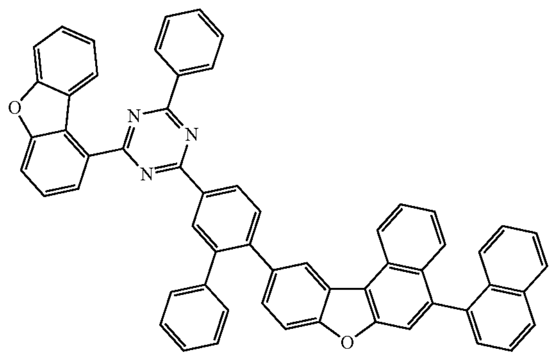
[99]
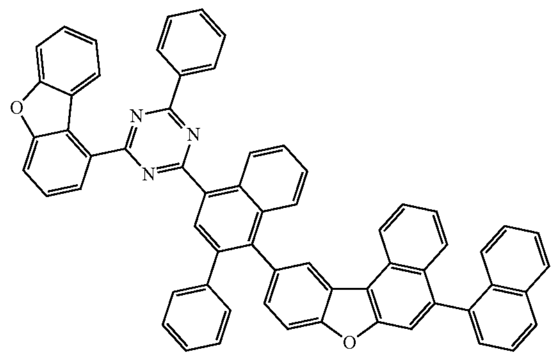
[100]
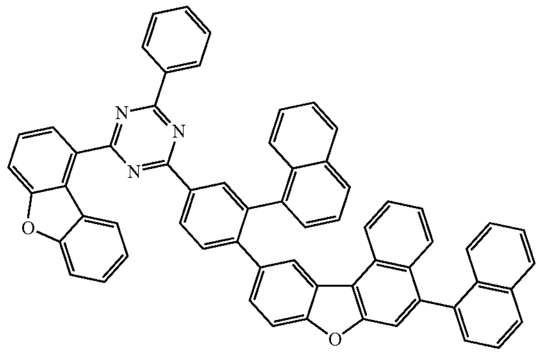
[101]
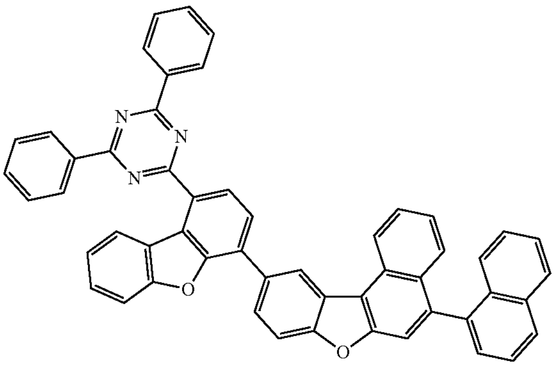
[102]
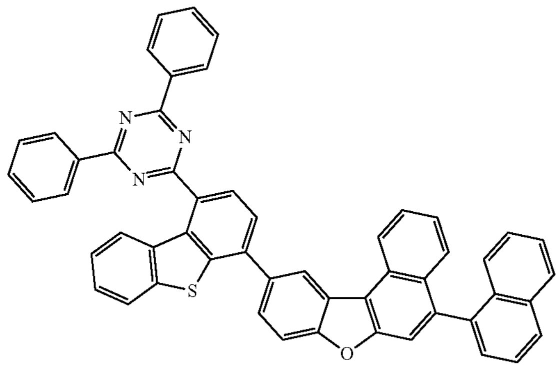
[103]
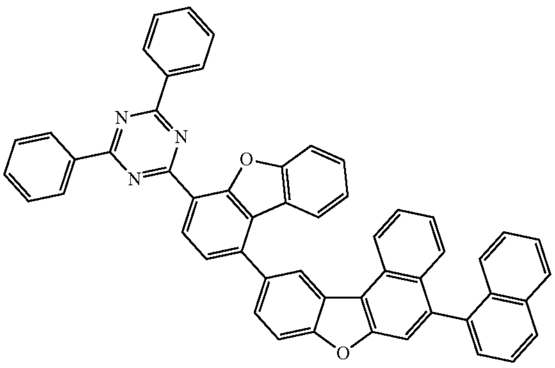
[104]
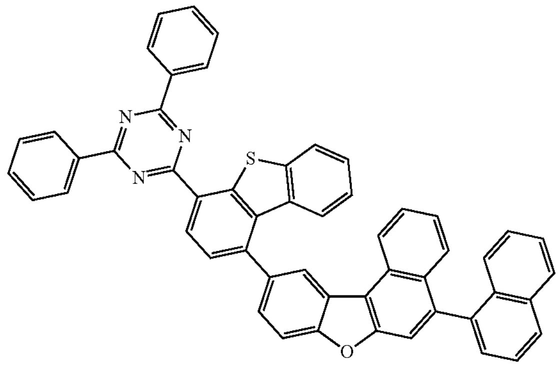
[105]
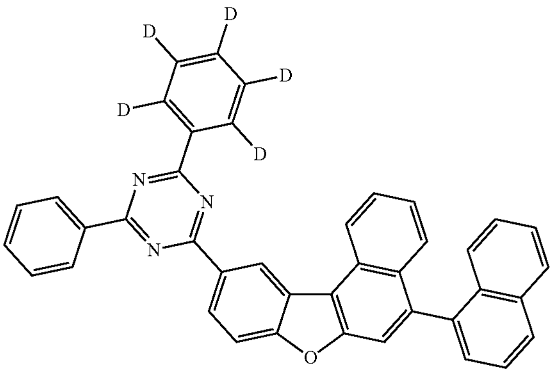

-continued
[106]
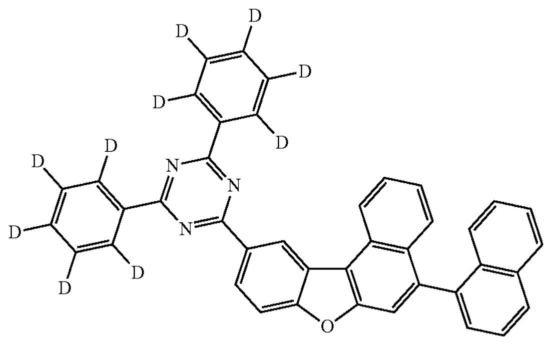
[107]
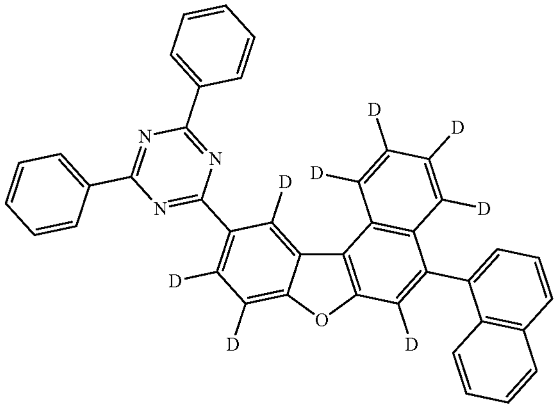
[108]
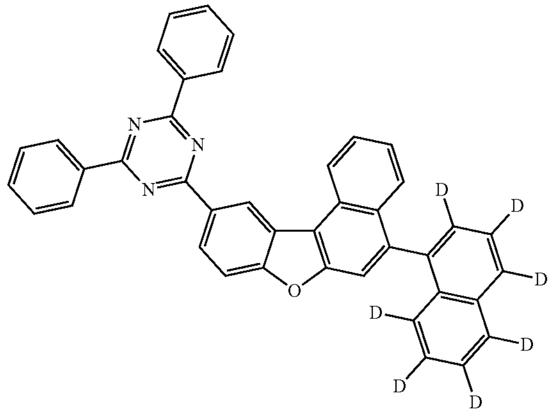
[109]
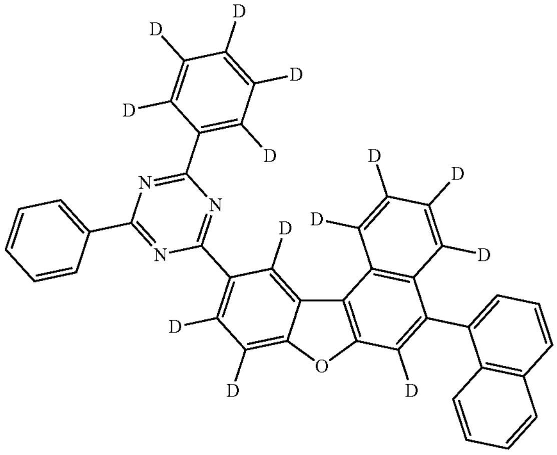
[110]
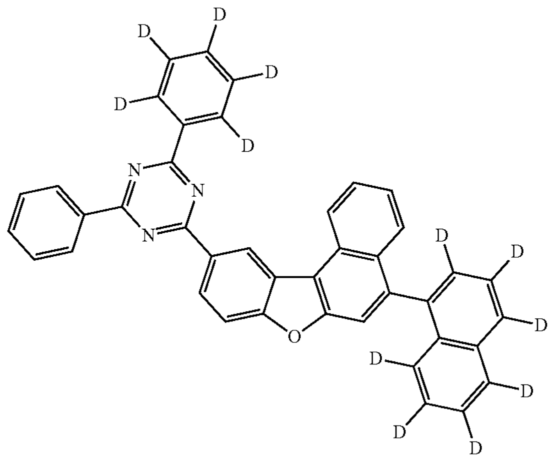
[111]
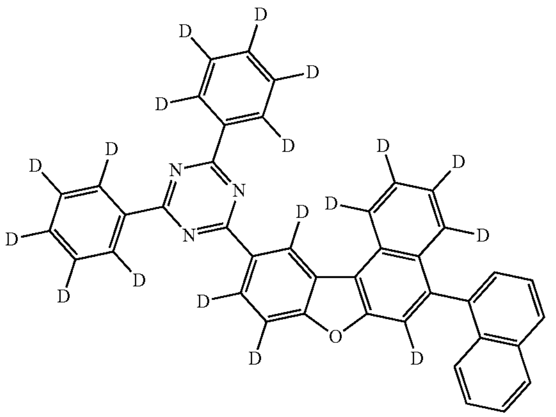

-continued
[112]
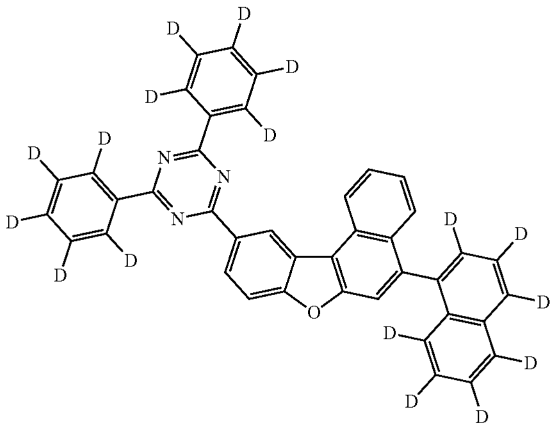
[113]
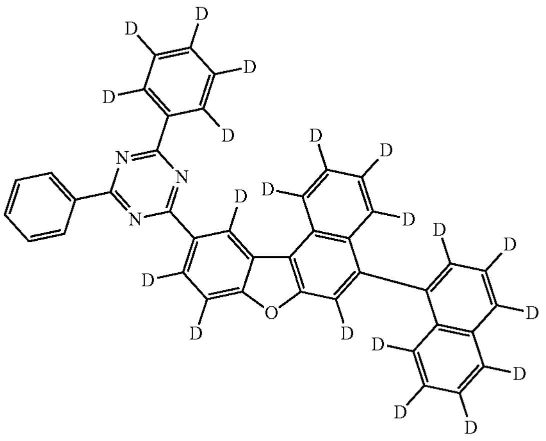
[114]
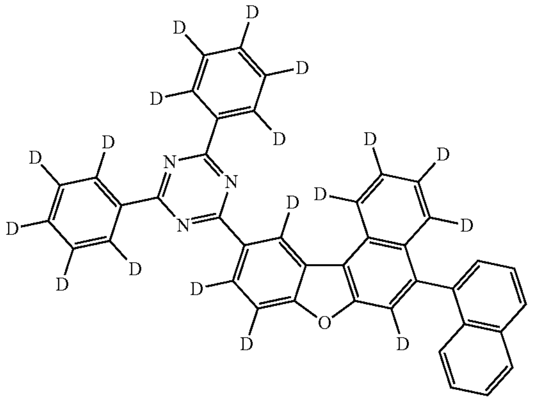
[115]
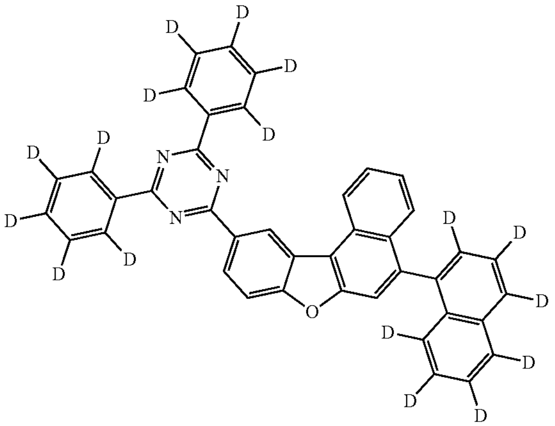
[116]
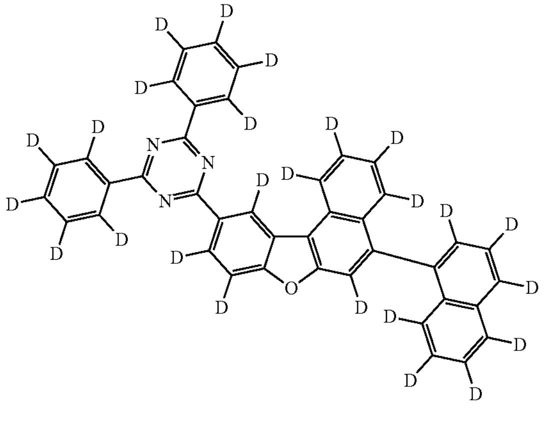
[117]
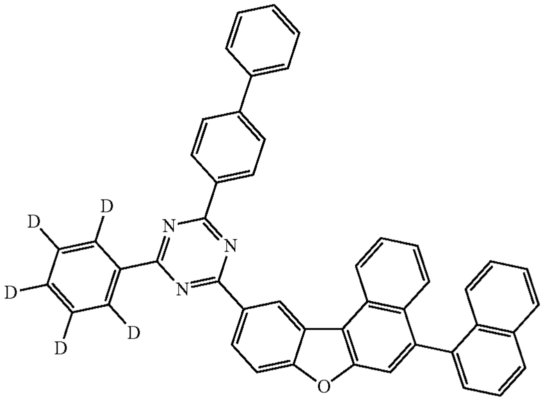

-continued
[118]
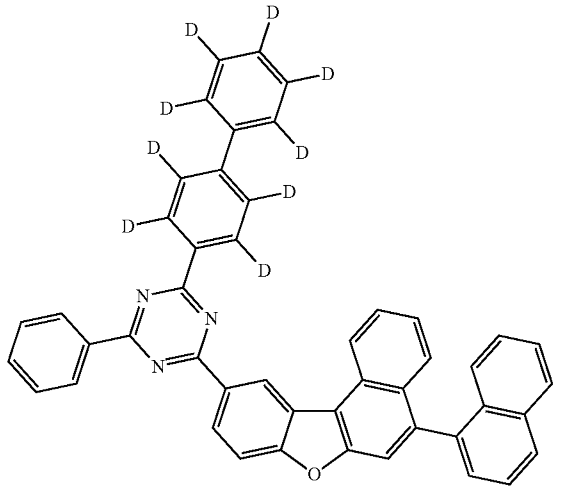
[119]
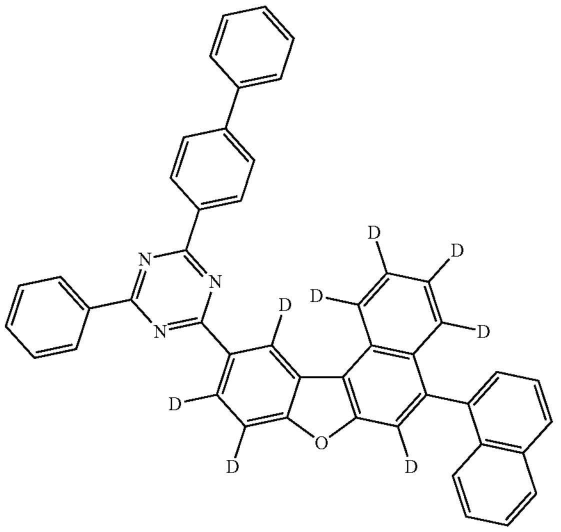
[120]
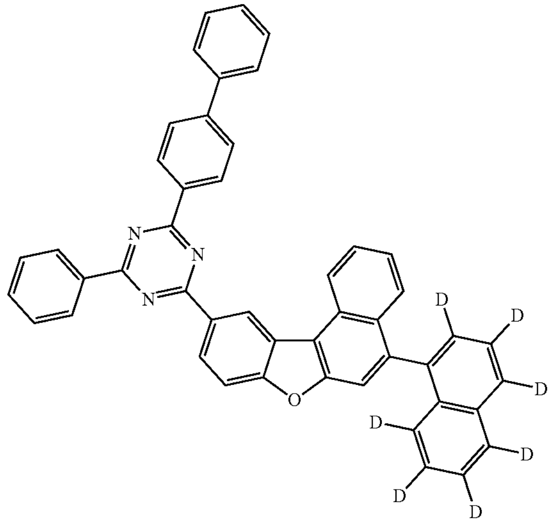
[121]
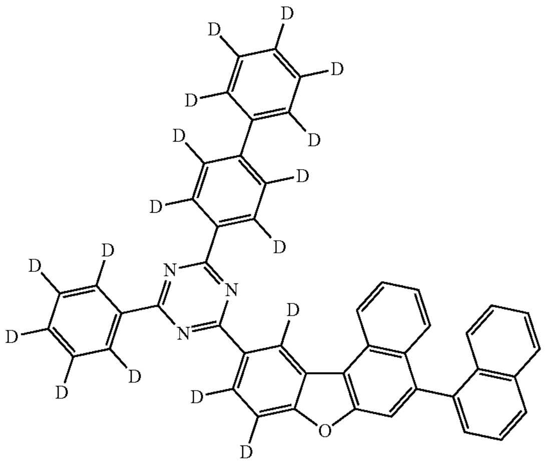
[122]
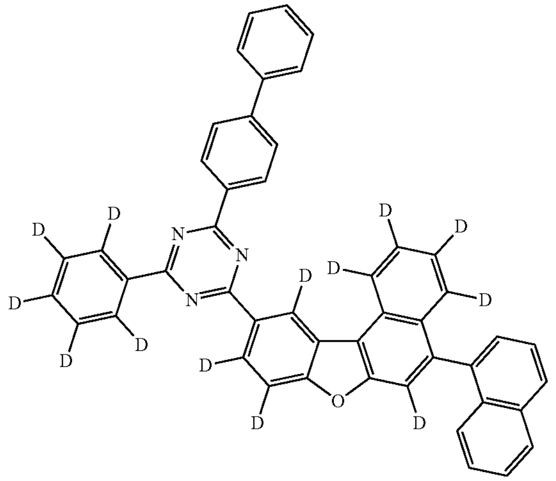
[123]
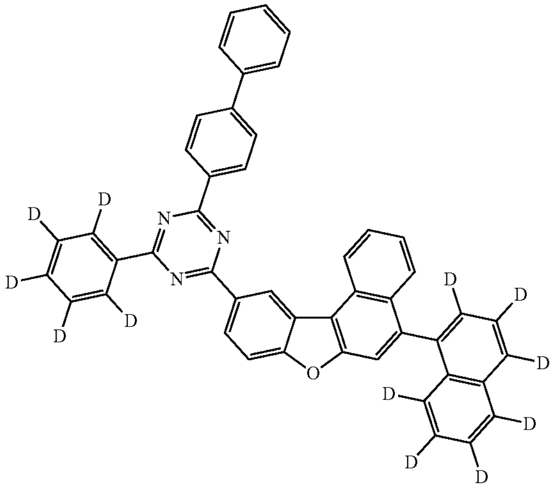

-continued
[124]
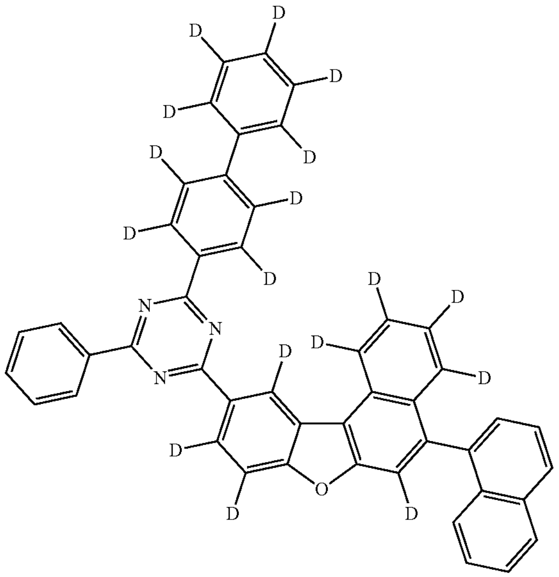
[125]
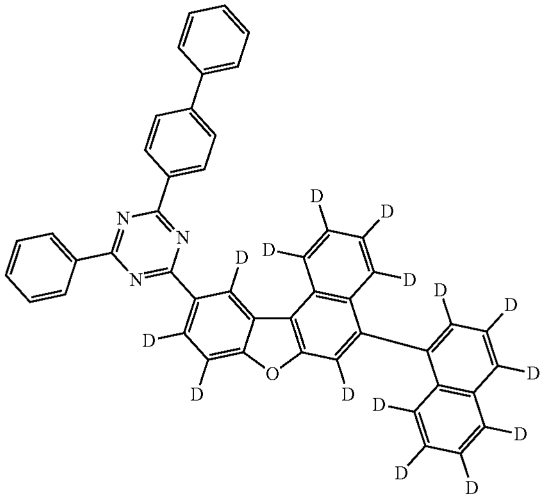
[126]
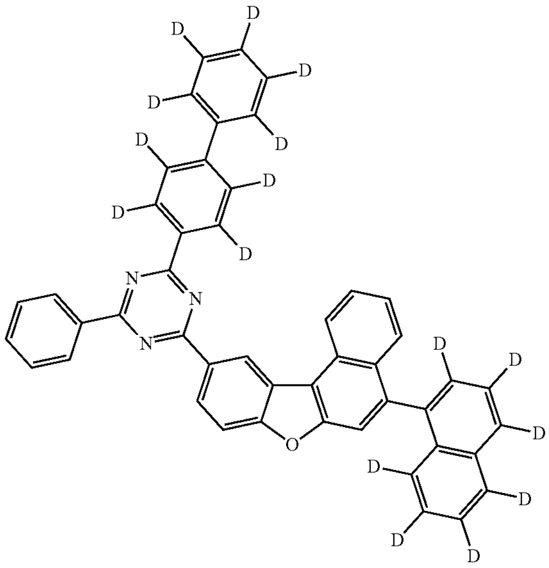
[127]
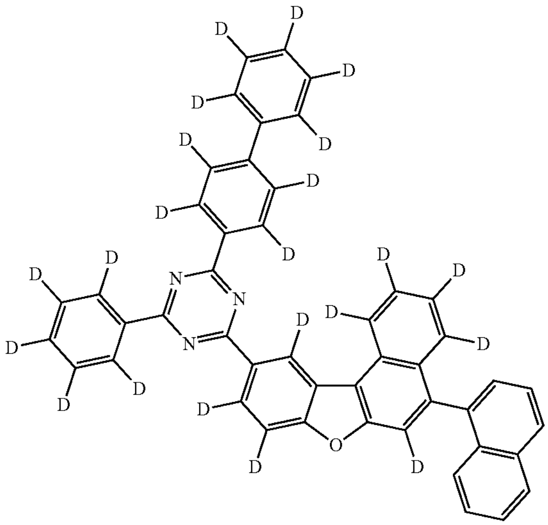

-continued
[128]
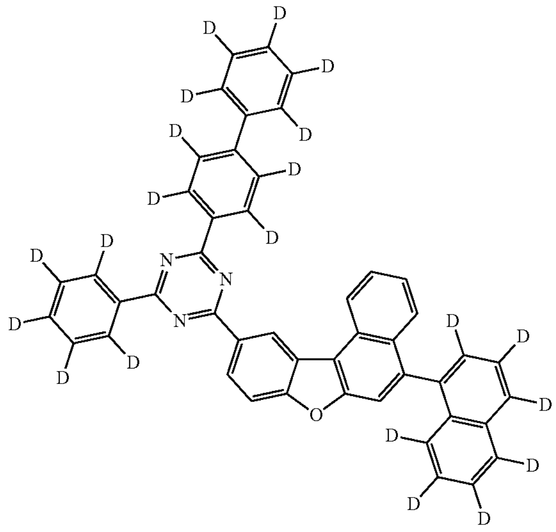
[129]
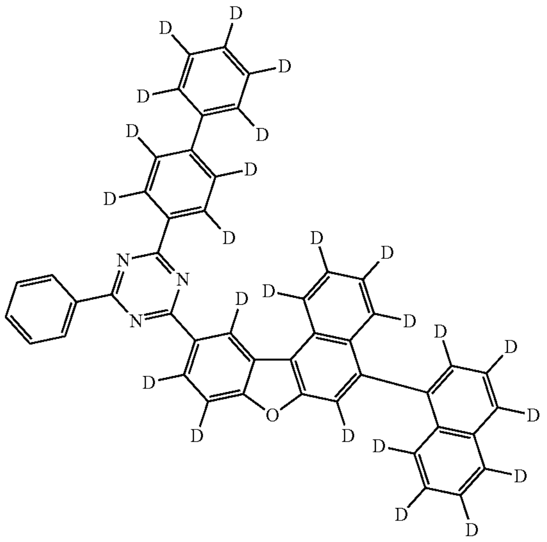
[130]
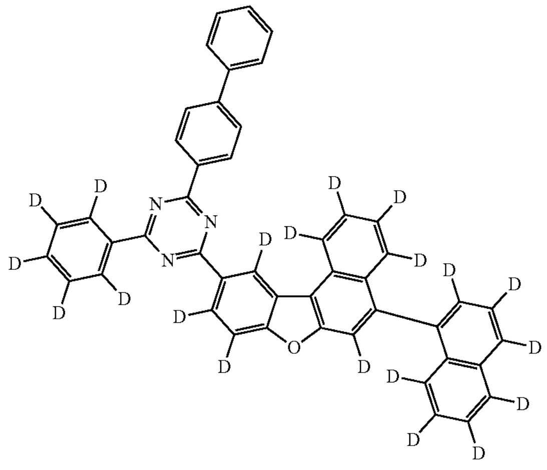
[131]
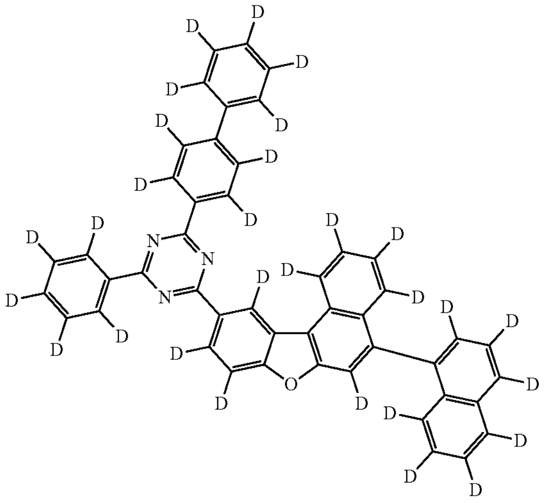
[132]
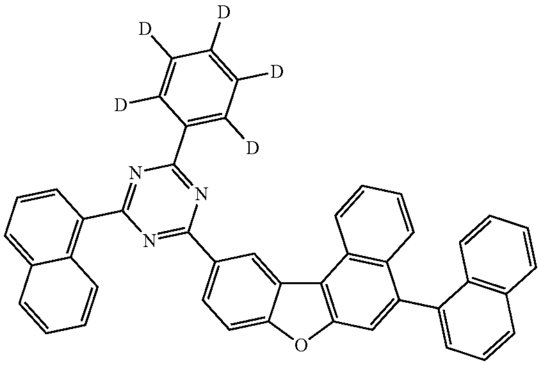
[133]
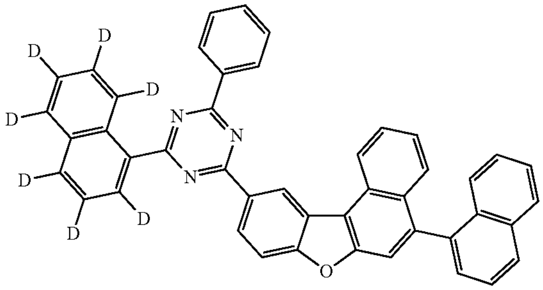

-continued
[134]
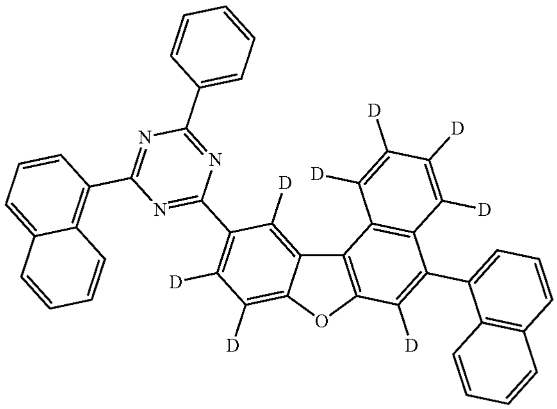
[135]
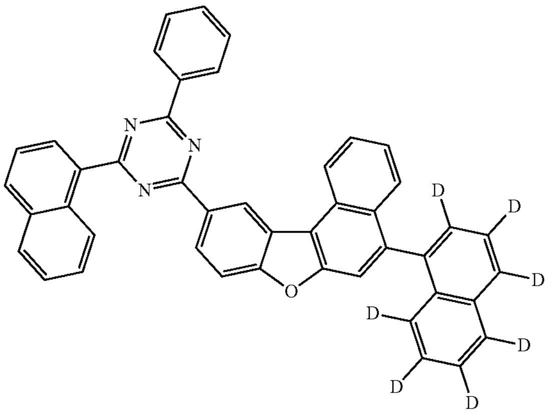
[136]
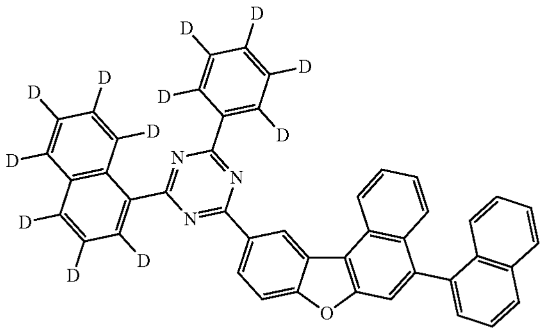
[137]
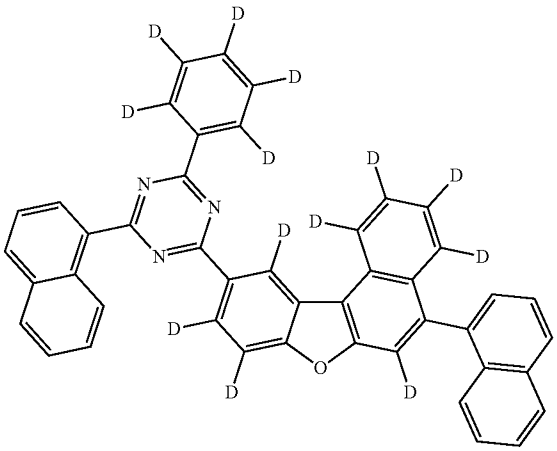
[138]
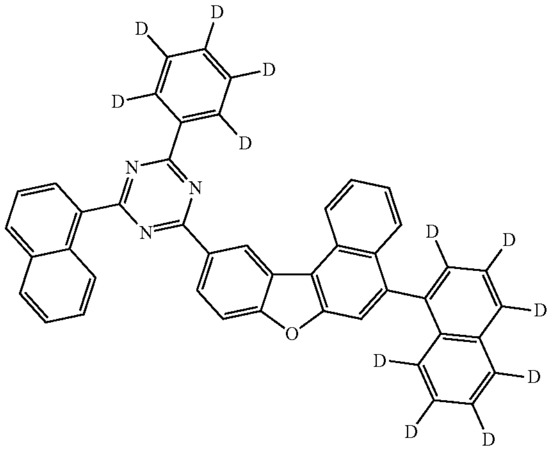
[139]
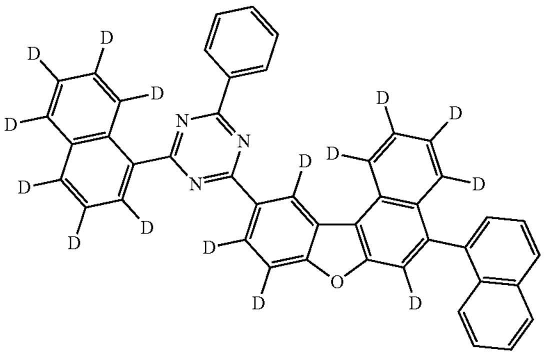

-continued
[140]
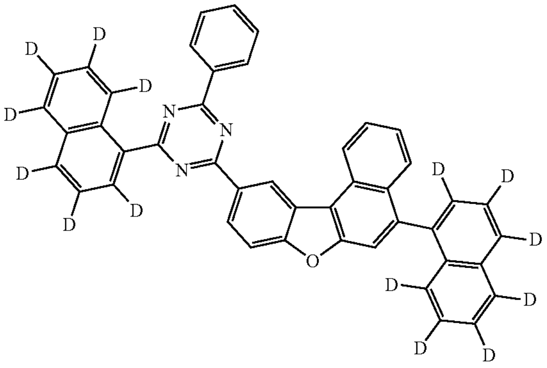
[141]
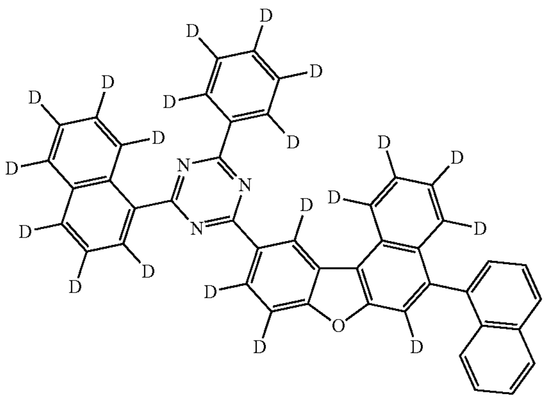
[142]
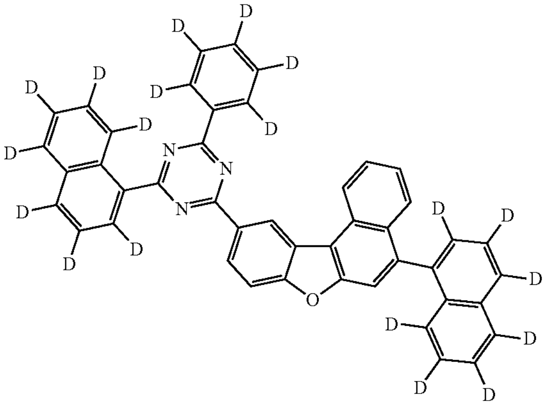
[143]
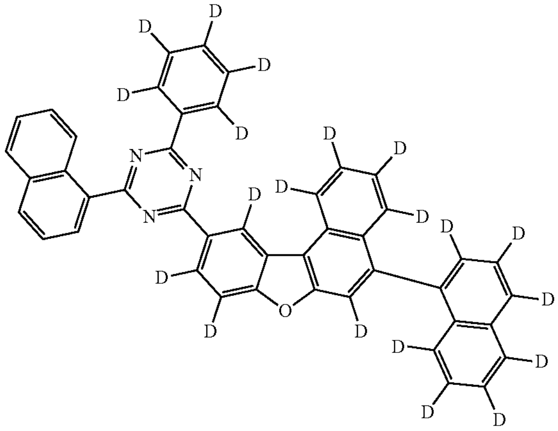
[144]
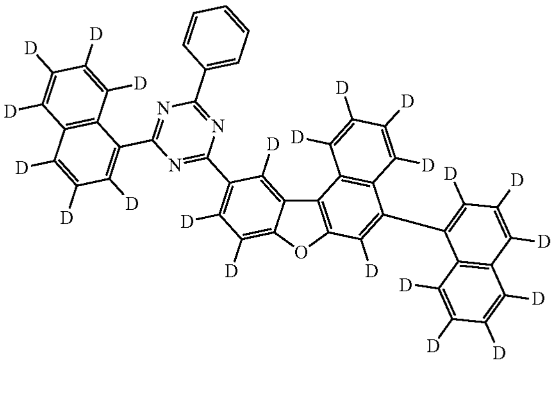
[145]
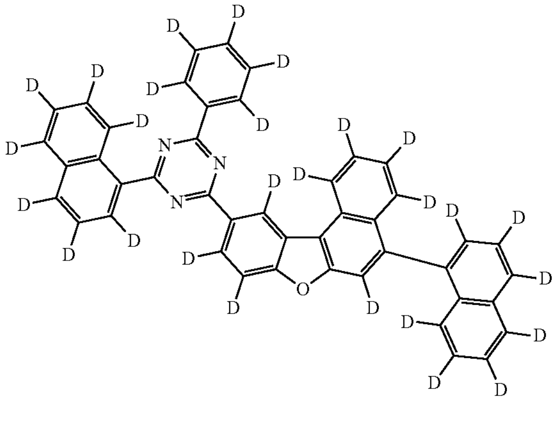

-continued
[146]
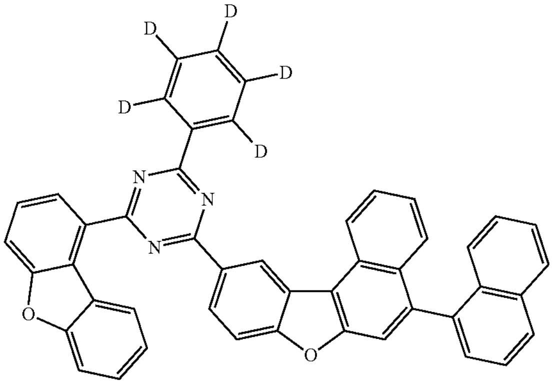
[147]
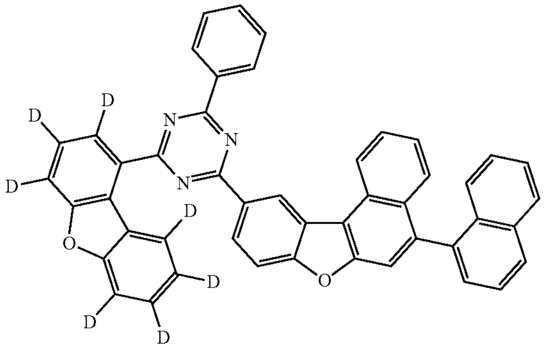
[148]
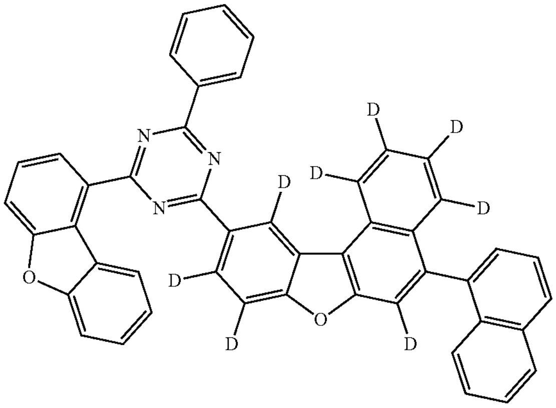
[149]
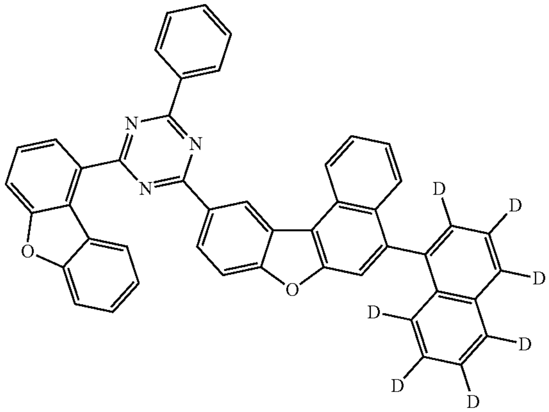
[150]
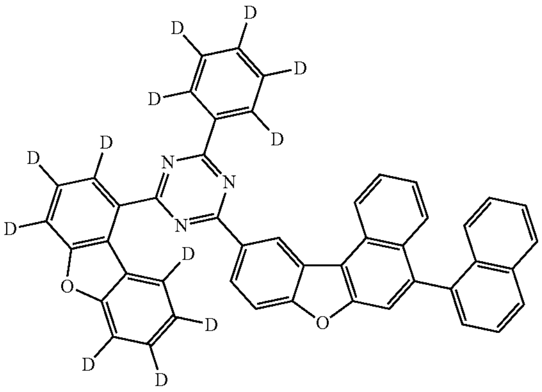
[151]
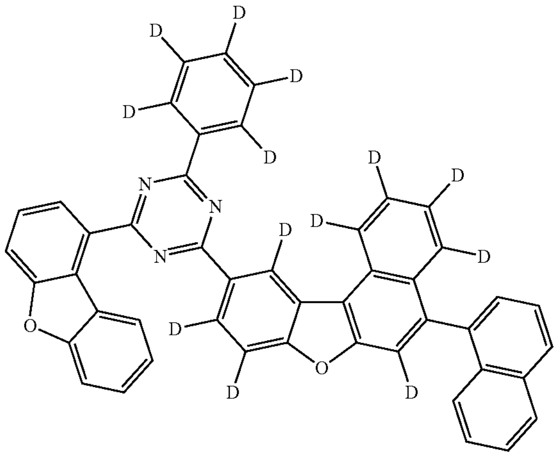

-continued
[152]
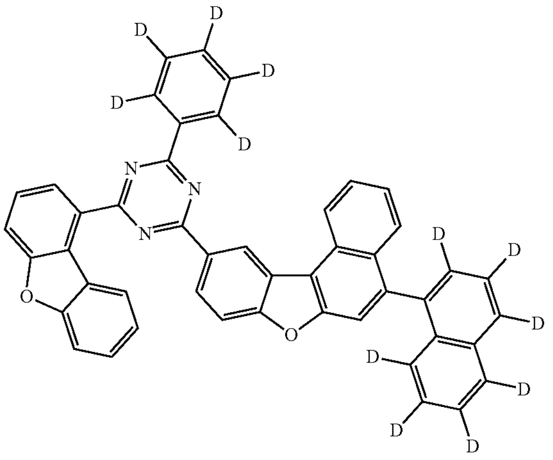
[153]
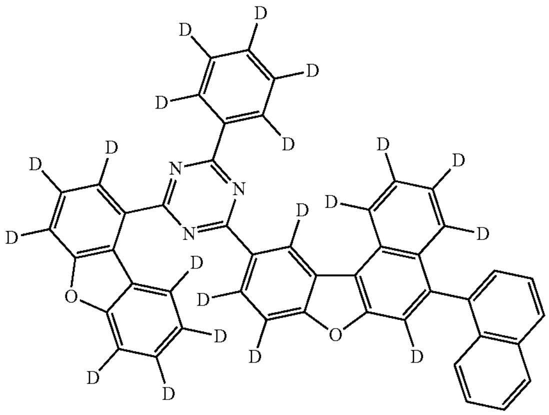
[154]
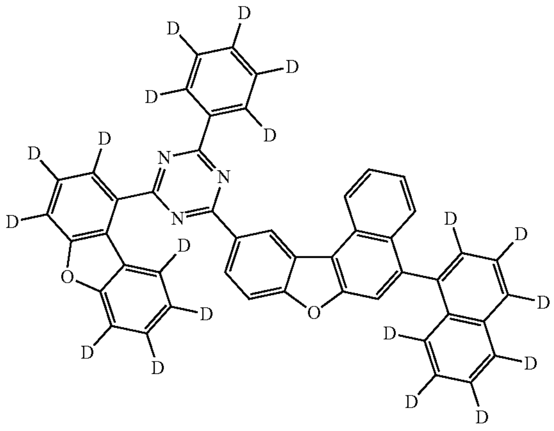
[155]
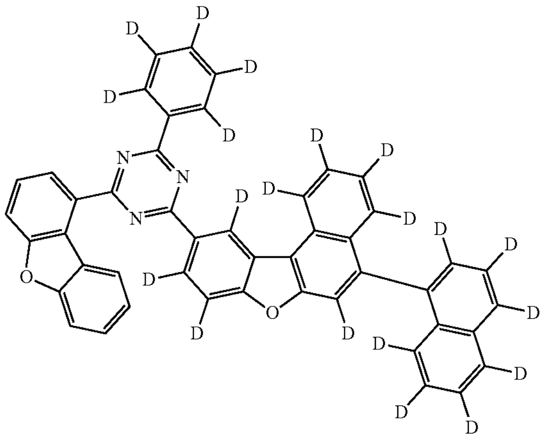
[156]
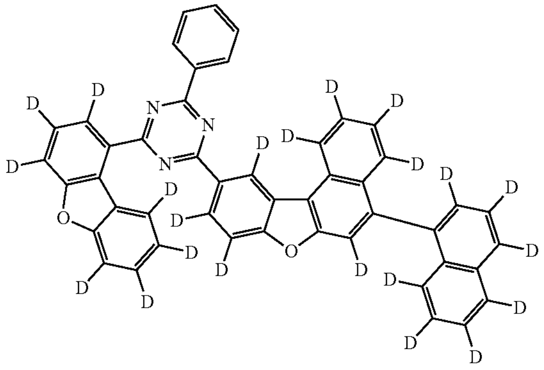
[157]
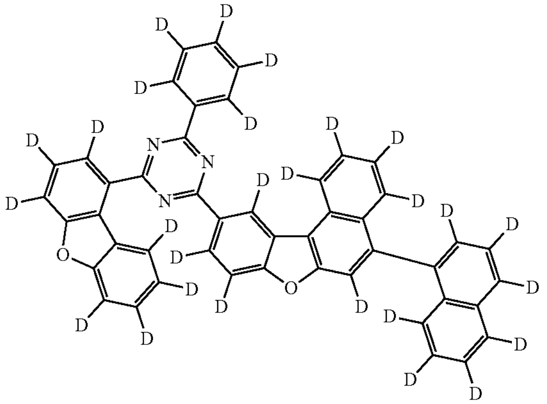

-continued
[158]
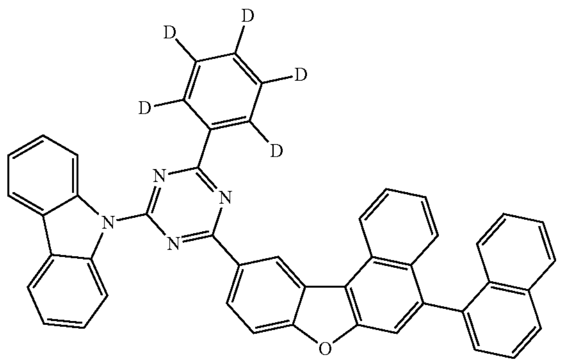
[159]
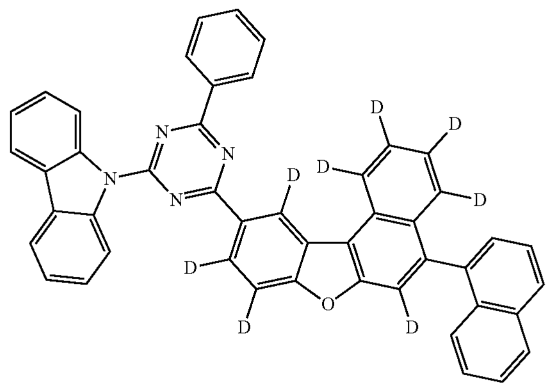
[160]
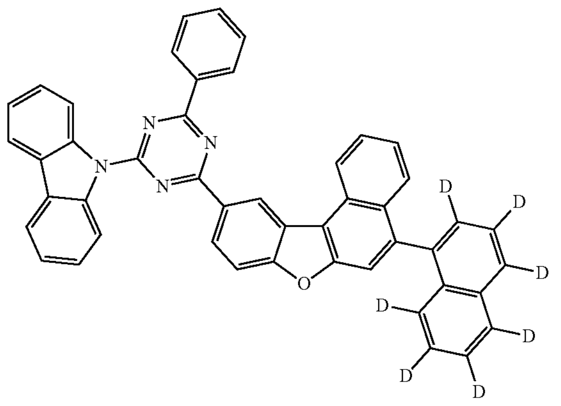
[161]
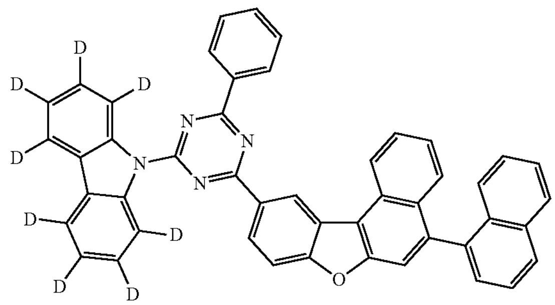
[162]
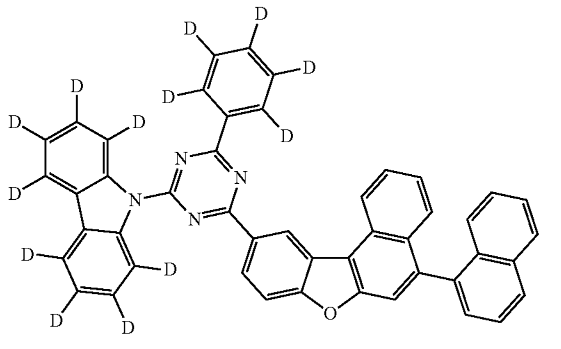
[163]
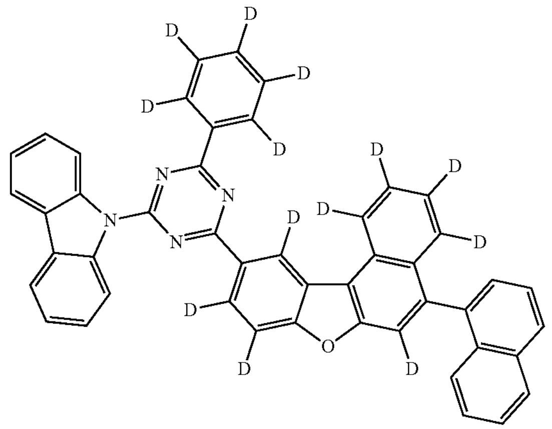

-continued

[164]

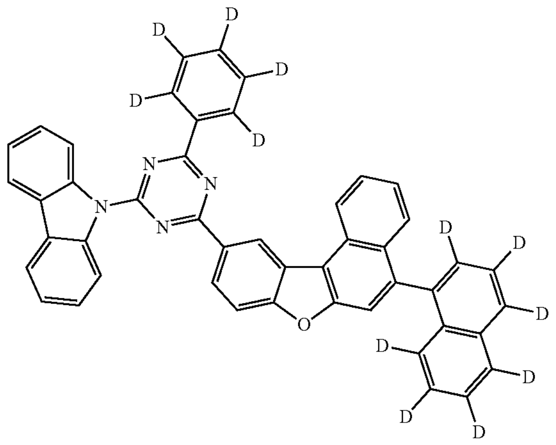

[165]

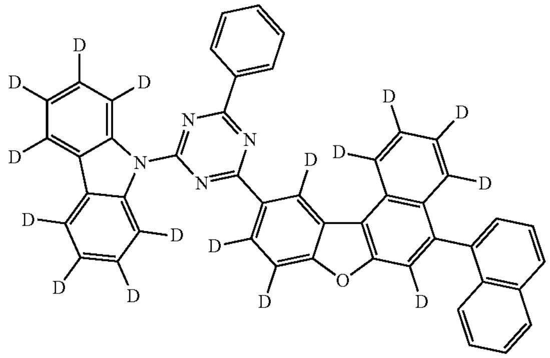

[166]

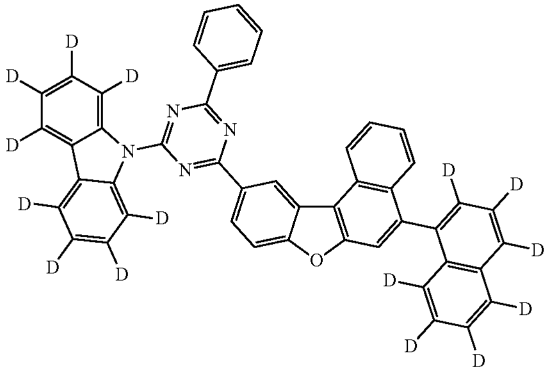

[167]

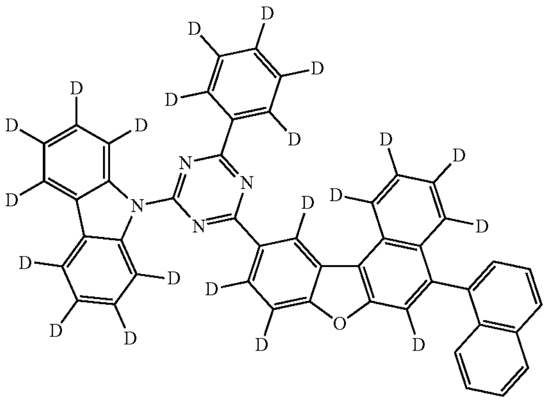

[168]

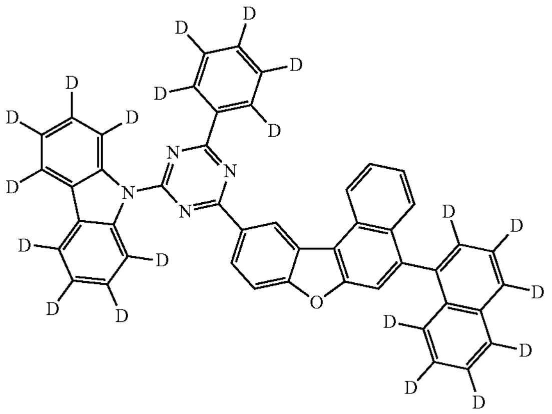

[169]

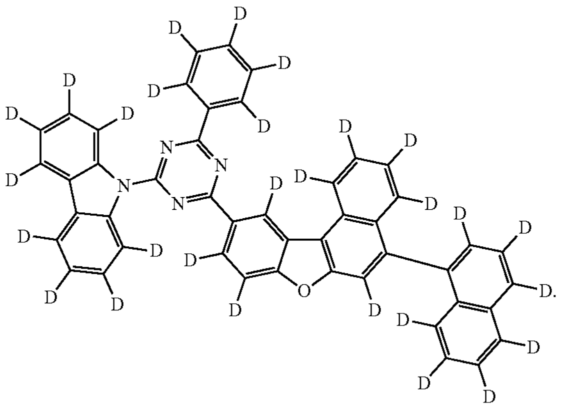

17. An organic optoelectronic device, comprising:

an anode and a cathode facing each other, and at least one organic layer between the anode and the cathode, wherein:

the at least one organic layer includes a light emitting layer, and the light emitting layer includes the compound for the organic optoelectronic device as claimed in claim 16.

18. The organic optoelectronic device as claimed in claim 17, wherein the compound for the organic optoelectronic device is a host of the light emitting layer.

19. A display device comprising the organic optoelectronic device as claimed in claim 17.

* * * * *